US009409995B2

(12) United States Patent
Foord et al.

(10) Patent No.: US 9,409,995 B2
(45) Date of Patent: Aug. 9, 2016

(54) PTK7 MODULATORS AND METHODS OF USE

(75) Inventors: Orit Foord, Foster City, CA (US); Scott J. Dylla, Mountain View, CA (US); Robert A. Stull, Alameda, CA (US); Alex Bankovich, San Francisco, CA (US); Alexandra Leida Liana Lazetic, San Jose, CA (US); Jeffrey Bernstein, San Francisco, CA (US)

(73) Assignee: Stemcentrx, Inc., South San Francisco, CA (US)

( * ) Notice: Subject to any disclaimer, the term of this patent is extended or adjusted under 35 U.S.C. 154(b) by 0 days.

(21) Appl. No.: 14/000,289

(22) PCT Filed: Feb. 17, 2012

(86) PCT No.: PCT/US2012/025726
§ 371 (c)(1),
(2), (4) Date: Nov. 27, 2013

(87) PCT Pub. No.: WO2012/112943
PCT Pub. Date: Aug. 23, 2012

(65) Prior Publication Data
US 2014/0105888 A1  Apr. 17, 2014

Related U.S. Application Data

(60) Provisional application No. 61/444,614, filed on Feb. 18, 2011.

(30) Foreign Application Priority Data

Sep. 2, 2011 (WO) ................ PCT/US2011/050451

(51) Int. Cl.
| | |
|---|---|
| *C07K 16/40* | (2006.01) |
| *A61K 39/395* | (2006.01) |
| *C07K 16/30* | (2006.01) |
| *A61K 47/48* | (2006.01) |

(52) U.S. Cl.
CPC ........... *C07K 16/40* (2013.01); *A61K 47/48646* (2013.01); *C07K 16/30* (2013.01); *C07K 2317/24* (2013.01); *C07K 2317/34* (2013.01); *C07K 2317/56* (2013.01); *C07K 2317/565* (2013.01); *C07K 2317/92* (2013.01); *C12N 2740/15043* (2013.01)

(58) Field of Classification Search
CPC ............... C07K 16/00–16/468; C07K 2317/30–2317/34; C07K 2317/77; C07K 2317/90–2317/94
See application file for complete search history.

(56) References Cited

U.S. PATENT DOCUMENTS

| | | | |
|---|---|---|---|
| 7,422,739 B2 | 9/2008 | Anderson et al. | |
| 7,619,068 B2 | 11/2009 | Pilkington et al. | |
| 7,659,374 B2 | 2/2010 | Wu et al. | |
| 7,744,877 B2 | 6/2010 | Anderson et al. | |
| 8,058,252 B2 | 11/2011 | Chouaib et al. | |
| 8,222,253 B2 | 7/2012 | Wang et al. | |
| 8,461,119 B2 | 6/2013 | Pasquale et al. | |
| 2007/0292414 A1 | 12/2007 | Duntsch et al. | |
| 2008/0138313 A1 | 6/2008 | Frankel | |
| 2009/0123371 A1 | 5/2009 | Debinski et al. | |
| 2009/0155255 A1 | 6/2009 | Glaser et al. | |
| 2010/0034826 A1* | 2/2010 | Terrett et al. ................ | 424/142.1 |
| 2010/0184119 A1 | 7/2010 | Bright et al. | |
| 2010/0273160 A1 | 10/2010 | Donahoe et al. | |
| 2011/0020221 A1 | 1/2011 | Berman et al. | |
| 2011/0280892 A1 | 11/2011 | Kinch et al. | |
| 2012/0083454 A1 | 4/2012 | Vescovi et al. | |
| 2013/0061340 A1 | 3/2013 | Dylla et al. | |
| 2013/0061342 A1 | 3/2013 | Dylla et al. | |
| 2013/0260385 A1 | 10/2013 | Dylla et al. | |
| 2015/0030636 A1 | 1/2015 | Dylla et al. | |
| 2015/0315293 A1* | 11/2015 | Damelin ................ | C07K 16/40 424/181.1 |

FOREIGN PATENT DOCUMENTS

| | | |
|---|---|---|
| CN | 101678075 A | 3/2010 |
| CN | 101939028 A | 1/2011 |
| EP | 0216846 | 4/1987 |
| EP | 0256055 | 2/1988 |
| EP | 0323997 | 7/1989 |
| EP | 0338841 | 10/1989 |
| EP | 2446895 | 5/2012 |
| KR | 2009 0099471 | 9/2009 |
| WO | WO 03/075957 | 9/2003 |
| WO | WO 2007/067730 | 6/2007 |
| WO | WO2007/067730 A2 * | 6/2007 |
| WO | WO 2008/149803 A1 | 12/2008 |
| WO | WO 2009/070767 A2 | 6/2009 |
| WO | WO 2009/073546 | 6/2009 |
| WO | WO 2009/157623 A1 | 12/2009 |
| WO | WO 2012/031280 | 3/2012 |
| WO | WO 2012/042021 | 4/2012 |

(Continued)

OTHER PUBLICATIONS

PJ Carter, Nat Rev Immunol, 2006; 6:343-357.*
Almagro & Fransson, Frontiers in Bioscience 2008; 13:1619-33.*
De Genst et al., Dev Comp Immunol 2006; 30:187-98.*
Botchkina et al, "Phenotypic Subpopulations of Metastatic Colon Cancer Stem Cells: Genomic Analysis", *Cancer Genomics & Proteomics* (2009) 6:19-30.
Cavard et al, "Gene expression profiling provides insights into the pathways involved in solid pseudopapillary neoplasm of the pancreas", *J Pathol* (2009) 218: 201-209.

(Continued)

*Primary Examiner* — Jessica H Roark
(74) *Attorney, Agent, or Firm* — Womble Carlye Sandridge & Rice, LLP

(57) ABSTRACT

PTK modulators, including antibodies and derivatives thereof, and methods of using such modulators to treat hyperproliferative disorders are provided.

29 Claims, 28 Drawing Sheets

(56) References Cited

FOREIGN PATENT DOCUMENTS

| WO | WO 2013/119964 | 8/2013 |
|---|---|---|
| WO | WO 2015/031698 | 3/2015 |

OTHER PUBLICATIONS

Soyuer et al, "Prognostic significance of CD9 expression in locally advanced gastric cancer treated with surgery and adjuvant chemoradiotherapy", *Pathology—Research and Practice* (2010) 206; 607-610.
Todaro et al, "Colon Cancer Stem Cells: Promise of Targeted Therapy", *Gastroenterology* (2010) 138:2151-2162.
Official Action dated Dec. 1, 2014 issued in Chinese application (No. 201280019016.6).
Official Action dated Sep. 29, 2014 issued in European application (No. 12705776.8).
Office action received Dec. 14, 2014 issued in Saudi Arabian application (No. 112330278.2).
Al-Hajj et al., "Self-renewal and solid tumor stem cells" *Oncogene* (2004) 23, 7274-7282.
Caddy et al., "Epidermal wound repair is regulated by the planar cell polarity signaling pathway." *Dev. Cell.* Jul. 12, 2010;19(1):138-47.
Dalerba et al. "Phenotypic characterization of human colorectal cancer stem cells" *Proc Natl Acad Sci U S A.* Jun. 12, 2007;104(24).
Dylla et al. "Colorectal Cancer Stem Cells Are Enriched in Xenogenic Tumors Following Chemotherapy" *PLoS ONE.* 2008; 3(6): e2428. 2008, PMCID: PMC2556496.
Easty et al. "Loss of Expression of Receptor Tyrosine Kinase Family Genes Ptk7 and Sek in Metastatic Melanoma" *Int J. Cancer.* (Jun. 11, 1997) 71(6):1061-5.
Endoh et al. "Prognostic Model of Pulmonary Adenocarcinoma by Expression Profiling of Eight Genes as Determined by Quantitative Real-Time Reverse Transcriptase Polymerase Chain Reaction" *J Clin Oncol.* Mar. 1, 2004; 22(5):811-9.
Forrest, Taylor et al.,"Genome-wide review of transcriptional complexity in mouse protein kinases and phosphatases." *Genome Biol.* 2006;7(1):R5.
Genbank accession No. NM_002821 *Homo sapiens* protein tyrosine kinase 7 (PTK7), transcript variant PTK7-1, mRNA, Dec. 1, 2013.
Genbank accession No. NP_002812 inactive tyrosine-protein kinase 7 isoform a precursor [*Homo sapiens*], Dec. 1, 2013.
Genbank accession No. NP_690619 inactive tyrosine-protein kinase 7 isoform b precursor [*Homo sapiens*], Dec. 1, 2013.
Genbank accession No. NP_690620 inactive tyrosine-protein kinase 7 isoform c precursor [*Homo sapiens*], Dec. 1, 2013.
Genbank accession No. NP_690621 inactive tyrosine-protein kinase 7 isoform d precursor [*Homo sapiens*], Dec. 1, 2013.
Golubkov, et al. (2012) "The Wnt/Planar Cell Polarity Protein-tyrosine Kinase-7 (PTK7) Is a Highly Efficient Proteolytic Target of Membrane Type-1 Matrix Metalloproteinase." *J Biol Chem.* Nov. 12, 2010; 285(46): 35740-35749.
Gorringe et al.,"Novel regions of chromosomal amplification at 6p21, 5p13, and 12q14 in gastric cancer identified by array comparative genomic hybridization " *Genes Chromosomes Cancer.* Mar. 2005; 42(3):247-59.
Haines, Christopher J., et al., "Human CD4+ T cell recent thymic emigrants are identified by protein tyrosine kinase 7 and have reduced immune function" *J Exp Med*, (2009) 206(2) pp. 275-285.
Hanks, Steven K. et al."Protein kinase catalytic domain sequence database: identification of conserved features of primary structure and classification of family members." *Methods Enzymol.* (1991) 200: 38-62.
Hoey, Timothy, et al."DLL4 Blockade Inhibits Tumor Growth and Reduces Tumor-Initiating Cell Frequency" *Cell Stem Cell.* Aug. 7, 2009; 5(2):168-77.
Huff et al.,"Strategies to eliminate cancer stem cells: Clinical implications" *European Journal of Cancer* (2006) 42: 1293-1297.

Jung, JW et al., "Organization of the human PTK7 gene encoding a receptor protein tyrosine kinase-like molecule and alternative splicing of its mRNA." *Biochim Biophys Acta.* Dec. 12, 2002;1579(2-3):153-63.
Katoh, Masuko, et al ,"Comparative integromics on non-canonical WNT or planar cell polarity signaling molecules: transcriptional mechanism of PTK7 in colorectal cancer and that of SEMA6A in undifferentiated ES cells." *Int J Mol Med.* Sep. 2007; 20(3): 405-9.
Kobus, FJ, "The GxxxG-containing transmembrane domain of the CCK4 oncogene does not encode preferential self-interactions." et al., *Biochemistry.* Feb. 8, 2005;44(5):1464-70.
Kroiher, M. et al., "Deceiving appearances: signaling by "dead" and "fractured" receptor protein-tyrosine kinases." *Bioessays.* Jan. 2001;23(1):69-76.
Lee ST, et al, "A survey of protein tyrosine kinase mRNAs expressed in normal human melanocytes." *Oncogene* Dec. 1993; 8(12):3403-10.
Lu et al., "PTK7/CCK-4 is a novel regulator of planar cell polarity in vertebrates." *Nature.* Jul. 1, 2004;430(6995):93-8.
Lu XY, et al "Cell cycle regulator gene CDC5L, a potential target for 6p12-p21 amplicon in osteosarcoma." *Mol Cancer Res.* Jun. 2008;6(6):937-46.
Meng, L. et al "Silencing of PTK7 in Colon Cancer Cells: Caspase-10-Dependent Apoptosis via Mitochondrial Pathway." *PLoS One.* Nov. 16, 2010;5(11):e14018.
Mossie et al., "Colon carcinoma kinase-4 defines a new subclass of the receptor tyrosine kinase family." *Oncogene* Nov. 16, 1995; 11(10): 2179-84.
Muller-Tidow, et al."High-Throughput Analysis of Genome-Wide Receptor Tyrosine Kinase Expression in Human Cancers Identifies Potential Novel Drug Targets." *Clin Cancer Res.* Feb. 15, 2004;10(4):1241-9.
Orsulic, S. et al "Expression of Eph receptors and ephrins is differentially regulated by E-cadherin", *Journal of Cell Science* 113, 1793-1802 (2000).
Paudyal, Damrau et al. "The novel mouse mutant, chuzhoi, has disruption of Ptk7 protein and exhibits defects in neural tube, heart and lung development and abnormal planar cell polarity in the ear." *BMC Dev Biol.* Aug. 12, 2010;10:87.
Piao et al., "Identification of novel deletion regions on chromosome arms 2q and 6p in breast carcinomas by amplotype analysis." *Genes Chromosomes Cancer.* Feb. 2001;30(2):113-22.
Prebet, Thomas et al. "The cell polarity PTK7 receptor acts as a modulator of the chemotherapeutic response in acute myeloid leukemia and impairs clinical outcome." *Blood* (2010) 116(13):2315-23.
Puppo et al., "Protein tyrosine kinase 7 has a conserved role in Wnt/β-catenin canonical signalling." *EMBO Rep.* Jan. 2011;12(1):43-9.
Retter et al., "VBASE2, an integrative V gene database" *Nucleic Acids Res.* Jan. 1, 2005;33(Database issue):D671-4.
Saha, S. et al.,"A phosphatase associated with metastasis of colorectal cancer." *Science.* Nov. 9, 2001; 294(5545): 1343-6.
Schmalhofer et al., "E-cadherin, β-catenin, and ZEB1 in malignant progression of cancer." *Cancer Metastasis Rev.* Jun. 2009; 28 (1-2):151-66.
Schulenburg, A. et al "Neoplastic stem cells: Current concepts and clinical perspectives" *Crit Rev Oncol Hematol.* 76 (2010) 79-98.
Shangguan, D. et al. "Cell-Specific Aptamer Probes for Membrane Protein Elucidation in Cancer Cells" *J Proteome Res.* May 2008; 7(5):2133-9.
Shin et al. "Soluble PTK7 inhibits tube formation, migration, and invasion of endothelial cells and angiogenesis", *Biochem Biophys Res Commun.* Jul. 11, 2008; 371(4) :793-8.
Shnitsar et al. "PTK7 recruits dsh to regulate neural crest migration", *Development.* Dec. 2008;135(24):4015-24.
Su, Y.A. et al "Undetectable and Decreased Expression of KIAA1949 (Phostensin) Encoded on Chromosome 6p21.33 in Human Breast Cancers Revealed by Transcriptome Analysis." *J Cancer.* Jun. 21, 2010; 1:38-50.
Toyofuku et al., "Dual roles of Sema6D in cardiac morphogenesis through region-specific association of its receptor, Plexin-A1, with off-track and vascular endothelial growth factor receptor type 2" *Genes Dev.* Feb. 15, 2004;18(4):435-47.

(56) References Cited

OTHER PUBLICATIONS

Visvader et al "Cancer stem cells in solid tumours: accumulating evidence and unresolved questions" *Nature Reviews Cancer* 8, 755-768 (Oct. 2008) PMID 18784658.
Wagner, G et al., "PlexinA1 interacts with PTK7 and is required for neural crest migration" *Biochem Biophys Res Commun.* Nov. 12, 2010;402(2):402-7.
Winberg et al.,"The Transmembrane Protein Off-Track Associates with Plexins and Functions Downstream of Semaphorin Signaling during Axon Guidance" *Neuron.* Oct. 11, 2001;32(1):53-62.
Xiao et al., "Structure elucidation and theoretical investigation of key steps in the biogenetic pathway of schisanartane nortriterpenoids by using DFT methods." *Chemistry.* 2008;14(36):11584-92.
Zantek, ND, et al.," E-cadherin regulates the function of the EphA2 receptor tyrosine kinase." *Cell Growth Differ.* Sep. 1999;10(9):629-38.
Zhou et al.,"Tumour-initiating cells: challenges and opportunities for anticancer drug discovery." *Nat Rev Drug Discov.* Oct. 2009;8(10):806-23.
International Search Report dated May 25, 2012 issued in PCT counterpart application (No. PCT/US2012/025726).
Written Opinion dated May 25, 2012 issued in PCT counterpart application (No. PCT/US2012/025726).
Official Action dated Feb. 28, 2014 issued in New Zealand counterpart application (No. 615285).
Official Action dated Jun. 4, 2014 issued in Saudi Arabian counterpart application (No. 112330278).
Office Action dated Apr. 8, 2015 issued in Australian patent application (No. 2012219313).
Office Action dated Oct. 23, 2015 issued in Chinese patent application (No. 201280019016.6).
Office Action dated May 25, 2015 issued in Colombian patent application (No. 13-216.891).
Office Action dated Jul. 26, 2015 issued in Colombian patent application (No. 13-216.891).
Office Action dated Oct. 13, 2015 issued in European patent application (No. 12705776.8).
Office Action dated Jun. 16, 2015 issued in New Zealand patent application (No. 615285).
Office Action dated Jun. 16, 2015 issued in New Zealand patent application (No. 708615).

\* cited by examiner

FIG. 1A

>gi|27886610|ref|NM_002821.3| Homo sapiens PTK7 protein tyrosine kinase 7 (PTK7), transcript variant PTK7-1, mRNA (SEQ ID NO: 1)

GCGGCGCGCGGGGACTCGGAGGTACTGGGCGCGCGCGGCTCCGGCTCGGGACGCCTCGGGACGCCTCGGG
GTCGGGCTCCGGCTGCGGCTGCTGCTGCGGCGCCCGCGCTCCGGTGCGCTCCGCCTCCTGTGCCCGCCGC
GGAGCGCAGTCTGCGCGCCCGCCGTGCGCCCTCAGCTCCTTTTCCTGAGCCCGCCGCGATGGGAGCTGCG
CGGGGATCCCCGGCCAGACCCCGCCGGTTGCCTCTGCTCAGCGTCCTGCTGCTGCCGCTGCTGGGCGGTA
CCCAGACAGCCATTGTCTTCATCAAGCAGCCGTCCTCCCAGGATGCACTGCAGGGGCGCCGGGCGCTGCT
TCGCTGTGAGGTTGAGGCTCCGGGCCCGGTACATGTGTACTGGCTGCTCGATGGGGCCCCTGTCCAGGAC
ACGGAGCGGCGTTTCGCCCAGGGCAGCAGCCTGAGCTTTGCAGCTGTGGACCGGCTGCAGGACTCTGGCA
CCTTCCAGTGTGTGGCTCGGGATGATGTCACTGGAGAAGAAGCCCGCAGTGCCAACGCCTCCTTCAACAT
CAAATGGATTGAGGCAGGTCCTGTGGTCCTGAAGCATCCAGCCTCGGAAGCTGAGATCCAGCCACAGACC
CAGGTCACACTTCGTTGCCACATTGATGGGCACCCTCGGCCCACCTACCAATGGTTCCGAGATGGGACCC
CCCTTTCTGATGGTCAGAGCAACCACACAGTCAGCAGCAAGGAGCGGAACCTGACGCTCCGGCCAGCTGG
TCCTGAGCATAGTGGGCTGTATTCCTGCTGCGCCCACAGTGCTTTTGGCCAGGCTTGCAGCAGCCAGAAC
TTCACCTTGAGCATTGCTGATGAAAGCTTTGCCAGGGTGGTGCTGGCACCCCAGGACGTGGTAGTAGCGA
GGTATGAGGAGGCCATGTTCCATTGCCAGTTCTCAGCCCAGCCACCCCCGAGCCTGCAGTGGCTCTTTGA
GGATGAGACTCCCATCACTAACCGCAGTCGCCCCCCACACCTCCGCAGAGCCACAGTGTTTGCCAACGGG
TCTCTGCTGCTGACCCAGGTCCGGCCACGCAATGCAGGGATCTACCGCTGCATTGGCCAGGGGCAGAGGG
GCCCACCCATCATCCTGGAAGCCACACTTCACCTAGCAGAGATTGAAGACATGCCGCTATTTGAGCCACG
GGTGTTTACAGCTGGCAGCGAGGAGCGTGTGACCTGCCTTCCCCCCAAGGGTCTGCCAGAGCCCAGCGTG
TGGTGGGAGCACGCGGGAGTCCGGCTGCCCACCCATGGCAGGGTCTACCAGAAGGGCCACGAGCTGGTGT
TGGCCAATATTGCTGAAAGTGATGCTGGTGTCTACACCTGCCACGCGGCCAACCTGGCTGGTCAGCGGAG
ACAGGATGTCAACATCACTGTGGCCACTGTGCCCTCCTGGCTGAAGAAGCCCCAAGACAGCCAGCTGGAG
GAGGGCAAACCCGGCTACTTGGATTGCCTGACCCAGGCCACACCAAAACCTACAGTTGTCTGGTACAGAA
ACCAGATGCTCATCTCAGAGGACTCACGGTTCGAGGTCTTCAAGAATGGGACCTTGCGCATCAACAGCGT
GGAGGTGTATGATGGGACATGGTACCGTTGTATGAGCAGCACCCCAGCCGGCAGCATCGAGGCGCAAGCC
CGTGTCCAAGTGCTGGAAAAGCTCAAGTTCACACCACCACCCCAGCCACAGCAGTGCATGGAGTTTGACA
AGGAGGCCACGGTGCCCTGTTCAGCCACAGGCCGAGAGAAGCCCACTATTAAGTGGGAACGGGCAGATGG
GAGCAGCCTCCCAGAGTGGGTGACAGACAACGCTGGGACCCTGCATTTTGCCCGGGTGACTCGAGATGAC
GCTGGCAACTACACTTGCATTGCCTCCAACGGGCCGCAGGGCCAGATTCGTGCCCATGTCCAGCTCACTG
TGGCAGTTTTTATCACCTTCAAAGTGGAACCAGAGCGTACGACTGTGTACCAGGGCCACACAGCCCTACT
GCAGTGCGAGGCCCAGGGGGACCCCAAGCCGCTGATTCAGTGGAAAGGCAAGGACCGCATCCTGGACCCC
ACCAAGCTGGGACCCAGGATGCACATCTTCCAGAATGGCTCCCTGGTGATCCATGACGTGGCCCCTGAGG
ACTCAGGCCGCTACACCTGCATTGCAGGCAACAGCTGCAACATCAAGCACACGGAGGCCCCCCTCTATGT
CGTGGACAAGCCTGTGCCGGAGGAGTCGGAGGGCCCTGGCAGCCCTCCCCCCTACAAGATGATCCAGACC

FIG. 1A (CONT.)

(SEQ ID NO: 1) Cont.

ATTGGGTTGTCGGTGGGTGCCGCTGTGGCCTACATCATTGCCGTGCTGGGCCTCATGTTCTACTGCAAGA
AGCGCTGCAAAGCCAAGCGGCTGCAGAAGCAGCCCGAGGGCGAGGAGCCAGAGATGGAATGCCTCAACGG
TGGGCCTTTGCAGAACGGGCAGCCCTCAGCAGAGATCCAAGAAGAAGTGGCCTTGACCAGCTTGGGCTCC
GGCCCCGCGGCCACCAACAAACGCCACAGCACAAGTGATAAGATGCACTTCCCACGGTCTAGCCTGCAGC
CCATCACCACGCTGGGGAAGAGTGAGTTTGGGGAGGTGTTCCTGGCAAAGGCTCAGGGCTTGGAGGAGGG
AGTGGCAGAGACCCTGGTACTTGTGAAGAGCCTGCAGAGCAAGGATGAGCAGCAGCAGCTGGACTTCCGG
AGGGAGTTGGAGATGTTTGGGAAGCTGAACCACGCCAACGTGGTGCGGCTCCTGGGGCTGTGCCGGGAGG
CTGAGCCCCACTACATGGTGCTGGAATATGTGGATCTGGGAGACCTCAAGCAGTTCCTGAGGATTTCCAA
GAGCAAGGATGAAAAATTGAAGTCACAGCCCCTCAGCACCAAGCAGAAGGTGGCCCTATGCACCCAGGTA
GCCCTGGGCATGGAGCACCTGTCCAACAACCGCTTTGTGCATAAGGACTTGGCTGCGCGTAACTGCCTGG
TCAGTGCCCAGAGACAAGTGAAGGTGTCTGCCCTGGGCCTCAGCAAGGATGTGTACAACAGTGAGTACTA
CCACTTCCGCCAGGCCTGGGTGCCGCTGCGCTGGATGTCCCCGAGGCCATCCTGGAGGGTGACTTCTCT
ACCAAGTCTGATGTCTGGGCCTTCGGTGTGCTGATGTGGGAAGTGTTTACACATGGAGAGATGCCCCATG
GTGGGCAGGCAGATGATGAAGTACTGGCAGATTTGCAGGCTGGGAAGGCTAGACTTCCTCAGCCCGAGGG
CTGCCCTTCCAAACTCTATCGGCTGATGCAGCGCTGCTGGGCCCTCAGCCCCAAGGACCGGCCCTCCTTC
AGTGAGATTGCCAGCGCCCTGGGAGACAGCACCGTGGACAGCAAGCCGTGAGGAGGGAGCCCGCTCAGGA
TGGCCTGGGCAGGGGAGGACATCTCTAGAGGGAAGCTCACAGCATGATGGGCAAGATCCCTGTCCTCCTG
GGCCCTGAGGCCCCTGCCCTAGTGCAACAGGCATTGCTGAGGTCTGAGCAGGGCCTGGCCTTTCCTCCTC
TTCCTCACCCTCATCCTTTGGGAGGCTGACTTGGACCCAAACTGGGCGACTAGGGCTTTGAGCTGGGCAG
TTTTCCCTGCCACCTCTTCCTCTATCAGGGACAGTGTGGGTGCCACAGGTAACCCCAATTTCTGGCCTTC
AACTTCTCCCCTTGACCGGGTCCAACTCTGCCACTCATCTGCCAACTTTGCCTGGGGAGGGCTAGGCTTG
GGATGAGCTGGGTTTGTGGGAGTTCCTTAATATTCTCAAGTTCTGGGCACACAGGGTTAATGAGTCTCT
TGGCCCACTGGTCCCACTTGGGGGTCTAGACCAGGATTATAGAGGACACAGCAAGTGAGTCCTCCCCACT
CTGGGCTTGTGCACACTGACCCAGACCCACGTCTTCCCCACCCTTCTCTCCTTTCCTCATCCTAAGTGCC
TGGCAGATGAAGGAGTTTTCAGGAGCTTTTGACACTATATAAACCGCCTTTTTGTATGCACCACGGGCG
GCTTTTATATGTAATTGCAGCGTGGGGTGGGTGGGCATGGGAGGTAGGGGTGGGCCCTGGAGATGAGGAG
GGTGGGCCATCCTTACCCCACACTTTTATTGTTGTCGTTTTTTGTTTGTTTTGTTTTTTGTTTTTGTTT
TTGTTTTTACACTCGCTGCTCTCAATAAATAAGCCTTTTTTACAACCTG

>gi|47938093|gb|AAH71557.1| PTK7 protein tyrosine kinase 7 [Homo sapiens]

(SEQ ID NO:2)

MGAARGSPARPRRLPLLSVLLLPLLGGTQTAIVFIKQPSSQDALQGRRALLRCEVEAPGPVHVYWLLDGA
PVQDTERRFAQGSSLSFAAVDRPQDSGTFQCVARDDVTGEEARSANASFNIKWIEAGPVVLKHPASEAEI
QPQTQVTLRCHIDGHPRPTYQWFRDGTPLSDGQSNHTVSSKERNLTLRPAGPEHSGLYSCCAHSAFGQAC
SSQNFTLSIADESFARVVLAPQDVVVARYEEAMFHCQFSAQPPPSLQWLFEDETPITNRSRPPHLRRATV
FANGSLLLTQVRPRNAGIYRCIGQQGRGPPIILEATLHLAEIEDMPLFEPRVFTAGSEERVTCLPPKGLP
EPSVWWEHAGVRLPTHGRVYQKGHELVLANIAESDAGVYTCHAANLAGQRRQDVNITVATVPSWLKKPQD
SQLEEGKPGYLDCLTQATPKPTVVWYRNQMLISEDSRFEVFKNGTLRINSVEVYDGTWYRCMSSTPAGSI
EAQARVQVLEKLKFTPPPQPQQCMEFDKEATVPCSATGREKPTIKWERADGSSLPEWVTDNAGTLHFARV
TRDDAGNYTCIASNGPQGQIRAHVQLTVAVFITFKVEPERTTVYQGHTALLQCEAQGDPKPLIQWKGKDR
ILDPTKLGPRMHIFQNGSLVIHDVAPEDSGRYTCIAGNSCNIKHTEAPLYVVDKPVPEESEGPGSPPPYK
MIQTIGLSVGAAVAYIIAVLGLMFYCKKRCKAKRLQKQPEGEEPEMECLNGGPLQNGQPSAEIQEEVALT
SLGSGPAATNKRHSTSDKMHFPRSSLQPITTLGKSEFGEVFLAKAQGLEEGVAETLVLVKSLQSKDEQQQ
LDFRRELEMFGKLNHANVVRLLGLCREAEPHYMVLEYVDLGDLKQFLRISKSKDEKLKSQPLSTKQKVAL
CTQVALGMEHLSNNRFVHKDLAARNCLVSAQRQVKVSALGLSKDVYNSEYHFRQAWVPLRWMSPEAILE
GDFSTKSDVWAFGVLMWEVFTHGEMPHGGQADDEVLADLQAGKARLPQPEGCPSKLYRLMQRCWALSPKD
RPSFSEIASALGDSTVDSKP

FIG. 1B

PTK7 isoforms

```
        signal peptide                        IG domain (1)
iso a  MGAARGSPARPRRLPLLSVLLLPLLGGTQTAIVFIKQPSSQDALQGRRALLRCEVEAPGPVHVYWLLDGA    70
iso d  MGAARGSPARPRRLPLLSVLLLPLLGGTQTAIVFIKQPSSQDALQGRRALLRCEVEAPGPVHVYWLLDGA
iso b  MGAARGSPARPRRLPLLSVLLLPLLGGTQTAIVFIKQPSSQDALQGRRALLRCEVEAPGPVHVYWLLDGA
iso c  MGAARGSPARPRRLPLLSVLLLPLLGGTQTAIVFIKQPSSQDALQGRRALLRCEVEAPGPVHVYWLLDGA iso a  PVQDTERRFAQGSSLSFAAVDRLQDSGTFQCVARDDVTGEEARSANASFNIKWIEAGPVVLKHPASEAEI   140
iso d  PVQDTERRFAQGSSLSFAAVDRLQDSGTFQCVARDDVTGEEARSANASFNIKWIEAGPVVLKHPASEAEI
iso b  PVQDTERRFAQGSSLSFAAVDRLQDSGTFQCVARDDVTGEEARSANASFNIKWIEAGPVVLKHPASEAEI
iso c  PVQDTERRFAQGSSLSFAAVDRLQDSGTFQCVARDDVTGEEARSANASFNIKWIEAGPVVLKHPASEAEI IGcam domain (2)
iso a  QPQTQVTLRCHIDGHPRPTYQWFRDGTPLSDGQSNHTVSSKERNLTLRPAGPEHSGLYSCCAHSAFGQAC   210
iso d  QPQTQVTLRCHIDGHPRPTYQWFRDGTPLSDGQSNHTVSSKERNLTLRPAGPEHSGLYSCCAHSAFGQAC
iso b  QPQTQVTLRCHIDGHPRPTYQWFRDGTPLSDGQSNHTVSSKERNLTLRPAGPEHSGLYSCCAHSAFGQAC
iso c  QPQTQVTLRCHIDGHPRPTYQWFRDGTPLSDGQSNHTVSSKERNLTLRPAGPEHSGLYSCCAHSAFGQAC IGcam domain (3)
iso a  SSQNFTLSIADESFARVVLAPQDVVVARYEEAMFHCQFSAQPPPSLQWLFEDETPITNRSRPPHLRRATV   280
iso d  SSQNFTLSIADESFARVVLAPQDVVVARYEEAMFHCQFSAQPPPSLQWLFEDETPITNRSRPPHLRRATV
iso b  SSQNFTLSIADESFARVVLAPQDVVVARYEEAMFHCQFSAQPPPSLQWLFEDETPITNRSRPPHLRRATV
iso c  SSQNFTLSIADESFARVVLAPQDVVVARYEEAMFHCQFSAQPPPSLQWLFEDETPITNRSRPPHLRRATV IGcam domain (4)
iso a  FANGSLLLTQVRPRNAGIYRCIGQGQRGPPIILEATLHLAEIEDMPLFEPRVFTAGSEERVTCLPPKGLP   350
iso d  FANGSLLLTQVRPRNAGIYRCIGQGQRGPPIILEATLHLAEIEDMPLFEPRVFTAGSEERVTCLPPKGLP
iso b  FANGSLLLTQVRPRNAGIYRCIGQGQRGPPIILEATLHLAEIEDMPLFEPRVFTAGSEERVTCLPPKGLP
iso c  FANGSLLLTQVRPRNAGIYRCIGQGQRGPPIILEATLHLAEIEDMPLFEPRVFTAGSEERVTCLPPKGLP iso a  EPSVWWEHAGVRLPTHGRVYQKGHELVLANIAESDAGVYTCHAANLAGQRRQDVNITVATVPSWLKKPQD   420
iso d  EPSVWWEHAGVRLPTHGRVYQKGHELVLANIAESDAGVYTCHAANLAGQRRQDVNITVATVPSWLKKPQD
iso b  EPSVWWEHAGVRLPTHGRVYQKGHELVLANIAESDAGVYTCHAANLAGQRRQDVNITVATVPSWLKKPQD
iso c  EPSVWWEHAGVRLPTHGRVYQKGHELVLANIAESDAGVYTCHAANLAGQRRQDVNITVA-----------

IGcam domain (5)
iso a  SQLEEGKPGYLDCLTQATPKPTVVWYRNQMLISEDSRFEVFKNGTLRINSVEVYDGTWYRCMSSTPAGSI   490
iso d  SQLEEGKPGYLDCLTQATPKPTVVWYRNQMLISEDSRFEVFKNGTLRINSVEVYDGTWYRCMSSTPAGSI
iso b  SQLEEGKPGYLDCLTQATPKPTVVWYRNQMLISEDSRFEVFKNGTLRINSVEVYDGTWYRCMSSTPAGSI
iso c  ----------------------------------------------------------------------

IGcam domain (6)
iso a  EAQARVQVLEKLKFTPPPQPQQCMEFDKEATVPCSATGREKPTIKWERADGSSLPEWVTDNAGTLHFARV   560
iso d  EAQARVQVLEKLKFTPPPQPQQCMEFDKEATVPCSATGREKPTIKWERADGSSLPEWVTDNAGTLHFARV
iso b  EAQARVQVL---------------------------------------DGSSLPEWVTDNAGTLHFARV
iso c  ------------------------------------------------NGSSLPEWVTDNAGTLHFARV IGcam domain (7)
iso a  TRDDAGNYTCIASNGPQGQIRAHVQLTVAVFITFKVEPERTTVYQGHTALLQCEAQGDPKPLIQWKGKDR   630
iso d  TRDDAGNYTCIASNGPQGQIRAHVQLTVAVFITFKVEPERTTVYQGHTALLQCEAQGDPKPLIQWK----
iso b  TRDDAGNYTCIASNGPQGQIRAHVQLTVAVFITFKVEPERTTVYQGHTALLQCEAQGDPKPLIQWKGKDR
iso c  TRDDAGNYTCIASNGPQGQIRAHVQLTVAVFITFKVEPERTTVYQGHTALLQCEAQGDPKPLIQWKGKDR iso a  ILDPTKLGPRMHIFQNGSLVIHDVAPEDSGRYTCIAGNSCNIKHTEAPLYVVDKPVPEESEGPGSPPPYK   700
iso d  -----------------------------------------------------DKPVPEESEGPGSPPPYK
iso b  ILDPTKLGPRMHIFQNGSLVIHDVAPEDSGRYTCIAGNSCNIKHTEAPLYVVDKPVPEESEGPGSPPPYK
iso c  ILDPTKLGPRMHIFQNGSLVIHDVAPEDSGRYTCIAGNSCNIKHTEAPLYVVDKPVPEESEGPGSPPPYK
```

FIG. 1C

```
           putative TM
iso a   MIQTIGLSVGAAVAYIIAVLGLMFYCKKRCKAKRLQKQPEGEEPEMECLNGGPLQNGQPSAEIQEEVALT    770
iso d   MIQTIGLSVGAAVAYIIAVLGLMFYCKKRCKAKRLQKQPEGEEPEMECLNGGPLQNGQPSAEIQEEVALT
iso b   MIQTIGLSVGAAVAYIIAVLGLMFYCKKRCKAKRLQKQPEGEEPEMECLNGGPLQNGQPSAEIQEEVALT
iso c   MIQTIGLSVGAAVAYIIAVLGLMFYCKKRCKAKRLQKQPEGEEPEMECLNGGPLQNGQPSAEIQEEVALT kinase domain     I                              II
iso a   SLGSGPAATNKRHSTSDKMHFPRSSLQPITTLGKSEEGEVFLAKAQGLEEGVAETLVLVKSLQSKDEQQQ    840
iso d   SLGSGPAATNKRHSTSDKMHFPRSSLQPITTLGKSEEGEVFLAKAQGLEEGVAETLVLVKSLQSKDEQQQ
iso b   SLGSGPAATNKRHSTSDKMHFPRSSLQPITTLGKSEEGEVFLAKAQGLEEGVAETLVLVKSLQSKDEQQQ
iso c   SLGSGPAATNKRHSTSDKMHFPRSSLQPITTLGKSEEGEVFLAKAQGLEEGVAETLVLVKSLQSKDEQQQ
                                 GxGxFGxV                              K III
iso a   IDERRELEMFGKLNHANVVRLLGLCREAEPHYMVLEYVDLGDLKQFLRISKSKDEKLKSQPLSTKQKVAL    910
iso d   IDERRELEMFGKLNHANVVRLLGLCREAEPHYMVLEYVDLGDLKQFLRISKSKDEKLKSQPLSTKQKVAL
iso b   IDERRELEMFGKLNHANVVRLLGLCREAEPHYMVLEYVDLGDLKQFLRISKSKDEKLKSQPLSTKQKVAL
iso c   IDERRELEMFGKLNHANVVRLLGLCREAEPHYMVLEYVDLGDLKQFLRISKSKDEKLKSQPLSTKQKVAL
                E VIB               VII                        VIII
iso a   CTQVALGMEHLSNNRFVHKDLAARNCLVSAQRQVKVSALLSKDVYNSEYYHFRQAWVPLRWMSPEATLE    980
iso d   CTQVALGMEHLSNNRFVHKDLAARNCLVSAQRQVKVSALLSKDVYNSEYYHFRQAWVPLRWMSPEATLE
iso b   CTQVALGMEHLSNNRFVHKDLAARNCLVSAQRQVKVSALLSKDVYNSEYYHFRQAWVPLRWMSPEATLE
iso c   CTQVALGMEHLSNNRFVHKDLAARNCLVSAQRQVKVSALLSKDVYNSEYYHFRQAWVPLRWMSPEATLE
                      HRDLxxxN         K--DFG                    P---W-APE IX
iso a   GDFSTKSDVWAFGVLMWEVFTHGEMPHGGQADDEVLADLQAGKARLPQPEGCPSKLYRLMQRCWALSPKD   1050
iso d   GDFSTKSDVWAFGVLMWEVFTHGEMPHGGQADDEVLADLQAGKARLPQPEGCPSKLYRLMQRCWALSPKD
iso b   GDFSTKSDVWAFGVLMWEVFTHGEMPHGGQADDEVLADLQAGKARLPQPEGCPSKLYRLMQRCWALSPKD
iso c   GDFSTKSDVWAFGVLMWEVFTHGEMPHGGQADDEVLADLQAGKARLPQPEGCPSKLYRLMQRCWALSPKD
            SDVWSxG                                                    CW XI
iso a   RPSFSEIASALGDSTVDSKP 1070    (SEQ ID NO:3)
iso d   RPSFSEIASALGDSTVDSKP         (SEQ ID NO:4)
iso b   RPSFSEIASALGDSTVDSKP         (SEQ ID NO:5)
iso c   RPSFSEIASALGDSTVDSKP         (SEQ ID NO:6)
            RP
```

FIG. 1C (CONT.)

Protein Sequences of Exemplary Murine and Humanized PTK7 Modulator Light Chain Variable Regions

FIG. 6A

Protein Sequences of Exemplary Murine and Humanized PTK7 Modulator Heavy Chain Variable Regions

Murine Heavy Chain Variable Regions

| mAb | FR1 | CDRH1 | FR2 | CDRH2 | FR3 | CDR3 | SEQ ID NO |
|---|---|---|---|---|---|---|---|
| SC6.2.35 | QVQMQQSGAELMKPGASVKLSCKAT | GYTFTGYW | IEWVKQRPGHGLEWIGE | ILPGSGRS | NSNEKFKGKATFTADTSSNTAYMQLSSLTTEDSAIYYC | ARGKLSWGCGTLVTVSA | 21 |
| SC6.10.2 | QVCLQQSGAELVRPGVSVKISCKGS | GYRFTDYP | IHWVKQSHAKSLEWIGI | ISTYYGDV | TNNPKFRGKATMTVDKSSTTAYMELARLTSEDSAIYYC | ARNDLFAYWGQGTLVTVSA | 23 |
| SC6.4.1 | SDVQLQESGPGLVKPSQSLSLTCTVT | GYSITSDYA | WNWIROFPGNKLEWMN | SYSGYT | NYNPSLKSRISITRDTSKNQFFLQLISVTTEDTATYYC | ARGDAYDVRRSTYYFDYWGCGTLTVSS | 25 |
| SC6.50.1 | QLEESSAELMCPGASVKVSCKAT | LEEGYTFTVYW | IEWVKQRPGHGLEWIGE | ILPGSSSTD | YNEKFKGKATFTADSSNTAYMQLSSLTTEDSAIYYC | ARGKLHWGCGTLVTVSA | 27 |
| SC6.3 | EVKLLESGGGLVQPGGSLKLSCAAS | GFDFSKDW | MSWVRQAPGKGLEWIGE | INPDSRTI | NYAPSLKDKFIISRENAKNTLYLQMSKVRSEDTALYYC | ARWDYDGGMDYWGQGTSVTVSS | 29 |
| SC6.4 | EVKLLESGGGLVQPGGSLKLSCAAS | GFDFSRYW | MSWVRQAPGKGLEWIGE | INPDSSTI | NYTPSLKDKFIISRDNAKNTLYLQMSKVRSEDTALYYC | ARPGYGNLFAYWGQGTLVTVSA | 31 |
| SC6.6 | EVQLQQSGPELVKPGASVKMSCKAS | GYTFTSY | VIHWVKQRPGQGLEWIGYI | INPFSDGT | KFTEKFKGKASLTSDKSSSTAYMELNSLTSEDSAVYYC | ARRGPYYGTAMDYWGQGTSVTVSS | 33 |
| SC6.7 | QVQLQQSGAELGRPGASVKLSCKDS | GYTITYW | MCQWVKQRPGQGLEWIGA | IYPGDGDT | RYPQKFKGKSTLSADKSSNTASMHLSSLASDDSAVYYC | SRGGSTNYDYDGFAYWGQGTLVTVSA | 35 |
| SC6.13 | QVQLQQSGAELMKPGASVKISCKAT | GYTFSNYW | IEWVKQRPGHGLEWIGE | ILPGRGST | NVNEKFKGKATFTADTSSNTAYMQLSSLTSEDSAVYYC | ARGKQYWGQGTLTVSS | 37 |
| SC6.14 | QVQLQQPGAELVKPGASVKLSCKAS | GYTFTSYW | MHWVKQRPGQGLEWIGE | INPSNGRS | NYNEKFKSKATLTVDKSSTAYMQLSSLTSEDSAVYFC | AHYDGSYGFFDYWGQGTLTVSS | 39 |
| SC6.15 | EVKLLESGGGLVQPGGSLKVSCTAS | GFDFSRYW | MSWVRQAPGKGLEWIGE | INPDSSTI | NYTPSLKDKFIISRDNAKNTLYLQMSKVRSEDTALYYC | ARPGYGNLFVYWGCGTLVTVSS | 41 |
| SC6.19 | EVKLLESGGGLVQPGGSLRLSCAAS | GFDFSKDW | MSWVRQAPGKGLEWIGE | INPDSSTI | NYA'PALKDKFIISRENAKNTLYLQMNKVRSEDTALYYC | ARWSTGLDYWGQGTTLVSS | 43 |
| SC6.20 | QVQLCQSGPELVKPGASVKISCKAS | GYPFSTSW | MNWVKQRPGKGLEWIGR | IYLGDGDT | NYNGKFTGKATLTADKSSSTVMQLSSLTSEDSAVYFC | ARWRGDYDYWGQGTTLVSS | 45 |
| SC6.21 | SDVQLQESGPGLVKPSQTLSLTCSVP | DYSITSDYH | WHWIRQFPGNKLEWMG | YISSRGST | NYNPSLKNRISITHDTSENQFPLKLTSVTTEDSATYYC | AGLSQLALDYWGQGTTLVSS | 47 |
| SC6.23 | QVTLKESGPGILKPSQTLSLTCSFS | GFSLSTSNMG | VGWIRQPSGKGLEWAH | IWWDDDK | YNPSLKSQLTISKDTSRNCVFLKITSVDTEDTATYC | VRSNYGYAWFAYWGQGTLVTVSA | 49 |
| SC6.24 | QVCLQQSGPEVVRPGVSVKISCKGS | GYTFTDYA | VHWVKLSHAKSLEWIGV | ISTYNDYT | YNNCQDFKGKAIMTVDKSSTAYMELARLTSEDSAIYYC | ARGNSYFYALDYWGCGTSVTVSS | 51 |
| SC6.26 | QVQLQQSGAELASPGTSVKLSCKAS | GYTFTFYG | ISWVKQKTGQGLEWIGE | IYPGSYNA | YNDKFKGKATLTADRSSSTAYMQLSSLTSEDSAVYFC | ARDYGDPYYYAMDYWGQGTSVTVSS | 53 |
| SC6.29 | EVKLLESGGGLVQPGGSQKLSCAAS | GFDFSRYW | MSWVRQAPGKGLEWIGE | INPDSSTV | NYTPSLKDKFIISRDNAKNTLYLQMSKVRSEDTALYYC | ARPGYGNLFVYWGGCTLVTVSA | 55 |
| SC6.41 | EVQLQQSGAEVRSGASVKLSCTAS | GLNIKDYY | MHWVNLRPEQGLEWIGW | IDPENGDT | EYAPEFQGKATMTADTSNTAYLQLSSLTSEDTAVYYC | NACNYGSAYGYWGQGTTLVSS | 57 |
| SC6.58 | EVKLLESGGGGLVQPGGSLKLSCAAS | GLNIKDYY | MSWVRQAPGKGLEWIGD | LNPDSSAI | NYTPSLKDKFIISRDNAKNTLYLQMSKVRSEDTALYYC | TLITTLVPYTMDFWGQGTSVTVSS | 59 |
| SC6.59 | EIHLVESGGGLVKPGGSLKVSCAAS | GFTFSRYA | MSWVRQTPEKRLEWVAT | ISGGGRYT | YPDLVKGRFTISRDIARTTLYLQMSSLRSEDTAMYYC | ARTARASNYAMDWGQGTSVTVSS | 61 |

Humanized Heavy Chain Variable Regions

| mAb | FR1 | CDRH1 | FR2 | CDRH2 | FR3 | CDR3 | SEQ ID NO |
|---|---|---|---|---|---|---|---|
| hSC6.23 | QITLKESGPTLVKPTQTLTLTCFS | GFSLSTSNMG | VGWIRQPPGKALEWLAH | IWWDDDK | YSPSLKSRLTITKDTSKNQVVLTMTNMDPVDTATYYC | VRSNYGYAWFAYWGQGTLVTVSS | 63 |
| hSC6.24 | QVCLVQSGPEVKKPGASVKVSCKAS | GYTFTDYA | VHWVRQAPGKRLEWIGV | ISTYNDYT | YNNQDFKGRVTMTRDTSASTAYMELSRLRSEDTAVYYC | ARGNSYFYALDYWGCGTSVTVSS | 65 |
| hSC6.41 | EVQLVQSGAEVKKPGASVKVSCKAS | GYTFKDYY | MHWVRCAPGQQGLEWMGW | IDPENGDT | EYAPEFQGRVTMTRDTSTSTVYMELSLRSEDTAVYYC | NACNYGSAYGYWGQGTTLVSS | 67 |
| hSC6.58 | EVQLVESGGGLVQPGGSLRLSCAAS | GFDFSRYW | MSWVRQAPGKGLEWIGD | LNPDSSAI | NYVDSVKGRFTISRDNAKNSLYLQMNSLRAEDTAVYYC | TLITTLVPYTMDFWGQGTSVTVSS | 69 |

FIG. 6B

Exemplary PTK7 Modulator Characteristics

| Clone | Bin | Affinity (nM) | Western Reactivity | Cynomolgus XR | Mouse XR |
|---|---|---|---|---|---|
| SC6.2.35 | B | <0.1[B] | NR | Yes | No |
| SC6.10.2 | A | 5.6[B] | ND | Yes | No |
| SC6.25.1 | C | 21[B] | NR | Yes | Yes |
| SC6.18 | D | 2[F] | ND | Yes | Yes |
| SC6.21 | E | <0.1[F] | ND | Yes | Yes |
| SC6.23 | F | 2.3[B] | ND | Yes | Yes |
| SC6.24 | A | 0.6[B] | ND | Yes | Yes |
| SC6.30 | A | <0.1[F] | ND | Yes | No |
| SC6.41 | H | 1.0[B] | ND | Yes | Yes |
| SC6.55 | A | 2[F] | ND | Yes | Yes |
| SC6.57 | ND | 0.2[F] | ND | Yes | Yes |
| SC6.58 | B | 0.5[B] | ND | Yes | Yes |

B – Biacore
F – ForteBio

FIG. 7B

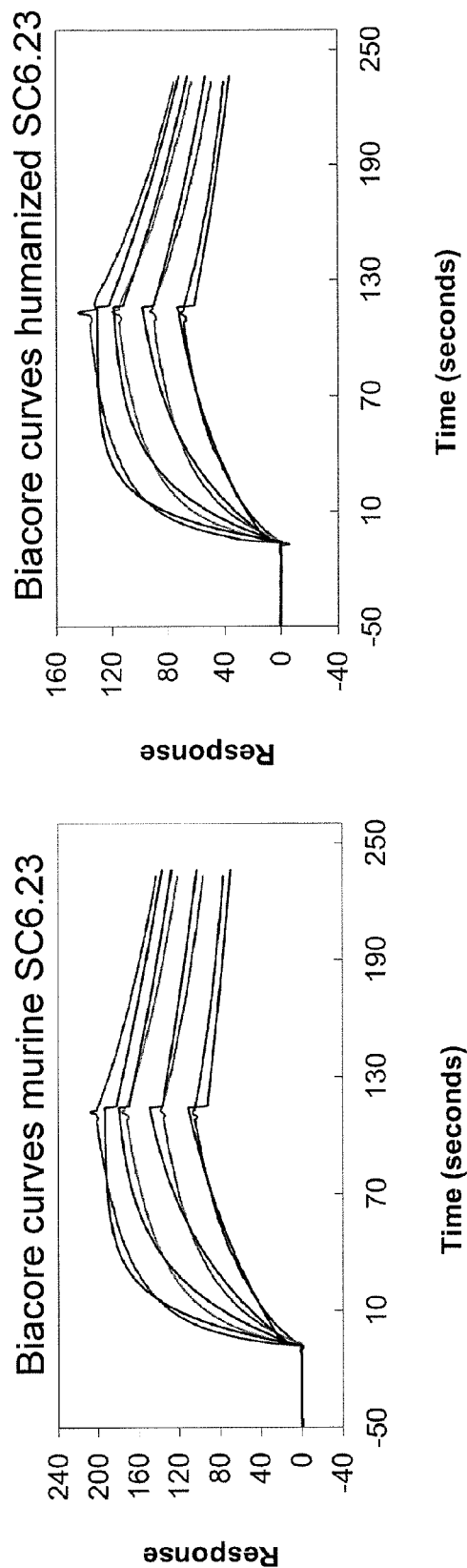

Translation of pEE12.4_ScRx6_2IgGs::IgG2Fc (Ig domains 1 & 2)

FIG. 8A

(SEQ ID NO: 70)

```
  1  AIVFIKQPSS QDALQGRRAL LRCEVEAPGP VHVYWLLDGA PVQDTERRFA
 51  QGSSLSFAAV DRLQDSGTFQ CVARDDVTGE EARSANASFN IKWIEAGPVV
101  LKHPASEAEI QPQTQVTLRC HIDGHPRPTY QWFRDGTPLS DGQSNHTVSS
151  KERNLTLRPA GPEHSGLYSC CAHSAFGQAC SSQNFTLSIA DESFARVVLA
201  PQDVVVHPVR SVECPPCPAP PVAGPSVFLF PPKPKDTLMI SRTPEVTCVV
251  VDVSHEDPEV QFNWYVDGVE VHNAKTKPRE EQFNSTFRVV SVLTVVHQDW
301  LNGKEYKCKV SNKGLPAPIE KTISKTKGQP REPQVYTLPP SREEMTKNQV
351  SLTCLVKGFY PSDIAVEWES NGQPENNYKT TPPMLDSDGS FFLYSKLTVD
401  KSRWQQGNVF SCSVMHEALH NHYTQKSLSL SPGK
```

Translation of pEE12.4_ScRx6_IgG3to7_IgG2Fc (Ig domains 3 to 7)

FIG. 8B

(SEQ ID NO: 71

```
  1  APQDVVVARY EEAMFHCQFS AQPPPSLQWL FEDETPITNR SRPPHLRRAT
 51  VFANGSLLLT QVRPRNAGIY RCIGQGQRGP PIILEATLHL AEIEDMPLFE
101  PRVFTAGSEE RVTCLPPKGL PEPSVWWEHA GVRLPTHGRV YQKGHELVLA
151  NIAESDAGVY TCHAANLAGQ RRQDVNITVA TVPSWLKKPQ DSQLEEGKPG
201  YLDCLTQATP KPTVVWYRNQ MLISEDSRFE VFKNGTLRIN SVEVYDGTWY
251  RCMSSTPAGS IEAQARVQVL EKLKFTPPPQ PQQCMEFDKE ATVPCSATGR
301  EKPTIKWERA DGSSLPEWVT DNAGTLHFAR VTRDDAGNYT CIASNGPQGQ
351  IRAHVQLTVA VFITFKVEPE RTTVYQGHTA LLQCEAQGDP KPLIQWKGKD
401  RILDPTKLGP RMHIFQNGSL VIHDVAPEDS GRYTCIAGNS CNIKHTEAPL
451  YVVDKPVPEE SEGPGSPPPY KMIQHPVRSV ECPPCPAPPV AGPSVFLFPP
501  KPKDTLMISR TPEVTCVVVD VSHEDPEVQF NWYVDGVEVH NAKTKPREEQ
551  FNSTFRVVSV LTVVHQDWLN GKEYKCKVSN KGLPAPIEKT ISKTKGQPRE
601  PQVYTLPPSR EEMTKNQVSL TCLVKGFYPS DIAVEWESNG QPENNYKTTP
651  PMLDSDGSFF LYSKLTVDKS RWQQGNVFSC SVMHEALHNH YTQKSLSLSP
701  GK*
``` pEE12.4_ScRx6_5IgGs::IgG2Fc (Ig domains 1 to 5)

FIG. 8C

(SEQ ID NO: 72)

```
  1  AIVFIKQPSS QDALQGRRAL LRCEVEAPGP VHVYWLLDGA PVQDTERRFA
 51  QGSSLSFAAV DRLQDSGTFQ CVARDDVTGE EARSANASFN IKWIEAGPVV
101  LKHPASEAEI QPQTQVTLRC HIDGHPRPTY QWFRDGTPLS DGQSNHTVSS
151  KERNLTLRPA GPEHSGLYSC CAHSAFGQAC SSQNFTLSIA DESFARVVLA
201  PQDVVARYE EAMFHCQFSA QPPPSLQWLF EDETPITNRS RPPHLRRATV
251  FANGSLLLTQ VRPRNAGIYR CIGQGQRGPP IILEATLHLA EIEDMPLFEP
301  RVFTAGSEER VTCLPPKGLP EPSVWWEHAG VRLPTHGRVY QKGHELVLAN
351  IAESDAGVYT CHAANLAGQR RQDVNITVAT VPSWLKKPQD SQLEEGKPGY
401  LDCLTQATPK PTVVWYRNQM LISEDSRFEV FKNGTLRINS VEVYDGTWYR
451  CMSSTPAGSI EAQARVQVLE KLKFTPPPQP HPVRSVECPP CPAPPVAGPS
501  VFLFPPKPKD TLMISRTPEV TCVVVDVSHE DPEVQFNWYV DGVEVHNAKT
551  KPREEQFNST FRVVSVLTVV HQDWLNGKEY KCKVSNKGLP APIEKTISKT
601  KGQPREPQVY TLPPSREEMT KNQVSLTCLV KGFYPSDIAV EWESNGQPEN
651  NYKTTPPMLD SDGSFFLYSK LTVDKSRWQQ GNVFSCSVMH EALHNHYTQK
701  SLSLSPGK
```

Translation of pEE12.4 ScRx6 IgG6&7 IgG2Fc (Ig domains 6 & 7)

FIG. 8D

(SEQ ID NO: 73)

```
  1  KFTPPPQPQQ  CMRFDKEATV  PCSATGREKP  TIKWFRADGS  SLPEWVTDNA
 51  GTLRFARVTR  DDAGNYTCIA  SNSPGQGIRA  HVQLTVAVFI  TPKVEPKTT
101  VYQGETALLQ  CEAQGDPKPI  IQWKGKDKIL  DPTKLGPRME  IFQNGSIVIH
151  DVAPEDSGRY  TCIAGNSCNI  KHTEAPLYVV  DKPVEESEG   PGSPPPYEMI
201  QHPVRSVECP  PCPAPPVAGP  SVFLFPPKPK  DTLMISRTPE  VTCVVVDVSE
251  EDPEVQFNWY  VDGVEVHNAK  TKPREEQFNS  TFRVVSVLTV  VHQDWLNGKE
301  YKCKVSNKGL  PAPIEKTISK  TKGQPREPQV  YTLPPSREEM  TKNQVSLSCL
351  VKGFYPSDIA  VEWESNGQPE  NNYKTTPPML  DSDGSFFLYS  KLTVDKSRWQ
401  QGNVFSCSVM  HEALHNHYTQ  KSLSLSPGK
```

Translation of pEE12.4 ScRx6 IgG2&3 IgG2Fc (Ig domains 2 & 3)

FIG. 8E

(SEQ ID NO: 74)

```
  1  EEARSANASF  NIKWIEAGPV  VLKHPASEAE  IQPQTQVTLR  CHIDGHPRPT
 51  YQWFRDGTPL  SDGQSNHTVS  SKERNLTLRP  AGPEHSGLYS  CCAHSAFGQA
101  CSSQNFTLSI  ADESFARVVL  APQDVVVARY  EEAMFHCQFS  AQPPPSLQWL
151  FEDETPITNR  SPPHLRRATV  FANGSLLLT   QVRPRNAGIY  RCIGQGQRGP
201  PIILEATLHL  AEHPVRSVEC  PPCPAPPVAG  PSVFLFPPKP  KDTLMISRTP
251  EVTCVVVDVS  HEDPEVQFNW  TVDGVEVHNA  KTKPREEQFN  STFRVVSVLT
301  VVHQDWLNGK  EYKCKVSNKG  LPAPIEKTIS  KTKGQPREPQ  VYTLPPSREE
351  MTKNQVSLTC  LVKGFYPSDI  AVEWESNGQP  ENNYKTTPPM  LDSDGSFFLY
401  SKLTVDKSRW  QQGNVFSCSV  MHEALHNHYT  QKSLSLSPGK
```

Translation of pEE12.4 ScRx6 4IgGs IgG2Fc (Ig domains 1 to 4)

FIG. 8F

(SEQ ID NO: 75)

```
  1  AIVFIKQPSS  QDALQGRKAL  LRCEVEAPGP  VHVYWLLDGA  PVQDTERRFA
 51  QGSSLSFAAV  DRLQDSGTFQ  CVARDDVTGE  EARSANASFN  IKWIEAGPVV
101  LKHPASEAEI  QPQTQVTLRC  HIDGHPRPTY  QWFRDGTPLS  DGQSNHTVSS
151  KERNLTLRPA  GPEHSGLYSC  CAHSAFGQAC  SSQNFTLSIA  DESFARVVLA
201  PQDVVVARYE  EAMFHCQFSA  QPPPSLQWLF  EDETPITNRS  PPHLRRATV
251  FANGSLLLTQ  VRPRNAGIYR  CIGQGQRGPP  IILEATLHLA  EHDMPLFEP
301  KVPTAGSEER  VTCLPPKGLS  EPEVWWEHAG  VRLPTHGRVY  QKGSELVLAN
351  IAESDAGVYT  CHAANLAGQR  RQDVNITVAH  PVRSVECPPC  PAPPVAGPSV
401  FLFPPKPKDT  LMISRTPEVT  CVVVDVSHED  PEVQFNWYVD  GVEVHNAKTK
451  PREEQFNSTF  RVVSVLTVVH  QDWLNGKEYK  CKVSNKGLPA  PIEKTISKTK
501  GQPREPQVYT  LPPSREEMTK  NQVSLTCLVK  GFYPSDIAVE  WESNGQPENN
551  YKTTPPMLDS  DGSFFLYSKL  TVDKSRWQQG  NVFSCSVMHE  ALHNHYTQKS
601  LSLSPGK
```

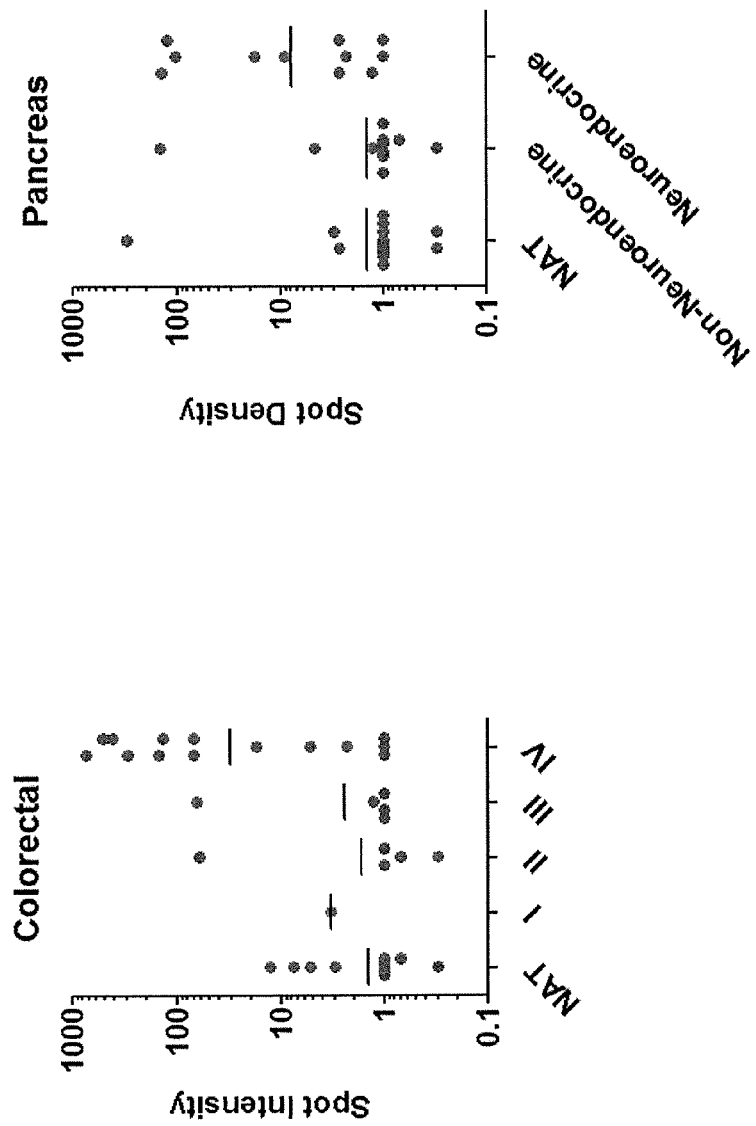

PTK7 Modulators Associate With K562 Cells and Internalize
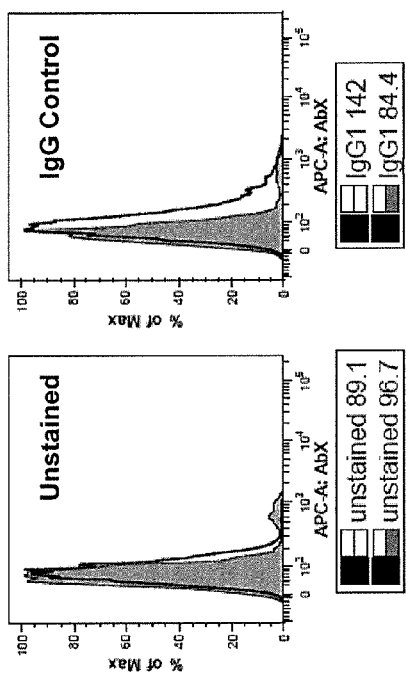
FIG. 10A
FIG. 10B
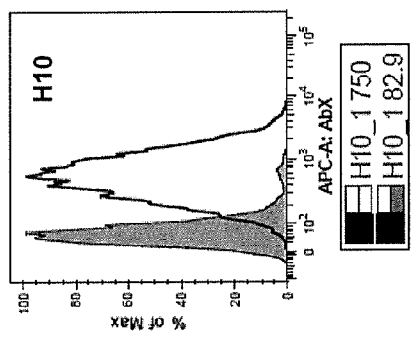
FIG. 10C PTK7 Modulators Associate With G401 Cells and Internalize

**PTK7 Modulators Mediate Toxin Delivery *In Vitro***

FIG. 11A

PTK7 Modulators Mediate Cell Killing
FIG. 11B
FIG. 11C
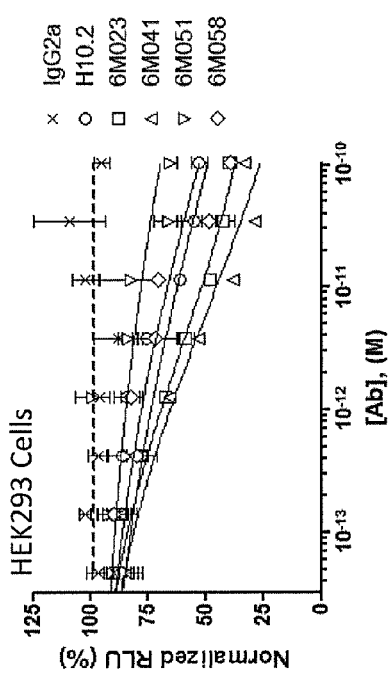
FIG. 11D

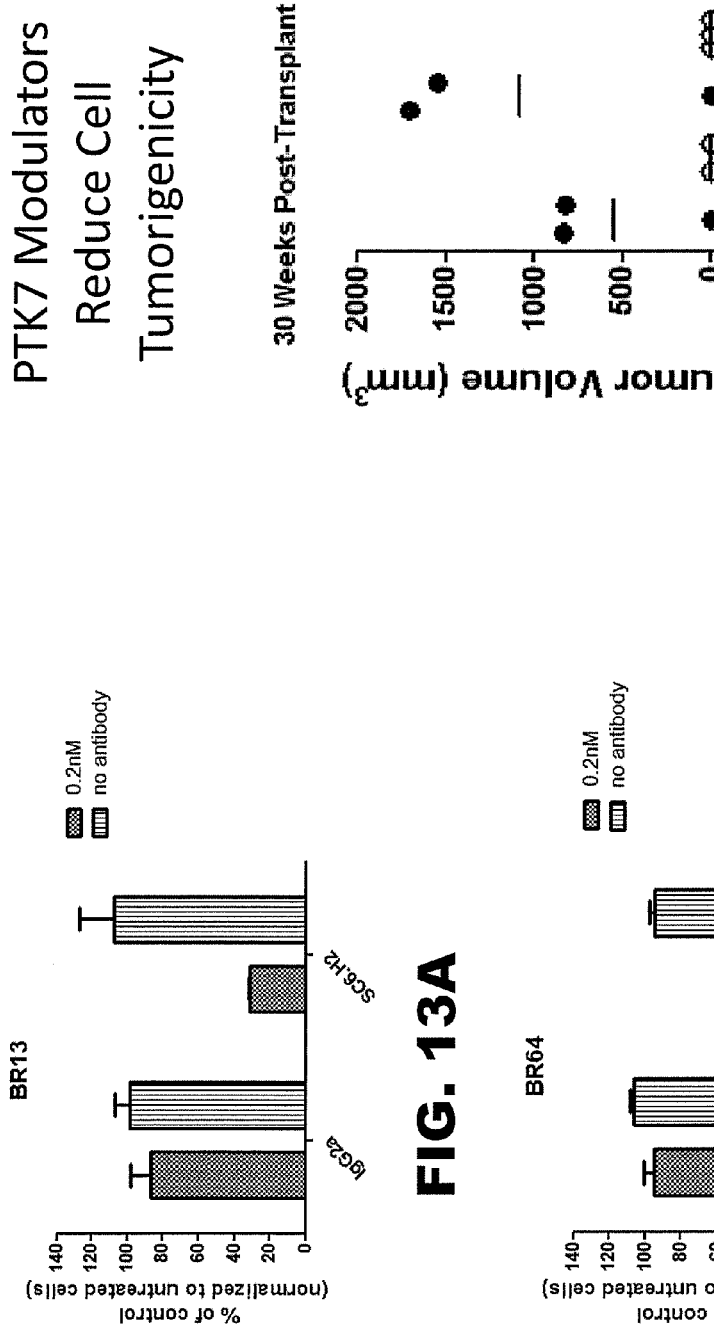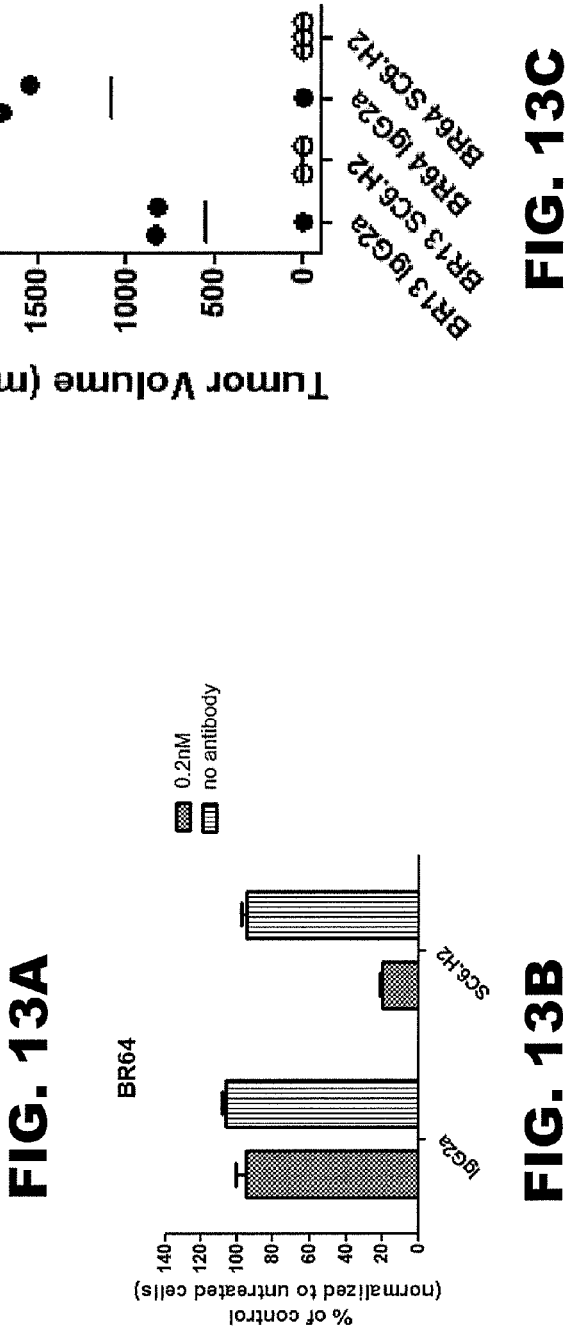
FIG. 13A  FIG. 13B  FIG. 13C

PTK7 MODULATORS AND METHODS OF USE

CROSS REFERENCED APPLICATIONS

This is a national stage of International Application No. PCT/US2012/025726 filed Feb. 17, 2012, which is a continuation-in-part of International Application No. PCT/US2011/050451, filed Sep. 2, 2011, and which claims the benefit of U.S. Provisional Patent Application No. 61/444,614, filed Feb. 18, 2011, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on 23 Nov. 2015, is named SUBS_SEQL.txt and is 166 kB in size.

FIELD OF THE INVENTION

This application generally relates to novel compositions and methods of their use in preventing, treating or ameliorating hyperproliferative disorders and any expansion, recurrence, relapse or metastasis thereof. In a broad aspect, the present invention relates to the use of protein tyrosine kinase 7 (PTK7) modulators, including anti-PTK7 antibodies and fusion constructs, for the treatment, diagnosis or prophylaxis of neoplastic disorders. Particularly preferred embodiments of the present invention provide for the use of such PTK7 modulators for the immunotherapeutic treatment of malignancies comprising a reduction in tumor initiating cell frequency.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. Differentiation and proliferation decisions are often controlled by numerous factors and signals that are balanced to maintain cell fate decisions and tissue architecture. Normal tissue architecture is largely maintained by cells responding to microenvironmental cues that regulate cell division and tissue maturation. Accordingly, cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including hyperproliferative disorders such as cancer.

Conventional treatments for cancer include chemotherapy, radiotherapy, surgery, immunotherapy (e.g., biological response modifiers, vaccines or targeted therapeutics) or combinations thereof. Sadly, far too many cancers are non-responsive or minimally responsive to such conventional treatments leaving few options for patients. For example, in some patients certain cancers exhibit gene mutations that render them non-responsive despite the general effectiveness of selected therapies. Moreover, depending on the type of cancer some available treatments, such as surgery, may not be viable alternatives. Limitations inherent in current standard of care therapeutics are particularly evident when attempting to care for patients who have undergone previous treatments and have subsequently relapsed. In such cases the failed therapeutic regimens and resulting patient deterioration may contribute to refractory tumors which often manifest themselves as a relatively aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies.

One promising area of research involves the use of targeted therapeutics to go after the tumorigenic "seed" cells that appear to underlie many cancers. To that end most solid tissues are now known to contain adult, tissue-resident stem cell populations generating the differentiated cell types that comprise the majority of that tissue. Tumors arising in these tissues similarly consist of heterogeneous populations of cells that also arise from stem cells, but differ markedly in their overall proliferation and organization. While it is increasingly recognized that the majority of tumor cells have a limited ability to proliferate, a minority population of cancer cells (commonly known as cancer stem cells or CSC) have the exclusive ability to extensively self-renew thereby enabling an inherent tumor reinitiating capacity. More specifically, the cancer stem cell hypothesis proposes that there is a distinct subset of cells (i.e. CSC) within each tumor (approximately 0.1-10%) that is capable of indefinite self-renewal and of generating tumor cells progressively limited in their replication capacity as a result of differentiation to tumor progenitor cells and, subsequently, to terminally differentiated tumor cells.

In recent years it has become more evident these CSC (also known as tumor perpetuating cells or TPC) might be more resistant to traditional chemotherapeutic agents or radiation and thus persist after standard of care clinical therapies to later fuel the growth of refractory tumors, secondary tumors and promote metastases. In this regard cancer stem cells have been implicated in promoting the migratory and invasive potential of various neoplasia. Moreover, growing evidence suggests that pathways that regulate organogenesis and/or the self-renewal of normal tissue-resident stem cells are deregulated or altered in CSC, resulting in the continuous expansion of self-renewing cancer cells and tumor formation. See generally Al-Hajj et al., 2004, PMID: 15378087; and Dalerba et al., 2007, PMID: 17548814; each of which is incorporated herein in its entirety by reference. Thus, the effectiveness of traditional, as well as more recent targeted treatment methods, has apparently been limited by the existence and/or emergence of resistant cancer cells that are capable of perpetuating the cancer even in face of these diverse treatment methods. Huff et al., European Journal of Cancer 42: 1293-1297 (2006) and Zhou et al., Nature Reviews Drug Discovery 8: 806-823 (2009) each of which is incorporated herein in its entirety by reference. Such observations are confirmed by the consistent inability of traditional debulking agents to substantially increase patient survival when suffering from solid tumors, and through the development of an increasingly sophisticated understanding as to how tumors grow, recur and metastasize. Accordingly, recent strategies for treating neoplastic disorders have recognized the importance of eliminating, depleting, silencing or promoting the differentiation of tumor perpetuating cells so as to diminish the possibility of tumor recurrence or metastasis leading to patient relapse.

Efforts to develop such strategies have incorporated recent work involving non-traditional xenograft (NTX) models, wherein primary human solid tumor specimens are implanted and passaged exclusively in immunocompromised mice. In numerous cancers such techniques confirm the existence of a subpopulation of cells with the unique ability to generate heterogeneous tumors and fuel their growth indefinitely. As previously hypothesized, work in NTX models has confirmed that identified CSC subpopulations of tumor cells appear more resistant to debulking regimens such as chemotherapy and radiation, potentially explaining the disparity between clinical response rates and overall survival. Further, employment of NTX models in CSC research has sparked a fundamental change in drug discovery and preclinical evaluation of drug candidates that may lead to CSC-targeted therapies having a major impact on tumor recurrence and metastasis thereby improving patient survival rates. While progress has been made, inherent technical difficulties associated with handling primary and/or xenograft tumor tissue, along with a lack of experimental platforms to characterize CSC identity and differentiation potential, pose major challenges. As such, there remains a substantial need to selectively target cancer stem cells and develop diagnostic, prophylactic or therapeutic compounds or methods that may be used in the treatment, prevention and/or management of hyperproliferative disorders.

SUMMARY OF THE INVENTION

These and other objectives are provided for by the present invention which, in a broad sense, is directed to methods, compounds, compositions and articles of manufacture that may be used in the treatment of PTK7 associated disorders (e.g., hyperproliferative disorders or neoplastic disorders). To that end, the present invention provides novel protein tyrosine kinase 7 (or PTK7) modulators that effectively target tumor cells and/or cancer stem cells and may be used to treat patients suffering from a wide variety of malignancies. As will be discussed in more detail herein, there are presently several known PTK7 isoforms and the disclosed modulators preferably comprise or associate with one or more of the same. Moreover, in certain embodiments the disclosed PTK7 modulators may comprise any compound that recognizes, competes, agonizes, antagonizes, interacts, binds or associates with a PTK7 polypeptide or gene (or fragment thereof) and modulates, adjusts, alters, changes or modifies the impact of the PTK7 protein on one or more physiological pathways. Thus, in a broad sense the present invention is generally directed to isolated PTK7 modulators and use thereof. In preferred embodiments the invention is more particularly directed to isolated PTK7 modulators comprising antibodies (i.e., antibodies that immunopreferentially bind, react with or associate with at least one isoform of PTK7). Moreover, as discussed extensively below, such modulators may be used to provide pharmaceutical compositions useful for the prophylaxis, diagnosis or treatment of proliferative disorders.

In selected embodiments of the invention, PTK7 modulators may comprise a PTK7 polypeptide or fragments thereof, either in an isolated form or fused or associated with other moieties (e.g., Fc-PTK7, PEG-PTK7 or PTK7 associated with a targeting moiety). In other selected embodiments PTK7 modulators may comprise PTK7 antagonists which, for the purposes of the instant application, shall be held to mean any construct or compound that recognizes, competes, interacts, binds or associates with PTK7 and neutralizes, eliminates, reduces, sensitizes, reprograms, inhibits or controls the growth of neoplastic cells including tumor initiating cells. In preferred embodiments the PTK7 modulators of the instant invention comprise anti-PTK7 antibodies, or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells. In particularly preferred embodiments the antibodies or immunoreactive fragments may be associated with or conjugated to one or more anti-cancer agents (e.g., a cytotoxic agent).

In selected embodiments compatible PTK7 modulators may comprise an antibody having a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58 and SEQ ID NO: 60 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, and SEQ ID NO: 61.

Of course, in view of the instant disclosure those skilled in the art could readily identify CDRs associated with each of the aforementioned heavy and light chain variable regions and use those CDRs to engineer or fabricate chimeric, humanized or CDR grafted antibodies without undue experimentation. As such, in selected embodiments the present invention is directed to anti-PTK7 antibodies comprising one or more CDRs from a variable region sequence set forth in FIG. 6A or FIG. 6B. In preferred embodiments such antibodies will comprise monoclonal antibodies and, in even more preferred embodiments will comprise chimeric, CDR grafted or humanized antibodies. As discussed in more detail below still other embodiments will comprise such antibodies conjugated or associated with one or more cytotoxic agents.

Accordingly, in other embodiments the instant invention will comprise a humanized PTK7 modulator selected from the group consisting of hSC6.23, hSC6.24, hSC6.41 and hSC6.58. Still other embodiments are directed to a PTK7 modulator comprising a humanized antibody wherein said humanized antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 62, SEQ ID NO: 64, SEQ ID NO: 66 and SEQ ID NO: 68 and wherein said heavy chain variable region comprises an amino acid sequence having at least 60% identity to an amino acid sequence selected from the group consisting of amino acid sequences as set forth in SEQ ID NO: 63, SEQ ID NO: 65, SEQ ID NO: 67 and SEQ ID NO: 69.

As previously indicated one aspect of the invention comprises the unexpected association of PTK7 polypeptides with cancer stem cells. Thus, in certain other embodiments the invention will comprise a PTK7 modulator that reduces the frequency of tumor initiating cells upon administration to a subject. Preferably the reduction in frequency will be determined using in vitro or in vivo limiting dilution analysis. In particularly preferred embodiments such analysis may be conducted using in vivo limiting dilution analysis comprising transplant of live human tumor cells into immunocompromised mice. Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodology such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, in another preferred embodiment of the instant invention comprises a method of treating a PTK7 associated disorder comprising administering a therapeutically effective amount of a PTK7 modulator to a subject in need thereof whereby the frequency of tumor initiating cells is reduced. Preferably the PTK7 associated disorder comprises a neoplastic disorder. Again, the reduction in the tumor initiating cell frequency will preferably be determined using in vitro or in vivo limiting dilution analysis.

In this regard it will be appreciated that the present invention is based, at least in part, upon the discovery that PTK7 immunogens are associated with tumor perpetuating cells (i.e., cancer stem cells) that are involved in the etiology of various neoplasia. More specifically, the instant application unexpectedly demonstrates that the administration of various exemplary PTK7 modulators can mediate, reduce, deplete, inhibit or eliminate tumorigenic signaling by tumor initiating cells (i.e., reduce the frequency of tumor initiating cells). This reduced signaling, whether by depletion, neutralization, reduction, elimination, reprogramming or silencing of the tumor initiating cells or by modifying tumor cell morphology (e.g., induced differentiation, niche disruption), in turn allows for the more effective treatment of PTK7 associated disorders by inhibiting tumorigenesis, tumor maintenance, expansion and/or metastasis and recurrence.

Besides the aforementioned association with cancer stem cells, there is evidence that PTK7 isoforms may be involved in angiogenesis, migration of endothelial cells and specific developmental signaling cascades that have been tied to oncogenesis (i.e., Wnt signaling pathways). Intervention in such cellular interactions, using the novel PTK7 modulators described herein, may thereby ameliorate or treat a disorder by more than one mechanism (i.e., tumor initiating cell reduction and disruption oncogenic pathway signaling) to provide additive or synergistic effects. Still other preferred embodiments may take advantage of the cellular internalization of cell surface PTK7 to deliver a modulator mediated anti-cancer agent. In this regard it will be appreciated that the present invention is not limited by any particular mechanism of action but rather encompasses the broad use of the disclosed modulators to treat PTK7 associated disorders (including various neoplasia).

Thus, other facets of the instant invention exploit the ability of the disclosed modulators to potentially disrupt oncogenic survival pathways while simultaneously silencing tumor initiating cells. Such multi-active PTK7 modulators (e.g., PTK7 antagonists) may prove to be particularly effective when used in combination with standard of care anti-cancer agents or debulking agents. Accordingly preferred embodiments of the instant invention comprise using the disclosed modulators as anti-metastatic agents for maintenance therapy following initial treatments. In addition, two or more PTK7 antagonists (e.g. antibodies that specifically bind to two discrete epitopes on PTK7) may be used in combination in accordance with the present teachings. Moreover, as discussed in some detail below, the PTK7 modulators of the present invention may be used in a conjugated or unconjugated state and, optionally, as a sensitizing agent in combination with a variety chemical or biological anti-cancer agents.

Accordingly another preferred embodiment of the instant invention comprises a method of sensitizing a tumor in a subject for treatment with an anti-cancer agent comprising the step of administering a PTK7 modulator to said subject. Other embodiments comprise a method of reducing metastasis following treatment comprising administering a PTK7 modulator to a subject in need thereof. In a particularly preferred aspect of the invention the PTK7 modulator will specifically result in a reduction of tumor initiating cell frequency is as determined using in vitro or in vivo limiting dilution analysis.

More generally preferred embodiments of the invention comprise a method of treating a PTK7 associated disorder in a subject in need thereof comprising the step of administering a PTK7 modulator to the subject. In particularly preferred embodiments the PTK7 modulator will be associated (e.g., conjugated) with an anti-cancer agent. In yet other embodiments the PTK7 modulator will internalize following association or binding with the PTK7 on or near the surface of the cell. Moreover the beneficial aspects of the instant invention, including any disruption of signaling pathways and collateral benefits, may be achieved whether the subject tumor tissue exhibits elevated levels of PTK7 or reduced or depressed levels of PTK7 as compared with normal adjacent tissue.

In yet another aspect the present invention will comprise a method of treating a subject suffering from neoplastic disorder comprising the step of administering a therapeutically effective amount of at least one internalizing PTK7 modulator. Preferred embodiments will comprise the administration of internalizing antibody modulators wherein, in other selected embodiments, the internalizing antibody modulators are conjugated or associated with a cytotoxic agent.

Other embodiments are directed to a method of treating a subject suffering from a PTK7 associated disorder comprising the step of administering a therapeutically effective amount of at least one depleting PTK7 modulator.

In yet another embodiment the present invention provides methods of maintenance therapy wherein the disclosed effectors or modulators are administered over a period of time following an initial procedure (e.g., chemotherapeutic, radiation or surgery) designed to remove at least a portion of the tumor mass. Such therapeutic regimens may be administered over a period of weeks, a period of months or even a period of years wherein the PTK7 modulators may act prophylactically to inhibit metastasis and/or tumor recurrence. In yet other embodiments the disclosed modulators may be administrated in concert with known debulking regimens to prevent or retard metastasis, tumor maintenance or recurrence.

It will further be appreciated that the PTK7 modulators of the instant invention may be fabricated and selected to react with a single isoform of PTK7 or a select few isoforms (i.e. provided by splice variants) of the protein or, conversely, may comprise a pan-PTK7 modulator that reacts or associates with some or all PTK7 isoforms (five have currently been identified). More specifically, as disclosed herein preferred modulators such as antibodies may be generated and selected so that they react with domains that are exhibited by single splice variants (e.g., at specific exon junctions) or with Ig domains that are conserved across multiple or all PTK7 isoforms. This is significant with respect to the instant invention in that certain isoforms may be preferably expressed on TIC and can therefore serve as therapeutic targets to provide for the selective reduction in tumorigenic cell frequency and/or depletion of cancer stem cell populations.

Accordingly, in a selected embodiment the invention comprises a pan-PTK7 modulator. In other selected embodiments the invention comprises a PTK7 modulator that immunospecifically associates with one or more splice variants or isoforms. Preferably the splice variants may be selected from the group consisting of isoform a, isoform b, isoform c and isoform d. In yet other embodiments the present invention comprises a method of treating a subject in need thereof comprising administering a therapeutically effective amount of a pan-PTK7 modulator. Still other embodiments comprise a method of treating a subject in need thereof comprising administering a therapeutically effective amount of a PTK7 modulator that immunospecifically associates with one or more isoforms.

Beyond the therapeutic uses discussed above it will also be appreciated that the modulators of the instant invention may be used to diagnose PTK7 related disorders and, in particular, hyperproliferative disorders. In some embodiments the modulator may be administered to the subject and detected or monitored in vivo. Those of skill in the art will appreciate that such modulators may be labeled or associated with markers or reporters as disclosed below and detected using any one of a number of standard techniques (e.g., MRI, CAT scan PET scan, etc.).

Thus, in some embodiments the invention will comprise a method of diagnosing, detecting or monitoring a PTK7 associated disorder in vivo in a subject in need thereof comprising the step of administering a PTK7 modulator.

In other instances the modulators may be used in an in vitro diagnostic setting using art-recognized procedures. As such, a preferred embodiment comprises a method of diagnosing a hyperproliferative disorder in a subject in need thereof comprising the steps of:

a. obtaining a tissue sample from said subject;
  b. contacting the tissue sample with at least one PTK7 modulator; and
  c. detecting or quantifying the PTK7 modulator associated with the sample.

Such methods may be easily discerned in conjunction with the instant application and may be readily performed using generally available commercial technology such as automatic plate readers, dedicated reporter systems, etc. In selected embodiments the PTK7 modulator will be associated with tumor perpetuating cells present in the sample. In other preferred embodiments the detecting or quantifying step will comprise a reduction of tumor initiating cell frequency and detection thereof. Moreover, limiting dilution analysis may be conducted as previously alluded to above and will preferably employ the use of Poisson distribution statistics to provide an accurate accounting as to the reduction of frequency.

In a similar vein the present invention also provides kits that are useful in the diagnosis and monitoring of PTK7 associated disorders such as cancer. To this end the present invention preferably provides an article of manufacture useful for diagnosing or treating PTK7 associated disorders comprising a receptacle comprising a PTK7 modulator and instructional materials for using said PTK7 modulator to treat or diagnose the PTK7 associated disorder.

Other preferred embodiments of the invention also exploit the properties of the disclosed modulators as an instrument useful for identifying, isolating, sectioning or enriching populations or subpopulations of tumor initiating cells through methods such as flow cytometric analysis, fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with a PTK7 modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE FIGURES

FIGS. 1A-1C depict, respectively, the nucleic acid sequence encoding human PTK7 (SEQ ID NO: 1), the amino acid sequence of an exemplary human PTK7 variant (SEQ ID NO: 2) and FIG. 1C depicts the aligned and notated sequences of four representative isoforms of PTK7 (SEQ ID NOS: 3-6) wherein the underlined section in FIG. 1A represents PTK7-1 open reading frame, the underlined section in FIG. 1B denotes an extracellular domain of PTK7 as defined herein and FIG. 1C shows a protein alignment of four known exemplary isoforms of the human PTK7 protein as reported in the Gene database at NCBI (Protein accessions: isoform a=NP_002812, isoform b=NP_690619; isoform c=NP_690620; isoform d=NP_690621) wherein FIG. 1C further discloses the motif peptides, "GxGxFGxV," "HRDLxxxN," and "SDVWSxG" as SEQ ID NOS: 11-13, respectively.

FIGS. 6A and 6B provide, in a tabular form, the contiguous amino acid sequences of heavy and light chain variable regions of a number of murine and humanized exemplary PTK7 modulators isolated, cloned and engineered as described in the Examples herein.

FIGS. 7A-7E provide, in graphical and tabular representations, physiochemical characteristics of exemplary PTK7 modulators wherein FIG. 7A depicts binding characteristics of certain modulators with respect to murine and human PTK7, FIG. 7B provides affinity, binning and cross-reactivity data for selected modulators, FIGS. 7C and 7D show comparative binding characteristics of a selected murine modulator and its humanized counterpart and FIG. 7E provides binding affinities for selected modulators with respect to human PTK7 and its murine ortholog.

FIGS. 8A-8G depict various PTK7 constructs in accordance with the instant invention wherein FIGS. 8A-8F provide the amino acid sequences of six PTK7 modulator variants in the form of Ig-PTK7-ECD constructs wherein the extracellular domain portion of each construct is varied and FIG. 8G schematically illustrates the seven Ig domains of the extracellular portion of PTK7 along with the ELISA derived binding regions of several PTK7 modulators as indicated by brackets.

FIGS. 9A-9E illustrate expression levels of PTK7 protein in different tumor lysates and in NTX samples wherein FIGS. 9A-9D depict tumor lysate levels for various tumors and disease stages as compared with normal adjacent tissue controls and FIG. 9E provides histograms illustrating the staining of human non-traditional xenografts with selected modulators where control staining (gray) was compared to staining on non-tumorogenic (dashed) and putative cancer stem cell populations (solid).

FIGS. 10A-10E graphically illustrate the capacity of a selected modulator of the instant invention to internalize upon binding with PTK7 on a cell surface wherein FIG. 10C shows the fluorescent shift associated with an exemplary modulator (i.e. SC6.10.2 termed H10 in FIG. 10C) and FIGS. 10A and 10B represent controls, FIG. 10D demonstrate that exemplary modulators from hybridoma supernatants may be screened for internalization as compared to purified controls (SC6.2.35, SC6.10.2 and SC6.25.1 termed H2.35, H10.2 and H25.1 respectively) and FIG. 10E illustrates the extent of internalization of various modulators (each data point represents a discrete modulator) where the dashed line denotes the background cutoff and the number of PTK7 molecules that are internalized by the cell in response to the binding event is plotted on the y axis.

FIGS. 11A-11D graphically illustrate the capability of the disclosed modulators to immunospecifically mediate the delivery of cytotoxic agents and promote cell killing wherein FIG. 11A depicts the use of three exemplary modulators (SC6.2.35, SC6.10.2 and SC6.25.3 termed H2.35, H10.2 and H25.3 respectively) as targeting moieties to direct cytotoxic payloads to cells expressing PTK7 and where FIGS. 11B-11D illustrate the ability of four additional exemplary modulators to eliminate three discrete cell lines wherein in each FIG. the downward sloping curve is indicative of cell killing through internalized toxin.

FIGS. 13A-13C are indicative of the capacity of the disclosed modulators to reduce the frequency of tumor perpetuating cells and inhibit their tumorigenic potential where FIGS. 13A and 13B show that modulator (i.e., SC6.2.35 labeled SC6.H2) mediated delivery of cytotoxic agents impacts the viability of two discrete NTX breast tumor cell populations and FIG. 13C depicts the reduced tumorigenicity of the treated cell lines upon implantation into immunocompromised mice.

DETAILED DESCRIPTION OF THE INVENTION

I. Introduction

Figure 2:
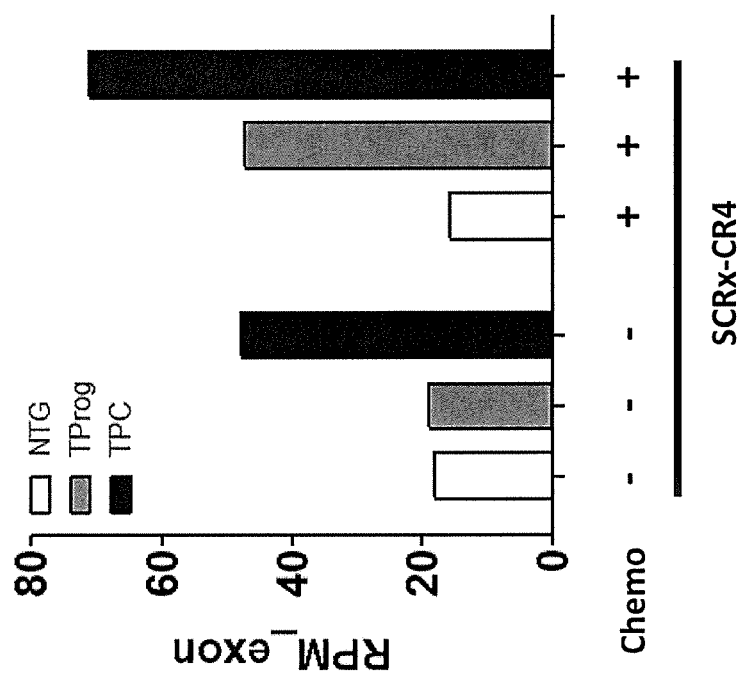
FIG. 2 is a graphical representation depicting the gene expression levels of PTK7 in untreated (−) and in irinotecan treated (+) mice as measured using whole transcriptome sequencing of highly enriched tumor progenitor cell (TProg), tumor perpetuating cell (TPC) and non-tumorigenic cell (NTG) populations obtained from a subset of a whole colorectal tumor specimen.

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

As previously alluded to, it has surprisingly been found that the expression of PTK7, including various isoforms, is associated with neoplastic growth and hyperproliferative disorders and that such ligands provide useful tumor markers which may be exploited in the treatment of related diseases. More specifically, it has been discovered that PTK7 modulators such as those disclosed herein may advantageously be used in the diagnosis, theragnosis, treatment or prevention of neoplastic disorders in subjects in need thereof. Accordingly, while preferred embodiments of the invention will be discussed extensively below, particularly in the context of cancer stem cells and their interactions with the disclosed modulators, those skilled in the art will appreciate that the scope of the instant invention is not limited by such exemplary embodiments. Rather, the present invention and the appended claims are broadly and expressly directed to PTK7 modulators and their use in the diagnosis, theragnosis, treatment or prevention of a variety of PTK7 associated or mediated disorders, including neoplastic or hyperproliferative disorders, regardless of any particular mechanism of action or specifically targeted tumor component.

It will further be appreciated that, in contrast to various prior art disclosures, the present invention is largely directed to immunospecific modulators of the various isoforms of PTK7 rather than general protein tyrosine kinase modulators. That is, while the class of protein tyrosine kinase receptors have been widely implicated in several types of disorders and generally targeted for therapeutic intervention, PTK7 specific modulators have heretofore attracted less attention. In part this may arise from the belief that interference with general PTK activity (particularly with small molecules that interact with conserved kinase domains) is more effective from a therapeutic standpoint as kinase redundancy would likely compensate for any specific antagonism of particular members of the class. Moreover, PTK7 reportedly comprises an inactive kinase domain (or pseudokinase domain) that may have discouraged its exploitation as a therapeutic target.

Conversely, the present invention comprises the use of immunospecific modulators that preferentially react with one or more isoforms of PTK7 to provide therapeutic benefits. As briefly discussed above in certain embodiments the modulators of the present invention may be generated and selected to associate with a single PTK7 isoform while in other embodiments the selected modulators may react with more than one isoform or all recognized isoforms of PTK7. In these latter embodiments the present invention may comprise modulators that associate or react with more than one PTK7 isoform thereby providing an unexpected additive or synergistic effect that may allow for quiescence of more than one PTK7 mediated pathway.

More generally, as demonstrated in the instant application, the disclosed immunospecific PTK7 modulators can effectively be used to target and eliminate or otherwise incapacitate tumorigenic cells and treat PTK7 associated disorders (e.g., neoplasia). As used herein a PTK7 associated disorder shall be held to mean any disorder or disease (including proliferative disorders) that is marked, diagnosed or identified by a phenotypic aberration of PTK7 expression during the course or etiology of the disease or disorder. In this regard the phenotypic aberration may, for example, comprise elevated or depressed levels of PTK7 expression, abnormal PTK7 expression on certain definable cell populations or abnormal PTK7 expression at an inappropriate phase or stage of a cell lifecycle.

Besides the general association discussed immediately above, the inventors have further discovered a heretofore unknown phenotypical association between selected tumor initiating cells (TIC) and PTK7. In this regard, it has been found that selected TICs express elevated levels of PTK7s when compared to normal tissue and non-tumorigenic cells (NTG), which together comprise much of a solid tumor. Thus, PTK7 isoforms comprise tumor associated markers (or antigens or immunogens) and have been found to provide effective agents for the detection and suppression of TIC and associated neoplasia due to altered levels of the proteins on cell surfaces or in the tumor microenvironment. More specifically, it has further been discovered that PTK7 modulators, including immunoreactive antagonists and antibodies that associate bind or react with the proteins, effectively reduce the frequency of tumor initiating cells and are therefore useful in eliminating, depleting, incapacitating, reducing, promoting the differentiation of, or otherwise precluding or limiting the ability of these tumor-initiating cells to lie dormant and/or continue to fuel tumor growth, metastasis or recurrence in a patient. As discussed in more detail below, the TIC tumor cell subpopulation is composed of both tumor perpetuating cells (TPC) and highly proliferative tumor progenitor cells (TProg).

In view of these discoveries, those skilled in the art will appreciate that the present invention further provides PTK7 modulators and their use in reducing the frequency of tumor initiating cells. As will be discussed extensively below, PTK7 modulators of the invention broadly comprise any compound that recognizes, reacts, competes, antagonizes, interacts, binds, agonizes, or associates with PTK7 or PTK7 or their genes. By these interactions, the PTK7 modulators thereby reduce or moderate the frequency of tumor initiating cells. Exemplary modulators disclosed herein comprise nucleotides, oligonucleotides, polynucleotides, peptides or polypeptides. In certain preferred embodiments the selected modulators will comprise antibodies to PTK7 or immunoreactive fragments or derivatives thereof. Such antibodies may be antagonistic or agonistic in nature and may optionally be conjugated or associated with a cytotoxic agent. In other embodiments, modulators within the instant invention will comprise a PTK7 construct comprising a PTK7 isoform or a reactive fragment thereof. It will be appreciated that such constructs may comprise fusion proteins and can include reactive domains from other polypeptides such as immunoglobulins or biological response modifiers. In still other aspects, the PTK7 modulator will comprise a nucleic acid assembly that exerts the desired effects at a genomic level. Still other modulators compatible with the instant teachings will be discussed in detail below.

Whichever form of modulator is ultimately selected it will preferably be in an isolated and purified state prior to introduction into a subject. In this regard an isolated PTK7 modulator shall be construed in a broad sense and in accordance with standard pharmaceutical practice to mean any preparation or composition comprising the modulator in a state substantially free of unwanted contaminants (biological or otherwise). As will be discussed in some detail below these preparations may be purified and formulated as desired using various art recognized techniques. Of course, it will be appreciated that such isolated preparations may be intentionally formulated or combined with inert or active ingredients as desired to improve the commercial, manufacturing or therapeutic aspects of the finished product and provide pharmaceutical compositions.

II. PTK7 Physiology

Protein tyrosine kinase (PTK7), also known as colon carcinoma kinase 4 (CCK4), is a receptor tyrosine kinase originally cloned from normal human melanocytes (Lee et al., *Oncogene* 8(12), 1993) and separately from colon carcinoma tissue (Mossie et al., *Oncogene* 11(10), 1995). The PTK7 gene is located at 6p21.1-p12.2. Five splice isoforms of human PTK7 have been cloned from testis cDNA (Jung, Ji et al., *Biochim Biophys Acta* 1579, 2002). The relative abundance of the isoforms with respect to one another differs between testis and hepatoma or colon carcinoma lines, but the functional significance of these isoforms, if any, is unknown. Bioinformatics analyses have suggested that the mouse may express a soluble Ptk7 isoform from alternatively spliced mRNAs (Forrest, Taylor et al., *Genome Biol* 7, 2006). For the purposes of the instant application it will be appreciated that the terms "PTK7" and "CCK4" may be used interchangeably and include splice variants, isoforms, species orthologs and homologs of human PTK7 unless otherwise dictated by contextual constraints. It will further be appreciated that the terms may also refer to any derivative or fragment of a native or variant form of PTK7 that contains an epitope to which a PTK7 protein modulator (e.g., an antibody or immunoreactive fragment) can specifically bind.

Full length PTK7 protein is a type I transmembrane protein, with a 674 amino acid extracellular domain (ECD), followed by a short TM spanning portion and a 345 amino acid cytoplasmic domain. A complete nucleic acid sequence of an exemplary isoform of human PTK7 (i.e., transcript variant PTK7-1) has Genbank accession number NM_002821 and is represented in FIG. 1A (SEQ ID NO: 1). Similarly, a full-length exemplary amino acid sequence of PTK7-1 protein is shown in FIG. 1B (SEQ ID NO: 2). Note that the PTK7 protein in SEQ ID NO: 2 differs from the translation product of the underlined nucleic acid sequence of SEQ ID NO: 1 (i.e. isoform a as shown in SEQ ID NO: 3) in that there is a point mutation (L->P) at position 93 in FIG. 1B. With regard to isoforms FIG. 1C shows the annotated alignment of amino acid sequences of four exemplary isoforms of PTK7 as reported in Genbank (Protein accessions: isoform a=NP_002812, SEQ ID NO: 3; isoform b=NP_690619, SEQ ID NO: 5; isoform c=NP_690620, SEQ ID NO: 6; isoform d=NP_690621, SEQ ID NO: 4). As previously alluded to the sequence set forth in isoform a corresponds to the translation product of the open reading frame from PTK7 variant 1 set forth in FIG. 1A and is the longest of the isoforms. The other splice isoforms encode extracellular domains lacking various Igcam domains relative to isoform a, as shown. All isoforms encode the same intracellular domain. Conserved submotifs in the catalytic domain of the protein serine/tyrosine kinases are shown below the PTK7 alignments, as are annotations of the changes in the PTK7 protein thought to render its kinase domain inactive (e.g., changes in subdomains I and VII).

In any event the mature full length PTK7 ECD comprises seven immunoglobulin-like domains while, as shown in FIG. 1C the various splice variants encode PTK7 isoforms that differ in their ECD structure. All isoforms contain a cytoplasmic domain with substantial homology to that found in the general class of tyrosine kinases. However, PTK7 lacks detectable tyrosine kinase activity and, as such, belongs to a subfamily of pseudokinases in which several amino acid changes in various conserved kinase subdomains lead to impaired binding of ATP (Kroiher et al. *Bioessays* 23(1), 2001). Specifically, key residues in subdomains I and VII are altered in PTK7 such that direct interactions with the non-transferable phosphates of ATP, as well as chelation of the $Mg^{2+}$ cofactor bridging these phosphates, would be impaired (Hanks et al., *Methods Enzymol* 200, 1991).

It will further be appreciated PTK7 polypeptides compatible with the instant invention may be in the form of a 'mature' protein or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag. Additional sequences which may provide stability during recombinant production may also be used. Such sequences may be optionally removed as required by incorporating a cleavable sequence as an additional sequence or part thereof. Thus, a PTK7 polypeptide as defined herein may comprise constructs fused to adjunct moieties including other polypeptides. Such additional sequences and affinity tags are well known in the art and may be generated using standard biochemical techniques.

The biological importance of PTK7 function despite its inactive kinase domain can be inferred from the presence of conserved orthologs from *Hydra* through *Drosophila* to chicken and human, each of which by sequence analysis is predicted to lack kinase activity (Kroiher et al., 2001). Based upon the high conservation of a specific TM domain motif associated with a propensity for helix-helix association and the fact that RTK typically dimerize in response to ligand engagement, it was suggested that TM domain may mediate PTK7 dimerization (Kroiher et al., 2001). A later study suggested that the PTK7 TM domain does not promote preferential self-association (Kobus et al., *Biochemistry* 44(5), 2005), but did not rule out heteromeric interactions with the TM domains of other RTKs or members of a signaling complex. Therefore, the PTK7 pseudokinase domain itself is not expected to directly transmit the signal, but it may interact as a scaffold for other molecules in the signaling pathway, or may recruit other tyrosine kinase(s) (Kroiher et al., 2001).

Human PTK7 is not expressed in adult colon although it is expressed in fetal colon and a variety of colon carcinoma derived cell lines (Mossie et al. supra, 1995), as well as in metastatic colorectal cancer (Saha et al., *Science* 294(5545) 2001). Other normal tissues and cells reported to express PTK7 include lung, thyroid and ovary (Mossie, Jallal et al. 1995), CD4+ recent thymic emigrant T-cells (Haines et al., *J Exp Med* 206(2) 2009), and normal myeloid progenitors and CD34+CD38– bone marrow cells (Prebet et al., *Blood* 116 (13), 2010). With respect to cancerous tissues, PTK7 expression has also been found in colon carcinoma cells (Mossie et al. 1995); in AML samples (Muller-Tidow, et al. *Clin Cancer Res* 10(4), 2004); in CD34-pre-TALL cells (Shangguan et al., *J Proteome Res* 7(5) 2008) and in gastric carcinoma (Gorringe et al., *Genes Chromosomes Cancer* 42(3), 2005). Interestingly, despite being cloned originally from normal melanocytes, PTK7 has been reported to be lost in metastatic melanoma (Easty et al., *Int J Cancer* 71(6), 1997). PTK7 also may be lost in certain breast cancers containing deletions of chromosome 6p21 (Piao et al., *Genes Chromosomes Cancer* 30(2), 2001), although expression is variable in breast cancer cell lines (Su et al., *J Cancer* 1 2010). PTK7 is also expressed lung adenocarcinoma, where stronger expression levels have been correlated with a more favorable prognosis in these tumors (Endoh et al., *J Clin Oncol* 22(5), 2004). Fine mapping of the amplifications of 6p12-p21 region in osteosarcomas has shown that increases in gene copy number do not necessarily result in overexpression of PTK7, as determined by qRT-PCR (Lu et al., *Mol Cancer Res* 6(6), 2008).

The ligand or ligands for PTK7 are n
Soyuer et al, "Prognostic significance of CD9 expression in locally advanced gastric cancer treated with surgery and adjuvant chemoradiotherapy", *Pathology—Research and Practice* (2010) 206; 607-610.
Todaro et al, "Colon Cancer Stem Cells: Promise of Targeted Therapy", *Gastroenterology* (2010) 138:2151-2162.
Official Action dated Dec. 1, 2014 issued in Chinese application (No. 201280019016.6).
Official Action dated Sep. 29, 2014 issued in European application (No. 12705776.8).
Office action received Dec. 14, 2014 issued in Saudi Arabian application (No. 112330278.2).
Al-Hajj et al., "Self-renewal and solid tumor stem cells" *Oncogene* (2004) 23, 7274-7282. ot known, although PTK7 has been linked to a variety of biological signaling pathways and developmental processes. The immunoglobulin-like ECD domain structure of the protein suggests that it may be a participant in or sensor of cell-cell contact and adhesion. The *Drosophila* ortholog of PTK7, OTK, has been associated with plexin as a potential co-receptor for semaphorin signaling during axon guidance (Winberg et al., *Neuron* 32(1), 2001). Recently an interaction between PlexinA1 and PTK7 in *Xenopus* has been demonstrated (Wagner et al., *Biochem Biophys Res Commun* 402(2) 2010) while the chick ortholog of PTK7, KLG, has been shown to interact with PlexinA1 and Sema6D in a complex important for chick cardiac morphogenesis ((Toyofuku et al., *Genes Dev* 18(4), 2004). Soluble PTK7 (sPTK7) was used to show a role for PTK7 in VEGF-induced angiogenesis, as well as in vitro tube formation, migration and invasion of human endothelial cells (Shin et al., *Biochem Biophys Res Commun* 371(4), 2008). Mouse PTK7 has also been linked to epidermal wound healing processes, which require actin cytoskeletal reorganization and cell migration (Caddy et al., *Dev Cell* 19(1), 2010).

With respect to specific signaling cascades, PTK7 appears to be a component of various Wnt signaling pathways important for development (Puppo et al., *EMBO Rep* 12(1), 2010). Mice expressing a null or severely hypomorphic mutation in Ptk7 die perinatally, displaying phenotypes consistent with a role for PTK7 in a planar cell polarity (PCP) pathway (Lu et al., *Nature* 430(6995), 2004). Similarly, chuzhoi mice containing mutant PTK7 proteins with a three amino acid insertion in the ECD display PCP-defective phenotypes (Paudyal, Damrau et al. 2010). Murine PTK7 has been shown to genetically interact with other PCP genes, including Vangl2 (Lu et al., 2004), Celsr1 (Paudyal, Damrau et al. 2010), Scrb1 and Grhl3 (Caddy et al., 2010). Membrane type-1 matrix metalloproteinase (MT1-MMP) cleaves PTK7 to release soluble PTK7 (i.e., sPTK7), and disregulation of the balance of MT1-MMP activity and sPTK7 production leads to convergent extension defects in zebrafish, also consistent with a role for PTK7 in a PCP pathway (Golubkov et al., *J Biol Chem* 285 (46), 2010). In *Xenopus*, PTK7 was found in complexes with dsh and the Wnt-receptor fz7 in non-canonical Wnt signaling pathways (Shnitsar et al., *Development* 135(24), 2008), whereas interactions between PTK7 and β-catenin could be shown to be dynamically affected by canonical Wnt signaling in mouse cells (Puppo et al., 2010). Additionally, a conserved TCF/LEF-transcription factor binding site in the PTK7 promoter suggests it is a Wnt response gene and may explain PTK7 up regulation in certain colorectal cancers, since these tumors are frequently disregulated for Wnt pathway signaling (Katoh, *Int J Mol Med* 20(3), 2007).

Within cancerous tissues, in addition to its potential for modulating the Wnt pathways described above, PTK appears to convey pro-proliferation and anti-apoptotic signals in the HCT116 colon carcinoma line, phenotypes which could be reversed by RNAi mediated knock-down of PTK7 (Meng et al., *PLoS One* 5(11), 2010). PTK7 anti-apoptotic signals conveyed resistance to anthracycline-mediated cell killing in AML blasts, which could be reversed using a soluble PTK7-Fc protein (Prebet et al., 2010). Overexpression of PTK7 by specific cancer cells has been exploited in a strategy to target delivery of daunorubicin to T-ALL cells in culture using aptamers that bind PTK7 and are subsequently internalized (Xiao et al., *Chemistry* 14(6), 2008).

In addition to the aforementioned characteristics the present disclosure demonstrates that the expression of PTK7 is elevated in various tumor initiating cell populations. Along with concomitant upregulation of PTK7 in at least some of the non-tumorigenic cells in the bulk tumor, this raises the possibility that PTK7 mediated ligand receptor interactions may be triggering cell signaling cascades linked to tumor proliferation, neoangiogenesis and/or tumor metastasis. While not wishing to be bound by any particular theory, it is believed that PTK7 modulators of the present invention (particularly antagonistic or neutralizing embodiments) act, at least in part, by either reducing or eliminating tumor initiating cell frequency thereby interfering with tumor propagation or survival in a different manner than traditional standard of care therapeutic regimens (e.g. irinotecan), or through immunotherapeutic signaling or delivering a payload able to kill PTK7 expressing cells. For example, a reduction in cancer stem cell activity by antagonizing PTK7 may include simply promoting cell proliferation in the face of chemotherapeutic regimens that eliminate proliferating cells, or inducing differentiation of the tumor initiating cell such that their self-renewal (i.e. unlimited proliferation and maintenance of multipotency) capacity is lost. Alternatively, in preferred embodiments recruitment of cytotoxic T-cells to PTK7 expressing cells, or delivery of a potent toxin conjugated to an anti-PTK7 antibody that is able to internalize, may selectively kill TPC.

III. Tumor Perpetuating Cells

In contrast to teachings of the prior art, the present invention provides PTK7 modulators that are particularly useful for targeting tumor initiating cells, and especially tumor perpetuating cells, thereby facilitating the treatment, management or prevention of neoplastic disorders. More specifically, as previously indicated it has surprisingly been found that specific tumor cell subpopulations express PTK7 and may modify localized coordination of morphogen signaling important to cancer stem cell self-renewal and cell survival. Thus, in preferred embodiments modulators of PTK7 may be used to reduce tumor initiating cell frequency in accordance with the present teachings and thereby facilitate the treatment or management of hyperproliferative diseases.

As used herein, the term tumor initiating cell (TIC) encompasses both tumor perpetuating cells (TPC; i.e., cancer stem cells or CSC) and highly proliferative tumor progenitor cells (termed TProg), which together generally comprise a unique subpopulation (i.e. 0.1-40%) of a bulk tumor or mass. For the purposes of the instant disclosure the terms tumor perpetuating cells and cancer stem cells or neoplastic stem cells are equivalent and may be used interchangeably herein. Conversely, TPC differ from TProg in that they can completely recapitulate the composition of tumor cells existing within a tumor and have unlimited self-renewal capacity as demonstrated by serial transplantation (two or more passages through mice) of low numbers of isolated cells. As will be discussed in more detail below fluorescence-activated cell sorting (FACS) using appropriate cell surface markers is a reliable method to isolate highly enriched cell subpopulations (e.g., >99.5% purity) due, at least in part, to its ability to discriminate between single cells and clumps of cells (i.e. doublets, etc.). Using such techniques it has been shown that when low cell numbers of highly purified TProg cells are transplanted into immunocompromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a non-tumorigenic cell (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such PTK7 positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non-TPC derived cells (e.g., fibroblasts/ stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many of the aforementioned prior art treatments, the novel compositions of the present invention preferably reduce the frequency of tumor initiating cells upon administration to a subject regardless of the form or specific target (e.g., genetic material, PTK7 antibody or ligand fusion construct) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert affects on the tumor environment or other cells, in turn allows for the more effective treatment of PTK7 associated disorders by inhibiting tumorigenesis, tumor maintenance and/or metastasis and recurrence.

Among the methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis are the preferred methods of calculating reduction of tumor initiating cell frequency, other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMCID: PMC2413402 & Hoey et al. 2009, PMID: 19664991; each of which is incorporated herein by reference in its entirety.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated conditions, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art recognized cell surface proteins known to enrich for tumor initiating cells (e.g., potentially compatible markers as are set forth in Example 1 below) and thereby measure TIC levels from various samples. In still another compatible method one skilled in the art might enumerate TIC frequency in situ (e.g., in a tissue section) by immunohistochemistry using one or more antibodies or reagents that are able to bind cell surface proteins thought to demarcate these cells.

Using any of the above-referenced methods it is then possible to quantify the reduction in frequency of TIC (or the TPC therein) provided by the disclosed PTK7 modulators (including those conjugated to cytotoxic agents) in accordance with the teachings herein. In some instances, the compounds of the instant invention may reduce the frequency of TIC (by a variety of mechanisms noted above, including elimination, induced differentiation, niche disruption, silencing, etc.) by 10%, 15%, 20%, 25%, 30% or even by 35%. In other embodiments, the reduction in frequency of TIC may be on the order of 40%, 45%, 50%, 55%, 60% or 65%. In certain embodiments, the disclosed compounds my reduce the frequency of TIC by 70%, 75%, 80%, 85%, 90% or even 95%.

Of course it will be appreciated that any reduction of the frequency of the TIC likely results in a corresponding reduction in the tumorigenicity, persistence, recurrence and aggressiveness of the neoplasia.

IV. PTK7 Modulators

In any event, the present invention is directed to the use of PTK7 modulators, including PTK7 antagonists, for the diagnosis, theragnosis, treatment and/or prophylaxis of various disorders including any one of a number of PTK7 associated malignancies. The disclosed modulators may be used alone or in conjunction with a wide variety of anti-cancer compounds such as chemotherapeutic or immunotherapeutic agents (e.g., therapeutic antibodies) or biological response modifiers. In other selected embodiments, two or more discrete PTK7 modulators may be used in combination to provide enhanced anti-neoplastic effects or may be used to fabricate multispecific constructs.

In certain embodiments, the PTK7 modulators of the present invention will comprise nucleotides, oligonucleotides, polynucleotides, peptides or polypeptides. Even more preferably the modulators will comprise soluble PTK7 (sPTK7) or a form, variant, derivative or fragment thereof including, for example, PTK7 fusion constructs (e.g., PTK7-Fc, PTK7-targeting moiety, etc.) or PTK7-conjugates (e.g., PTK7-PEG, PTK7-cytotoxic agent, PTK7-brm, etc.). It will also be appreciated that, in other embodiments, the PTK7 modulators comprise antibodies or immunoreactive fragments or derivatives thereof. In particularly preferred embodiments the modulators of the instant invention will comprise neutralizing antibodies or derivatives or fragments thereof. In other embodiments the PTK7 modulators may comprise internalizing antibodies or fragments thereof. In still other embodiments the PTK7 modulators may comprise depleting antibodies or fragments thereof. Moreover, as with the aforementioned fusion constructs, these antibody modulators may be conjugated, linked or otherwise associated with selected cytotoxic agents, polymers, biological response modifiers (BRMs) or the like to provide directed immunotherapies with various (and optionally multiple) mechanisms of action. As alluded to above such antibodies may be pan-PTK7 antibodies and associate with two or more PTK7 isoforms or immunospecific antibodies that selectively react with a single isoform. In yet other embodiments the modulators may operate on the genetic level and may comprise compounds as antisense constructs, siRNA, micro RNA and the like.

It will further be appreciated that the disclosed PTK7 modulators may deplete, silence, neutralize, eliminate or inhibit growth, propagation or survival of tumor cells, particularly TPC, and/or associated neoplasia through a variety of mechanisms, including agonizing or antagonizing selected pathways or eliminating specific cells depending, for example, on the form of PTK7 modulator, any associated payload or dosing and method of delivery. Accordingly, while preferred embodiments disclosed herein are directed to the depletion, inhibition or silencing of specific tumor cell subpopulations such as tumor perpetuating cells, it must be emphasized that such embodiments are merely illustrative and not limiting in any sense. Rather, as set forth in the appended claims, the present invention is broadly directed to PTK7 modulators and their use in the treatment, management or prophylaxis of various PTK7 associated hyperproliferative disorders irrespective of any particular mechanism or target tumor cell population.

In the same sense disclosed embodiments of the instant invention may comprise one or more PTK7 antagonists that associate with PTK7. To that end it will be appreciated that PTK7 antagonists of the instant invention may comprise any ligand, polypeptide, peptide, fusion protein, antibody or immunologically active fragment or derivative thereof that recognizes, reacts, binds, combines, competes, associates or otherwise interacts with the PTK7 protein or fragment thereof and eliminates, silences, reduces, inhibits, hinders, restrains or controls the growth of tumor initiating cells or other neoplastic cells including bulk tumor or NTG cells. In selected embodiments the PTK7 modulators comprise PTK7 antagonists.

As used herein an antagonist refers to a molecule capable of neutralizing, blocking, inhibiting, abrogating, reducing or interfering with the activities of a particular or specified protein, including the binding of receptors to ligands or the interactions of enzymes with substrates. More generally antagonists of the invention may comprise antibodies and antigen-binding fragments or derivatives thereof, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. Antagonists may also include small molecule inhibitors, fusion proteins, receptor molecules and derivatives which bind specifically to the protein thereby sequestering its binding to its substrate target, antagonist variants of the protein, antisense molecules directed to the protein, RNA aptamers, and ribozymes against the protein.

As used herein and applied to two or more molecules or compounds, the terms recognizes or associates shall be held to mean the reaction, binding, specific binding, combination, interaction, connection, linkage, uniting, coalescence, merger or joining, covalently or non-covalently, of the molecules whereby one molecule exerts an effect on the other molecule.

Moreover, as demonstrated in the examples herein, some modulators of human PTK7 may, in certain cases, cross-react with PTK7 from a species other than human (e.g., murine). In other cases exemplary modulators may be specific for one or more isoforms of human PTK7 and will not exhibit cross-reactivity with PTK7 orthologs from other species. Of course, in conjunction with the teachings herein such embodiments may comprise pan-PTK7 antibodies that associate with two or more isoforms from a single species or antibodies that exclusively associate with a single isoform.

In any event, and as will be discussed in more detail below, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, anti-cancer agents, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated herein the selected conjugate may be covalently or non-covalently linked to the PTK7 modulator in various molar ratios depending, at least in part, on the method used to effect the conjugation.

V. Antibodies a. Overview

As previously alluded to particularly preferred embodiments of the instant invention comprise PTK7 modulators in the form of antibodies that preferentially associate with one or more isoforms of PTK7. The term antibody is used in the broadest sense and specifically covers synthetic antibodies, monoclonal antibodies, oligoclonal or polyclonal antibodies, multiclonal antibodies, recombinantly produced antibodies, intrabodies, multispecific antibodies, bispecific antibodies, monovalent antibodies, multivalent antibodies, human antibodies, humanized antibodies, chimeric antibodies, CDR-grafted antibodies, primatized antibodies, Fab fragments, F(ab') fragments, single-chain FvFcs (scFvFc), single-chain Fvs (scFv), anti-idiotypic (anti-Id) antibodies and any other immunologically active antibody fragments so long as they exhibit the desired biological activity (i.e., immunospecific or immunopreferential PTK7 association or binding). In a broader sense, the antibodies of the present invention include immunoglobulin molecules and immunologically active fragments of immunoglobulin molecules, i.e., molecules that contain an antigen binding site, where these fragments may or may not be fused to another immunoglobulin domain including, but not limited to, an Fc region or fragment thereof. Further, as outlined in more detail herein, the terms antibody and antibodies specifically include Fc variants as described below, including full length antibodies and variant Fc-Fusions comprising Fc regions, or fragments thereof, optionally comprising at least one amino acid residue modification and fused to an immunologically active fragment of an immunoglobulin.

As discussed in more detail below, the generic terms antibody or immunoglobulin comprises five distinct classes of antibody that can be distinguished biochemically and, depending on the amino acid sequence of the constant domain of their heavy chains, can readily be assigned to the appropriate class. For historical reasons, the major classes of intact antibodies are termed IgA, IgD, IgE, IgG, and IgM. In humans, the IgG and IgA classes may be further divided into recognized subclasses (isotypes), i.e., IgG1, IgG2, IgG3, IgG4, IgA1, and IgA2 depending on structure and certain biochemical properties. It will be appreciated that the IgG isotypes in humans are named in order of their abundance in serum with IgG1 being the most abundant.

While all five classes of antibodies (i.e. IgA, IgD, IgE, IgG, and IgM) and all isotypes (i.e., IgG1, IgG2, IgG3, IgG4, IgA1, and IgA2), as well as variations thereof, are within the scope of the present invention, preferred embodiments comprising the IgG class of immunoglobulin will be discussed in some detail solely for the purposes of illustration. It will be understood that such disclosure is, however, merely demonstrative of exemplary compositions and methods of practicing the present invention and not in any way limiting of the scope of the invention or the claims appended hereto.

In this respect, human IgG immunoglobulins comprise two identical light polypeptide chains of molecular weight approximately 23,000 Daltons, and two identical heavy chains of molecular weight 53,000-70,000 depending on the isotype. Heavy-chain constant domains that correspond to the different classes of antibodies are denoted by the corresponding lower case Greek letter $\alpha$, $\delta$, $\epsilon$, $\gamma$, and $\mu$, respectively. The light chains of the antibodies from any vertebrate species can be assigned to one of two clearly distinct types, called kappa ($\kappa$) and lambda ($\lambda$), based on the amino acid sequences of their constant domains. Those skilled in the art will appreciate that the subunit structures and three-dimensional configurations of different classes of immunoglobulins are well known.

The four chains are joined by disulfide bonds in a Y configuration wherein the light chains bracket the heavy chains starting at the mouth of the Y and continuing through the variable region to the dual ends of the Y. Each light chain is linked to a heavy chain by one covalent disulfide bond while two disulfide linkages in the hinge region join the heavy chains. The respective heavy and light chains also have regularly spaced intrachain disulfide bridges the number of which may vary based on the isotype of IgG.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. In this regard, it will be appreciated that the variable domains of both the light ($V_L$) and heavy ($V_H$) chain portions determine antigen recognition and specificity. Conversely, the constant domains of the light chain ($C_L$) and the heavy chain ($C_H1$, $C_H2$ or $C_H3$) confer and regulate important biological properties such as secretion, transplacental mobility, circulation half-life, complement binding, and the like. By convention the numbering of the constant region domains increases as they become more distal from the antigen binding site or amino-terminus of the antibody. Thus, the amino or N-terminus of the antibody comprises the variable region and the carboxy or C-terminus comprises the constant region. Thus, the $C_H3$ and $C_L$ domains actually comprise the carboxy-terminus of the heavy and light chain, respectively.

The term variable refers to the fact that certain portions of the variable domains differ extensively in sequence among immunoglobulins and these hot spots largely define the binding and specificity characteristics of a particular antibody. These hypervariable sites manifest themselves in three segments, known as complementarity determining regions (CDRs), in both the light-chain and the heavy-chain variable domains respectively. The more highly conserved portions of variable domains flanking the CDRs are termed framework regions (FRs). More specifically, in naturally occurring monomeric IgG antibodies, the six CDRs present on each arm of the antibody are short, non-contiguous sequences of amino acids that are specifically positioned to form the antigen binding site as the antibody assumes its three dimensional configuration in an aqueous environment.

The framework regions comprising the remainder of the heavy and light variable domains show less inter-molecular variability in amino acid sequence. Rather, the framework regions largely adopt a $\beta$-sheet conformation and the CDRs form loops which connect, and in some cases form part of, the $\beta$-sheet structure. Thus, these framework regions act to form a scaffold that provides for positioning the six CDRs in correct orientation by inter-chain, non-covalent interactions. The antigen-binding site formed by the positioned CDRs defines a surface complementary to the epitope on the immunoreactive antigen. This complementary surface promotes the non-covalent binding of the antibody to the immunoreactive antigen epitope. It will be appreciated that the position and composition of CDRs can be readily identified by one of ordinary skill in the art using the definitions provided herein.

As discussed in more detail below all or part of the heavy and light chain variable regions may be recombined or engineered using standard recombinant and expression techniques to provide effective antibodies. That is, the heavy or light chain variable region from a first antibody (or any portion thereof) may be mixed and matched with any selected portion of the heavy or light chain variable region from a second antibody. For example, in one embodiment, the entire light chain variable region comprising the three light chain CDRs of a first antibody may be paired with the entire heavy chain variable region comprising the three heavy chain CDRs of a second antibody to provide an operative antibody. Moreover, in other embodiments, individual heavy and light chain CDRs derived from various antibodies may be mixed and matched to provide the desired antibody having optimized characteristics. Thus, an exemplary antibody may comprise three light chain CDRs from a first antibody, two heavy chain CDRs derived from a second antibody and a third heavy chain CDR from a third antibody.

Figure 6A:
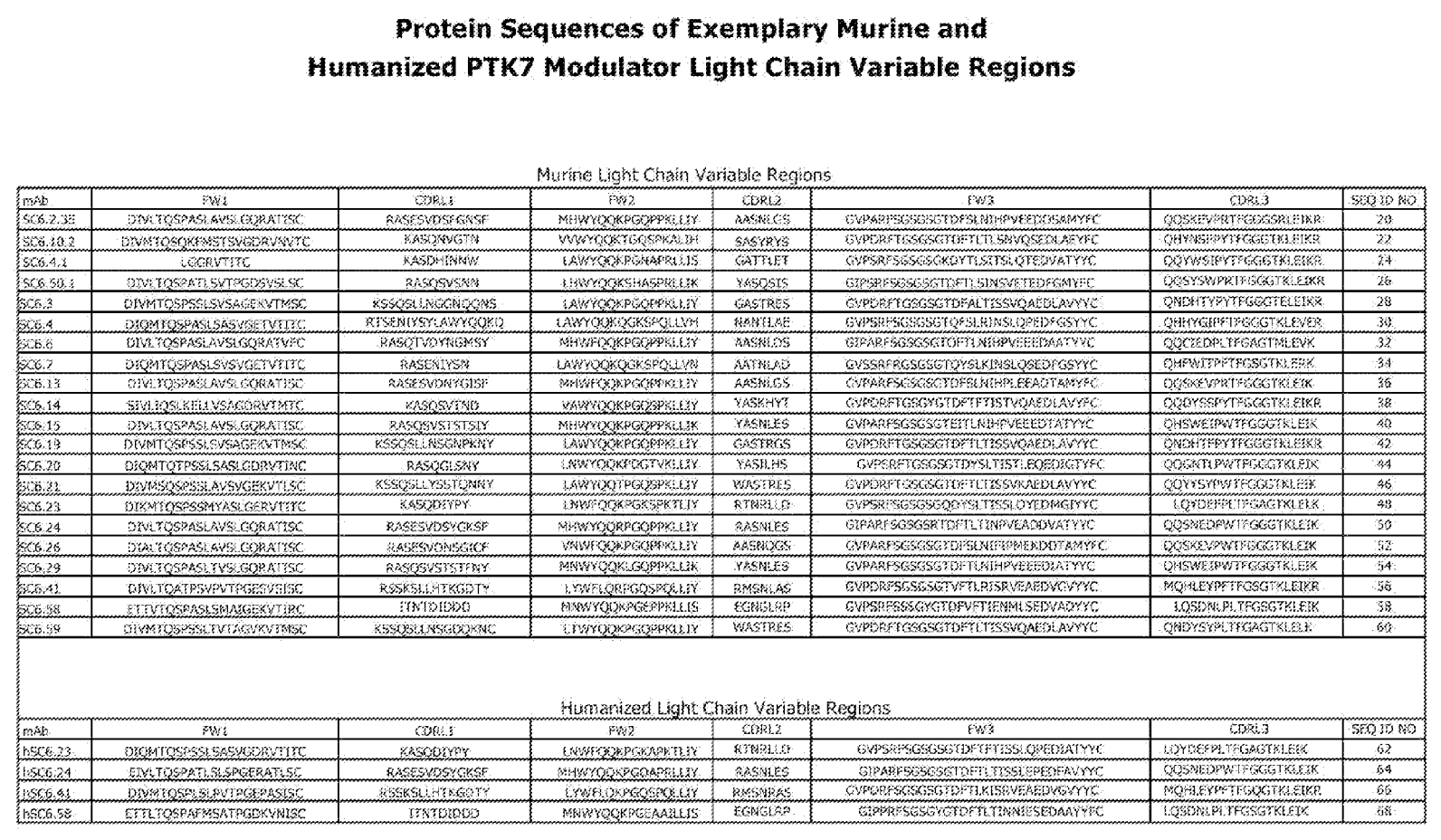

More specifically, in the context of the instant invention it will be appreciated that any of the disclosed heavy and light chain CDRs derived from the murine variable region amino acid sequences set forth in FIG. 6A or FIG. 6B may be rearranged in this manner to provide optimized anti-PTK7 (e.g. anti-hPTK7) antibodies in accordance with the instant teachings. That is, one or more of the CDRs derived from the contiguous light chain variable region amino acid sequences set forth in FIG. 6A (SEQ ID NOS: 20-60, even numbers) or the contiguous heavy chain variable region amino acid sequences set forth in FIG. 6B (SEQ ID NOS: 21-61, odd numbers) may be incorporated in a PTK7 modulator and, in particularly preferred embodiments, in a CDR grafted or humanized antibody that immunospecifically associates with one or more PTK7 isoforms. Examples of light (SEQ ID NOS: 62-68, even numbers) and heavy (SEQ ID NOS: 63-69, odd numbers) chain variable region amino acid sequences of such humanized modulators are also set forth in FIGS. 6A and 6B. Taken together these novel amino acid sequences depict twenty-one murine and four humanized exemplary modulators in accordance with the instant invention. Moreover, corresponding nucleic acid sequences of each of the twenty-one exemplary murine modulators and four humanized modulators set forth in FIGS. 6A and 6B are included in the sequence listing appended to the instant application (SEQ ID NOS: 120-169).

In any event, the complementarity determining regions residue numbers may be defined as those of Kabat et al. (1991, NIH Publication 91-3242, National Technical Information Service, Springfield, Va.), specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of spacer residues in the numbering system, to be used for the Fv region. In addition, the identity of certain individual residues at any given Kabat site number may vary from antibody chain to antibody chain due to interspecies or allelic divergence. See also Chothia et al., J. Mol. Biol. 196:901-917 (1987); Chothia et al., Nature 342, pp. 877-883 (1989), MacCallum et al., J. Mol. Biol. 262:732-745 (1996) and S. Dubel, ed., *Handbook of Therapeutic Antibodies*, 3$^{rd}$ ed., WILEY-VCH Verlag GmbH and Co. (2007), where the definitions include overlapping or subsets of amino acid residues when compared against each other. Each of the aforementioned references is incorporated herein by reference in its entirety and the amino acid residues which comprise binding regions or CDRs as defined by each of the above cited references and are set forth for comparison below.

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 50-58 | 47-58 |
| $V_H$ CDR3 | 95-102 | 95-102 | 93-101 |

-continued

|  | Kabat[1] | Chothia[2] | MacCallum[3] |
|---|---|---|---|
| $V_L$ CDR1 | 24-34 | 23-34 | 30-36 |
| $V_L$ CDR2 | 50-56 | 50-56 | 46-55 |
| $V_L$ CDR3 | 89-97 | 89-97 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As discussed herein one skilled in the art could readily define, identify derive and/or enumerate the CDRs as defined by Kabat et al., Chothia et al. or MacCallum et al. for each respective heavy and light chain sequence set forth in FIG. 6A or FIG. 6B. Accordingly, each of the subject CDRs and antibodies comprising CDRs defined by all such nomenclature are expressly included within the scope of the instant invention. More broadly the term variable region CDR amino acid residue includes amino acids in a CDR as identified using any sequence or structure based method as set forth above.

As used herein the term variable region framework (FR) amino acid residues refers to those amino acids in the framework region of an Ig chain. The term framework region or FR region as used herein, includes the amino acid residues that are part of the variable region, but are not part of the CDRs (e.g., using the Kabat definition of CDRs). Therefore, a variable region framework is a non-contiguous sequence between about 100-120 amino acids in length but includes only those amino acids outside of the CDRs.

For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. (e.g., CDR-L1 23-34, CDR-L2 50-56, CDR-L3 89-97; CDR-H1 26-32, CDR-H2 50-58, CDR-H3 95-102) or McCallum et al. the framework region boundaries are separated by the respective CDR termini as described above.

With the aforementioned structural considerations in mind, those skilled in the art will appreciate that the antibodies of the present invention may comprise any one of a number of functional embodiments. In this respect, compatible antibodies may comprise any immunoreactive antibody (as the term is defined herein) that provides the desired physiological response in a subject. While any of the disclosed antibodies may be used in conjunction with the present teachings, certain embodiments of the invention will comprise chimeric, humanized or human monoclonal antibodies or immunoreactive fragments thereof. Yet other embodiments may, for example, comprise homogeneous or heterogeneous multimeric constructs, Fc variants and conjugated or glycosylationally altered antibodies. Moreover, it will be understood that such configurations are not mutually exclusive and that compatible individual antibodies may comprise one or more of the functional aspects disclosed herein. For example, a compatible antibody may comprise a single chain diabody with humanized variable regions or a fully human full length IgG3 antibody with Fc modifications that alter the glycosylation pattern to modulate serum half-life. Other exemplary b. Antibody Generation As is well known, and shown in the Examples herein, various host animals, including rabbits, mice, rats, etc. may be inoculated and used to provide antibodies in accordance with the teachings herein. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with a PTK7 immunogen (e.g., soluble PTK7 or sPTK7) which may comprise selected isoforms and/or peptides, or live cells or cell preparations expressing the desired protein, antibodies and/or antibody-producing cells can be obtained from the animal using art recognized techniques. In some embodiments, polyclonal anti-PTK7 antibody-containing serum is obtained by bleeding or sacrificing the animal. The serum may be used for research purposes in the form obtained from the animal or, in the alternative, the anti-PTK7 antibodies may be partially or fully purified to provide immunoglobulin fractions or homogeneous antibody preparations.

c. Monoclonal Antibodies

While polyclonal antibodies may be used in conjunction with certain aspects of the present invention, preferred embodiments comprise the use of PTK7 reactive monoclonal antibodies. As used herein, the term monoclonal antibody or mAb refers to an antibody obtained from a population of substantially homogeneous antibodies, i.e., the individual antibodies comprising the population are identical except for possible mutations, e.g., naturally occurring mutations, that may be present in minor amounts. Thus, the modifier monoclonal indicates the character of the antibody as not being a mixture of discrete antibodies and may be used in conjunction with any type of antibody. In certain embodiments, such a monoclonal antibody includes an antibody comprising a polypeptide sequence that binds or associates with PTK7, wherein the PTK7-binding polypeptide sequence was obtained by a process that includes the selection of a single target binding polypeptide sequence from a plurality of polypeptide sequences.

In preferred embodiments, antibody-producing cell lines are prepared from cells isolated from the immunized animal. After immunization, the animal is sacrificed and lymph node and/or splenic B cells are immortalized by means well known in the art as shown in the appended Examples). Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. If fusion with myeloma cells is used, the myeloma cells preferably do not secrete immunoglobulin polypeptides (a non-secretory cell line). As set forth in the Examples below immortalized cells may be screened using a PTK7 (including selected isoforms), or an immunoreactive portion thereof. In a preferred embodiment, the initial screening is performed using an enzyme-linked immunoassay (ELISA) or a radioimmunoassay.

More generally, discrete monoclonal antibodies consistent with the present invention can be prepared using a wide variety of techniques known in the art including hybridoma, recombinant techniques, phage display technologies, yeast libraries, transgenic animals (e.g. a XenoMouse® or HuMAb Mouse®) or some combination thereof. For example, monoclonal antibodies can be produced using hybridoma techniques such as broadly described above and taught in more detail in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) each of which is incorporated herein. Using the disclosed protocols, antibodies are preferably raised in mammals by multiple subcutaneous or intraperitoneal injections of the relevant antigen and an adjuvant. As previously discussed, this immunization generally elicits an immune response that comprises production of antigen-reactive antibodies (that may be fully human if the immunized animal is transgenic) from activated splenocytes or lymphocytes. While the resulting antibodies may be harvested from the serum of the animal to provide polyclonal preparations, it is generally more desirable to isolate individual lymphocytes from the spleen, lymph nodes or peripheral blood to provide homogenous preparations of monoclonal antibodies. Most typically, the lymphocytes are obtained from the spleen and immortalized to provide hybridomas.

For example, as described above, the selection process can be the selection of a unique clone from a plurality of clones, such as a pool of hybridoma clones, phage clones, or recombinant DNA clones. It should be understood that a selected PTK7 binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include discrete antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins that may be cross-reactive.

d. Chimeric Antibodies

In another embodiment, the antibody of the invention may comprise chimeric antibodies derived from covalently joined protein segments from at least two different species or types of antibodies. It will be appreciated that, as used herein, the term chimeric antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)). In one exemplary embodiment, a chimeric antibody in accordance with the teachings herein may comprise murine $V_H$ and $V_L$ amino acid sequences and constant regions derived from human sources. In other compatible embodiments a chimeric antibody of the present invention may comprise a CDR grafted or humanized antibody as described herein.

Generally, a goal of making a chimeric antibody is to create a chimera in which the number of amino acids from the intended subject species is maximized. One example is the CDR-grafted antibody, in which the antibody comprises one or more complementarity determining regions (CDRs) from a particular species or belonging to a particular antibody class or subclass, while the remainder of the antibody chain(s) is/are identical with or homologous to a corresponding sequence in antibodies derived from another species or belonging to another antibody class or subclass. For use in humans, the variable region or selected CDRs from a rodent antibody often are grafted into a human antibody, replacing the naturally occurring variable regions or CDRs of the human antibody. These constructs generally have the advantages of providing full strength modulator functions (e.g., CDC, ADCC, etc.) while reducing unwanted immune responses to the antibody by the subject.

e. Humanized Antibodies

Similar to the CDR grafted antibody is a humanized antibody. Generally, a humanized antibody is produced from a monoclonal antibody raised initially in a non-human animal. As used herein humanized forms of non-human (e.g., murine) antibodies are chimeric antibodies that contain a minimal sequence derived from a non-human immunoglobulin. In one embodiment, a humanized antibody is a human immunoglobulin (recipient or acceptor antibody) in which residues from a CDR of the recipient antibody are replaced by residues from a CDR of a non-human species (donor antibody) such as mouse, rat, rabbit, or nonhuman primate having the desired specificity, affinity, and/or capacity.

Generally humanization of an antibody comprises an analysis of the sequence homology and canonical structures of both the donor and recipient antibodies. In selected embodiments, the recipient antibody may comprise consensus sequences. To create consensus human frameworks, frameworks from several human heavy chain or light chain amino acid sequences may be aligned to identify a consensus amino acid sequence. Moreover, in many instances, one or more framework residues in the variable domain of the human immunoglobulin are replaced by corresponding non-human residues from the donor antibody. These framework substitutions are identified by methods well known in the art, e.g., by modeling of the interactions of the CDR and framework residues to identify framework residues important for antigen binding and sequence comparison to identify unusual framework residues at particular positions. Such substitutions help maintain the appropriate three-dimensional configuration of the grafted CDR(s) and often improve infinity over similar constructs with no framework substitutions. Furthermore, humanized antibodies may comprise residues that are not found in the recipient antibody or in the donor antibody. These modifications may be made to further refine antibody performance using well-known techniques.

CDR grafting and humanized antibodies are described, for example, in U.S. Pat. Nos. 6,180,370, 5,693,762, 5,693,761, 5,585,089, and 5,530,101. In general, a humanized antibody will comprise substantially all of at least one, and typically two, variable domains, in which all or substantially all of the CDRs correspond to those of a non-human immunoglobulin, and all or substantially all of the framework regions are those of a human immunoglobulin sequence. The humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1: 105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409. Still another method is termed humaneering and is described, for example, in U.S. 2005/0008625. For the purposes of the present application the term humanized antibodies will be held to expressly include CDR grafted antibodies (i.e. human antibodies comprising one or more grafted non-human CDRs) with no or minimal framework substitutions.

Additionally, a non-human anti-PTK7 antibody may also be modified by specific deletion of human T cell epitopes or deimmunization by the methods disclosed in WO 98/52976 and WO 00/34317. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed peptide threading can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and $V_L$ can be constructed by mutagenesis or other synthetic methods (e.g., de novo synthesis, cassette replacement, and so forth). A mutagenized variable sequence can, optionally, be fused to a human constant region.

In selected embodiments, at least 60%, 65%, 70%, 75%, or 80% of the humanized antibody variable region residues will correspond to those of the parental framework region (FR) and CDR sequences. In other embodiments at least 85% or 90% of the humanized antibody residues will correspond to those of the parental framework region (FR) and CDR sequences. In a further preferred embodiment, greater than 95% of the humanized antibody residues will correspond to those of the parental framework region (FR) and CDR sequences.

Humanized antibodies may be fabricated using common molecular biology and biomolecular engineering techniques as described herein. These methods include isolating, manipulating, and expressing nucleic acid sequences that encode all or part of immunoglobulin Fv variable regions from at least one of a heavy or light chain. Sources of such nucleic acid are well known to those skilled in the art and, for example, may be obtained from a hybridoma, eukaryotic cell or phage producing an antibody or immunoreactive fragment against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, I. A. et al. (1992) J. Mol. Biol. 227:776-798; Cook, G. P. et al. (1995) Immunol. Today 16: 237-242;

Chothia, D. et al. (1992) J. Mol. Bio. 227:799-817; and Tomlinson et al. (1995) EMBO J. 14:4628-4638. The V BASE directory provides a comprehensive directory of human immunoglobulin variable region sequences (See Retter et al., (2005) Nuc Acid Res 33: 671-674). These sequences can be used as a source of human sequence, e.g., for framework regions and CDRs. As set forth herein consensus human framework regions can also be used, e.g., as described in U.S. Pat. No. 6,300,064.

f. Human Antibodies

In addition to the aforementioned antibodies, those skilled in the art will appreciate that the antibodies of the present invention may comprise fully human antibodies. For the purposes of the instant application the term human antibody comprises an antibody which possesses an amino acid sequence that corresponds to that of an antibody produced by a human and/or has been made using any of the techniques for making human antibodies as disclosed herein. This definition of a human antibody specifically excludes a humanized antibody comprising non-human antigen-binding residues.

Human antibodies can be produced using various techniques known in the art. As alluded to above, phage display techniques may be used to provide immunoactive binding regions in accordance with the present teachings. Thus, certain embodiments of the invention provide methods for producing anti-PTK7 antibodies or antigen-binding portions thereof comprising the steps of synthesizing a library of (preferably human) antibodies on phage, screening the library with a selected PTK7 or an antibody-binding portion thereof, isolating phage that binds PTK7, and obtaining the immunoreactive fragments from the phage. By way of example, one method for preparing the library of antibodies for use in phage display techniques comprises the steps of immunizing a non-human animal comprising human or non-human immunoglobulin loci with the selected PTK7 or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. More particularly, DNA encoding the $V_H$ and $V_L$ domains are recombined together with an scFv linker by PCR and cloned into a phagemid vector (e.g., p CANTAB 6 or pComb 3 HSS). The vector may then be electroporated in *E. coli* and then the *E. coli* is infected with helper phage. Phage used in these methods are typically filamentous phage including fd and M13 and the $V_H$ and $V_L$ domains are usually recombinantly fused to either the phage gene III or gene VIII.

Recombinant human anti-PTK7 antibodies of the invention may be isolated by screening a recombinant combinatorial antibody library prepared as above. In a preferred embodiment, the library is a scFv phage display library, generated using human $V_L$ and $V_H$ cDNAs prepared from mRNA isolated from B cells. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology 9:1370-1372 (1991); Hay et al., Hum. Antibod. Hybridomas 3:81-85 (1992); Huse et al., Science 246:1275-1281 (1989); McCafferty et al., Nature 348:552-554 (1990); Griffiths et al., EMBO J. 12:725-734 (1993); Hawkins et al., J. Mol. Biol. 226:889-896 (1992); Clackson et al., Nature 352:624-628 (1991); Gram et al., Proc. Natl. Acad. Sci. USA 89:3576-3580 (1992); Garrad et al., Bio/Technology 9:1373-1377 (1991); Hoogenboom et al., Nuc. Acid Res. 19:4133-4137 (1991); and Barbas et al., Proc. Natl. Acad. Sci. USA 88:7978-7982 (1991).

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 described a method for inducing mutagenesis in a complementarity determining region of an immunoglobulin light chain to create a library of light chain genes. Another effective approach is to recombine the $V_H$ or $V_L$ domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with a dissociation constant $K_d$ ($k_{off}/k_{on}$) of about $10^{-9}$ M or less.

It will further be appreciated that similar procedures may be employed using libraries comprising eukaryotic cells (e.g., yeast) that express binding pairs on their surface. As with phage display technology, the eukaryotic libraries are screened against the antigen of interest (i.e., PTK7) and cells expressing candidate-binding pairs are isolated and cloned. Steps may be taken to optimize library content and for affinity maturation of the reactive binding pairs. See, for example, U.S. Pat. No. 7,700,302 and U.S. Ser. No. 12/404,059. In one embodiment, the human antibody is selected from a phage library, where that phage library expresses human antibodies (Vaughan et al. Nature Biotechnology 14:309-314 (1996): Sheets et al. Proc. Natl. Acad. Sci. 95:6157-6162 (1998)); Hoogenboom and Winter, J. Mol. Biol, 227:381 (1991); Marks et al., J. Mol. Biol, 222:581 (1991)). In other embodiments human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545, 806; 5,569,825; 5,625,126; 5,633,425; 5,661,016, and U.S. Pat. Nos. 6,075,181 and 6,150,584 regarding XenoMouse® technology along with the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody may be prepared via immortalization of human B-lymphocytes producing an antibody directed against a target antigen (such B lymphocytes may be recovered from an individual suffering from a neoplastic disorder or may have been immunized in vitro). See, e.g., Cole et al., Monoclonal Antibodies and Cancer Therapy, Alan R. Liss, p. 77 (1985); Boerner et al., J. Immunol, 147 (1):86-95 (1991); and U.S. Pat. No. 5,750,373.

VI. Antibody Characteristics

No matter how obtained or which of the aforementioned forms the antibody modulator takes (e.g., humanized, human, etc.) the preferred embodiments of the disclosed modulators may exhibit various characteristics. In this regard anti-PTK7 antibody-producing cells (e.g., hybridomas or yeast colonies) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

a. Neutralizing Antibodies

In particularly preferred embodiments the modulators of the instant invention will comprise neutralizing antibodies or derivative or fragment thereof. The term neutralizing antibody or neutralizing antagonist refers to an antibody or antagonist that binds to or interacts with a PTK7 molecule and prevents binding or association of the ligand to any binding partner thereby interrupting the biological response (e.g., phosphorylation or VEGF-induced angiogenesis) that otherwise would result from the interaction of the molecules. In assessing the binding and specificity of an antibody or immunologically functional fragment or derivative thereof, an antibody or fragment will substantially inhibit binding of the ligand to its binding partner or substrate when an excess of antibody reduces the quantity of binding partner bound to the target molecule by at least about 20%, 30%, 40%, 50%, 60%, 70%, 80%, 85%, 90%, 95%, 97%, 99% or more as measured, for example, by phosphorylation or selected substrates (Shin et al, Biochem and Biophys Res Com, Vol. 371:4) or in an in vitro competitive binding assay. In the case of antibodies to PTK7 for example, a neutralizing antibody or antagonist will preferably diminish the phosphorylation ability of PTK7 with regard to a specific substrate by at least about 20%, 30%, 40%, 50%, 60%, 70%, 80%, 85%, 90%, 95%, 97%, 99% or more. It will be appreciated that this diminished activity may be measured directly using art recognized techniques or may be measured by the impact such reduction will have on secondary activities such as angiogenesis.

b. Internalizing Antibodies

While evidence indicates that PTK7 or selected isoforms thereof may be present in a soluble form, at least some PTK7 likely remains associated with the cell surface thereby allowing for internalization of the disclosed modulators. Accordingly, the anti-PTK7 antibodies of the instant invention may be internalized, at least to some extent, by cells that express PTK7. For example, an anti-PTK7 antibody that binds to PTK7 on the surface of a tumor-initiating cell may be internalized by the tumor-initiating cell. In particularly preferred embodiments such anti-PTK7 antibodies may be associated with or conjugated to anti-cancer agents such as cytotoxic moieties that kill the cell upon internalization.

As used herein, an anti-PTK7 antibody that internalizes is one that is taken up by the cell upon binding to PTK7 associated with a mammalian cell. The internalizing antibody includes antibody fragments, human or humanized antibody and antibody conjugates. Internalization may occur in vitro or in vivo. For therapeutic applications, internalization may occur in vivo. The number of antibody molecules internalized may be sufficient or adequate to kill a PTK7-expressing cell, especially a PTK7-expressing tumor initiating cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell. Whether an anti-PTK7 antibody internalizes upon binding PTK7 on a mammalian cell can be determined by various assays including those described in the Examples below (e.g., Examples 12 and 13). Methods of detecting whether an antibody internalizes into a cell are also described in U.S. Pat. No. 7,619,068 which is incorporated herein by reference in its entirety.

c. Depleting Antibodies

In other preferred embodiments the modulators of the instant invention will comprise depleting antibodies or derivatives or fragments thereof. The term depleting antibody refers to an antibody or fragment that binds to or associates with a PTK7 on or near the cell surface and induces, promotes or causes the death, incapacitation or elimination of the cell (e.g., by complement-dependent cytotoxicity or antibody-dependent cellular cytotoxicity). In some embodiments discussed more fully below the selected depleting antibodies will be associated or conjugated to a cytotoxic agent. Preferably a depleting antibody will be able to remove, incapacitate, eliminate or kill at least 20%, 30%, 40%, 50%, 60%, 70%, 80%, 85%, 90%, 95%, 97%, or 99% of tumor perpetuating cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below (e.g., Examples 13 and 14) may be used to monitor and quantify the depletion of tumorigenic cells or tumor perpetuating cells in accordance with the teachings herein.

d. Epitope Binding

It will further be appreciated the disclosed anti-PTK7 antibodies will associate with, or bind to, discrete epitopes or determinants presented by the selected target(s). As used herein the term epitope refers to that portion of the target antigen capable of being recognized and specifically bound by a particular antibody. When the antigen is a polypeptide such as PTK7, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. More specifically, the skilled artisan will appreciate the term epitope includes any protein determinant capable of specific binding to an immunoglobulin or T-cell receptor or otherwise interacting with a molecule. Epitopic determinants generally consist of chemically active surface groupings of molecules such as amino acids or carbohydrate or sugar side chains and generally have specific three dimensional structural characteristics, as well as specific charge characteristics. Additionally an epitope may be linear or conformational. In a linear epitope, all of the points of interaction between the protein and the interacting molecule (such as an antibody) occur linearly along the primary amino acid sequence of the protein. In a conformational epitope, the points of interaction occur across amino acid residues on the protein that are linearly separated from one another.

Once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731.

As used herein, the term binning refers to a method to group antibodies based on their antigen binding characteristics. The assignment of bins is somewhat arbitrary, depending on how different the observed binding patterns of the antibodies tested. Thus, while the technique is a useful tool for categorizing antibodies of the instant invention, the bins do not always directly correlate with epitopes and such initial determinations of epitope binding should be further confirmed by other art recognized methodology as described herein.

With this caveat one can determine whether a selected primary antibody (or fragment thereof) binds to the same epitope or cross competes for binding with a second antibody by using methods known in the art and set forth in the Examples herein. In one embodiment, one allows the primary antibody of the invention to bind to PTK7 under saturating conditions and then measures the ability of the secondary antibody to bind to PTK7. If the test antibody is able to bind to PTK7 at the same time as the primary anti-PTK7 antibody, then the secondary antibody binds to a different epitope than the primary antibody. However, if the secondary antibody is not able to bind to PTK7 at the same time, then the secondary antibody binds to the same epitope, an overlapping epitope, or an epitope that is in close proximity to the epitope bound by the primary antibody. As known in the art and detailed in the Examples below, the desired data can be obtained using solid phase direct or indirect radioimmunoassay (RIA), solid phase direct or indirect enzyme immunoassay (EIA), sandwich competition assay, a Biacore™ system (i.e., surface plasmon resonance—GE Healthcare), a ForteBio® Analyzer (i.e., biolayer interferometry—ForteBio, Inc.) or flow cytometric methodology. The term surface plasmon resonance, as used herein, refers to an optical phenomenon that allows for the analysis of real-time specific interactions by detection of alterations in protein concentrations within a biosensor matrix. In a particularly preferred embodiment, the analysis is performed using a Biacore or ForteBio instrument as demonstrated in the Examples below.

The term compete when used in the context of antibodies means competition between antibodies as determined by an assay in which the antibody or immunologically functional fragment under test prevents or inhibits specific binding of a reference antibody to a common antigen. Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

Besides epitope specificity the disclosed antibodies may be characterized using a number of different physical characteristics including, for example, binding affinities, melting temperature (Tm), and isoelectric points.

e. Binding Affinity

In this respect, the present invention further encompasses the use of antibodies that have a high binding affinity for a selected PTK7 or, in the case of pan-antibodies, more than one type of PTK7. An antibody of the invention is said to specifically bind its target antigen when the dissociation constant $K_d$ ($k_{off}/k_{on}$) is $\leq 10^{-8}$M. The antibody specifically binds antigen with high affinity when the $K_d$ is $\leq 5\times10^{-9}$M, and with very high affinity when the $K_d$ is $\leq 5\times10^{-10}$M. In one embodiment of the invention, the antibody has a $K_d$ of $\leq 10^{-9}$M and an off-rate of about $1\times10^{-4}$/sec. In one embodiment of the invention, the off-rate is $<1\times10^{-5}$/sec. In other embodiments of the invention, the antibodies will bind to PTK7 with a $K_d$ of between about $10^{-8}$M and $10^{-10}$M, and in yet another embodiment it will bind with a $K_d \leq 2\times10^{-10}$M. Still other selected embodiments of the present invention comprise antibodies that have a disassociation constant or $K_d$ ($k_{off}/k_{on}$) of less than $10^{-2}$M, less than $5\times10^{-2}$M, less than $10^{-3}$M, less than $5\times10^{-3}$M, less than $10^{-4}$M, less than $5\times10^{-4}$M, less than $10^{-5}$M, less than $5\times10^{-5}$M, less than $10^{-6}$M, less than $5\times10^{-6}$M, less than $10^{-7}$M, less than $5\times10^{-7}$M, less than $10^{-8}$M, less than $5\times10^{-8}$M, less than $10^{-9}$M, less than $5\times10^{-9}$M, less than $10^{-10}$M, less than $5\times10^{-10}$M, less than $10^{-11}$M, less than $5\times10^{-11}$M, less than $10^{-12}$M, less than $5\times10^{-12}$M, less than $10^{-13}$M, less than $5\times10^{-13}$M, less than $10^{-14}$M, less than $5\times10^{-14}$M, less than $10^{-15}$M or less than $5\times10^{-15}$M.

In specific embodiments, an antibody of the invention that immunospecifically binds to PTK7 has an association rate constant or $k_{on}$ rate (PTK7 (Ab)+antigen (Ag) $\xrightarrow{k_{on}}$ Ab-Ag) of at least $10^5$M$^{-1}$s$^{-1}$, at least $2\times10^5$M$^{-1}$s$^{-1}$, at least $5\times10^5$M$^{-1}$s$^{-1}$, at least $10^6$M$^{-1}$s$^{-1}$, at least $5\times10^6$M$^{-1}$s$^{-1}$, at least $10^7$M$^{-1}$s$^{-1}$, at least $5\times10^7$M$^{-1}$s$^{-1}$, or at least $10^8$M$^{-1}$s$^{-1}$.

In another embodiment, an antibody of the invention that immunospecifically binds to PTK7 has a disassociation rate constant or $k_{off}$ rate (PTK7 (Ab)+antigen (Ag) $\xrightarrow{k_{off}}$ Ab-Ag) of less than $10^{-1}$ s$^{-1}$, less than $5\times10^{-1}$ s$^{-1}$, less than $10^{-2}$ s$^{-1}$, less than $5\times10^{-2}$ s$^{-1}$ less than $10^{-3}$ s$^{-1}$ than $5\times10^{-3}$ s$^{-1}$, less than $10^{-4}$ s$^{-1}$ less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$ less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$ or less than $10^{-10}$ s$^{-1}$.

In other selected embodiments of the present invention anti-PTK7 antibodies will have an affinity constant or $K_a$ ($k_{on}/k_{off}$) of at least $10^2$M$^{-1}$, at least $5\times10^2$M$^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$ at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12} M^{-1}$, at least $5 \times 10^{12} M^{-1}$, at least $10^{13} M^{-1}$, at least $5 \times 10^{13} M^{-1}$, at least $10^{14} M^{-1}$, at least $5 \times 10^{14} M^{-1}$, at least $10^{15} M^{-1}$ or at least $5 \times 10^{15} M^{-1}$.

f. Isoelectric Points

In addition to the aforementioned binding properties, anti-PTK7 antibodies and fragments thereof, like all polypeptides, have an Isoelectric Point (pI), which is generally defined as the pH at which a polypeptide carries no net charge. It is known in the art that protein solubility is typically lowest when the pH of the solution is equal to the isoelectric point (pI) of the protein. Therefore it is possible to optimize solubility by altering the number and location of ionizable residues in the antibody to adjust the pI. For example the pI of a polypeptide can be manipulated by making the appropriate amino acid substitutions (e.g., by substituting a charged amino acid such as a lysine, for an uncharged residue such as alanine). Without wishing to be bound by any particular theory, amino acid substitutions of an antibody that result in changes of the pI of said antibody may improve solubility and/or the stability of the antibody. One skilled in the art would understand which amino acid substitutions would be most appropriate for a particular antibody to achieve a desired pI.

The pI of a protein may be determined by a variety of methods including but not limited to, isoelectric focusing and various computer algorithms (see for example Bjellqvist et al., 1993, Electrophoresis 14:1023). In one embodiment, the pI of the anti-PTK7 antibodies of the invention is between is higher than about 6.5, about 7.0, about 7.5, about 8.0, about 8.5, or about 9.0. In another embodiment, the pI of the anti-PTK7 antibodies of the invention is between is higher than 6.5, 7.0, 7.5, 8.0, 8.5, or 9.0. In yet another embodiment, substitutions resulting in alterations in the pI of antibodies of the invention will not significantly diminish their binding affinity for PTK7. As discussed in more detail below, it is specifically contemplated that the substitution(s) of the Fc region that result in altered binding to FcγR may also result in a change in the pI. In a preferred embodiment, substitution(s) of the Fc region are specifically chosen to effect both the desired alteration in FcγR binding and any desired change in pI. As used herein, the pI value is defined as the pI of the predominant charge form.

g. Thermal Stability

It will further be appreciated that the Tm of the Fab domain of an antibody can be a good indicator of the thermal stability of an antibody and may further provide an indication of the shelf life. Tm is merely the temperature of 50% unfolding for a given domain or sequence. A lower Tm indicates more aggregation/less stability, whereas a higher Tm indicates less aggregation/more stability. Thus, antibodies or fragments or derivatives having higher Tm are preferable. Moreover, using art-recognized techniques it is possible to alter the composition of the anti-PTK7 antibodies or domains thereof to increase or optimize molecular stability. See, for example, U.S. Pat. No. 7,960,142. Thus, in one embodiment, the Fab domain of a selected antibody has a Tm value higher than at least 50° C., 55° C., 60° C., 65° C., 70° C., 75° C., 80° C., 85° C., 90° C., 95° C., 100° C., 105° C., 110° C., 115° C. or 120° C. In another embodiment, the Fab domain of an antibody has a Tm value higher than at least about 50° C., about 55° C., about 60° C., about 65° C., about 70° C., about 75° C., about 80° C., about 85° C., about 90° C., about 95° C., about 100° C., about 105° C., about 110° C., about 115° C. or about 120° C. Thermal melting temperatures (Tm) of a protein domain (e.g., a Fab domain) can be measured using any standard method known in the art, for example, by differential scanning calorimetry (see, e.g., Vermeer et al., 2000, Biophys. J. 78:394-404; Vermeer et al., 2000, Biophys. J. 79: 2150-2154 both incorporated herein by reference).

VII. PTK7 Modulator Fragments and Derivatives

Whether the agents of the present invention comprise intact fusion constructs, antibodies, fragments or derivatives, the selected modulators will react, bind, combine, complex, connect, attach, join, interact or otherwise associate with PTK7 and thereby provide the desired anti-neoplastic effects. Those of skill in the art will appreciate that modulators comprising anti-PTK7 antibodies interact or associate with PTK7 through one or more binding sites expressed on the antibody. More specifically, as used herein the term binding site comprises a region of a polypeptide that is responsible for selectively binding to a target molecule of interest (e.g., enzyme, antigen, ligand, receptor, substrate or inhibitor). Binding domains comprise at least one binding site (e.g. an intact IgG antibody will have two binding domains and two binding sites). Exemplary binding domains include an antibody variable domain, a receptor-binding domain of a ligand, a ligand-binding domain of a receptor or an enzymatic domain. For the purpose of the instant invention the typical active region of PTK7 (e.g., as part of an Fc-PTK7 fusion construct) may comprise a binding site for a substrate or promote phosphorylation.

a. Fragments

Regardless of which form of the modulator (e.g. chimeric, humanized, etc.) is selected to practice the invention, it will be appreciated that immunoreactive fragments of the same may be used in accordance with the teachings herein. In the broadest sense, the term antibody fragment comprises at least a portion of an intact antibody (e.g. a naturally occurring immunoglobulin). More particularly the term fragment refers to a part or portion of an antibody or antibody chain (or PTK7 molecule in the case of Fc fusions) comprising fewer amino acid residues than an intact or complete antibody or antibody chain. The term antigen-binding fragment refers to a polypeptide fragment of an immunoglobulin or antibody that binds antigen or competes with intact antibody (i.e., with the intact antibody from which they were derived) for antigen binding (i.e., specific binding). As used herein, the term fragment of an antibody molecule includes antigen-binding fragments of antibodies, for example, an antibody light chain ($V_L$), an antibody heavy chain ($V_H$), a single chain antibody (scFv), a F(ab')2 fragment, a Fab fragment, an Fd fragment, an Fv fragment, single domain antibody fragments, diabodies, linear antibodies, single-chain antibody molecules and multi-specific antibodies formed from antibody fragments. Similarly, an active fragment of PTK7 comprises a portion of the PTK7 molecule that retains its ability to interact with PTK7 substrates or receptors and modify them in a manner similar to that of an intact PTK7 (e.g., phosphorylation—though maybe with somewhat less efficiency).

Those skilled in the art will appreciate fragments can be obtained via chemical or enzymatic treatment of an intact or complete modulator (e.g., antibody or antibody chain) or by recombinant means. In this regard, while various antibody fragments are defined in terms of the digestion of an intact antibody, one of skill will appreciate that such fragments may be synthesized de novo either chemically or by using recombinant DNA methodology. Thus, the term antibody, as used herein, explicitly includes antibodies or fragments or derivatives thereof either produced by the modification of whole antibodies or synthesized de novo using recombinant DNA methodologies.

More specifically, papain digestion of antibodies produces two identical antigen-binding fragments, called Fab fragments, each with a single antigen-binding site, and a residual Fc fragment, whose name reflects its ability to crystallize readily. Pepsin treatment yields an F(ab')$_2$ fragment that has two antigen-binding sites and is still capable of cross-linking antigen. The Fab fragment also contains the constant domain of the light chain and the first constant domain ($C_H1$) of the heavy chain. Fab' fragments differ from Fab fragments by the addition of a few residues at the carboxy terminus of the heavy-chain $C_H1$ domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known. See, e.g., Fundamental Immunology, W. E. Paul, ed., Raven Press, N.Y. (1999), for a more detailed description of other antibody fragments.

It will further be appreciated that an Fv fragment is an antibody fragment that contains a complete antigen recognition and binding site. This region is made up of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

In other embodiments an antibody fragment, for example, is one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

b. Derivatives

In another embodiment, it will further be appreciated that the modulators of the invention may be monovalent or multivalent (e.g., bivalent, trivalent, etc.). As used herein the term valency refers to the number of potential target (i.e., PTK7) binding sites associated with an antibody. Each target binding site specifically binds one target molecule or specific position or locus on a target molecule. When an antibody of the instant invention comprises more than one target binding site (multivalent), each target binding site may specifically bind the same or different molecules (e.g., may bind to different ligands or different antigens, or different epitopes or positions on the same antigen). For the purposes of the instant invention, the subject antibodies will preferably have at least one binding site specific for human PTK7. In one embodiment the antibodies of the instant invention will be monovalent in that each binding site of the molecule will specifically bind to a single PTK7 position or epitope. In other embodiments, the antibodies will be multivalent in that they comprise more than one binding site and the different binding sites specifically associate with more than a single position or epitope. In such cases the multiple epitopes may be present on the selected PTK7 polypeptide or spice variant or a single epitope may be present on PTK7 while a second, different epitope may be present on another molecule or surface. See, for example, U.S.P.N. 2009/0130105.

As alluded to above, multivalent antibodies may immunospecifically bind to different epitopes of the desired target molecule or may immunospecifically bind to both the target molecule as well as a heterologous epitope, such as a heterologous polypeptide or solid support material. While preferred embodiments of the anti-PTK7 antibodies only bind two antigens (i.e. bispecific antibodies), antibodies with additional specificities such as bispecific antibodies are also encompassed by the instant invention. Examples of bispecific antibodies include, without limitation, those with one arm directed against PTK7 and the other arm directed against any other antigen (e.g., a modulator cell marker). Methods for making bispecific antibodies are known in the art. Traditional production of full-length bispecific antibodies is based on the coexpression of two immunoglobulin heavy chain-light chain pairs, where the two chains have different specificities (Millstein et al., 1983, Nature, 305:537-539). Other more sophisticated compatible multispecific constructs and methods of their fabrication are set forth in U.S.P.N. 2009/0155255.

In yet other embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and/or $C_H3$ regions. In one example, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., PTK7), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210. According to another approach described in WO96/27011, a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory cavities of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies also include cross-linked or heteroconjugate antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

VIII. PTK7 Modulators—Constant Region Modifications a. Fc Region and Fc Receptors In addition to the various modifications, substitutions, additions or deletions to the variable or binding region of the disclosed modulators (e.g., Fc-PTK7 or anti-PTK7 antibodies) set forth above, those skilled in the art will appreciate that selected embodiments of the present invention may also comprise substitutions or modifications of the constant region (i.e. the Fc region). More particularly, it is contemplated that the PTK7 modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding, enhanced or reduced ADCC or CDC activity, altered glycosylation and/or disulfide bonds and modified binding specificity. In this regard it will be appreciated that these Fc variants may advantageously be used to enhance the effective anti-neoplastic properties of the disclosed modulators.

The term Fc region herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A functional Fc region possesses an effector function of a native sequence Fc region. Exemplary effector functions include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

Fc receptor or FcR describes a receptor that binds to the Fc region of an antibody. In some embodiments, an FcR is a native human FcR. In some embodiments, an FcR is one that binds an IgG antibody (a gamma receptor) and includes receptors of the FcγRI, Fc.RII, and FcγRIII subclasses, including allelic variants and alternatively spliced forms of those receptors. FcγII receptors include FcγRIIA (an activating receptor) and FcγRIIB (an inhibiting receptor), which have similar amino acid sequences that differ primarily in the cytoplasmic domains thereof. Activating receptor Fcγ RIIA contains an immunoreceptor tyrosine-based activation motif (ITAM) in its cytoplasmic domain. Inhibiting receptor FγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126: 330-41 (1995). Other FcRs, including those to be identified in the future, are encompassed by the term FcR herein. The term Fc receptor or FcR also includes the neonatal receptor, FcRn, which, in certain instances, is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

b. Fc Functions

As used herein complement dependent cytotoxicity and CDC refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, J. Immunol. Methods, 202:163, may be performed.

Further, antibody-dependent cell-mediated cytotoxicity or ADCC refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the target arm cytotoxic cells and are absolutely required for such killing. Lysis of the target cell is extracellular, requires direct cell-to-cell contact, and does not involve complement.

PTK7 modulator variants with altered FcR binding affinity or ADCC activity is one which has either enhanced or diminished FcR binding activity and/or ADCC activity compared to a parent or unmodified antibody or to a modulator comprising a native sequence Fc region. The modulator variant which displays increased binding to an FcR binds at least one FcR with better affinity than the parent or unmodified antibody or to a modulator comprising a native sequence Fc region. A variant which displays decreased binding to an FcR, binds at least one FcR with worse affinity than the parent or unmodified antibody or to a modulator comprising a native sequence Fc region. Such variants which display decreased binding to an FcR may possess little or no appreciable binding to an FcR, e.g., 0-20% binding to the FcR compared to a native sequence IgG Fc region, e.g. as determined techniques well known in the art.

As to FcRn, the antibodies of the instant invention also comprise or encompass Fc variants with modifications to the constant region that provide half-lives (e.g., serum half-lives) in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies (or Fc containing molecules) of the present invention in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

c. Glycosylation Modifications

In still other embodiments, glycosylation patterns or compositions of the antibodies of the invention are modified. More particularly, preferred embodiments of the present invention may comprise one or more engineered glycoforms, i.e., an altered glycosylation pattern or altered carbohydrate composition that is covalently attached to a molecule comprising an Fc region. Engineered glycoforms may be useful for a variety of purposes, including but not limited to enhancing or reducing effector function, increasing the affinity of the antibody for a target antigen or facilitating production of the antibody. In cases where reduced effector function is desired, it will be appreciated that the molecule may be engineered to express in an aglycosylated form. Such carbohydrate modifications can be accomplished by, for example, altering one or more sites of glycosylation within the antibody sequence. That is, one or more amino acid substitutions can be made that result in elimination of one or more variable region framework glycosylation sites to thereby eliminate glycosylation at that site (see e.g. U.S. Pat. Nos. 5,714,350 and 6,350,861. Conversely, enhanced effector functions or improved binding may be imparted to the Fc containing molecule by engineering in one or more additional glycosylation sites.

Additionally or alternatively, an Fc variant can be made that has an altered glycosylation composition, such as a hypofucosylated antibody having reduced amounts of fucosyl residues or an antibody having increased bisecting GlcNAc structures. These and similar altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed. See, for example, Shields, R. L. et al. (2002) J. Biol. Chem. 277: 26733-26740; Umana et al. (1999) Nat. Biotech. 17:176-1, as well as, European Patent No: EP 1,176,195; PCT Publications WO 03/035835; WO 99/54342, Umana et al, 1999, Nat. Biotechnol 17:176-180; Davies et al., 20017 Biotechnol Bioeng 74:288-294; Shields et al, 2002, J Biol Chem 277: 26733-26740; Shinkawa et al., 2003, J Biol Chem 278:3466-3473) U.S. Pat. No. 6,602,684; U.S. Ser. Nos. 10/277,370; 10/113,929; PCT WO 00/61739A1; PCT WO 01/292246A1; PCT WO 02/311140A1; PCT WO 02/30954A1; Potillegent™ technology (Biowa, Inc.); GlycoMAb™ glycosylation engineering technology (GLYCART biotechnology AG); WO 00061739; EA01229125; U.S.P.N. 2003/0115614; Okazaki et al., 2004, JMB, 336: 1239-49.

IX. Modulator Expression a. Overview

DNA encoding the desired PTK7 modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, the isolated DNA (which may be modified) can be used to clone constant and variable region sequences for the manufacture antibodies as described in U.S. Pat. No. 7,709,611.

This exemplary method entails extraction of RNA from the selected cells, conversion to cDNA, and amplification by PCR using antibody specific primers. Suitable primers are well known in the art and, as exemplified herein, are readily available from numerous commercial sources. It will be appreciated that, to express a recombinant human or non-human antibody isolated by screening of a combinatorial library, the DNA encoding the antibody is cloned into a recombinant expression vector and introduced into host cells including mammalian cells, insect cells, plant cells, yeast, and bacteria. In yet other embodiments, the modulators are introduced into and expressed by simian COS cells, NSO cells, Chinese Hamster Ovary (CHO) cells or myeloma cells that do not otherwise produce the desired construct. As will be discussed in more detail below, transformed cells expressing the desired modulator may be grown up in relatively large quantities to provide clinical and commercial supplies of the fusion construct or immunoglobulin.

Whether the nucleic acid encoding the desired portion of the PTK7 modulator is obtained or derived from phage display technology, yeast libraries, hybridoma based technology, synthetically or from commercial sources, it is to be understood that the present invention explicitly encompasses nucleic acid molecules and sequences encoding PTK7 modulators including fusion proteins and anti-PTK7 antibodies or antigen-binding fragments or derivatives thereof. The invention further encompasses nucleic acids or nucleic acid molecules (e.g., polynucleotides) that hybridize under high stringency, or alternatively, under intermediate or lower stringency hybridization conditions (e.g., as defined below), to polynucleotides complementary to nucleic acids having a polynucleotide sequence that encodes a modulator of the invention or a fragment or variant thereof. The term nucleic acid molecule or isolated nucleic acid molecule, as used herein, is intended to include at least DNA molecules and RNA molecules. A nucleic acid molecule may be single-stranded or double-stranded, but preferably is double-stranded DNA. Moreover, the present invention comprises any vehicle or construct, incorporating such modulator encoding polynucleotide including, without limitation, vectors, plasmids, host cells, cosmids or viral constructs.

The term isolated nucleic acid means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

More specifically, nucleic acids that encode a modulator, including one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing are also provided. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. These nucleic acids can be single-stranded or double-stranded and can comprise RNA and/or DNA nucleotides, and artificial variants thereof (e.g., peptide nucleic acids). Nucleic acids encoding modulators of the invention, including antibodies or immunoreactive fragments or derivatives thereof, have preferably been isolated as described above.

b. Hybridization and Identity

As indicated, the invention further provides nucleic acids that hybridize to other nucleic acids under particular hybridization conditions. Methods for hybridizing nucleic acids are well known in the art. See, e.g., Current Protocols in Molecular Biology, John Wiley & Sons, N.Y. (1989), 6.3.1-6.3.6. For the purposes of the instant application, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1× SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. More generally, for the purposes of the instant disclosure the term substantially identical with regard to a nucleic acid sequence may be construed as a sequence of nucleotides exhibiting at least about 85%, or 90%, or 95%, or 97% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

It will further be appreciated that nucleic acids may, according to the invention, be present alone or in combination with other nucleic acids, which may be homologous or heterologous. In preferred embodiments, a nucleic acid is functionally linked to expression control sequences that may be homologous or heterologous with respect to said nucleic acid. In this context the term homologous means that a nucleic acid is also functionally linked to the expression control sequence naturally and the term heterologous means that a nucleic acid is not functionally linked to the expression control sequence naturally.

c. Expression

A nucleic acid, such as a nucleic acid expressing RNA and/or protein or peptide, and an expression control sequence are functionally linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term expression control sequence comprises according to the invention promoters, ribosome binding sites, enhancers and other control elements that regulate transcription of a gene or translation of mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region that includes a promoter sequence for transcriptional control of the functionally linked nucleic acid. Expression control sequences may also comprise enhancer sequences or upstream activator sequences.

According to the invention the term promoter or promoter region relates to a nucleic acid sequence which is located upstream (5') to the nucleic acid sequence being expressed and controls expression of the sequence by providing a recognition and binding site for RNA-polymerase. The promoter region may include further recognition and binding sites for further factors that are involved in the regulation of transcription of a gene. A promoter may control the transcription of a prokaryotic or eukaryotic gene. Furthermore, a promoter may be inducible and may initiate transcription in response to an inducing agent or may be constitutive if transcription is not controlled by an inducing agent. A gene that is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term expression is used in its most general meaning and comprises the production of RNA or of RNA and protein/peptide. It also comprises partial expression of nucleic acids. Furthermore, expression may be carried out transiently or stably.

In a preferred embodiment, a nucleic acid molecule is according to the invention present in a vector, where appropriate with a promoter, which controls expression of the nucleic acid. The term vector is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors may comprise plasmids, phagemids, bacteriophages or viral genomes. The term plasmid as used herein generally relates to a construct of extrachromosomal genetic material, usually a circular DNA duplex, which can replicate independently of chromosomal DNA.

In practicing the present invention it will be appreciated that many conventional techniques in molecular biology, microbiology, and recombinant DNA technology are optionally used. Such conventional techniques relate to vectors, host cells and recombinant methods as defined herein. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., supra Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla. Methods of making nucleic acids (e.g., by in vitro amplification, purification from cells, or chemical synthesis), methods for manipulating nucleic acids (e.g., site-directed mutagenesis, by restriction enzyme digestion, ligation, etc.), and various vectors, cell lines and the like useful in manipulating and making nucleic acids are described in the above references. In addition, essentially any polynucleotide (including, e.g., labeled or biotinylated polynucleotides) can be custom or standard ordered from any of a variety of commercial sources.

Thus, in one aspect, the present invention provides recombinant host cells allowing recombinant expression of antibodies of the invention or portions thereof. Antibodies produced by expression in such recombinant host cells are referred to herein as recombinant antibodies. The present invention also provides progeny cells of such host cells, and antibodies produced by the same.

The term recombinant host cell (or simply host cell), as used herein, means a cell into which a recombinant expression vector has been introduced. It should be understood that recombinant host cell and host cell mean not only the particular subject cell but also the progeny of such a cell. Because certain modifications may occur in succeeding generations due to either mutation or environmental influences, such progeny may not, in fact, be identical to the parent cell, but are still included within the scope of the term host cell as used herein. Such cells may comprise a vector according to the invention as described above.

In another aspect, the present invention provides a method for making an antibody or portion thereof as described herein.

According to one embodiment, said method comprises culturing a cell transfected or transformed with a vector as described above, and retrieving the antibody or portion thereof.

As indicated above, expression of an antibody of the invention (or fragment or variants thereof) preferably comprises expression vector(s) containing a polynucleotide that encodes the desired anti-PTK7 antibody. Methods that are well known to those skilled in the art can be used to construct expression vectors comprising antibody coding sequences and appropriate transcriptional and translational control signals. These methods include, for example, in vitro recombinant DNA techniques, synthetic techniques, and in vivo genetic recombination. Embodiments of the invention, thus, provide replicable vectors comprising a nucleotide sequence encoding an anti-PTK7 antibody of the invention (e.g., a whole antibody, a heavy or light chain of an antibody, a heavy or light chain variable domain of an antibody, or a portion thereof, or a heavy or light chain CDR, a single chain Fv, or fragments or variants thereof), operably linked to a promoter. In preferred embodiments such vectors may include a nucleotide sequence encoding the heavy chain of an antibody molecule (or fragment thereof), a nucleotide sequence encoding the light chain of an antibody (or fragment thereof) or both the heavy and light chain.

Once the nucleotides of the present invention have been isolated and modified according to the teachings herein, they may be used to produce selected modulators including anti-PTK7 antibodies or fragments thereof.

X. Modulator Production and Purification

Using art recognized molecular biology techniques and current protein expression methodology, substantial quantities of the desired modulators may be produced. More specifically, nucleic acid molecules encoding modulators, such as antibodies obtained and engineered as described above, may be integrated into well known and commercially available protein production systems comprising various types of host cells to provide preclinical, clinical or commercial quantities of the desired pharmaceutical product. It will be appreciated that in preferred embodiments the nucleic acid molecules encoding the modulators are engineered into vectors or expression vectors that provide for efficient integration into the selected host cell and subsequent high expression levels of the desired PTK7 modulator.

Preferably nucleic acid molecules encoding PTK7 modulators and vectors comprising these nucleic acid molecules can be used for transfection of a suitable mammalian, plant, bacterial or yeast host cell though it will be appreciated that prokaryotic systems may be used for modulator production. Transfection can be by any known method for introducing polynucleotides into a host cell. Methods for the introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors. Methods of transforming mammalian cells are well known in the art. See, e.g., U.S. Pat. Nos. 4,399,216, 4,912, 040, 4,740,461, and 4,959,455. Further, methods of transforming plant cells are well known in the art, including, e.g., *agrobacterium*-mediated transformation, biolistic transformation, direct injection, electroporation and viral transformation. Methods of transforming bacterial and yeast cells are also well known in the art.

Moreover, the host cell may be co-transfected with two expression vectors of the invention, for example, the first vector encoding a heavy chain derived polypeptide and the second vector encoding a light chain derived polypeptide. The two vectors may contain identical selectable markers that enable substantially equal expression of heavy and light chain polypeptides. Alternatively, a single vector may be used which encodes, and is capable of expressing, both heavy and light chain polypeptides. In such situations, the light chain is preferably placed before the heavy chain to avoid an excess of toxic free heavy chain. The coding sequences for the heavy and light chains may comprise cDNA or genomic DNA.

a. Host-Expression Systems

Varieties of host-expression vector systems, many commercially available, are compatible with the teachings herein and may be used to express the modulators of the invention. Such host-expression systems represent vehicles by which the coding sequences of interest may be expressed and subsequently purified, but also represent cells which may, when transformed or transfected with the appropriate nucleotide coding sequences, express a molecule of the invention in situ. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant virus expression vectors (e.g., cauliflower mosaic virus, CaMV; tobacco mosaic virus, TMV) or transfected with recombinant plasmid expression vectors (e.g., Ti plasmid) containing modulator coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of a modulator, vectors which direct the expression of high levels of fusion protein products that are readily purified may be desirable. Such vectors include, but are not limited to, the *E. coli* expression vector pUR278 (Ruther et al., EMBO 1. 2:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) may be used as a vector to express foreign genes. The virus grows in *Spodoptera frugiperda* cells. The coding sequences may be cloned individually into non-essential regions (for example, the polyhedrin gene) of the virus and placed under control of an AcNPV promoter (for example, the polyhedrin promoter).

In mammalian host cells, a number of viral-based expression systems may be used to introduce the desired nucleotide sequence. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the molecule in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Enzymol. 153:51-544 (1987)). Thus, compatible mammalian cell lines available as hosts for expression are well known in the art and include many immortalized cell lines available from the American Type Culture Collection (ATCC). These include, inter alia, Chinese hamster ovary (CHO) cells, NSO cells, SP2 cells, HEK-293T cells, 293 Freestyle cells (Life Technologies), NIH-3T3 cells, HeLa cells, baby hamster kidney (BHK) cells, African green monkey kidney cells (COS), human hepatocellular carcinoma cells (e.g., Hep G2), A549 cells, and a number of other cell lines.

For long-term, high-yield production of recombinant proteins stable expression is preferred. Accordingly, cell lines that stably express the selected modulator may be engineered using standard art recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the molecule. Such engineered cell lines may be particularly useful in screening and evaluation of compositions that interact directly or indirectly with the molecule.

A number of selection systems are well known in the art and may be used including, but not limited to, the herpes simplex virus thymidine kinase (Wigler et al., Cell 11:223 (1977)), hypoxanthineguanine phosphoribosyltransferase (Szybalska & Szybalski, Proc. Natl. Acad. Sci. USA 48:202 (1992)), and adenine phosphoribosyltransferase (Lowy et al., Cell 22:8 17 (1980)) genes can be employed in tk–, hgprt– or aprt– cells, respectively. Also, antimetabolite resistance can be used as the basis of selection for the following genes: dhfr, which confers resistance to methotrexate (Wigler et al., Natl.

Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62: 191-217 (1993); TIB TECH 11(5):155-215 (May, 1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981). It will be appreciated that one particularly preferred method of establishing a stable, high yield cell line comprises the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 each of which is incorporated herein by reference.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function and/or purification of the protein. Different host cells have characteristic and specific mechanisms for the post-translational processing and modification of proteins and gene products. As known in the art appropriate cell lines or host systems can be chosen to ensure the desired modification and processing of the expressed polypeptide. To this end, eukaryotic host cells that possess the cellular machinery for proper processing of the primary transcript, glycosylation, and phosphorylation of the gene product are particularly effective for use in the instant invention. Accordingly, particularly preferred mammalian host cells include, but are not limited to, CHO, VERY, BHK, HeLa, COS, NSO, MDCK, 293, 3T3, W138, as well as breast cancer cell lines such as, for example, BT483, Hs578T, HTB2, BT2O and T47D, and normal mammary gland cell line such as, for example, CRL7O3O and HsS78Bst. Depending on the modulator and the selected production system, those of skill in the art may easily select and optimize appropriate host cells for efficient expression of the modulator.

b. Chemical Synthesis

Besides the aforementioned host cell systems, it will be appreciated that the modulators of the invention may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). For example, a peptide corresponding to a polypeptide fragment of the invention can be synthesized by use of a peptide synthesizer. Furthermore, if desired, nonclassical amino acids or chemical amino acid analogs can be introduced as a substitution or addition into a polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

c. Transgenic Systems

The PTK7 modulators of the invention also can be produced transgenically through the generation of a mammal or plant that is transgenic for the immunoglobulin heavy and light chain sequences (or fragments or derivatives or variants thereof) of interest and production of the desired compounds in a recoverable form. In connection with the transgenic production in mammals, anti-PTK7 antibodies, for example, can be produced in, and recovered from, the milk of goats, cows, or other mammals. See, e.g., U.S. Pat. Nos. 5,827,690, 5,756, 687, 5,750,172, and 5,741,957. In some embodiments, non-human transgenic animals that comprise human immunoglobulin loci are immunized with PTK7 or an immunogenic portion thereof, as described above. Methods for making antibodies in plants are described, e.g., in U.S. Pat. Nos. 6,046,037 and 5,959,177.

In accordance with the teachings herein non-human transgenic animals or plants may be produced by introducing one or more nucleic acid molecules encoding a PTK7 modulator of the invention into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999). In some embodiments, the transgenic non-human animals have a targeted disruption and replacement by a targeting construct that encodes, for example, a heavy chain and/or a light chain of interest. In one embodiment, the transgenic animals comprise and express nucleic acid molecules encoding heavy and light chains that specifically bind to PTK7. While anti-PTK7 antibodies may be made in any transgenic animal, in particularly preferred embodiments the non-human animals are mice, rats, sheep, pigs, goats, cattle or horses. In further embodiments the non-human transgenic animal expresses the desired pharmaceutical product in blood, milk, urine, saliva, tears, mucus and other bodily fluids from which it is readily obtainable using art recognized purification techniques.

It is likely that modulators, including antibodies, expressed by different cell lines or in transgenic animals will have different glycosylation patterns from each other. However, all modulators encoded by the nucleic acid molecules provided herein, or comprising the amino acid sequences provided herein are part of the instant invention, regardless of the glycosylation state of the molecule, and more generally, regardless of the presence or absence of post-translational modification(s). In addition the invention encompasses modulators that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc. Various post-translational modifications are also encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. Moreover, as set forth in the text and Examples below the polypeptides may also be modified with a detectable label, such as an enzymatic, fluorescent, radioisotopic or affinity label to allow for detection and isolation of the modulator.

d. Purification

Once a modulator of the invention has been produced by recombinant expression or any one of the other techniques disclosed herein, it may be purified by any method known in the art for purification of immunoglobulins, or more generally by any other standard technique for the purification of proteins. In this respect the modulator may be isolated. As used herein, an isolated PTK7 modulator is one that has been identified and separated and/or recovered from a component of its natural environment. Contaminant components of its natural environment are materials that would interfere with diagnostic or therapeutic uses for the polypeptide and may include enzymes, hormones, and other proteinaceous or non-proteinaceous solutes. Isolated modulators include a modulator in situ within recombinant cells because at least one component of the polypeptide's natural environment will not be present.

When using recombinant techniques, the PTK7 modulator (e.g. an anti-PTK7 antibody or derivative or fragment thereof) can be produced intracellularly, in the periplasmic space, or directly secreted into the medium. If the desired molecule is produced intracellularly, as a first step, the particulate debris, either host cells or lysed fragments, may be removed, for example, by centrifugation or ultrafiltration. For example, Carter, et al., Bio/Technology 10:163 (1992) describe a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The modulator (e.g., fc-PTK7 or anti-PTK7 antibody) composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the selected construct. Protein A can be used to purify antibodies that are based on human IgG1, IgG2 or IgG4 heavy chains (Lindmark, et al., J Immunol Meth 62:1 (1983)). Protein G is recommended for all mouse isotypes and for human IgG3 (Guss, et al., EMBO J. 5:1567 (1986)). The matrix to which the affinity ligand is attached is most often agarose, but other matrices are available. Mechanically stable matrices such as controlled pore glass or poly(styrene-divinyl)benzene allow for faster flow rates and shorter processing times than can be achieved with agarose. Where the antibody comprises a $C_H3$ domain, the Bakerbond ABX™ resin (J. T. Baker; Phillipsburg, N.J.) is useful for purification. Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

XI. Conjugated PTK7 Modulators

Once the modulators of the invention have been purified according to the teachings herein they may be linked with, fused to, conjugated to (e.g., covalently or non-covalently) or otherwise associated with pharmaceutically active or diagnostic moieties or biocompatible modifiers. As used herein the term conjugate will be used broadly and held to mean any molecule associated with the disclosed modulators regardless of the method of association. In this respect it will be understood that such conjugates may comprise peptides, polypeptides, proteins, polymers, nucleic acid molecules, small molecules, mimetic agents, synthetic drugs, inorganic molecules, organic molecules and radioisotopes. Moreover, as indicated above the selected conjugate may be covalently or non-covalently linked to the modulator and exhibit various molar ratios depending, at least in part, on the method used to effect the conjugation.

In preferred embodiments it will be apparent that the modulators of the invention may be conjugated or associated with proteins, polypeptides or peptides that impart selected characteristics (e.g., biotoxins, biomarkers, purification tags, etc.). More generally, in selected embodiments the present invention encompasses the use of modulators or fragments thereof recombinantly fused or chemically conjugated (including both covalent and non-covalent conjugations) to a heterologous protein or polypeptide wherein the polypeptide comprises at least 10, at least 20, at least 30, at least 40, at least 50, at least 60, at least 70, at least 80, at least 90 or at least 100 amino acids. The construct does not necessarily need to be directly linked, but may occur through linker sequences. For example, antibodies may be used to target heterologous polypeptides to particular cell types expressing PTK7, either in vitro or in vivo, by fusing or conjugating the modulators of the present invention to antibodies specific for particular cell surface receptors. Moreover, modulators fused or conjugated to heterologous polypeptides may also be used in in vitro immunoassays and may be compatible with purification methodology known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

a. Biocompatible Modifiers

In a preferred embodiment, the modulators of the invention may be conjugated or otherwise associated with biocompatible modifiers that may be used to adjust, alter, improve or moderate modulator characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored). PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

b. Diagnostic or Detection Agents

In other preferred embodiments, modulators of the present invention, or fragments or derivatives thereof, are conjugated to a diagnostic or detectable agent, marker or reporter which may be a biological molecule (e.g., a peptide or nucleotide), a small molecule, fluorophore, or radioisotope. Labeled modulators can be useful for monitoring the development or progression of a hyperproliferative disorder or as part of a clinical testing procedure to determine the efficacy of a particular therapy including the disclosed modulators (i.e. theragnostics) or to determine a future course of treatment. Such markers or reporters may also be useful in purifying the selected modulator, separating or isolating TIC or in preclinical procedures or toxicology studies.

Such diagnosis and detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused to marker sequences, such as a peptide or fluorophore to facilitate purification or diagnostic procedures such as immunohistochemistry or FACs. In preferred embodiments, the marker amino acid sequence is a hexa-histidine peptide (SEQ ID NO: 7), such as the tag provided in a pQE vector (Qiagen Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

c. Therapeutic Moieties

As previously alluded to the modulators or fragments or derivatives thereof may also be conjugated, linked or fused to or otherwise associated with a therapeutic moiety such as anti-cancer agents, a cytotoxin or cytotoxic agent, e.g., a cytostatic or cytocidal agent, a therapeutic agent or a radioactive metal ion, e.g., alpha or beta-emitters. As used herein a cytotoxin or cytotoxic agent includes any agent or therapeutic moiety that is detrimental to cells and may inhibit cell growth or survival. Examples include paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional cytotoxins comprise auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (PBDs, Spirogen, Ltd). Furthermore, in one embodiment the PTK7 modulators of the instant invention may be associated with anti-CD3 binding molecules to recruit cytotoxic T-cells and have them target the tumor initiating cells (BiTE technology; see e.g., Fuhrmann, S. et. al. Annual Meeting of AACR Abstract No. 5625 (2010) which is incorporated herein by reference).

Additional compatible therapeutic moieties comprise cytotoxic agents including, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

The selected modulators can also be conjugated to therapeutic moieties such as radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Exemplary radioisotopes that may be compatible with this aspect of the invention include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium (103Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{75}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, $^{117}$Tin, $^{225}$Ac, $^{76}$Br and $^{211}$At. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

PTK7 modulators of the present invention may also be conjugated to a therapeutic moiety or drug that modifies a given biological response (e.g., biological response modifiers or BRMs). That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622, 929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337 each of which is incorporated herein by reference. The association of a modulator with a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

More generally, techniques for conjugating therapeutic moieties or cytotoxic agents to modulators are well known. Moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119. In preferred embodiments a PTK7 modulator that is conjugated to a therapeutic moiety or cytotoxic agent may be internalized by a cell upon binding to a PTK7 molecule associated with the cell surface thereby delivering the therapeutic payload.

XII. Diagnostics and Screening a. Diagnostics

As indicated, the present invention provides in vitro or in vivo methods for detecting, diagnosing or monitoring hyperproliferative disorders and methods of screening cells from a patient to identify tumorigenic cells including TPCs. Such methods include identifying an individual having cancer for treatment or monitoring progression of a cancer comprising contacting the patient or a sample obtained from a patient with a selected PTK7 modulator as described herein and detecting presence or absence, or level of association of the modulator to bound or free PTK7 in the sample. When the modulator comprises an antibody or immunologically active fragment thereof the association with particular PTK7 in the sample likely denotes that the sample may contain tumor perpetuating cells (e.g., a cancer stem cells) indicating that the individual having cancer may be effectively treated with a PTK7 modulator as described herein. The methods may further comprise a step of comparing the level of binding to a control. Conversely, when the selected modulator is Fc-PTK7 the binding properties of the selected PTK7 may be exploited and monitored (directly or indirectly, in vivo or in vitro) when in contact with the sample to provide the desired information. Other diagnostic or theragnostic methods compatible with the teachings herein are well known in the art and can be practiced using commercial materials such as dedicated reporting systems.

In a particularly preferred embodiment the modulators of the instant invention may be used to detect and quantify PTK7 levels in a patient sample (e.g., plasma or blood) which may, in turn, be used to detect, diagnose or monitor PTK7 associated disorders including hyperproliferative disorders. In related embodiments the modulators of the instant invention may be used to detect, monitor and/or quantify circulating tumor cells either in vivo or in vitro (see, for example, WO 2012/0128801 which is incorporated herein by reference). In still other preferred embodiments the circulating tumor cells may comprise cancer stem cells.

Exemplary compatible assay methods include radioimmunoassays, enzyme immunoassays, competitive-binding assays, fluorescent immunoassay, immunoblot assays, Western Blot analysis, flow cytometry assays, and ELISA assays. More generally detection of PTK7 in a biological sample or the measurement of PTK7 enzymatic activity (or inhibition thereof) may be accomplished using any art-known assay. Compatible in vivo theragnostics or diagnostics may comprise art recognized imaging or monitoring techniques such as magnetic resonance imaging (MRI), computerized tomography (e.g. CAT scan), positron tomography (e.g., PET scan) radiography, ultrasound, etc. Those skilled in the art will readily be able to recognize and implement appropriate detection, monitoring or imaging techniques (often comprising commercially available sources) based on the etiology, pathological manifestation or clinical progression of the disorder.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in-vivo. In another embodiment, the size and shape of secondary tumors are analyzed. In some embodiments, further ex vivo analysis is performed.

In another embodiment, the invention provides a method of analyzing cancer progression and/or pathogenesis in vivo including determining cell metastasis or detecting and quantifying the level of circulating tumor cells. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

In certain examples, the tumorigenic cells in a subject or a sample from a subject may be assessed or characterized using the disclosed modulators prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

b. Screening

The PTK7 modulators and cells, cultures, populations and compositions comprising the same, including progeny thereof, can also be used to screen for or identify compounds or agents (e.g., drugs) that affect a function or activity of tumor initiating cells or progeny thereof by interacting with PTK7 (e.g., the polypeptide or genetic components thereof). The invention therefore further provides systems and methods for evaluation or identification of a compound or agent that can affect a function or activity tumor initiating cells or progeny thereof by associating with PTK7 or its substrates. Such compounds and agents can be drug candidates that are screened for the treatment of a hyperproliferative disorder, for example. In one embodiment, a system or method comprises tumor initiating cells exhibiting PTK7 and a compound or agent (e.g., drug), wherein the cells and compound or agent (e.g., drug) are in contact with each other.

The invention further provides methods of screening and identifying PTK7 modulators or agents and compounds for altering an activity or function of tumor initiating cells or progeny cells. In one embodiment, a method includes contacting tumor initiating cells or progeny thereof with a test agent or compound; and determining if the test agent or compound modulates an activity or function of the PTK7 associated tumor initiating cells.

A test agent or compound modulating a PTK7 related activity or function of such tumor initiating cells or progeny thereof within the population identifies the test agent or compound as an active agent. Exemplary activity or function that can be modulated include changes in cell morphology, expression of a marker, differentiation or de-differentiation, maturation, proliferation, viability, apoptosis or cell death neuronal progenitor cells or progeny thereof.

Contacting, when used in reference to cells or a cell culture or method step or treatment, means a direct or indirect interaction between the composition (e.g., a PTK7 associated cell or cell culture) and another referenced entity. A particular example of a direct interaction is physical interaction. A particular example of an indirect interaction is where a composition acts upon an intermediary molecule which in turn acts upon the referenced entity (e.g., cell or cell culture).

In this aspect of the invention modulates indicates influencing an activity or function of tumor initiating cells or progeny cells in a manner compatible with detecting the effects on cell activity or function that has been determined to be relevant to a particular aspect (e.g., metastasis or proliferation) of the tumor initiating cells or progeny cells of the invention. Exemplary activities and functions include, but are not limited to, measuring morphology, developmental markers, differentiation, proliferation, viability, cell respiration, mitochondrial activity, membrane integrity, or expression of markers associated with certain conditions. Accordingly, a compound or agent (e.g., a drug candidate) can be evaluated for its effect on tumor initiating cells or progeny cells, by contacting such cells or progeny cells with the compound or agent and measuring any modulation of an activity or function of tumor initiating cells or progeny cells as disclosed herein or would be known to the skilled artisan.

Methods of screening and identifying agents and compounds include those suitable for high throughput screening, which include arrays of cells (e.g., microarrays) positioned or placed, optionally at pre-determined locations or addresses. High-throughput robotic or manual handling methods can probe chemical interactions and determine levels of expression of many genes in a short period of time. Techniques have been developed that utilize molecular signals (e.g., fluorophores) and automated analyses that process information at a very rapid rate (see, e.g., Pinhasov et al., Comb. Chem. High Throughput Screen. 7:133 (2004)). For example, microarray technology has been extensively utilized to probe the interactions of thousands of genes at once, while providing information for specific genes (see, e.g., Mocellin and Rossi, Adv. Exp. Med. Biol. 593:19 (2007)).

Such screening methods (e.g., high-throughput) can identify active agents and compounds rapidly and efficiently. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish), optionally at defined locations, for identification of potentially therapeutic molecules. Libraries that can be screened include, for example, small molecule libraries, phage display libraries, fully human antibody yeast display libraries (Adimab, LLC), siRNA libraries, and adenoviral transfection vectors.

XIII. Pharmaceutical Preparations and Therapeutic Uses a. Formulations and Routes of Administration Depending on the form of the modulator along with any optional conjugate, the mode of intended delivery, the disease being treated or monitored and numerous other variables, compositions of the instant invention may be formulated as desired using art recognized techniques. That is, in various embodiments of the instant invention compositions comprising PTK7 modulators are formulated with a wide variety of pharmaceutically acceptable carriers (see, e.g., Gennaro, *Remington: The Science and Practice of Pharmacy with Facts and Comparisons: Drugfacts Plus*, 20th ed. (2003); Ansel et al., *Pharmaceutical Dosage Forms and Drug Delivery Systems*, 7$^{th}$ ed., Lippencott Williams and Wilkins (2004); Kibbe et al., *Handbook of Pharmaceutical Excipients*, 3$^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the PTK7 modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics of the modulator. Suitable excipients include but are not limited to stabilizing agents, wetting and emulsifying agents, salts for varying osmolarity, encapsulating agents, buffers, and skin penetration enhancers.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising PTK7 modulators may be administered in vivo, to a subject in need thereof, by various routes, including, but not limited to, oral, intravenous, intra-arterial, subcutaneous, parenteral, intranasal, intramuscular, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

b. Dosages

Similarly, the particular dosage regimen, i.e., dose, timing and repetition, will depend on the particular individual and that individual's medical history. Empirical considerations such as pharmacokinetics (e.g., half-life, clearance rate, etc.) will contribute to the determination of the dosage. Frequency of administration may be determined and adjusted over the course of therapy, and is based on reducing the number of hyperproliferative or neoplastic cells, including tumor initiating cells, maintaining the reduction of such neoplastic cells, reducing the proliferation of neoplastic cells, or delaying the development of metastasis. Alternatively, sustained continuous release formulations of a subject therapeutic composition may be appropriate. As alluded to above various formulations and devices for achieving sustained release are known in the art.

From a therapeutic standpoint the pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In general, the PTK7 modulators of the invention may be administered in an amount in the range of about 10 μg/kg body weight to about 100 mg/kg body weight per dose. In certain embodiments, the PTK7 modulators of the invention may be administered in an amount in the range of about 50 μg/kg body weight to about 5 mg/kg body weight per dose. In certain other embodiments, the PTK7 modulators of the invention may be administered in an amount in the range of about 100 μg/kg body weight to about 10 mg/kg body weight per dose. Optionally, the PTK7 modulators of the invention may be administered in an amount in the range of about 100 μg/kg body weight to about 20 mg/kg body weight per dose. Further optionally, the PTK7 modulators of the invention may be administered in an amount in the range of about 0.5 mg/kg body weight to about 20 mg/kg body weight per dose. In certain embodiments the compounds of present invention are provided a dose of at least about 100 μg/kg body weight, at least about 250 μg/kg body weight, at least about 750 μg/kg body weight, at least about 3 mg/kg body weight, at least about 5 mg/kg body weight, at least about 10 mg/kg body weight is administered.

Other dosing regimens may be predicated on Body Surface Area (BSA) calculations as disclosed in U.S. Pat. No. 7,744, 877 which is incorporated herein by reference in its entirety. As is well known in the art the BSA is calculated using the patient's height and weight and provides a measure of a subject's size as represented by the surface area of his or her body. In selected embodiments of the invention using the BSA the modulators may be administered in dosages from 10 mg/m² to 800 mg/m². In other preferred embodiments the modulators will be administered in dosages from 50 mg/m² to 500 mg/m² and even more preferably at dosages of 100 mg/m², 150 mg/m², 200 mg/m², 250 mg/m², 300 mg/m², 350 mg/m², 400 mg/m² or 450 mg/m². Of course it will be appreciated that, regardless of how the dosages are calculated, multiple dosages may be administered over a selected time period to provide an absolute dosage that is substantially higher than the individual administrations.

In any event, the PTK7 modulators are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the PTK7 modulator is administered to a subject one or more times. More particularly, an effective dose of the modulator is administered to the subject once a month, more than once a month, or less than once a month. In certain embodiments, the effective dose of the PTK7 modulator may be administered multiple times, including for periods of at least a month, at least six months, or at least a year. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the disclosed modulators.

Dosages and regimens may also be determined empirically for the disclosed therapeutic compositions in individuals who have been given one or more administration(s). For example, individuals may be given incremental dosages of a therapeutic composition produced as described herein. To assess efficacy of the selected composition, a marker of the specific disease, disorder or condition can be followed as described previously. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

c. Combination Therapies

Combination therapies contemplated by the invention may be particularly useful in decreasing or inhibiting unwanted neoplastic cell proliferation (e.g. endothelial cells), decreasing the occurrence of cancer, decreasing or preventing the recurrence of cancer, or decreasing or preventing the spread or metastasis of cancer. In such cases the compounds of the instant invention may function as sensitizing or chemosensitizing agent by removing the TPC propping up and perpetuating the tumor mass (e.g. NTG cells) and allow for more effective use of current standard of care debulking or anti-cancer agents. That is, a combination therapy comprising a PTK7 modulator and one or more anti-cancer agents may be used to diminish established cancer e.g., decrease the number of cancer cells present and/or decrease tumor burden, or ameliorate at least one manifestation or side effect of cancer. As such, combination therapy refers to the administration of a PTK7 modulator and one or more anti-cancer agent that includes, but is not limited to, cytotoxic agents, cytostatic agents, chemotherapeutic agents, targeted anti-cancer agents, biological response modifiers, immunotherapeutic agents, cancer vaccines, anti-angiogenic agents, cytokines, hormone therapies, radiation therapy and anti-metastatic agents.

According to the methods of the present invention, there is no requirement for the combined results to be additive of the effects observed when each treatment (e.g., anti-PTK7 antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

To practice combination therapy according to the invention, a PTK7 modulator (e.g., anti-PTK7 antibody) in combination with one or more anti-cancer agent may be administered to a subject in need thereof in a manner effective to result in anti-cancer activity within the subject. The PTK7 modulator and anti-cancer agent are provided in amounts effective and for periods of time effective to result in their combined presence and their combined actions in the tumor environment as desired. To achieve this goal, the PTK7 modulator and anti-cancer agent may be administered to the subject simultaneously, either in a single composition, or as two or more distinct compositions using the same or different administration routes.

Alternatively, the modulator may precede, or follow, the anti-cancer agent treatment by, e.g., intervals ranging from minutes to weeks. In certain embodiments wherein the anti-cancer agent and the antibody are applied separately to the subject, the time period between the time of each delivery is such that the anti-cancer agent and modulator are able to exert a combined effect on the tumor. In a particular embodiment, it is contemplated that both the anti-cancer agent and the PTK7 modulator are administered within about 5 minutes to about two weeks of each other.

In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent. The PTK7 modulator and one or more anti-cancer agent (combination therapy) may be administered once, twice or at least the period of time until the condition is treated, palliated or cured. Preferably, the combination therapy is administered multiple times. The combination therapy may be administered from three times daily to once every six months. The administering may be on a schedule such as three times daily, twice daily, once daily, once every two days, once every three days, once weekly, once every two weeks, once every month, once every two months, once every three months, once every six months or may be administered continuously via a minipump. As previously indicated the combination therapy may be administered via an oral, mucosal, buccal, intranasal, inhalable, intravenous, subcutaneous, intramuscular, parenteral, intratumor or topical route. The combination therapy may be administered at a site distant from the site of the tumor. The combination therapy generally will be administered for as long as the tumor is present provided that the combination therapy causes the tumor or cancer to stop growing or to decrease in weight or volume.

In one embodiment a PTK7 modulator is administered in combination with one or more anti-cancer agents for a short treatment cycle to a subject in need thereof. The duration of treatment with the antibody may vary according to the particular anti-cancer agent used. The invention also contemplates discontinuous administration or daily doses divided into several partial administrations. An appropriate treatment time for a particular anti-cancer agent will be appreciated by the skilled artisan, and the invention contemplates the continued assessment of optimal treatment schedules for each anti-cancer agent.

The present invention contemplates at least one cycle, preferably more than one cycle during which the combination therapy is administered. An appropriate period of time for one cycle will be appreciated by the skilled artisan, as will the total number of cycles, and the interval between cycles. The invention contemplates the continued assessment of optimal treatment schedules for each modulator and anti-cancer agent. Moreover, the invention also provides for more than one administration of either the anti-PTK7 antibody or the anti-cancer agent. The modulator and anti-cancer agent may be administered interchangeably, on alternate days or weeks; or a sequence of antibody treatment may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the PTK7 modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed modulators one or more times even though there is little or no indication of disease using standard diagnostic procedures. In some embodiments the effectors will be administered on a regular schedule over a period of time. For example the PTK7 modulators could be administered weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the modulators of the present invention may be used to prophylactically to prevent or reduce the possibility of tumor metastasis following a debulking procedure. As used in the instant disclosure a debulking procedure is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy or ablation. At appropriate times readily determined by one skilled in the art in view of the instant disclosure the PTK7 modulators may be administered as suggested by clinical and diagnostic or theragnostic procedures to reduce tumor metastasis. The modulators may be administered one or more times at pharmaceutically effective dosages as determined using standard techniques. Preferably the dosing regimen will be accompanied by appropriate diagnostic or monitoring techniques that allow it to be modified as necessary.

d. Anti-Cancer Agents

As used herein the term anti-cancer agent means any agent that can be used to treat a cell proliferative disorder such as cancer, including cytotoxic agents, cytostatic agents, anti-angiogenic agents, debulking agents, chemotherapeutic agents, radiotherapy and radiotherapeutic agents, targeted anti-cancer agents, biological response modifiers, antibodies, and immunotherapeutic agents. It will be appreciated that, in selected embodiments as discussed above, anti-cancer agents may comprise conjugates and may be associated with modulators prior to administration.

The term cytotoxic agent means a substance that decreases or inhibits the function of cells and/or causes destruction of cells, i.e., the substance is toxic to the cells. Typically, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, e.g., cytotoxic RNases, such as extracellular pancreatic RNases; DNase I, including fragments and/or variants thereof.

A chemotherapeutic agent means a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in the formulation CHOP.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, an esperamicin, chromoprotein enediyne antiobiotic chromophores, aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; Gemzar® gemcitabine; 6-thioguanine; mercaptopurine; methotrexate; platinum analogs, vinblastine; platinum; etoposide (VP-16); ifosfamide; mitoxantrone; vincristine; NAVELBINE" vinorelbine; novantrone; teniposide; edatrexate; daunomycin; aminopterin; xeloda; ibandronate; irinotecan (Camptosar, CPT-11), topoisomerase inhibitor RFS 2000; difluoromethylornithine (DMFO); retinoids; capecitabine; combretastatin; leucovorin (LV); oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators (SERMs), aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides; ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above. Other embodiments comprise the use of immunotherapeutic agents, such as antibodies, approved for cancer therapy including, but not limited to, rituximab, trastuzumab, gemtuzumab ozogamcin, alemtuzumab, ibritumomab tiuxetan, tositumomab, bevacizumab, cetuximab, patitumumab, ofatumumab, ipilimumab and brentuximab vedotin. Those skilled in the art will be able to readily identify additional anti-cancer agents that are compatible with the teachings herein.

e. Radiotherapy

The present invention also provides for the combination of PTK7 modulators with radiotherapy (i.e., any mechanism for inducing DNA damage locally within tumor cells such as gamma.-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

f. Neoplastic Conditions

Whether administered alone or in combination with an anti-cancer agent or radiotherapy, the PTK7 modulators of the instant invention are particularly useful for generally treating neoplastic conditions in patients or subjects which may include benign or malignant tumors (e.g., renal, liver, kidney, bladder, breast, gastric, ovarian, colorectal, prostate, pancreatic, lung, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly preferred targets for treatment with therapeutic compositions and methods of the present invention are neoplastic conditions comprising solid tumors. In other preferred embodiments the modulators of the present invention may be used for the diagnosis, prevention or treatment of hematologic malignancies. Preferably the subject or patient to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma). In certain preferred embodiments, the cancerous cells are selected from the group of solid tumors including but not limited to breast cancer, non-small cell lung cancer (NSCLC), small cell lung cancer, pancreatic cancer, colon cancer, prostate cancer, sarcomas, renal metastatic cancer, thyroid metastatic cancer, and clear cell carcinoma.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

In yet other preferred embodiments the PTK7 modulators may be used to effectively treat certain myeloid and hematologic malignancies including leukemias such as chronic lymphocytic leukemia (CLL or B-CLL) or acute myeloid leukemia AML. Such leukemias are predominantly a disease of the elderly that starts to increase in incidence after fifty years of age and reaches a peak by late sixties. CLL generally involves the proliferation of neoplastic peripheral blood lymphocytes. Clinical finding of CLL involves lymphocytosis, lymphadenopatliy, splenomegaly, anemia and thrombocytopenia. AML is also called acute myelogenous leukemia, acute myeloblastic leukemia, acute granulocytic leukemia, and acute nonlymphocytic leukemia. The underlying pathophysiology in AML consists of a maturational arrest of bone marrow cells in the earliest stages of development. In the case of either disorder treatment regimens can readily be derived by those skilled in the art in view of the instant disclosure using clinically accepted procedures.

The present invention also provides for a preventative or prophylactic treatment of subjects who present with benign or precancerous tumors. It is not believed that any particular type of tumor or neoplastic disorder should be excluded from treatment using the present invention. However, the type of tumor cells may be relevant to the use of the invention in combination with secondary therapeutic agents, particularly chemotherapeutic agents and targeted anti-cancer agents.

Still other preferred embodiments of the instant invention comprise the use of PTK7 modulators to treat subjects suffering from solid tumors. In such subjects many of these solid tumors comprise tissue exhibiting various genetic mutations that may render them particularly susceptible to treatment with the disclosed effectors. For example, KRAS, APC and CTNNB1 and CDH1 mutations are relatively common in patients with colorectal cancer. Moreover, patients suffering from tumors with these mutations are usually the most refractory to current therapies; especially those patients with KRAS mutations. KRAS activating mutations, which typically result in single amino acid substitutions, are also implicated in other difficult to treat malignancies, including lung adenocarcinoma, mucinous adenoma, and ductal carcinoma of the pancreas.

Currently, the most reliable prediction of whether colorectal cancer patients will respond to EGFR- or VEGF-inhibiting drugs, for example, is to test for certain KRAS "activating" mutations. KRAS is mutated in 35-45% of colorectal cancers, and patients whose tumors express mutated KRAS do not respond well to these drugs. For example, KRAS mutations are predictive of a lack of response to panitumumab and cetuximab therapy in colorectal cancer (Lievre et al. *Cancer Res* 66:3992-5; Karapetis et al. *NEJM* 359:1757-1765). Approximately 85% of patients with colorectal cancer have mutations in the APC gene (Markowitz & Bertagnolli. *NEJM* 361:2449-60), and more than 800 APC mutations have been characterized in patients with familial adenomatous polyposis and colorectal cancer. A majority of these mutations result in a truncated APC protein with reduced functional ability to mediate the destruction of beta-catenin. Mutations in the beta-catenin gene, CTNNB1, can also result in increased stabilization of the protein, resulting in nuclear import and subsequent activation of several oncogenic transcriptional programs, which is also the mechanism of oncogenesis resulting from failure of mutated APC to appropriately mediate beta-catenin destruction, which is required to keep normal cell proliferation and differentiation programs in check.

Loss of CDH1 (E-cadherin) expression is yet another common occurrence in colorectal cancer, often observed in more advanced stages of the disease. E-cadherin is the central member of adherin junctions that connect and organize cells in epithelial layers. Normally E-cadherin physically sequesters beta-catenin (CTNNB1) at the plasma membrane; loss of E-cadherin expression in colorectal cancer results in localization of beta-catenin to the nucleus and transcriptional activation of the beta-catenin/WNT pathway. Aberrant beta-catenin/WNT signaling is central to oncogenesis and nuclear beta-catenin has been implicated in cancer stemness (Schmalhofer et al., 2009 PMID 19153669). E-cadherin is required for the expression and function of EphA2 a known binding partner for PTK7 ligands in epithelia cells (Dodge Zantek et al., 1999 PMID 10511313; Orsulic S and Kemler R, 2000 PMID 10769210). Using modulators that bind to PTK7 ligands and agonize with or antagonize receptor binding may modify, interrupt or reverse the pro-oncogenic processes. Alternatively, PTK7 modulators may preferentially bind to tumor cells with aberrant PTK7 interactions based on the binding preferences of the PTK7 modulators. Hence patients with cancers carrying the above mentioned genetic traits may benefits from treatment with aforementioned PTK7 modulators.

XIV. Articles of Manufacture

Pharmaceutical packs and kits comprising one or more containers, comprising one or more doses of a PTK7 modulator are also provided. In certain embodiments, a unit dosage is provided wherein the unit dosage contains a predetermined amount of a composition comprising, for example, an anti-PTK7 antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of a PTK7 modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). Such kits will generally contain in a suitable container a pharmaceutically acceptable formulation of the PTK7 modulator and, optionally, one or more anti-cancer agents in the same or different containers. The kits may also contain other pharmaceutically acceptable formulations, either for diagnosis or combined therapy. For example, in addition to the PTK7 modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the PTK7 modulator with an anti-cancer agent or diagnostic agent (e.g., see U.S. Pat. No. 7,422,739 which is incorporated herein by reference in its entirety).

More specifically the kits may have a single container that contains the PTK7 modulator, with or without additional components, or they may have distinct containers for each desired agent. Where combined therapeutics are provided for conjugation, a single solution may be pre-mixed, either in a molar equivalent combination, or with one component in excess of the other. Alternatively, the PTK7 modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the PTK7 modulator composition is used for treating cancer, for example colorectal cancer.

In other preferred embodiments the modulators of the instant invention may be used in conjunction with, or comprise, diagnostic or therapeutic devices useful in the diagnosis or treatment of proliferative disorders. For example, in on preferred embodiment the compounds and compositions of the instant invention may be combined with certain diagnostic devices or instruments that may be used to detect, monitor, quantify or profile cells or marker compounds involved in the etiology or manifestation of proliferative disorders. In particularly preferred embodiments the devices may be used to detect, monitor and/or quantify circulating tumor cells either in vivo or in vitro (see, for example, WO 2012/0128801 which is incorporated herein by reference). In still other preferred embodiments, and as discussed above, the circulating tumor cells may comprise cancer stem cells.

XV. Research Reagents

Other preferred embodiments of the invention also exploit the properties of the disclosed modulators as an instrument useful for identifying, isolating, sectioning or enriching populations or subpopulations of tumor initiating cells through methods such as flow cytometry, fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Ser. Nos. 12/686,359, 12/669,136 and 12/757,649 each of which is incorporated herein by reference in its entirety).

XVI. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual, Cold Spring Harbor Laboratory Press, Cold Spring Harbor, N.Y. (1998); and Coligan et al., Short Protocols in Protein Science, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

All references or documents disclosed or cited within this specification are, without limitation, incorporated herein by reference in their entirety. Moreover, any section headings used herein are for organizational purposes only and are not to be construed as limiting the subject matter described.

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Enrichment of Tumor Initiating Cell Populations

To characterize the cellular heterogeneity of solid tumors as they exist in cancer patients, elucidate the identity of tumor perpetuating cells (TPC; i.e. cancer stem cells: CSC) using particular phenotypic markers and identify clinically relevant therapeutic targets, a large non-traditional xenograft (NTX) tumor bank was developed and maintained using art recognized techniques. The NTX tumor bank, comprising a large number of discrete tumor cell lines, was propagated in immunocompromised mice through multiple passages of heterogeneous tumor cells originally obtained from numerous cancer patients afflicted by a variety of solid tumor malignancies. The continued availability of a large number of discrete early passage NTX tumor cell lines having well defined lineages greatly facilitate the identification and isolation of TPC as they allow for the reproducible and repeated characterization of cells purified from the cell lines. More particularly, isolated or purified TPC are most accurately defined retrospectively according to their ability to generate phenotypically and morphologically heterogeneous tumors in mice that recapitulate the patient tumor sample from which the cells originated. Thus, the ability to use small populations of isolated cells to generate fully heterogeneous tumors in mice is strongly indicative of the fact that the isolated cells comprise TPC. In such work the use of minimally passaged NTX cell lines greatly simplifies in vivo experimentation and provides readily verifiable results. Moreover, early passage NTX tumors also respond to therapeutic agents such as irinotecan (i.e. Camptosar®), which provides clinically relevant insights into underlying mechanisms driving tumor growth, resistance to current therapies and tumor recurrence.

As the NTX tumor cell lines were established the constituent tumor cell phenotypes were analyzed using flow cytometry to identify discrete markers that might be used to characterize, isolate, purify or enrich tumor initiating cells (TIC) and separate or analyze TPC and TProg cells within such populations. In this regard the inventors employed a proprietary proteomic based platform (i.e. PhenoPrint™ Array) that provided for the rapid characterization of cells based on protein expression and the concomitant identification of potentially useful markers. The PhenoPrint Array is a proprietary proteomic platform comprising hundreds of discrete binding molecules, many obtained from commercial sources, arrayed in 96 well plates wherein each well contains a distinct antibody in the phycoerythrin fluorescent channel and multiple additional antibodies in different fluorochromes arrayed in every well across the plate. This allows for the determination of expression levels of the antigen of interest in a subpopulation of selected tumor cells through rapid inclusion of relevant cells or elimination of non-relevant cells via non-phycoerythrin channels. When the PhenoPrint Array was used in combination with tissue dissociation, transplantation and stem cell techniques well known in the art (Al-Hajj et al., 2004, Dalerba et al., 2007 and Dylla et al., 2008, all supra, each of which is incorporated herein by reference in its entirety), it was possible to effectively identify relevant markers and subsequently isolate and transplant specific human tumor cell subpopulations with great efficiency.

Accordingly, upon establishing various NTX tumor cell lines as is commonly done for human tumors in severely immune compromised mice, the tumors were resected from mice upon reaching 800-2,000 mm$^3$ and the cells were dissociated into single cell suspensions using art-recognized enzymatic digestion techniques (See for example U.S.P.N. 2007/0292414 which is incorporated herein). Data obtained from these suspensions using the PhenoPrint Array provided both absolute (per cell) and relative (vs. other cells in the population) surface protein expression on a cell-by-cell basis, leading to more complex characterization and stratification of cell populations. More specifically, use of the PhenoPrint Array allowed for the rapid identification of proteins or markers that prospectively distinguished TIC or TPC from NTG bulk tumor cells and tumor stroma and, when isolated from NTX tumor models, provided for the relatively rapid characterization of tumor cell subpopulations expressing differing levels of specific cell surface proteins. In particular, proteins with heterogeneous expression across the tumor cell population allow for the isolation and transplantation of distinct, and highly purified, tumor cell subpopulations expressing either high and low levels of a particular protein or marker into immune-compromised mice, thereby facilitating the assessment of whether TPC were enriched in one subpopulation or another.

The term enriching is used synonymously with isolating cells and means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

As used herein a marker, in the context of a cell or tissue, means any characteristic in the form of a chemical or biological entity that is identifiably associated with, or specifically found in or on a particular cell, cell population or tissue including those identified in or on a tissue or cell population affected by a disease or disorder. As manifested, markers may be morphological, functional or biochemical in nature. In preferred embodiments the marker is a cell surface antigen that is differentially or preferentially expressed by specific cell types (e.g., TPC) or by cells under certain conditions (e.g., during specific points of the cell life cycle or cells in a particular niche). Preferably, such markers are proteins, and more preferably, possess an epitope for antibodies, aptamers or other binding molecules as known in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes, ability to migrate under particular conditions and the ability to differentiate along particular lineages. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

In a related sense the term marker phenotype in the context of a tissue, cell or cell population (e.g., a stable TPC phenotype) means any marker or combination of markers that may be used to characterize, identify, separate, isolate or enrich a particular cell or cell population (e.g., by FACS). In specific embodiments, the marker phenotype is a cell surface phenotype that may be determined by detecting or identifying the expression of a combination of cell surface markers.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, ADAM9, oncostatin M, Lgr5, Lgr6, CD324, CD325, nestin, Sox I, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPA1, PTS, CEACAM6, NID2, STEAP, ABCA3, CRIM1, IL1R1, OPN3, DAF, MUC1, MCP, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.N. 2007/0292414, 2008/0175870, 2010/0275280, 2010/0162416 and 2011/0020221 each of which is incorporated herein by reference. It will be appreciated that a number of these markers were included in the PhenoPrint Array described above.

Similarly, non-limiting examples of cell surface phenotypes associated with cancer stem cells of certain tumor types include CD44$^{hi}$CD24$^{low}$, ALDH$^+$, CD133$^+$, CD123$^+$, CD34$^+$CD38$^-$, CD44$^+$CD24$^-$, CD46$^{hi}$CD324$^+$CD66c$^-$, CD133$^+$CD34$^+$CD10$^-$CD19$^-$, CD138$^-$CD34$^-$CD19$^+$, CD133$^+$RC2$^+$, CD44$^+$α$_2$β$_1$$^{hi}$CD133$^+$, CD44$^+$CD24$^+$ESA$^+$, CD271$^+$, ABCB5$^+$as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), prostate ("PR"), kidney ("KDY"), melanoma ("Mel"), ovarian ("OV"), and head and neck cancer ("HN") tumor cells, regardless of whether the tumor specimens being analyzed were primary patient tumor specimens or patient-derived NTX tumors.

Cells with negative expression (i.e."−") are herein defined as those cells expressing less than, or equal to, the 95$^{th}$ percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the 95$^{th}$ percentile of expression observed with an isotype control antibody using the FMO staining procedure described above are herein defined as "positive" (i.e."+"). As defined herein there are various populations of cells broadly defined as "positive." First, cells with low expression (i.e. "lo") are generally defined as those cells with observed expression above the 95$^{th}$ percentile determined using FMO staining with an isotype control antibody and within one standard deviation of the 95$^{th}$ percentile of expression observed with an isotype control antibody using the FMO staining procedure described above. Cells with "high" expression (i.e. "hi") may be defined as those cells with observed expression above the 95$^{th}$ percentile determined using FMO staining with an isotype control antibody and greater than one standard deviation above the 95$^{th}$ percentile of expression observed with an isotype control antibody using the FMO staining procedure described above. In other embodiments the 99$^{th}$ percentile may preferably be used as a demarcation point between negative and positive FMO staining and in particularly preferred embodiments the percentile may be greater than 99%.

Using techniques such as those described above to quickly identify and rank colorectal tumor antigens based on expression intensity and heterogeneity across several NTX tumors from colorectal cancer patients, candidate TPC antigens were further assessed by comparison of tumor versus normal adjacent tissue and then selected based, at least in part, on the up- or down-regulation of the particular antigen in malignant cells. Moreover, systematic analysis of a variety of cell surface markers for their ability to enrich for the ability to transplant fully heterogeneous tumors into mice (i.e. tumorigenic ability), and subsequent combination of these markers substantially improved the resolution of the method and improved the ability to tailor fluorescence activated cell sorting (FACS) techniques to identify and characterize distinct, highly enriched tumor cell subpopulations that exclusively contained all tumor generating ability upon transplantation (i.e. tumor initiating cells).

To reiterate, the term tumor initiating cell (TIC) or tumorigenic (TG) cell encompasses both Tumor Perpetuating Cells (TPC; i.e. cancer stem cells) and highly proliferative Tumor Progenitor cells (TProg), which together generally comprise a unique subpopulation (i.e. 0.1-25%) of a bulk tumor or mass; the characteristics of which are defined above. The majority of tumor cells characterized in this fashion are devoid of this tumor forming ability, and can thus be characterized as non-tumorigenic (NTG). Surprisingly, it was observed that most distinct markers identified using the proprietary PhenoPrint Array did not demonstrate an ability to enrich tumor initiating cell populations in colorectal tumors using standard FACS protocols, but that distinct marker combinations could be used to identify two subpopulations of tumor initiating cells: TPC and TProg. Those skilled in the art will recognize that the defining difference between TPC and TProg, though both are tumor initiating in primary transplants, is the ability of TPC to perpetually fuel tumor growth upon serial transplantation at low cell numbers. Furthermore, the marker/proteins used in combination to enrich for both TPC and TProg were unknown to be associated with cells containing such activity in any tissue or neoplasm prior to discovery by current inventors though others have defined cell surface markers or enzymatic activity that can similarly be used to enrich for tumorigenic cells (Dylla et al 2008, supra). As set forth below, specific tumor cell subpopulations isolated using cell surface marker combinations alluded to above were then analyzed using whole transcriptome next generation sequencing to identify and characterize differentially expressed genes.

Example 2

Isolation and Analysis of RNA Samples From Enriched Tumor Initiating Cell Populations The established colorectal NTX tumor line SCRX-CR4 was passaged as described in Example 1 and used to initiate tumors in immune compromised mice. Once the mean tumor burden reached ~300 mm$^3$ the mice were randomized and treated with 15 mg/kg irinotecan, 25 mg/kg gemcitabine, or vehicle control (PBS) twice weekly for a period of at least twenty days prior to euthanization. Tumors were then removed and TPC, TProg and NTG cells, respectively, were isolated from freshly resected colorectal NTX tumors and, similarly, TG and NTG cells were isolated from pancreatic NTX tumors, generally using the technique set out in Example 1. More particularly, cell populations were isolated by FACS and immediately pelleted and lysed in Qiagen RLT-plus RNA lysis buffer (Qiagen, Inc.). The lysates were then stored at −80° C. until used. Upon thawing, total RNA was extracted using the Qiagen RNeasy isolation kit (Qiagen, Inc.) following vendor's instructions and quantified on the Nanodrop (Thermo Scientific) and a Bioanalyzer 2100 (Agilent Technologies) again using the vendor's protocols and recommended instrument settings. The resulting total RNA preparation was suitable for genetic sequencing and analysis.

Total RNA samples obtained from the respective cell populations isolated as described above from vehicle or chemotherapeutic agent-treated mice were prepared for whole transcriptome sequencing using an Applied Biosystems SOLiD 3.0 (Sequencing by Oligo Ligation/Detection) next generation sequencing platform (Life Technologies), starting with 5 ng of total RNA per sample. The data generated by the SOLiD platform mapped to 34,609 genes from the human genome and was able to detect PTK7, in several samples.

Generally the SOLiD3 next generation sequencing platform enables parallel sequencing of clonally-amplified RNA/DNA fragments linked to beads. Sequencing by ligation with dye-labeled oligonucleotides is then used to generate 50 base reads of each fragment that exists in the sample with a total of greater than 50 million reads generating a much more accurate representation of the mRNA transcript level expression of proteins in the genome. The SOLiD3 platform is able to capture not only expression, but SNPs, known and unknown alternative splicing events, and potentially new exon discoveries based solely on the read coverage (reads mapped uniquely to genomic locations). Thus, use of this next generation platform allowed the determination of differences in transcript level expression as well as differences or preferences for specific splice variants of those expressed mRNA transcripts. Moreover, analysis with the SOLiD3 platform using a modified whole transcriptome protocol from Applied Biosystems only required approximately 5 ng of starting material pre-amplification. This is significant as extraction of total RNA from sorted cell populations where the TPC subset of cells is, for example, vastly smaller in number than the NTG or bulk tumors and thus results in very small quantities of usable starting material.

Duplicate runs of sequencing data from the SOLiD3 platform were normalized and transformed and fold ratios calculated as is standard industry practice. As seen in FIG. 2, PTK7 gene expression levels (expressed as reads per million mapped to exons; RPM_exon) were measured in respective SCRx-CR4 tumor cell subpopulations. An analysis of the data showed that PTK7 was up-regulated at the transcript level between 2-4 fold over the NTG population, and 50-200% over the TProg population, in vehicle or irinotecan treated mice, respectively.

The observations detailed above show that PTK7 expression is generally elevated in TPC populations and suggests that PTK7 may play an important role in tumorigenesis and tumor maintenance, thus constituting an interesting target for immunotherapeutic approaches.

Example 3

Real-Time PCR Analysis of PTK7 in Enriched Tumor Initiating Cell Populations

To validate the differential PTK7 expression observed by whole transcriptome sequencing in TPC populations versus TProg and NTG cells in colorectal cancer, and TG versus NTG cells in pancreatic cancer, TaqMan® quantitative real-time PCR was used to measure gene expression levels in respective cell populations isolated from various NTX lines as set forth above. It will be appreciated that such real-time PCR analysis allows for a more direct and rapid measurement of gene expression levels for discrete targets using primers and probe sets specific to a particular gene of interest. TaqMan® real-time quantitative PCR was performed on an Applied Biosystems 7900HT Machine (Life Technologies), which was used to measure PTK7 and PTK7 gene expression in multiple patient-derived NTX line cell populations and corresponding controls. Moreover, the analysis was conducted as specified in the instructions supplied with the TaqMan System and using commercially available PTK7 and PTK7 primer/probe sets (Life Technologies).

Figure 3:
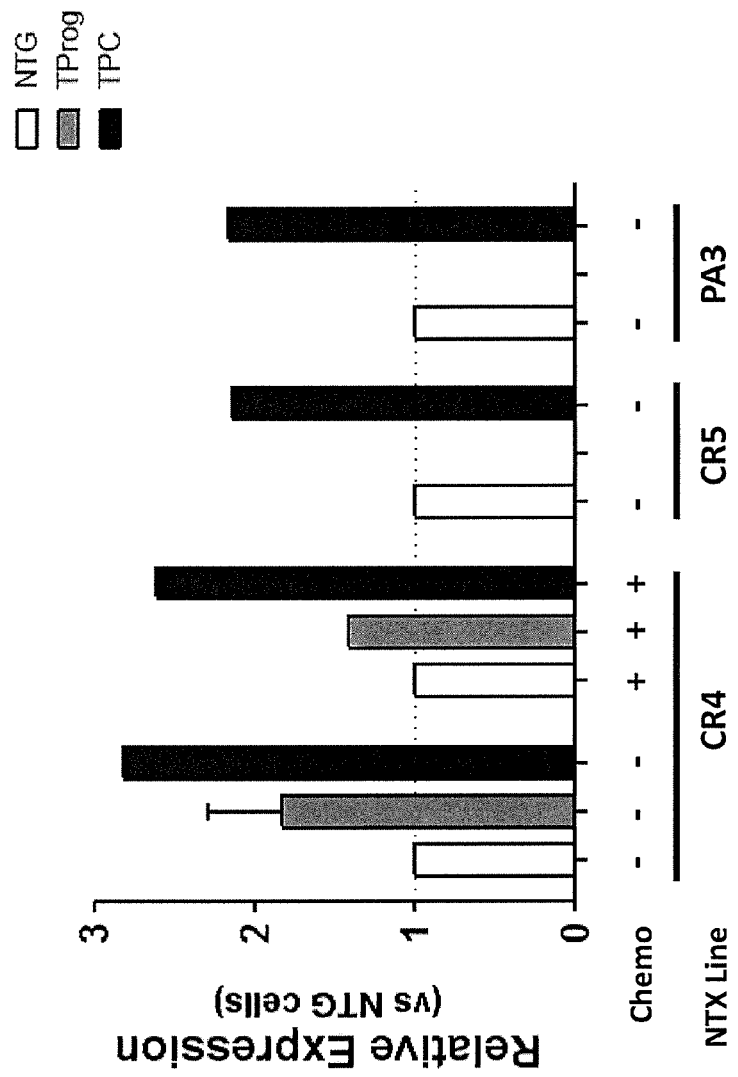
FIG. 3 is a graphical representation showing the relative gene expression levels of human PTK7 in highly enriched tumor progenitor cell (TProg) and tumor perpetuating cell (TPC) populations obtained from mice bearing one of three different non-traditional xenograft (NTX) colorectal or pancreatic tumor cell lines, and normalized against non-tumorigenic (NTG) enriched cell populations as measured using quantitative RT-PCR.

As seen in FIG. 3, quantitative real-time PCR interrogation of gene expression was conducted using NTG and TPC populations isolated from 2 distinct colorectal NTX tumor lines (SCRX-CR4 & CR5) and a pancreatic tumor line (SCRX-PA3). TProg cell populations were also separated and analyzed for SCRx-CR4. The data set forth in FIG. 3 shows that PTK7 gene expression is elevated more than 2-fold in colorectal TPC, when compared versus NTG cells from the same tumors. PTK7 was also elevated more than 2-fold in TPC in mice undergoing treatment with irinotecan, and in the TIC cell population of pancreatic tumors (e.g. SCRx-PA3). The observation of elevated PTK7 expression in NTX TPC preparations as compared with NTG cell controls from both colorectal and pancreatic patient-derived NTX tumors using the widely accepted methodology of real-time quantitative PCR confirms the more sensitive SOLiD3 whole transcriptome sequencing data of the previous Example. Such findings further support the observed association between PTK7 expression levels and cells underlying tumorigenesis, resistance to therapy and recurrence.

Example 4

Expression of PTK7s in Unfractionated Colorectal Tumor Specimens

In light of the fact that PTK7 gene expression was found to be elevated in TPC populations from colorectal tumors when compared with TProg and NTG cells from the same tumors, experiments were conducted to determine whether elevated PTK7 expression was also detectable in unfractionated colorectal tumor samples versus normal adjacent tissue (NAT). Measurements were also made to determine how the expression of PTK7 in tumors compares with levels in normal tissue specimens (NL).

More specifically custom Tumor Scan qPCR (Origene Technologies) 384-well arrays containing 110 colorectal patient tumor specimens at different stages, normal adjacent tissue, and 48 normal tissues were designed and fabricated using art known techniques. Using the procedures detailed in Example 3 and the same PTK7 specific primer/probe sets, TaqMan® real-time quantitative PCR was performed in the wells of the custom plates.

Figures 4A, 4B:
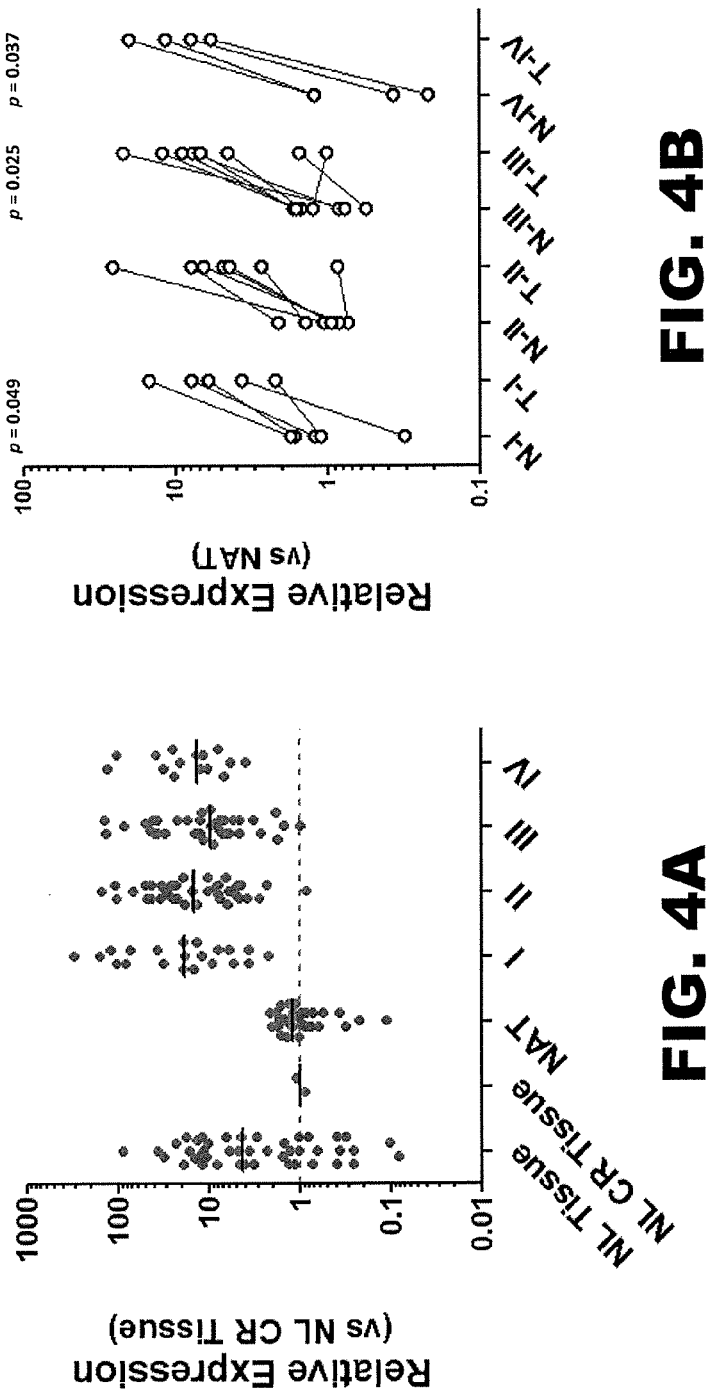
FIGS. 4A and 4B are graphical representations showing the relative gene expression levels of human PTK7 as measured using RT-PCR in whole colorectal tumor specimens from patients with Stage I-IV disease, as normalized against the mean of expression in normal colon and rectum tissue (FIG. 4A) or matched with normal adjacent tissue (FIG. 4B).

FIGS. 4A and 4B show the results of the expression data in a graphical format normalized against the mean expression in normal colon and rectum tissue. More particularly, FIG. 4A summarizes data generated using 168 tissue specimens, obtained from 110 colorectal cancer patients at various stages of the disease (I-IV), (35 tissue specimens of which are normal adjacent (NAT) tissue from colorectal cancer patients) and 48 normal tissues from other locations (NL Tissue). In the plot, data from each tissue specimen/patient is represented by a dot, with the geometric mean value of each population demarcated on the X-axis represented as a line. Similarly, FIG. 4B contains data from 24 matched colorectal patient specimens obtained from tumor (T) or normal adjacent tissue (N) at various stages of the disease (I-IV). Here the plotted data is presented on a sample by sample basis with linkage between the respective tumor and normal adjacent tissue from individual patients. Expression of PTK7 is clearly higher in the majority of matched tumor versus normal adjacent tissue, with the differential expression in Stages 3 and 4 reaching statistical significance ($n \geq 4$, $P \leq 0.037$).

Both FIGS. 4A and 4B indicate that, in all four stages presented, the expressed level of the PTK7 gene is elevated in a majority of colorectal tumors and in matched tumor specimens versus normal adjacent tissue. Moreover, the mean PTK7 gene expression in any Stage of colorectal cancer appears elevated versus most normal tissues that were evaluated (FIG. 4A). These results demonstrate that PTK7 expression is increased in colorectal cancer and, when coupled with the above observations that PTK7 expression is greatest in colorectal TPC and pancreatic TIC, suggests that therapeutic targeting of cancer stem cells expressing PTK7 may provide a therapeutic benefit to cancer patients.

Example 5

Differential Expression of PTK7 in Exemplary Tumor Samples

To further assess PTK7 gene expression in additional colorectal cancer patient tumor samples and tumor specimens from patients diagnosed with 1 of 18 different solid tumor types, Taqman® qRT-PCR was performed using TissueScan qPCR (Origene Technologies) 384-well arrays, which were custom fabricated as described in Example 4 but including solid tumor samples from eighteen different tumor types rather than just colorectal samples. The results of the measurements are presented in FIGS. 5A and 5B and show that gene expression of PTK7 is significantly elevated in a number of solid tumor types.

Figures 5A, 5B:
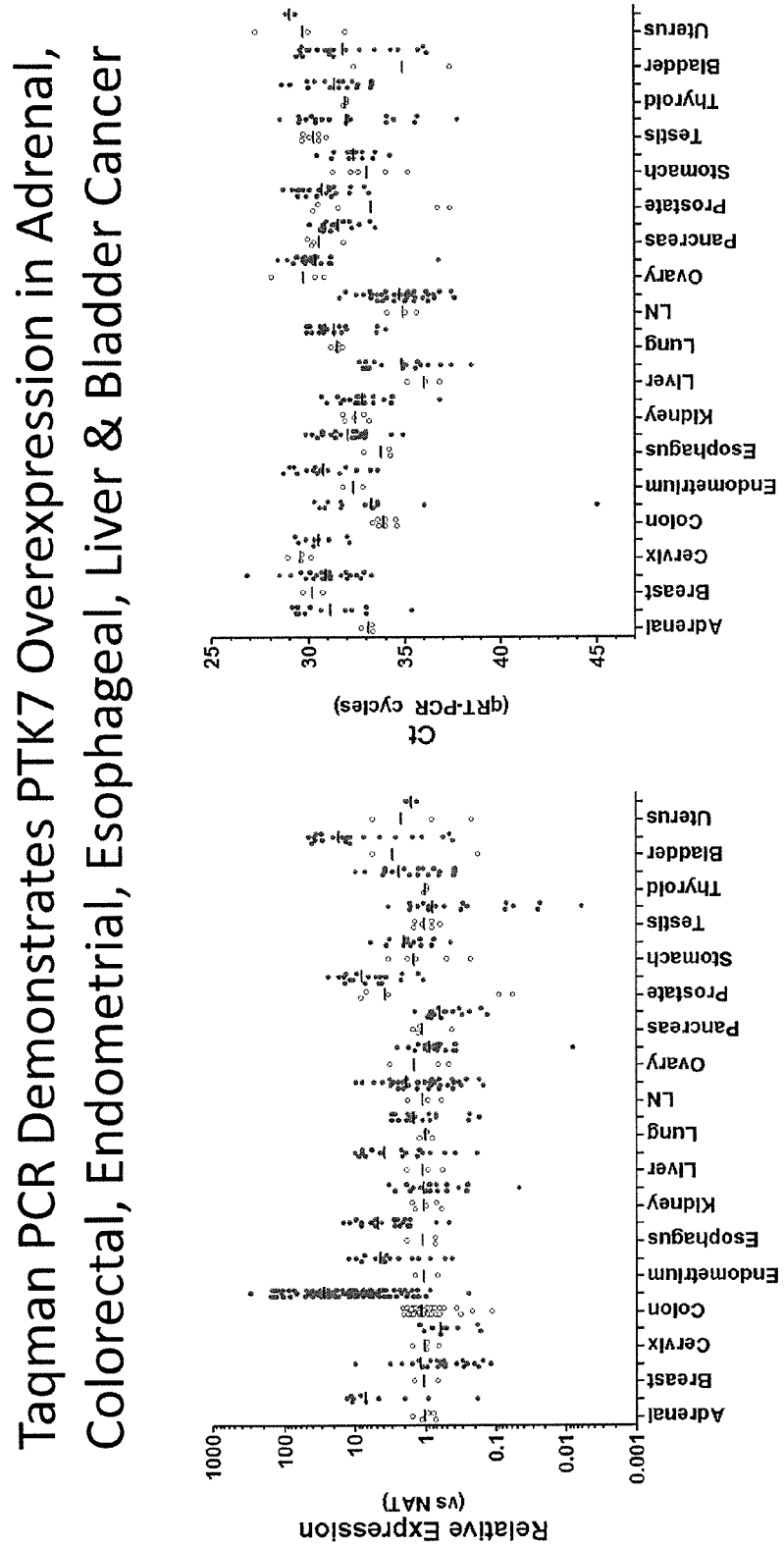
FIGS. 5A and 5B are graphical representations showing the relative or absolute gene expression levels, respectively, of human PTK7 genes as measured by RT-PCR in whole tumor specimens (grey dot) or matched NAT (white dots) from patients with one of eighteen different solid tumor types.

In this regard, FIGS. 5A and 5B show the relative and absolute gene expression levels, respectively, of human PTK7 in whole tumor specimens (grey dots) or matched normal adjacent tissue (NAT; white dots) from patients with one of eighteen different solid tumor types. In FIG. 5A, data is normalized against mean gene expression in NAT for each tumor type analyzed. In FIG. 5B, the absolute expression of PTK7 was assessed in various tissues/tumors, with the data being plotted as the number of cycles (Ct) needed to reach exponential amplification by quantitative real-time PCR. Specimens not amplified were assigned a Ct value of 45, which represents the last cycle of amplification in the experimental protocol. Each dot represents an individual tissue specimen, with the mean value represented as a black line.

Using the custom assembled OriGene TissueScan Array, it was observed that the majority of patients diagnosed with colorectal cancer and most patients diagnosed with adrenal, endometrial, esophageal, liver, thyroid and bladder cancer had significantly more PTK7 gene expression in their tumors versus NAT, suggesting that PTK7 might play a role in tumorigenesis and/or tumor progression in these tumors. There were also subsets of lung and prostate cancer patients with elevated PTK7 expression versus NAT. What was also clear from these studies is that PTK7 gene expression was generally moderate in most NAT samples; with the highest expression being observed in the breast, cervix, ovary, pancreas, testis and bladder. Again, these data suggest that elevated PTK7 expression is indicative, and potentially dispositive, as to tumorigenesis or tumor perpetuation in patients presenting with selected hyperproliferative disorders.

Example 6

Construction and Expression of PTK7 Immunogens

In order to generate and characterize certain PTK7 modulators in accordance with the instant invention two forms of PTK7 immunogen were constructed and expressed. Initially a commercial expression vector, pCMV6-XL4-PTK7, was purchased from Origene, Inc. The sequence of the full length ORF (underlined portion of FIG. 1A) was continued, then subcloned by PCR into the EcoRI and NotI sites of the pCDH-EF1-MCS-T2A-GFP lentiviral vector (System Biosciences). This lentiviral vector expresses the full length PTK7 protein fused to a T2A ribosomal skip peptide and a GFP selectable marker, enabling multicistronic expression in transduced cells. This lentiviral vector was used to transduce 293T cells or BALB/c 3T3 cells according to standard protocols. In addition, pCMV6-XL4-PTK7 was used to transiently express PTK7 protein on the surface of 293T cells 48-hours after transfection of the cells using polyethenimine. Plasma membrane preparations were obtained from PTK7 over-expressing cells using differential centrifugation.

In other instances, soluble PTK7 immunogens were prepared and expressed using the pEE12.4 expression vector (Lonza AG) into which the portion of the PTK7 cDNA encoding the extracellular domain (ECD) of the protein, encoded by the sequence denoted by the underlined amino acids in FIG. 1B). In a first instance the ECD fragment was subcloned in-frame downstream of an IgK leader sequence and upstream of an 8×His epitope tag (SEQ ID NO: 8). Soluble His-tagged PTK7 ECD immunogen was produced by transient transfection of CHO-KSV cells, and the secreted protein purified from the cell supernatant using Ni-NTA resins and standard methods (Qiagen Inc.). In addition to the aforementioned PTK7-ECD-His construct, plasma preps and transfected cells described above, a Fc-PTK7-ECD construct was also generated and expressed. This process was initiated by PCR amplification of the ECD fragment set forth in FIG. 1B using the high fidelity KOD Hot Start DNA Polymerase (EMD Chemicals). The forward primer used in this PCR reaction had PTK7 sequence: GCCATTGTCTTCATCAAG-CAGCC (SEQ ID NO: 9) and also included a 5' HindIII restriction site and murine IgG Kappa signal peptide/leader sequence for secretion of the product into the culture supernatant. The reverse primer used to amplify these constructs had PTK7 sequence: CTGGATCATCTTGTAGGGGGGAG (SEQ ID NO: 10) and included a 5' DraIII and BglII restriction site allowing for cloning upstream of the human IgG2 Fc protein which was ordered as a synthesized gene (DNA 2.0 Inc.).

Amplified or sub-cloned products were then moved into the final expression vector pEE12.4 (Lonza AG) using HindIII and EcoRI restriction sites, and fidelity was confirmed by DNA sequencing. Plasmids were transiently transfected into either CHO-S or 293T suspension cells and purified by either nickel affinity column for His-tagged protein or Protein A for the Fc fusion product. The products were further purified by size exclusion chromatography using a Superdex200 column (GE Healthcare) in phosphate buffered saline (PBS), pH 7.2 with the purified fusion protein being quantified using the Bradford method (Bradford, 1976: PMID 942051).

Example 7

Generation of Anti-PTK7 Antibodies Using hPTK7 Immunogens

PTK-7 modulators in the form of murine antibodies were produced in accordance with the teachings herein through inoculation, respectively, with BALB/3T3 or HEK 293 cells over expressing full length hPTK7, hPTK7-His or hPTK7-Fc fabricated as set forth in the previous Example. In this respect three strains of female mice (3 each: Balb/c, CD-1, FVB) were immunized with preparations of the aforementioned PTK7 immunogens. The mice were all immunized via the footpad route with 10 μg of the selected PTK7 construct or $1\times10^6$ cells in each case emulsified with an equal volume of TiterMax® or alum adjuvant.

Either FACS or solid-phase ELISA assays was used to screen mouse sera for mouse IgG antibodies specific for human PTK7. For the ELISAs, plates were coated with PTK7-His at different concentrations ranging from 0.01-1 μg/mL in PBS overnight. After washing with PBS containing 0.02% (v/v) Tween 20, the wells were blocked with 3% (w/v) BSA in PBS or 2% FCS in PBS, 200 μL/well for 1 hour at RT. Mouse serum dilutions were incubated on the PTK7-His coated plates at 50 μL/well at RT for 1 hour. The plates are washed and then incubated with 50 μL/well HRP-labeled goat anti-mouse IgG diluted 1:10,000 in 3% BSA-PBS or 2% FCS in PBS for 1 hour at RT. The plates were washed and 100 μL/well of the TMB substrate solution (Thermo Scientific 34028) was added for 15 minutes at RT. Finally an equal volume of 2M $H_2SO_4$ was added to stop substrate development and analyzed by spectrophotometer at OD 450.

As indicated murine sera were also tested for anti-PTK7 antibodies by FACS against cells over expressing human PTK7 co-transduced with GFP. Briefly $1\times10^5$ BALB/3T3 cells per well were transduced with human PTK7 and GFP were incubated for 30 minutes with 100 ul mouse serum diluted 1:100 in PBS/2% FCS. Cells were washed PBS/2% FCS and then incubated with 50 uL per sample DyeLight 649 labeled goat-anti-mouse IgG, Fc fragment specific secondary diluted 1:200 in PBS/2% FCS. After a 15 minute incubation cells were washed 2 times with PBS/2% FCS and re-suspended in PBS/2% FCS with DAPI and analyzed by FACS.

Sera positive immunized mice were sacrificed and draining lymph nodes (popliteal and inguinal, if enlarged) were dissected out and used as a source for antibody producing cells. Single cell suspension of B cells ($375\times10^6$ cells) were fused with non-secreting P3x63Ag8.653 myeloma cells (ATCC #CRL-1580) at a ratio of 1:1 by electrofusion. Cell electrofusion was performed using the BTX Hybrimmune System or an ECM2001, (both BTX Harvard Apparatus) as per the manufacturer's instructions. Following electrofusion cells were resuspended in hybridoma selection medium supplemented with Azaserine (Sigma #A9666) (DMEM (Cellgro cat#15-017-CM) medium containing, 15% Fetal Clone I serum (Hyclone), 10% BM Condimed (Roche Applied Sciences), 1 mM sodium pyruvate, 4 mM L-glutamine, 100 IU Penicillin-Streptomycin, 50 μM 2-mercaptoethanol, and 100 μM hypoxanthine). In a first fusion cells were plated at $2\times10^4$/ well in flat bottom microtiter plates, followed by two weeks incubation in selective HAT medium (Sigma, CRL P-7185). In a second fusion the cells were plated post fusion in four T225 flasks at 90 ml selection medium per flask. The flasks were then placed in a humidified 37° C. incubator containing 5% $CO_2$ and 95% air for 6-7 days.

After growth the library comprising the cells from the second fusion in the T225s is sorted using a FACSAria I cell sorter and plated at one cell per well in Falcon 96 well U-bottom plates (both BD Biosciences). Any remaining unused hybridoma library cells were frozen for future testing if necessary. The selected hybridomas were then grown in 200 uL of culture medium containing 15% Fetal Clone I serum (Hyclone), 10% BM-Condimed (Roche Applied Sciences), 1 mM sodium pyruvate, 4 mM L-glutamine, 100 IU Penicillin-Streptamycin, 50 μM 2-mercaptoethanol, and 100 μM hypoxanthine. After 10-14 days of growth for both fusions in 96 well plates the supernatants from each well were assayed for antibodies reactive for murine PTK7 using an ELISA or FACS assay.

Briefly, 96 well plates (VWR, 610744) were coated with 1 μg/mL murine PTK7-His in sodium carbonate buffer overnight at 4° C. The plates were washed and blocked with 2% FCS-PBS for one hour at 37° C. and used immediately or kept at 4° C. Undiluted hybridoma supernatants were incubated on the plates for one hour at RT. The plates are washed and probed with HRP labeled goat anti-mouse IgG diluted 1:10, 000 in 1% BSA-PBS for one hour at RT. Following incubation with substrate solution as described above the plates were read at OD 450.

Growth positive hybridoma wells secreting mouse immunoglobulins were also screened for human PTK7 specificity using a FACS assay similar to that described above. Briefly $1\times10^5$ per well BALB/3T3 cells transduced with human PTK7 and GFP were incubated for 30 minutes with 25-100 uL hybridoma supernatant. Cells were washed PBS/2% FCS twice and then incubated with 50 uL per sample DyeLight 649 labeled goat-anti-mouse IgG, Fc fragment specific secondary diluted 1:200 in PBS/2% FCS. After a 15 minute incubation cells were washed 2 times with PBS/2% FCS and re-suspended in PBS/2% FCS with DAPI (Life Technologies) and analyzed by FACS. For the second fusion the resulting PTK7 specific clonal hybridomas were expanded and cryopreserved in CS-10 freezing medium (Biolife Solutions) and stored in liquid nitrogen.

For the first fusion sub-cloning was performed on selected antigen-positive wells using limited dilution plating. Plates were visually inspected for the presence of single colony growth and supernatants from single colony wells then screened by antigen-specific ELISAs and FACS confirmation as described above. The resulting clonal populations were expanded and cryopreserved in freezing medium (90% FBS, 10% DMSO) and stored in liquid nitrogen.

For the first fusion PTK7 secreting hybridomas from positive wells (4 hits OD405@20 min >0.75) were selected for further characterization.

A second fusion seeded over 48 plates (4608 wells) resulted in approximately a 65% cloning efficiency with hundreds of hits. Selected clones provided several dozen murine antibodies that were immunospecific for human PTK7, some of which also cross-reacted with murine PTK7.

Example 8

Sequencing and Humanization of PTK7 Modulators

8(a) Sequencing:

Based on the foregoing, a number of exemplary distinct monoclonal antibodies that bind immobilized human and antibodies that cross-react with the mouse PTK7 with apparently high affinity were selected for sequencing and further analysis. As shown in a tabular fashion in FIGS. 6A and 6B, sequence analysis of the light chain variable regions (FIG. 6A) and heavy chain variable regions (FIG. 6B) from selected monoclonal antibodies generated in Example 7 confirmed that many had novel complementarity determining regions and often displayed novel VDJ arrangements. Note that the complementarity determining regions set forth in FIGS. 6A and 6B were derived from VBASE2 analvis.

More specifically, FIG. 6A depicts the contiguous amino acid sequences of twenty-one novel murine light chain variable regions from anti-PTK7 antibodies (SEQ ID NOS: 20-60, even numbers) and four humanized light chain variable regions (SEQ ID NOS: 62-68, even numbers) derived from representative murine light chains. Similarly, FIG. 6B depicts the contiguous amino acid sequences of twenty-one novel murine heavy chain variable regions (SEQ ID NOS: 21-61, odd numbers) from the same anti-PTK7 antibodies and four humanized heavy chain variable regions (SEQ ID NOS: 63-69, odd numbers) from the same murine antibodies as those providing the humanized light chains. Thus, taken together FIGS. 6A and 6B provide the annotated sequences of twenty-one murine anti-PTK7 antibodies (termed SC6.2.35, SC6.10.2, SC6.4.1, SC6.50.1, SC6.3, SC6.4, SC6.6, SC6.7, SC6.13, SC6.14, SC6.15, SC6.19, SC6.20, SC6.21, SC6.23, SC6.24, SC6.26, SC6.29, SC6.41, SC6.58 and SC6.59) and four humanized antibodies (termed hSC6.23, hSC6.24, hSC6.41 and hSC6.58). Note that the designations SC6.4.1 and SC6.4 merely reflect a naming anomaly and that the modulators actually comprise two discrete antibodies with novel heavy and light chain variable region sequences.

For the purposes of the instant application the SEQ ID NOS of each particular antibody are sequential. Thus mAb SC6.2.35 comprises SEQ ID NOS: 20 and 21 for the light and heavy chain variable regions respectively. In this regard SC6.10.2 comprises SEQ ID NOS: 22 and 23, SC6.4.1 comprises SEQ ID NOS: 24 and 25, and so on. Moreover, corresponding nucleic acid sequences for each antibody amino acid sequence in FIGS. 6A and 6B are included in the instant application as a sequence listing appended hereto. The included nucleic acid sequences comprise SEQ ID NOS that are one hundred greater than the corresponding amino acid sequence (heavy or light chain). Thus, nucleic acid sequences encoding the heavy and light chain variable region amino acid sequences of mAb SC6.2.35 (i.e., SEQ ID NOS: 20 and 21) comprise SEQ ID NOS: 120 and 121. The other antibody nucleic acid sequences, including those encoding humanized constructs are numbered similarly.

As a first step in sequencing exemplary modulators the selected hybridoma cells were lysed in Trizol® reagent (Life Technologies) to prepare the RNA. In this regard between $10^4$ and $10^5$ cells were resuspended in 1 ml Trizol and shaken vigorously after addition of 200 μL of chloroform. Samples were then centrifuged at 4° C. for 10 minutes and the aqueous phase was transferred to a fresh microfuge tube where an equal volume of isopropanol was added. The tubes were again shaken vigorously and allowed to incubate at room temperature for 10 minutes before being centrifuged at 4° C. for 10 minutes. The resulting RNA pellets were washed once with 1 ml of 70% ethanol and dried briefly at room temperature before being resuspended in 40 μL of DEPC-treated water. The quality of the RNA preparations was determined by fractionating 3 μL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse VH repertoire, in combination with 3' mouse Cγ primer specific for all mouse Ig isotypes. A 400 bp PCR fragment of the VH was sequenced from both ends using the same PCR primers. Similarly thirty-two 5' Vk leader sequence primer mix designed to amplify each of the Vk mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the V kappa light chain and four for the V gamma heavy chain (γ1). The QIAGEN One Step RT-PCR kit was used for amplification, (Qiagen, Inc.). This kit provides a blend of Sensiscript and Omniscript Reverse Transcriptases, HotStarTaq DNA Polymerase, dNTP mix, buffer and Q-Solution, a novel additive that enables efficient amplification of "difficult" (e.g., GC-rich) templates. The extracted PCR products were directly sequenced using specific V region primers. Nucleotide sequences were analyzed using IMGT to identify germ line V, D and J gene members with the highest sequence homology. The derived sequences were compared to known germ line DNA sequences of the Ig V- and J-regions using V-BASE2 (Retter et al., supra) and by alignment of $V_H$ and $V_L$ genes to the mouse germ line database.

Reaction mixtures were prepared that included 3 μL of RNA, 0.5 of 100 μM of either heavy chain or kappa light chain primers 5 μL of 5×RT-PCR buffer, 1 μL dNTPs, 1 μL of enzyme mix containing reverse transcriptase and DNA polymerase, and 0.4 μL of ribonuclease inhibitor RNasin (Promega BioSystems). The reaction mixture contains all of the reagents required for both reverse transcription and PCR. The thermal cycler program was RT step 50° C. for 30 minutes 95° C. for 15 minutes followed by 30 cycles of (95° C. for 30 seconds, 48° C. for 30 seconds, 72° C. for 1.0 minutes). There was then a final incubation at 72° C. for 10 minutes.

To prepare the PCR products for direct DNA sequencing, they were purified using the QIAquick™ PCR Purification Kit according to the manufacturer's protocol. The DNA was eluted from the spin column using 50 μL of sterile water and then sequenced directly from both strands. Again the resulting DNA sequences were analyzed using VBASE2 (data not shown) to provide the annotated sequences set forth in FIGS. 6A and 6B. More specifically, as discussed above, the annotated amino acid sequences of twenty-one murine anti-PTK7 antibody heavy and light chain variable regions are set forth FIGS. 6A and 6B.

8(b) Humanization:

Four of the murine antibodies generated in Example 7 were humanized using complementarity determining region (CDR) grafting. Human frameworks for heavy and light chains were selected based on sequence and structure similarity with respect to functional human germline genes. In this regard structural similarity was evaluated by comparing the mouse canonical CDR structure to human candidates with the same canonical structures as described in Chothia et al. (supra).

More particularly murine antibodies SC6.23, SC6.24, SC6.41 and SC6.58 were humanized using a computer-aided CDR-grafting method (Abysis Database, UCL Business Plc.) and standard molecular engineering techniques to provide hSC6.23, hSC6.24, hSC6.41 and hSC6.58 modulators. The human framework regions of the variable regions were selected based on their highest sequence homology to the mouse framework sequence and its canonical structure. For the purposes of the analysis the assignment of amino acids to each of the CDR domains is in accordance with the Kabat et al. numbering. Several humanized antibody variants were made in order to generate the optimal humanized antibody with the humanized antibodies generally retaining the antigen-binding complementarity-determining regions (CDRs) from the mouse hybridoma in association with human framework regions. Ultimately it was found that humanized SC6.23, SC6.24, SC6.41 and SC6.58 mAbs bind to the human PTK7 antigen with similar affinity to their murine counterparts as measured using the Biacore system.

Molecular engineering procedures were conducted using art-recognized techniques. To that end total mRNA was extracted from the hybridomas according to the manufacturer's protocol (Trizol® Plus RNA Purification System, Life Technologies). A sequence specific 5' leader sequence primer, designed to amplify each hybridoma, was used in combination with 3' human Cγ1 primer to amplify and clone the variable regions of each humanized antibody. Similarly a 5' Vk leader sequence designed specifically to amplify each of the Vk regions combined with a single reverse primer specific to the human kappa constant region were used to amplify and clone the kappa light chain. The amplified fragments were cloned as chimeric human gamma1/kappa chains and served as a bench mark for each humanized mAb.

From the nucleotide sequence information, data regarding V, D and J gene segments of the heavy and light chains of SC6.23, SC6.24, SC6.41 and SC6.58 were obtained. Based on the sequence data new primer sets specific to the leader sequence of the Ig $V_H$ and $V_K$ chain of the antibodies were designed for cloning of the recombinant monoclonal antibody. Subsequently the V-(D)-J sequences were aligned with mouse Ig germ line sequences. Heavy chain genes of SC6.23 were identified as VH36096 (V), DSP2.3 (D) and JH3. The heavy chain genes of SC6.24 were identified as VHJ558 (V), DSP2.7 (D) and JH4. The heavy chain genes of SC6.41 were identified as IGHV14-4 (V), DFL16.1 (D) and JH2. The heavy chain genes of SC6.58 were identified as IGHV4-1 (V), DFL16.1 (D) and JH4. All four light chains were K class. Light chains genes were identified as IGKV14-111 and JK5 for the SC6.23 mAb, IGKV3-5 and JK1 for the SC6.24 mAb, IGKV2-137 and JK4 germ line sequence for the SC6.41 mAb and IGKV17-121 and JK4 germ line sequences for SC6.58 kappa light chain. These results are summarized in the TABLE 1 immediately below.

TABLE 1

| Clone | VH | DH | JH | VL | JL |
|---|---|---|---|---|---|
| SC6.23 | VH3609 | DSP2.3 | JH3 | IGKV14-111 | JK5 |
| SC6.24 | VHJ558 | DSP2.7 | JH4 | IGKV3-5 | JK1 |
| SC6.41 | IGHV14-4 | DFL16.1 | JH2 | IGKV2-137 | JK4 |
| SC6.58 | IGHV4-1 | DFL16.1 | JH4 | IGKV17-121 | JK4 |

The obtained heavy and light chain sequences from all four clones were aligned to the functional human variable region sequences and reviewed for homology and canonical structure. The result the heavy and light chain analysis are shown below in TABLES 2 and 3 respectively.

TABLE 2

| mAb | human VH | human DH | human JH | % homology to human germ line sequence | % homology to mouse sequence |
|---|---|---|---|---|---|
| hSC6.23 | VH2-5 | IGHD5-5 | JH4 | 91 | 81 |
| hSC6.24 | VH1-3 | IGHD4-23 | JH6 | 82 | 82 |
| hSC6.41 | VH1-46 | IGHD4-23 | JH4 | 79 | 88 |
| hSC6.58 | VH3-7 | IGHD2-8 | JH6 | 86 | 88 |

TABLE 3

| mAb | human VK | human JK | % homology to human germ line sequence | % homology to mouse sequence |
|---|---|---|---|---|
| hSC6.23 | O8 | JK5 | 91 | 81 |
| hSC6.24 | L6 | JK1 | 82 | 82 |
| hSC6.41 | A3/A19 | JK1 | 79 | 88 |
| hSC6.58 | B2 | JK4 | 86 | 88 |

As the germ line selection and CDR grafting processes provided antibodies that generally retained their binding characteristics, there was apparently little need to insert murine residues in most of the constructs.

As alluded to above the amino acid sequences of the humanized heavy variable region chains and the humanized kappa light chains for all four antibodies are shown in FIGS. 6A and 6B (SEQ ID NOS: 62-69) and the corresponding nucleic acid sequences (SEQ ID NOS: 162-169) are set forth in the appended sequence listing.

More particularly the amino acid sequences and corresponding nucleic acid sequences of the humanized SC6.23 light chain (SEQ ID NOS: 62 and 162), and the humanized heavy chain (SEQ ID NOS: 63 and 163) are shown in FIGS. 6A and 6B and in the sequence listing. Similarly, the amino acid sequences and corresponding nucleic acid sequences of the humanized SC6.24 light chain (SEQ ID NOS: 64 and 164), and the humanized heavy chain (SEQ ID NOS: 65 and 165) are shown in the same manner. Another embodiment of the invention is illustrated by the amino acid sequences and corresponding nucleic acid sequences of the humanized SC6.41 light chain (SEQ ID NOS: 66 and 166), and the humanized heavy chain (SEQ ID NOS: 67 and 167). In yet another embodiment the amino acid sequences and corresponding nucleic acid sequences of the humanized SC6.58 light chain (SEQ ID NOS: 68 and 168), and the humanized heavy chain (SEQ ID NOS: 69 and 169) are depicted. As demonstrated in the Examples below each of the aforementioned humanized antibodies functions as an effective PTK7 modulator in accordance with the teachings herein.

In any event the disclosed modulators were expressed and isolated using art recognized techniques. To that end synthetic humanized variable DNA fragments (Integrated DNA Technologies) of both heavy chains were cloned into human IgG1 expression vector. The variable light chain fragments were cloned into human C-kappa expression vector. Antibodies were expressed by co-transfection of the heavy and the light chain into CHO cells.

More particularly, for antibody production directional cloning of the murine and humanized variable gene PCR products into human immunoglobulin expression vectors was undertaken. All primers used in Ig gene-specific PCRs included restriction sites (AgeI and XhoI for IgH, XmaI and DraIII for IgK, which allowed direct cloning into expression vectors containing the human IgG1, and IGK constant regions, respectively. In brief, PCR products were purified with Qiaquick PCR purification kit (Qiagen, Inc.) followed by digestion with AgeI and XhoI (IgH), XmaI and DraIII (IgK), respectively. Digested PCR products were purified prior to ligation into expression vectors. Ligation reactions were performed in a total volume of 10 µL with 200 U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates (100 µg/mL). The AgeI-EcoRI fragment of the $V_H$ region was than inserted into the same sites of pEE6.4HuIgG1 (Lonza AG) expression vector while the synthetic XmaI-DraIII $V_K$ insert was cloned into the XmaI-DraIII sites of the respective pEE12.4Hu-Kappa expression vector.

Cells producing humanized antibodies were generated by transfection of HEK 293 cells with the appropriate plasmids using 293fectin. In this respect plasmid DNA was purified with QIAprep Spin columns (Qiagen). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 µg/mL streptomycin, 100 U/mL penicillin G (all from Life Technologies).

For transient transfections cells were grown to 80% confluency. Equal amounts of IgH and corresponding IgL chain vector DNA (12.5 µg of each vector DNA) was added to 1.5 mL Opti-MEM mixed with 50 µL HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 min and stored at 4° C. Recombinant chimeric and humanized antibodies were purified with Protein G beads (GE Healthcare).

Example 9

Characteristics of PTK7 Modulators

9(a) General Modulator Characteristics

Figure 7A:
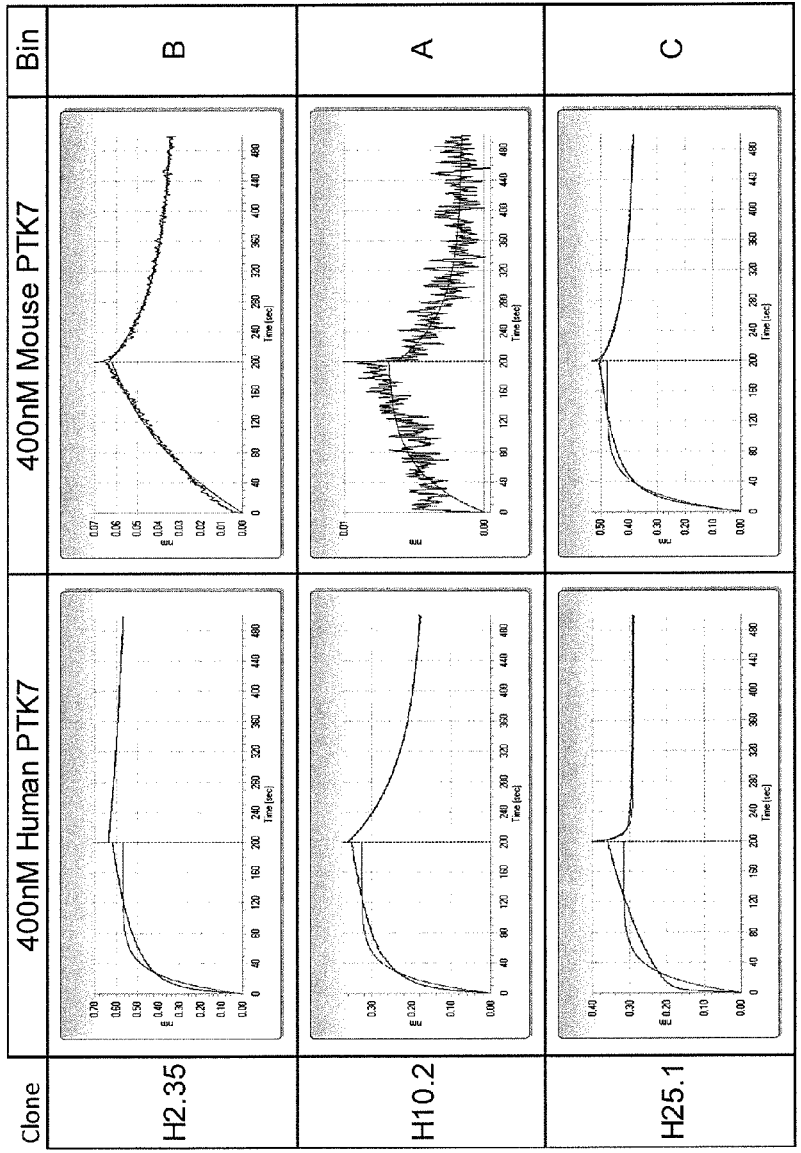

Various methods were used to analyze the immunochemical characteristics of selected PTK7 modulators (both murine and humanized) generated as set forth above. Specifically, a number of these antibodies were characterized as to affinity, kinetics, binning, and cross reactivity with regard to cynomolgus and murine homologs (e.g., by ForteBio). The reactivity of the modulators was also measured by Western blot using reduced and non-reduced samples to provide some indication as to whether epitopes were linear or not. In addition to the murine and human antigen binding data set forth in FIG. 7A, results of the antibody characterization for selected murine modulators are set forth in tabular form in FIG. 7B. Finally, as shown in FIGS. 7C-7E affinities for selected murine had humanized modulators were measured using bio-layer interferometry analysis on a ForteBio RED (ForteBio, Inc.) with a standard antigen concentration series. In general, the selected modulators exhibited relatively high affinities in the nanomolar range.

In accordance with the instant invention modulator affinity was measured in three ways to ensure accuracy. First, binding signal was measured for a fixed amount of antibody probed against serial dilutions of antigen in an ELISA to determine relative modulator activity (data not shown). Second, the affinities and kinetic constants $k_{on}$ and $k_{off}$ of the selected effectors were then measured using bio-layer interferometry analysis on a ForteBio RED (ForteBio, Inc.) with a standard antigen concentration series. Finally, the affinity of selected modulators was measured by surface plasmon resonance (Biacore System, GE Healthcare). Based on a standard antigen concentration series and using a 1:1 Langmuir binding model, the $K_d$ of the antibody binding to antigen and the kinetic constants $k_{on}$ and $k_{off}$ were determined (e.g., see FIGS. 7C and 7E) using techniques common in the art. Generally the selected effectors, whether murine or humanized, exhibited relatively high affinities in the nanomolar range. In the table in FIG. 7B a superscript B designates affinity measurements made on Biacore while superscript F designates measurements made on ForteBio.

Preliminary work was also conducted to determine whether the epitope recognized by the PTK7 effector comprises contiguous amino acids or is formed by noncontiguous amino acids juxtaposed by secondary structure of the antigen. In this respect Western blots were run under reducing (e.g., using 0.5M DTT) and non-reducing conditions. More specifically, using standard electrophoresis techniques well known in the art, PTK7 antigen in both states was run on gels and blotted before exposure to the selected modulators. As set forth in FIG. 7B two PTK7 modulators were tested that apparently reacted only with antigen where disulphide bonds were intact (NR). The remaining PTK7 modulators were not tested for Western blot activity.

With regard to antibody binning, a ForteBio Octet Red96 Analyzer (ForteBio, Inc.) was used per manufacturer's instructions and an art recognized sandwich method [Analytical Biochemistry 386:172-180 (2009) to identify antibodies which bound to the same or different bins. Briefly, an antibody (Ab1) was captured onto an anti-mouse capture chip before a high concentration of nonbinding antibody at 15 ug/mL (100 nM) was used to block the chip and establish a baseline. Monomeric recombinant hPTK7-His (isoform a) as provided for in Example 6 (at 500 nM) was then captured by the specific antibody (Ab1) and the tip was dipped into a well with either the same antibody (Ab1) as a control or into a well with a different antibody (Ab2) where both antibodies are at 4 ug/mL (25 nM). If additional binding was observed with a new antibody, then Ab1 and Ab2 were determined to be in a different bin. If no further binding occurred, similar to the control Ab1, then Ab2 was determined to be in the same bin. This process can be expanded to screen large libraries of unique antibodies using a full row of antibodies representing unique bins in a 96-well plate. Exemplary data for three representative modulators is shown in FIG. 7A for both human and murine PTK7 antigen. FIG. 7A illustrates that while SC6.10.2 did not bind mouse at all, SC6.2.35 bound at about 10% of human and SC6.25.1 bound to mouse PTK7-His with identical affinity (note; the antibodies are denoted H2.35, H10.2 and H25.1 in FIG. 7A). It was further determined that each of these tested antibodies resided in a different bin. In a similar manner binning analysis was conducted for nine additional PTK7 modulators with the results shown in FIG. 7B. These data identified at least seven distinct bins recognized by the tested modulators. ND in the tables indicates that the data was not determined.

Finally, cross-reactivity with regard to cynomolgus and murine PTK7 homologs were evaluated in with a ForteBio using a concentration series comprising recombinantly expressed, monomeric antigen. As listed in FIG. 7B a number of the exemplary modulators were reactive with mouse PTK7, while all antibodies cross-reacted with the highly similar cynomolgus PTK7.

9(b) Humanized Modulator Characteristics

Using techniques set forth above in this Example the humanized constructs hSC6.23, hSC6.24, hSC6.41 and hSC6.58 were analyzed to determine their binding characteristics. Additionally, humanized antibody binding was directly compared with the parent murine antibody for both antibodies to identify any subtle changes in rate constants brought about by the humanization process.

More specifically, the affinity of murine SC6.23 was measured by a Biacore using surface plasmon resonance (SPR) to provide the results set forth in FIG. 7C. Based on a concentration series of 25, 12.5, and 6.25 nM (generating the curves from top to bottom in the FIGS. 7C and 7D) and using a 1:1 Langmuir binding model, the $K_d$ of the antibody binding to antigen was estimated to be 2.3 nM. Similar experiments then run with the humanized SC6.23 construct showed equivalent results (FIG. 7D) indicating that the humanization process had not adversely impacted the affinity. In this regard the measurements indicated that the humanized construct had an affinity of 3.9 nM which is well within the acceptable limits for therapeutic antibodies. Similar measurements for each of the humanized constructs described in Example 8 are set forth in FIG. 7E and, along with the other techniques set out in this Example, show that the disclosed humanized PTK7 modulators possess desirable qualities for therapeutic antibodies.

Example 10

Epitope Determination of Selected PTK7 Modulators

In order to further refine binning data and determine the epitope regions defined by selected PTK7 modulators generated as set forth above, several different variants of the PTK7 ECD were constructed and expressed. More specifically PTK7 deletion mutants were designed using primers which amplified various PTK7 Ig domains and fused these to the BglII restriction site upstream of the human IgG2 Fc domain, ordered as a synthetic gene (DNA 2.0). These Fc fusion proteins were then cloned into the pEE12.4 expression vector (Lonza AG) using HindIII and EcoRI restriction sites. Isolated endotoxin free Plasmids DNA (Qiagen Inc.) were used for transfection of adherent 293 cell using 293Fectin (Life Technologies). Supernatants from 293 transfected cells were harvested 72 hours post transfection. Specifically the following deletion constructs fused to the Fc region were designed:

1. PTK7 ECD Ig domains 1-2 (SEQ ID NO: 70) FIG. 8A
2. PTK7 ECD Ig domains 3-7 (SEQ ID NO: 71) FIG. 8B
3. PTK7 ECD Ig domains 1-5 (SEQ ID NO: 72) FIG. 8C
4. PTK7 ECD Ig domains 6-7 (SEQ ID NO: 73) FIG. 8D
5. PTK7 ECD Ig domains 2-3 (SEQ ID NO: 74) FIG. 8E
6. PTK7 ECD Ig domains 1-4 (SEQ ID NO: 75) FIG. 8F
7. PTK7 ECD Ig domains 1-7 (SEQ ID NO: 3) FIG. 1C-ECD Amino acid sequences for the first six of these constructs are set forth in FIGS. 8A-8F (comprising the selected PTK7 ECD along with the Fc region). The sequence for the seventh construct comprises the extracellular domain of isoform a (SEQ ID NO: 3) as set forth in FIG. 1C fused to the Fc domain.

Using these constructs several modulators were tested for their ability to recognize PTK7 proteins with deletions of defined Ig domains. Through an ELISA assay comprising the use of domain deleted constructs and run under standard conditions. In this regard PTK7 Ig domain Fc fusions were captured on ELISA plate coated with goat anti-human IgG Fc-specific (Jackson Immunoresearch) antibody. The ability of each murine anti-PTK7 antibody to bind the various deletion Fc fusion proteins was then detected with HRP-labeled goat anti-mouse Fc-specific antibody.

Using this assay exemplary modulators were identified as being directed against particular PTK7 Ig domains. An example of ELISA results defines each representative detected epitope or binding pattern and is included in TABLE 4 immediately below.

TABLE 4

| Ig Domains | 1-2 | 2-3 | 1-4 | 1-5 | 3-7 | 6-7 | 1-7 | Binding domain |
| --- | --- | --- | --- | --- | --- | --- | --- | --- |
| SC6.2.35 | + | − | + | + | − | − | + | Ig domains 1-2 |
| SC6.39 | + | + | + | + | − | − | + | Ig domain 2 |
| SC6.25.1 | − | + | + | + | − | − | + | Ig domains 2-3 |
| SC6.10.2 | − | − | + | + | − | − | + | Ig domains 1-4 |
| SC6.18 | − | − | − | − | + | − | + | Ig domains 3-7 |
| SC6.11 | − | − | − | − | − | − | + | Ig domains 1-7 |

Figure 8G:
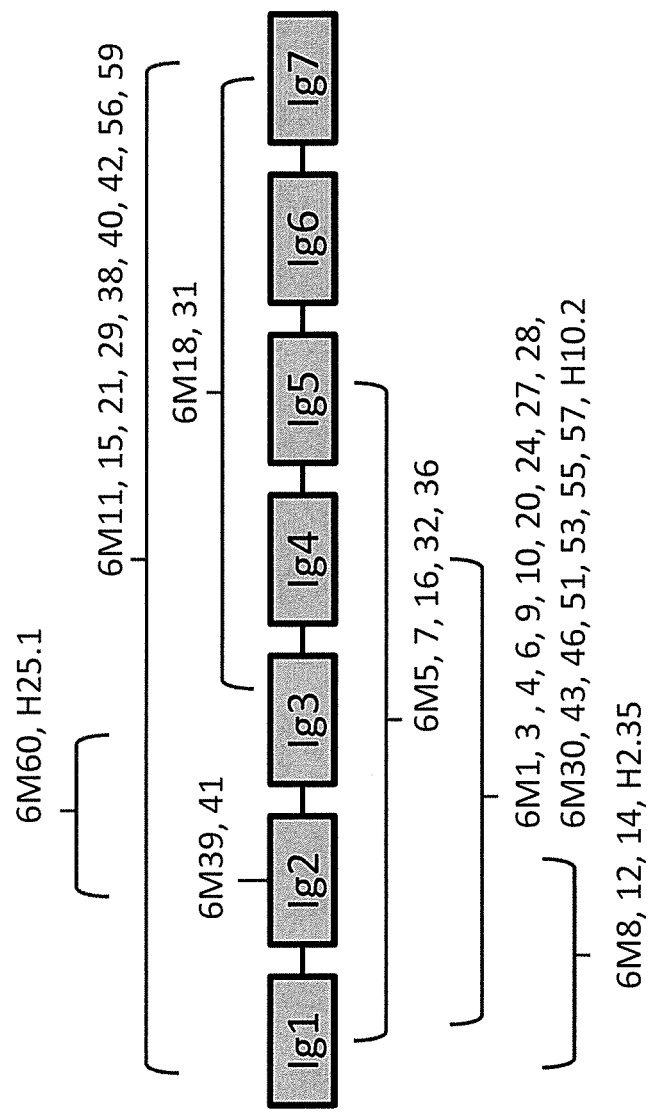

The anti-PTK7 monoclonal antibodies apparently recognize several different epitopes based on the different patterns of positive binding in the ELISA assay (Table 4 and FIG. 8G). Note that in FIG. 8G the modulators are listed as 6M rather that SC6 and SC6.2.35 and SC6.10.2 are listed as H2.35 and H10.2. None of the antibodies bind only to an epitope within Ig domains 6-7, but these two domains may contribute to the secondary/tertiary structure of the Ig3-7 Fc fusion construct which was bound by SC6.18 and SC6.31 (NOT IN TABLE). Moreover, three antibodies (SC6.2.35, SC6.4.1 and SC6.10.2) recognize an epitope in the first four Ig domains and none of the antibodies bind to an epitope in within Ig domains 6-7. In the first four Ig domains SC6.2.35 binds to an epitope within domains 1-2. SC6.4.1 recognizes an epitope within the boundaries of Ig domains 2 and 3. Conversely SC6.10.2 appears sensitive to any deletions within the first four Ig domains, and therefore all four Ig like domains are likely involved in defining the epitope SC6.10.2. Similarly some antibodies only bound to the full-length construct, Ig domains 1-7, indicating that the Ig deletions may have disrupted some of the binding sites or secondary structure of these epitopes. FIG. 8G provides a schematic representation of these binding patterns including additional antibodies and comparable data showing binding localization of the disclosed modulators where the 7 Ig domains of PTK7 ECD are

Example 11

PTK7 Protein Expression in Exemplary Tumor Samples

After documenting elevated gene expression levels and generating antibodies against PTK7 in the previous Examples, evidence was sought for corresponding PTK7 protein expression in selected patient tumor populations. In this respect, reverse phase cancer protein lysate arrays (ProteoScan™ Arrays; OriGene Technologies) comprising 4 dilutions of 432 tissue lysates from 11 tumor types, or their respective normal adjacent tissue, were provided along with controls consisting of HEK 293 cells without or with TP53-overexpression driven by an exogenous promoter. PTK7 protein expression in the lysates on this array was detected using a mouse monoclonal PTK7 antibody generated as set forth in Example 7 and that recognizes PTK7 protein by Western Blot (e.g. clone SC6.2.35). Colorimetric detection reagents and protocols were provided by the manufacturer of the ProteoScan Arrays; spots on the fabricated array were converted to a digital image using a flatbed scanner using BZScan2 Java Software (INSERM-TAGC) to quantify spot intensity.

Figures 9C, 9D:
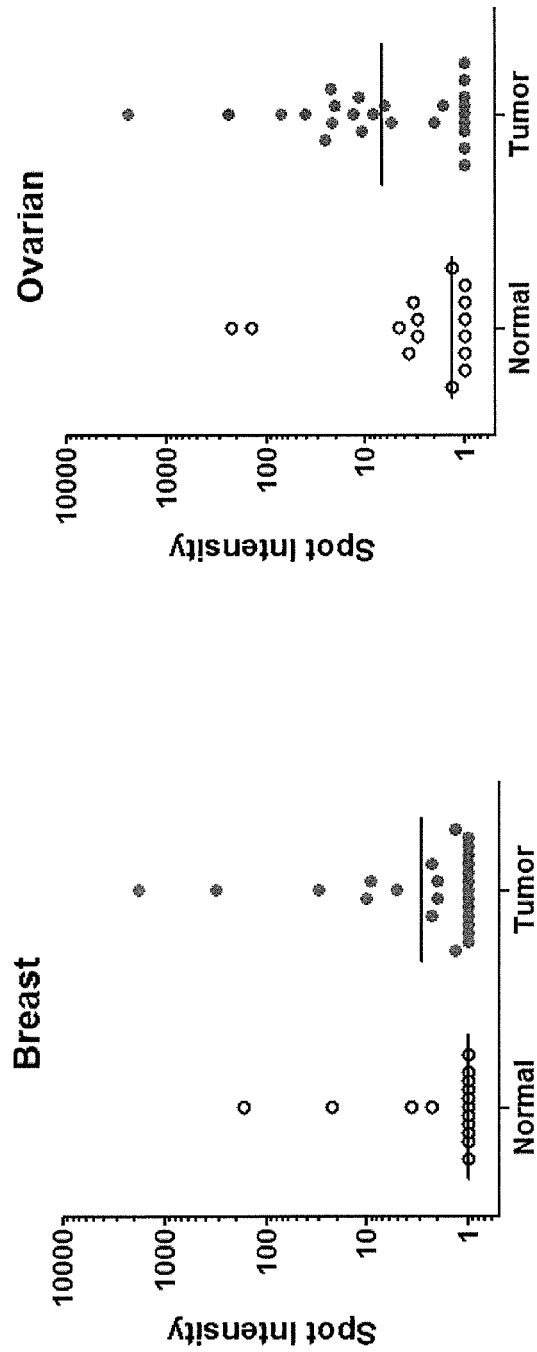

Results of such assays indicate that expression of the PTK7 protein is upregulated in a subset of melanoma, non-small cell lung carcinoma (NSCLC), small cell lung carcinoma (SCLC), colorectal, pancreatic, breast and ovarian cancer patient-derived tumor samples. Exemplary data from these assays for selected tumors are shown in FIGS. 9A-9D. More specifically, FIG. 9A shows that PTK7 protein expression appears significantly elevated in a subset of colorectal tumor specimens; especially in patients with Stage IV disease when compared to normal adjacent tissue or tumor tissue from specimens obtained from earlier stages of disease. As shown in FIG. 9B PTK7 protein expression was also elevated in most neuroendocrine pancreatic tumors, as well as in subsets of patients with breast (FIG. 9C) and ovarian (FIG. 9D) cancer, respectively. Data was generated as described above and represented as average pixel intensity per spot (spot intensity). The horizontal black bar in each sample represents the mean for specimens in each respective category.

These data support the observations in above Examples that PTK7 overexpression is associated with TIC and/or TPC in colorectal cancer, and may be involved in proliferation and/or survival. In view of the forgoing Examples showing: a) PTK7 gene expression is predominantly associated with the TPC cell subpopulation in colorectal cancer and the TG cell subpopulation in pancreatic tumors; b) that PTK7 protein expression is higher on the TIC cell subpopulation; c) PTK7 protein expression is elevated in whole tumor specimens from late stage colorectal cancer; and d) the general observation is that TIC are more frequent in late stage tumors, it appears that PTK7 is associated with those cells underlying tumor growth, resistance to therapy and tumor recurrence, thus reinforcing the proposition that PTK7 may play in integral role in supporting TPC and/or TIC in the aforementioned tumors.

In view of these results expression of PTK7 was assessed within the non-tumorigenic (NTG) and cancer stem cell (CSC) populations of human breast (BR), lung (LU), ovary (OV), colon (CR), and kidney (KDY) tumor xenografts using flow cytometry. As set forth in Example 1 NTG and CSC-enriched populations may be identified, monitored and enriched using phenotypic markers $CD46^{-/lo}CD324^-$ and $CD46^{hi}CD324^+$, respectively. Accordingly, human tumor xenografts from immunocompromised mice were harvested, dissociated, and co-stained with commercially available anti-CD46, anti-CD324, and anti-PTK7 (Miltenyi Biotech) antibodies before assessing PTK7 expression using flow cytometry in the $CD46^{-/lo}CD324^-$ NTG population and $CD46^{hi}CD324^+$ CSC population. More specifically, flow cytometry analysis was conducted using standard techniques on a BD FACSCanto™ II flow cytometer (BD Biosciences) with isotype-stained and fluorescence minus one (FMO) controls employed to confirm staining specificity.

Figure 9E:
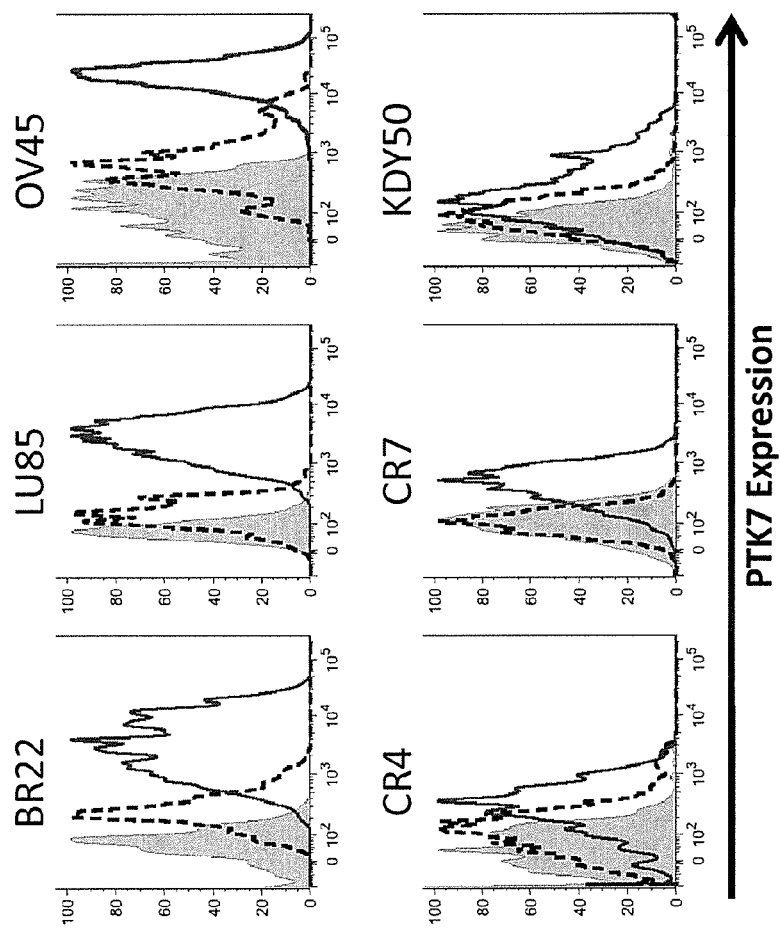

The results for exemplary breast, lung, ovarian, colorectal and kidney tumors samples are shown in FIG. 9E where the isotype control is marked in solid grey, the NTG cell population is represented by the hatched line and the CSC-enriched population is shown by the solid line. It will be appreciated that, whereas surface PTK7 staining was relatively low in the NTG populations of each of these tumors, surface PTK7 staining was markedly elevated in the CSC-enriched populations. These results have since been confirmed (data not shown) using a number of the disclosed modulators and is representative of more than twenty five unique NTX lines tested (comprising various solid tumors).

The correlated expression pattern of PTK7 with other surface markers of TPC was further delineated functionally in tumorigenicity studies in NSCLC and ovarian cancer. $PTK7^-$ and $PTK7^+$ tumor populations were isolated from dissociated human tumor xenografts stained as described above by fluorescence activated cell sorting (FACS), and equivalent numbers were mixed with Matrigel (BD Biosciences) and subcutaneously transplanted into NOD/SCID recipient mice. Whereas $PTK7^-$ cells failed to produce tumors in recipient mice, $PTK7^+$ tumor cells consistently produced rapidly growing tumors with both NSCLC and ovarian carcinomas. Thus, in accordance with the teachings herein PTK7 functionally delineates TPC in ovarian cancer and NSCLC and provides further evidence as to the utility of the disclosed modulators as diagnostic and theragnostic agents.

Example 12

Selected PTK7 Modulators are Internalized by K562 and G401 Cells

PTK7 modulators from hybridomas that were generated by immunizing mice as described above were screened for their ability to internalize in K562 and G401 cells.

In this regard K562 cells at a starting concentration of $10^6$/mL (single cell suspension) were blocked with Human TruStain (Biolegend, Inc., 422302) for 10 minutes at room temperature. Cells were diluted to $50 \times 10^3$ cells per reaction. Duplicate samples were stained for 30 minutes on ice with antibody supernatant for a final volume of 50 uL, then washed with FACS staining medium (FSM; 2% fetal bovine serum/Hank's buffered saline solution/25 mM HEPES [pH7.4]; Mediatech, Inc.) to remove unbound antibody. This was followed by a second stain with donkey anti-mouse Alexa647 (Life Technologies) for 30 minutes on ice. Cells were then washed again to remove unbound antibody and samples were resuspended in internalization medium (2% fetal bovine serum/Iscove's Modified Dulbecco's Medium) and incubated in 5% CO2 @ 37° C. (or 4° C. for the control) for 1 hour to allow internalization. The reaction was stopped by transferring samples to ice and adding ice cold FSM. To remove any antibody that did not internalize and remained on the cell surface, samples were treated with low pH phosphate buffered saline (PBS [pH2.0]) for 10 minutes on ice. Following this "acid-strip" step, samples were washed extensively with FSM, resuspended in 150 uL of FSM containing 2 ug/ml of DAPI (Life Technologies) and analyzed on a BD FACS Canto flow cytometer. Any increase in fluorescence over that detected from cells incubated on ice in this experiment resulted from the ability of antibody internalization, which protects the fluorescent molecule from being stripped off the cell surface during the low pH phosphate buffer treatment. All incubations were performed in FACS staining medium unless otherwise stated.

When screening individual clones of PTK7 antibody-containing hybridoma supernatants using the acid strip protocol described above, several supernatants showed a positive shift in fluorescence vs. unstained cells and IgG negative control antibodies (FIGS. 10A and 10B). Antibody internalization was observed with several anti-PTK7 antibodies, as demonstrated by the ability of these antibodies to protect the Alexa647 secondary antibody from acid stripping and resulting in a shift in fluorescence to the right. Antibody clone SC6.10.2 (i.e., H10 in FIG. 10C) is an example of typical internalization ability by anti-PTK7 antibodies with this activity. Compared to the IgG controls, approximately 15% of the PTK7 antibody-containing supernatants (4 of 27) induced internalization. Using the K562 cells this data demonstrates that a subset of antibodies able to bind PTK7 ECD engage the antigen as it is presented on cells and are able to internalize efficiently.

Figure 10D:
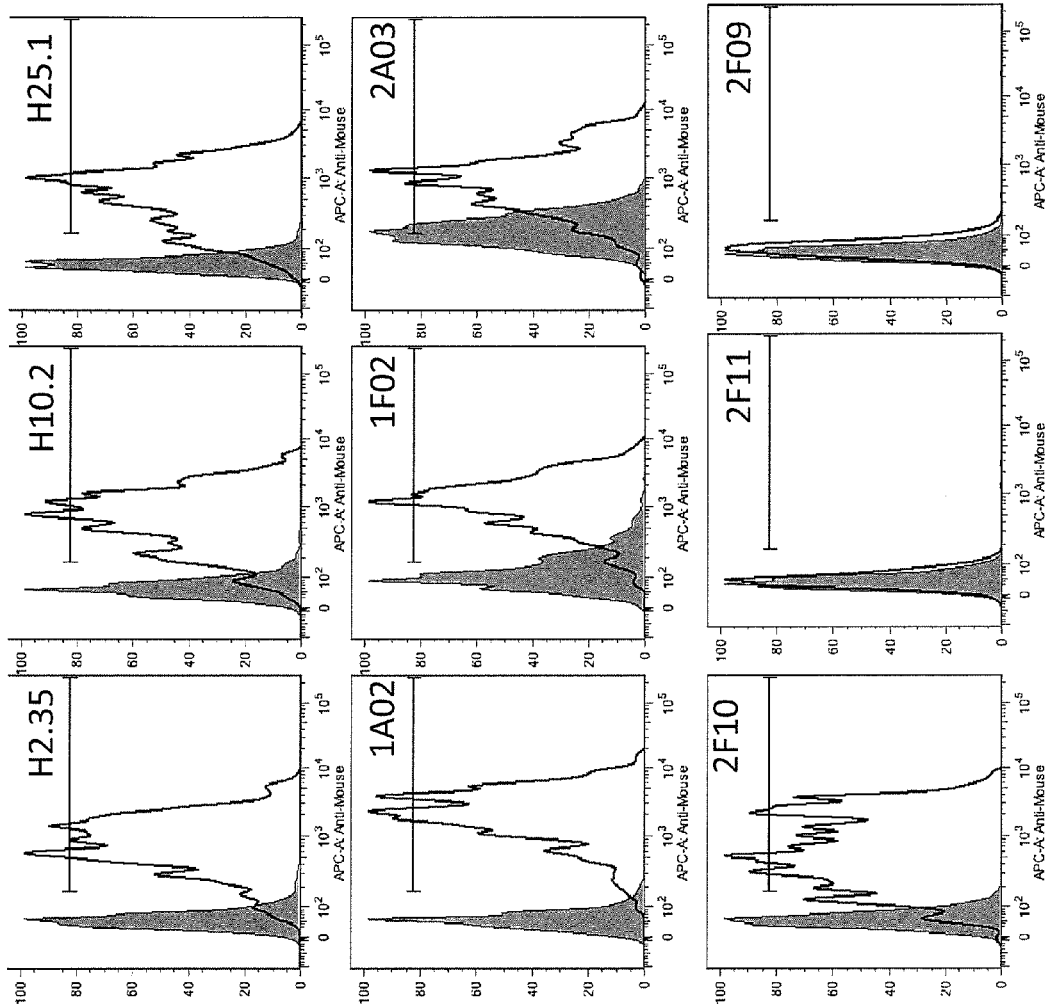

Further evidence indicating that the disclosed modulators can mediate internalization in various exemplary cell lines is shown in FIG. 10D. More specifically a glioblastoma cell line (G401 Wilm's Tumor cells) was found to express high levels of PTK7 (data not shown) suggesting that this cell line may be may be more sensitive under selected assay conditions and therefore able to more effectively identify modulators able to induce internalization. Generally using these cells with the aforementioned acid-strip procedure 170 unique hybridoma supernatants from Example 7 were screened to determine if they contained internalizing antibodies. Purified antibodies SC6.2.35, SC6.10.2 and SC6.25.3 (denoted H2.35, H10.2 and H25.3 in FIG. 10D) which were identified in the above mentioned screen were used as positive controls (FIG. 10D). The internalization capacity of modulators present in six exemplary supernatants (identified by well designation) are shown immediately below the controls. With this more refined assay the data shows that numerous modulators provided by the immunization procedure discussed above were able to bind PTK7 and internalize (as evidenced by 1A02, 1F02, 2A03 and 2F10) although not every clone (2F11 and 2F09) possessed this ability.

Figure 10E:
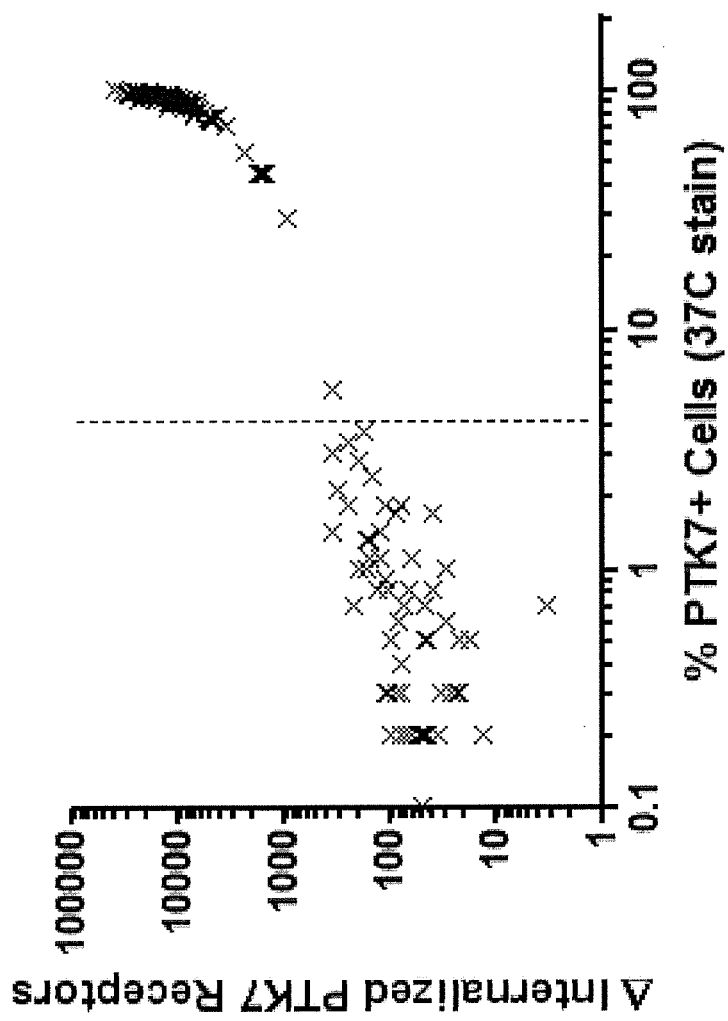

In yet a further demonstration as to the properties of the disclosed modulators, all screened antibodies that bound to the G401 cells in a significant way were found to internalize to some extent (FIG. 10E). As represented by the dashed line in FIG. 10E positive cell staining was set to 4% based on mouse isotype control antibodies which showed nonspecific staining of 0-3% of cells. Mean fluorescence intensities of G401 cells stained with each antibody were measured after the acid-strip step (i.e., post internalization) at 37° C. and 4° C. and interpolated to relative receptor numbers per cells using 8-peak Rainbow beads (BD Spherotech #559123) which contain known numbers of fluorescent molecules. Numbers of internalized receptors were calculated by subtracting receptor numbers obtained from samples undergoing the internalization step at the 4° C. (control) from the one at 37° C. It was noted that PTK7 specific antibodies are heterogeneous in their ability to induce internalization given a ten-fold difference in numbers of internalized receptors independent of the level of cell binding (upper right quadrant of FIG. 10E).

Example 13

PTK7 Modulators Facilitate Delivery of Cytotoxic Agents

Targeting of a cytotoxic drug stably linked to an antibody represents an empowered antibody approach that might have great therapeutic benefit for patients with solid tumors. To determine whether the internalizing PTK7-specific antibodies described above were able to mediate the delivery of a cytotoxic agent to live cells, an in vitro cell killing assay was performed wherein streptavidin conjugated to the ribosome-inactivating protein saporin (Advanced Targeting Systems) was bound to biotinylated PTK7 antibodies, and the ability of these saporin complexes to internalize and kill cells was measured 72 hours later by measuring cell viability.

Specifically, $1 \times 10^4$ G401 Wilm's Tumor cells per well were plated in wells of a 96-well plate. PTK7 modulators in the form of anti-PTK7 antibodies as described above were purified from supernatants, biotinylated and then diluted to 20 mg/mL. An aliquot of each antibody was mixed 1:1 with streptavidin-ZAP (Advanced Targeting Systems), vortexed for 5 seconds and then incubated at room temperature for 1 hour. Three additional serial 10-fold dilutions of the antibody-saporin complexes were then made and 50 uL of each mixture, respectively, was added to G401 cell containing wells. The cell/antibody-saporin mixture was then incubated at 37° C./5% $CO_2$ for 24 hours. Following this incubation, cells were spun down in round-bottom 96-well plates, supernatant was removed, and 100 uL of fresh culture medium was added to each well. The cells were then incubated for an additional 72 hours before viable cell numbers were enumerated using CellTiter-Glo (Promega Inc.) per the manufacturer's protocol.

Figure 11A:
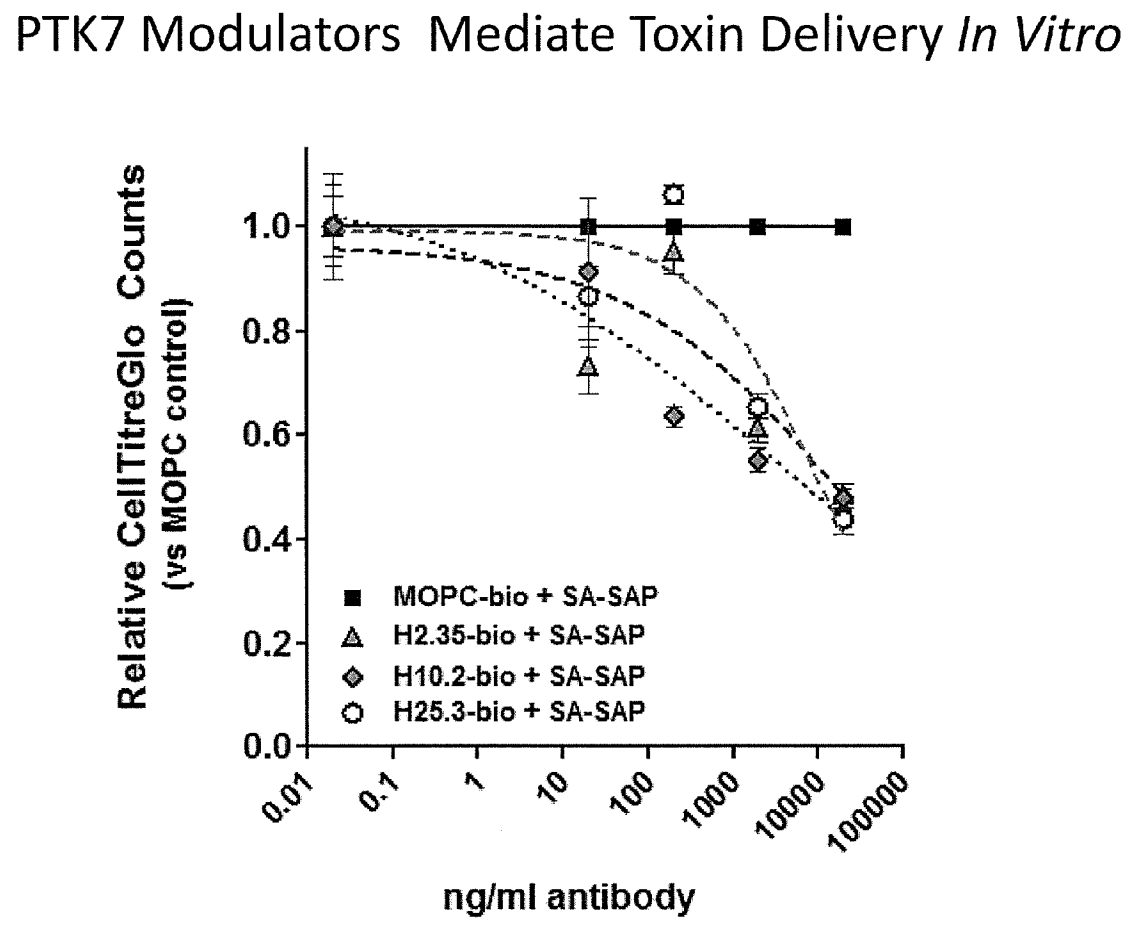

Using the cell killing assay described above, exemplary internalizing PTK7 modulators comprising antibodies from clones SC6.2.35, SC6.10.2 and SC6.25.3 (denoted H2.35, H10.2 and H25.3 in FIG. 11A) were shown to mediate saporin toxin internalization and cell killing. More particularly FIG. 11A clearly demonstrate the ability of these modulators effect cell killing through PTK7 mediated internalization as opposed to a non-specific isotype control antibody (i.e. MOPC). Such data demonstrates that the disclosed modulators are immunospecific for PTK7 and are effectively able to mediate the delivery of a cytotoxic payload and kill PTK7 positive cells through cell surface association.

In an extension of the aforementioned killing assay the delivery of a cytotoxic payload via PTK7 specific antibodies was demonstrated using four more exemplary modulators (SC6.23, SC6.41, SC6.51 and SC6.58) with SC6.10.2 used as a positive control. To this end the following cell types were plated into 96 well tissue culture plates in their respective culture media (500 cells per well) one day before the addition of antibodies and toxin: G401 Wilm's Tumor cells, HEK293T engineered using retroviral transduction to express PTK7 molecules on their cell surface (herein denoted as 293.PTK7 cells) and HEK293T which function as a control.

For this assay purified PTK7 modulators at various concentrations were added to the wells containing the plated cells. Following addition of the modulators a fixed amount of anti-mouse IgG Fab fragment covalently linked to saporin (Fab-ZAP, Advanced Targeting Systems, #IT-48) at a concentration of 4 nM was added to the wells and the cultures were incubated for 72 hours. Viable cell numbers were determined as described above using CellTiter-Glo. Raw luminescence counts using cultures containing cells with the saporin-Fab fragment (but no modulator) were set as 100% reference values and all other counts calculated accordingly (referred to as "Normalized RLU").

Using this assay, it was demonstrated that all tested PTK7 antibodies (but not isotype control antibodies) were able to kill target cells (FIGS. 11B-11D) where FIGS. 11B, 11C and 11D illustrate the modulator impact on G401 cells, 293.PTK7 cells and HEK293T cells respectively. It will be appreciated that modulator mediated internalization and killing is dependent on cell type (compare FIGS. 11B—G401 cells and 11D—HEK293T cells), expression level of PTK7 on the target cells (compare FIG. 11C—293.PTK7 cells and 11D—HEK293T cells) and the intrinsic ability of the various modulators to internalize. The assay further demonstrates that internalization primarily occurs because of binding of the PTK7-specific antibody to the cell surface without the need for additional crosslinking. Based on the data used to generate the dose response curves of FIGS. 11B-11D (and similarly derived values for additional modulators—not shown) the half-maximal effective concentration ("EC50") was determined for each of the tested modulators/target cell combination. More specifically TABLE 5 immediately below lists the EC50 (in pM) for thirteen modulators as determined for each of the three target cells using the assay described immediately above. ND indicates that value was not determined.

TABLE 5

PTK7 Modulator Mediated Delivery of a Cytotoxic Agent

| Modulator | G401 Cells | 293.PTK7 Cells | HEK293T Cells |
| --- | --- | --- | --- |
| IgG2b Control | No killing | No killing | No killing |
| SC6.2.35 | 1.1 | 0.65 | 0.45 |
| SC6.10.2 | 4.7 | 1.1 | 156 |
| SC6.25.1 | 223 | 10.9 | 97.6 |
| SC6.8 | 2.8 | 3.5 | ND |
| SC6.21 | ~200 | 30.6 | ND |
| SC6.23 | 2.6 | 1.1 | 3.0 |
| SC6.24 | 6.7 | 2.3 | 11.0 |
| SC6.30 | 314 | 19.7 | ND |
| SC6.41 | 2.6 | 2.3 | 5.7 |
| SC6.51 | 105 | 12.6 | 8100 |
| SC6.53 | 4.5 | 1.9 | 14.2 |
| SC6.55 | 8.8 | 4.2 | ND |
| SC6.58 | 35.1 | 10.4 | 86.8 |

While some variation as to killing was noted among the individual modulators there were some general trends that are evident from the data in TABLE 5. In this regard the modulators were generally more effective in mediating cell killing of the engineered PTK overexpressing 293 cells than either the G401 cells or wild type 293 cells. Of interest, many of the tested modulators were relatively effective at mediating the killing of non-engineered G401 tumor cells that are known to express PTK7 on the cell surface. Such reproducible results are indicative as to the therapeutic potential of a broad range of internalizing PTK7 modulators as exemplified herein.

Example 14

PTK7 Modulators Facilitate Delivery of Cytotoxic Agents to Tumorigenic Cells

To corroborate the results of the previous Example and demonstrate that PTK7 modulators can mediate toxin internalization and cell killing of primary human tumor cells, mouse lineage-depleted NTX cells (i.e. human tumor cells propagated as low-passage xenografts in immunocompromised mice) were plated and subsequently exposed to anti-PTK7 antibodies and Fab-ZAP.

Specifically, NTX tumors derived from lung (LU), ovarian (OV) cancer and melanoma (SK) patients were dissociated into a single cell suspension and plated on Primaria™ plates (BD Biosciences) in growth factor supplemented serum free media using common art recognized techniques that favor cancer stem cell proliferation. After 3-5 days of culture at 37° C./5% $CO_2$/5% $O_2$ the cells were contacted with an isotype control (IgG2a) antibody or one of three murine anti-PTK7 antibodies (SC6.2.35, SC6.10.2, or SC6.25.1 at 0.1 nM; − labeled SC6.H2, SC6.H10 and SC6.H25), and Fab-ZAP (at 40 nM) as generally set forth in the previous Example. Modulator-mediated saporin cytotoxicity was then assessed by quantifying the remaining number of cells using CellTiter Glo as per the manufacturer's instructions 5-7 days later. The results were normalized to untreated cells.

Figure 12:
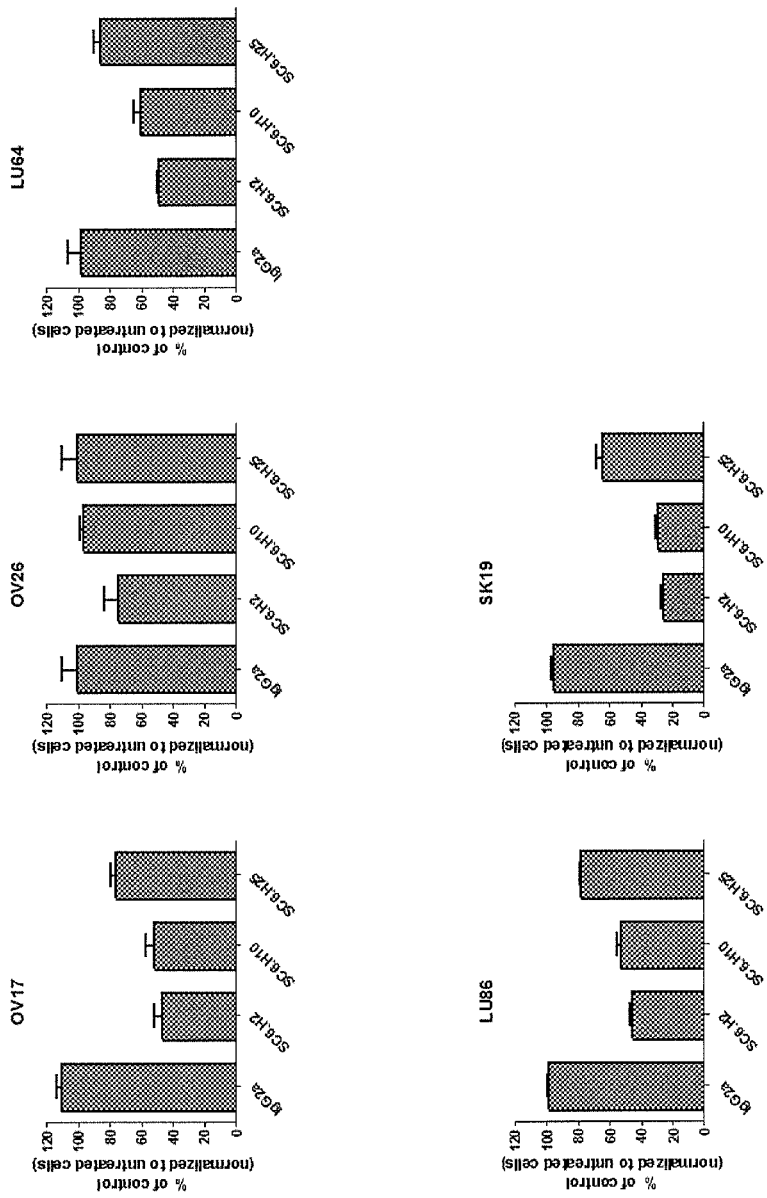
FIG. 12 evidences the ability of three exemplary PTK7 modulators to immunospecifically mediate the delivery of cytotoxic agents and thereby reduce tumor cell viability in a variety NTX tumor cell lines.

As seen in FIG. 12 exposure to each of the tested modulators (though not the isotype control) resulted in reduced viable cell numbers for all tumor types. In this respect it will be appreciated that the amount of cell killing is apparently dependant on the specific tumor cell line as well as on the particular modulator. These data indicate that the modulators of the instant invention can immunospecifically associate with various antigen expressing cells from various tumor types, internalize and thereby mediate the killing of the constituent cells. Moreover, the ability of the disclosed modulators to do this with respect to NTX tumor cell lines cultured under conditions that favor cancer stem cell proliferation as previously described is strongly indicative of their ability to selectively eliminate cancer stem cells.

Example 15

PTK7 Modulators Reduce Cancer Stem Cell Tumorigenicity

To further confirm the ability of the disclosed modulators to reduce the frequency of cancer stem cells and impact their tumorigenic potential, NTX breast tumor cells were treated with SC6.2.35 and subsequently implanted into immunocompromised mice.

In this regard two breast cancer patient-derived NTX tumors (BR13 and BR64) were dissociated and the human tumor cells were cultured under conditions known in the art to maintain tumorigenic cells, and treated with a PTK7 modulator (and isotype control) and Fab-ZAP as set forth in the previous Example. Cytotoxicity was then measured in terms of cell viability using Cell Titer Glo per the manufacturer's instructions fourteen days post treatment. Again the results were normalized to untreated cells.

As seen in FIGS. 13A and 13B respectively the breast tumor cells derived from BR13 (FIG. 13A) and from BR64 (FIG. 13B) were largely eliminated through the PTK7 modulator mediated immunospecific association and internalization of the saporin cytotoxic agent. More specifically treatment with the PTK7 modulator SC6.2.35 (SC6.H2) at 0.2 nM resulted in the elimination of approximately 70-80% of the cells whereas the IgG2a control treated cells were largely unaffected. The findings are consistent with results seen in Example 13 and further demonstrate the broad applicability of the instant invention based on the ability of the disclosed modulators to eliminate tumor perpetuating cells derived from a variety of tumors.

In order to confirm that the disclosed modulators eliminate tumor initiating cells, the treated preparations from the two breast cancer cell lines were transplanted into mice to determine whether tumor initiating cells remained alive. More specifically, cells from triplicate wells were each harvested independently, washed in PBS containing 2% BSA, resuspended in 100 ul and then transplanted into individual immunocompromised mice generally using the procedures set forth in Example 1. Mice were monitored weekly for tumor growth and any tumors that arose were measured to calculate their volume. Only mice transplanted with NTX BR13 and BR64 cells treated with the IgG control developed tumors whereas those transplanted with cells contacted with PTK7 modulators did not. These results demonstrate that TIC are eliminated by PTK7 modulators able to mediate toxin deliver (FIG. 13C).

A review of the data shows that the implantation of live cells remaining after treatment of either breast cancer cell line with PTK7 modulator and saporin does not result in the formation of tumors. Conversely, the control cells from both breast cancer cell lines (i.e., those that were treated with the isotype control antibody) were able to reinitiate tumor growth upon implantation. In particular, two of the three mice implanted with each control cell line (BR22 and BR64) developed measurable tumors indicating that the implanted cells included tumor perpetuating cells. More significantly, the inability of the modulator treated cells to form tumors strongly implies that the cells that were implanted did not include tumor perpetuating cells. That is, it is likely that treatment with the PTK7 modulator/saporin combination selectively targeted and eliminated tumor perpetuating cells in accordance with the instant invention. In any event these data demonstrate that treatment with the disclosed modulators is effective at reducing the tumorigenic potential of tumor cells.

Example 16

Humanized PTK7 Modulators Mediate the Delivery of Cytotoxic Agents

As preferred embodiments of the present invention will likely employ humanized PTK7 modulators in a therapeutic setting, work was performed to demonstrate that humanized anti-PTK7 antibodies (fabricated as set forth in Example 8) function as effective mediators of cell killing through delivery of cytotoxic agents.

More particularly, three exemplary humanized PTK7 modulators (hSC6.23, hSC6.58 and hSC6.24) were employed to mediate the introduction of a cytotoxic payload and eliminate tumorigenic cells in accordance with the teachings herein. Generally using the protocol set forth in Example 13 above HEK293 cells engineered to express PTK7 (i.e. 293.PTK7 cells) were exposed to different concentrations of the selected modulators and saporin linked to an anti-human Fab (Fab-ZAP human, Advanced Targeting Systems). Following incubation the cells were washed and modulator-mediated saporin cytotoxicity was then assessed by quantifying the remaining number of cells using CellTiter Glo as per the manufacturer's instructions 5-7 days later. The results were normalized to untreated cells and are graphically presented in FIG. 14.

Figure 14:
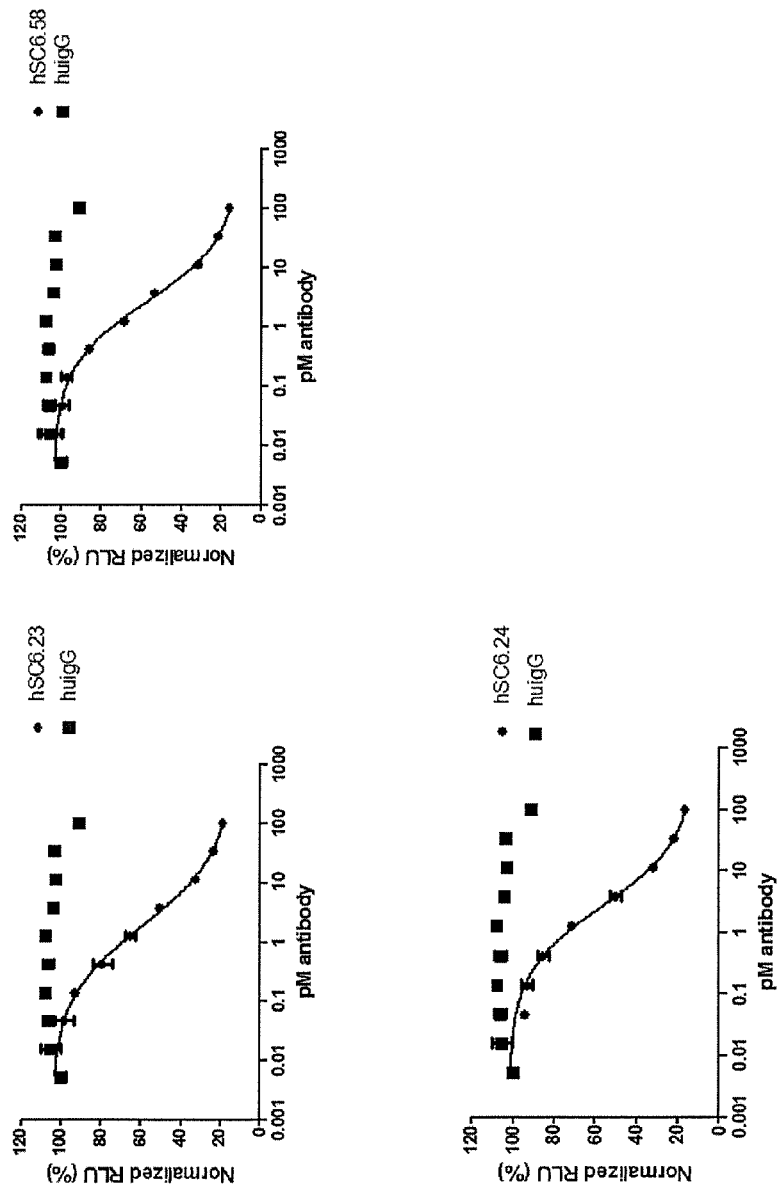
FIG. 14 demonstrates the capability of exemplary humanized PTK7 modulators of the instant invention to effectively mediate the immunospecific delivery and internalization of cytotoxic agents to PTK7 expressing cells.

Examination of the curves set forth in FIG. 14 shows that all three of the tested PTK7 modulators were very effective at inducing internalization of the cytotoxic payload reducing cell viability. In this respect each of the modulators provided a 50% reduction in cell viability at a concentration between 1 and 10 µM and a reduction of greater than 80% in cell viability at a concentration of 100 µM. Again, in accordance with the instance disclosure these data are indicative of highly effective modulators that can immunospecifically mediate the delivery of cytotoxic agents to selected cell populations.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. An antibody comprising a chimeric, CDR-grafted, or humanized antibody, or fragment thereof, which specifically binds to PTK7, comprising:
   (a) CDR-L1, CDR-L2 and CDR-L3 of a light chain variable region set forth as SEQ ID NO: 62 and CDR-H1, CDR-H2 and CDR-H3 of a heavy chain variable region set forth as SEQ ID NO: 63; or
   (b) CDR-L1, CDR-L2 and CDR-L3 of a light chain variable region set forth as SEQ ID NO: 64 and CDR-H1, CDR-H2 and CDR-H3 of a heavy chain variable region set forth as SEQ ID NO: 65.

2. The antibody of claim 1, which is a neutralizing antibody.

3. The antibody of claim 1, which is an internalizing antibody.

4. The antibody of claim 1, which specifically binds to a PTK7 isoform selected from the group consisting of isoform a, isoform b, isoform c, and isoform d.

5. The antibody of claim 4, which specifically binds to PTK7 isoform a.

6. The antibody of claim 1 comprising:
   (a) a heavy chain variable region comprising an amino acid sequence TSNMGVG (SEQ ID NO: 170) for CDR1, an amino acid sequence HIWWDDDKYYSPSLKS (SEQ ID NO: 171) for CDR2, and an amino acid sequence SNYGYAWFAY (SEQ ID NO: 172) for CDR3; and
   (b) a light chain variable region comprising an amino acid sequence KASQDIYPYLN (SEQ ID NO: 173) for CDR1, an amino acid sequence RTNRLLD (SEQ ID NO: 174) for CDR2, and an amino acid sequence LQYDEFPLT (SEQ ID NO: 175) for CDR3.

7. The antibody of claim 1 comprising a heavy chain variable region having an amino acid sequence that is at least 60% identical to SEQ ID NO: 63 and a light chain variable region having an amino acid sequence that is at least 60% identical to SEQ ID NO: 62.

8. The antibody of claim 7 comprising a heavy chain variable region set forth as SEQ ID NO: 63 and a light chain variable region set forth as SEQ ID NO: 62.

9. The antibody of claim 1 comprising:
   (a) a heavy chain variable region comprising an amino acid sequence DYAVH (SEQ ID NO: 176) for CDR1, an amino acid sequence VISTYNDYTYNNQDFKG (SEQ ID NO: 177) for CDR2, and an amino acid sequence GNSYFYALDY (SEQ ID NO: 178) for CDR3; and
   (b) a light chain variable region comprising an amino acid sequence RASESVDSYGKSFMH (SEQ ID NO: 179) for CDR1, an amino acid sequence RASNLES (SEQ ID NO: 180) for CDR2, and an amino acid sequence QQSNEDPWT (SEQ ID NO: 181) for CDR3.

10. The antibody of claim 1 comprising a heavy chain variable region having an amino acid sequence that is at least 60% identical to SEQ ID NO: 65 and a light chain variable region having an amino acid sequence that is at least 60% identical to SEQ ID NO: 64.

11. The antibody of claim 10 comprising a heavy chain variable region set forth as SEQ ID NO: 65 and a light chain variable region set forth as SEQ ID NO: 64.

12. The antibody of claim 1 comprising a heavy chain variable region set forth as SEQ ID NO: 63 or 65.

13. The antibody of claim 1 comprising a light chain variable region set forth as SEQ ID NO: 62 or 64.

14. The antibody of claim 1 comprising:
(a) a heavy chain variable region set forth as SEQ ID NO: 63, and a light chain variable region set forth as SEQ ID NO: 62; or
(b) a heavy chain variable region set forth as SEQ ID NO: 65, and a light chain variable region set forth as SEQ ID NO: 64.

15. The antibody of claim 1, which is conjugated, linked or otherwise associated with a cytotoxic agent.

16. The antibody of claim 8, which is conjugated, linked or otherwise associated with a cytotoxic agent.

17. The antibody of claim 11, which is conjugated, linked or otherwise associated with a cytotoxic agent.

18. A pharmaceutical composition comprising the antibody of claim 1.

19. A pharmaceutical composition comprising the antibody of claim 8.

20. A pharmaceutical composition comprising the antibody of claim 11.

21. An antibody conjugate comprising a chimeric, CDR-grafted, or humanized antibody, or a fragment thereof, which specifically binds to PTK7, which antibody is conjugated, linked or otherwise associated with a cytotoxic agent, wherein the antibody conjugate comprises:
(a) a light chain variable region comprising CDR-L1, CDR-L2 and CDR-L3 of SEQ ID NO: 62 and a heavy chain variable region comprising CDR-H1, CDR-H2 and CDR-H3 of SEQ ID NO: 63; or
(b) a light chain variable region comprising CDR-L1, CDR-L2 and CDR-L3_of SEQ ID NO: 64 and a heavy chain variable region comprising CDR-H1, CDR-H2 and CDR-H3 of SEQ ID NO: 65.

22. A pharmaceutical composition comprising the antibody conjugate of claim 21.

23. A nucleic acid encoding a heavy chain variable region set forth as SEQ ID NO: 63 or 65, or a light chain variable region set forth as SEQ ID NO: 62 or 64.

24. A vector comprising the nucleic acid of claim 23.

25. A host cell comprising the nucleic acid of claim 23.

26. The antibody of claim 1 comprising:
(a) a heavy chain variable region comprising an amino acid sequence GFSLSTSNM (SEQ ID NO: 182) for CDR1, an amino acid sequence WWDDD (SEQ ID NO: 183) for CDR2, and an amino acid sequence SNYGYAWFAY (SEQ ID NO: 172) for CDR3; and
(b) a light chain variable region comprising an amino acid sequence KASQDIYPYLN (SEQ ID NO: 173) for CDR1, an amino acid sequence RTNRLLD (SEQ ID NO: 174) for CDR2, and an amino acid sequence LQYDEFPLT (SEQ ID NO: 175) for CDR3.

27. The antibody of claim 1 comprising:
(a) a heavy chain variable region comprising an amino acid sequence GYTFTDY (SEQ ID NO: 184) for CDR1, an amino acid sequence STYNDY (SEQ ID NO: 185) for CDR2, and an amino acid sequence GNSYFYALDY (SEQ ID NO: 178) for CDR3; and
(b) a light chain variable region comprising an amino acid sequence RASESVDSYGKSFMH (SEQ ID NO: 179) for CDR1, an amino acid sequence RASNLES (SEQ ID NO: 180) for CDR2, and an amino acid sequence QQSNEDPWT (SEQ ID NO: 181) for CDR3.

28. The antibody of claim 1 comprising:
(a) a heavy chain variable region comprising an amino acid sequence STSNMGVG (SEQ ID NO: 186) for CDR1, an amino acid sequence WLAHIWWDDDKY (SEQ ID NO: 187) for CDR2, and an amino acid sequence VRSNYGYAWFA (SEQ ID NO: 188) for CDR3; and
(b) a light chain variable region comprising an amino acid sequence YPYLNWF (SEQ ID NO: 189) for CDR1,an amino acid sequence TLIYRTNRLL (SEQ ID NO: 190) for CDR2, and an amino acid sequence LQYDEFPL (SEQ ID NO: 191) for CDR3.

29. The antibody of claim 1 comprising:
(a) a heavy chain variable region comprising an amino acid sequence TDYAVH (SEQ ID NO: 192) for CDR1, an amino acid sequence WIGVISTYNDYTY (SEQ ID NO: 193) for CDR2, and an amino acid sequence ARGNSYFYALD (SEQ ID NO: 194) for CDR3; and
(b) a light chain variable region comprising an amino acid sequence DSYGKSFMHWY (SEQ ID NO: 195) for CDR1, an amino acid sequence LLIYRASNLE (SEQ ID NO: 196) for CDR2, and an amino acid sequence QQSNEDPW (SEQ ID NO: 197) for CDR3.

* * * * *

SEQUENCE LISTING

```
<160> NUMBER OF SEQ ID NOS: 197

<210> SEQ ID NO 1
<211> LENGTH: 4249
<212> TYPE: DNA
<213> ORGANISM: Homo sapiens

<400> SEQUENCE: 1
gcggcgcgcg gggactcgga ggtactgggc gcgcgcggct ccggctcggg acgcctcggg      60
acgcctcggg gtcgggctcc ggctgcggct gctgctgcgg cgcccgcgct ccggtgcgct     120
ccgcctcctg tgcccgccgc ggagcgcagt ctgcgcgccc gccgtgcgcc ctcagctcct     180
tttcctgagc ccgccgcgat gggagctgcg cggggatccc cggccagacc ccgccggttg     240
cctctgctca gcgtcctgct gctgccgctg ctgggcggta cccagacagc cattgtcttc     300
atcaagcagc cgtcctccca ggatgcactg cagggcgcc gggcgctgct tcgctgtgag     360
gttgaggctc cgggcccggt acatgtgtac tggctgctcg atgggcccc tgtccaggac     420 acggagcggc gtttcgccca gggcagcagc ctgagctttg cagctgtgga ccggctgcag     480
```

```
gactctggca ccttccagtg tgtggctcgg gatgatgtca ctggagaaga agcccgcagt      540
gccaacgcct ccttcaacat caaatggatt gaggcaggtc ctgtggtcct gaagcatcca      600
gcctcggaag ctgagatcca gccacagacc caggtcacac ttcgttgcca cattgatggg      660
caccctcggc ccacctacca atggttccga gatgggaccc ccctttctga tggtcagagc      720
aaccacacag tcagcagcaa ggagcggaac ctgacgctcc ggccagctgg tcctgagcat      780
agtgggctgt attcctgctg cgcccacagt gcttttggcc aggcttgcag cagcagaac       840 ttcaccttga gcattgctga tgaaagcttt gccagggtgg tgctggcacc ccaggacgtg      900
gtagtagcga ggtatgagga ggccatgttc cattgccagt tctcagccca gccaccccg       960 agcctgcagt ggctctttga ggatgagact cccatcacta accgcagtcg cccccacac     1020 ctccgcagag ccacagtgtt tgccaacggg tctctgctgc tgacccaggt ccggccacgc    1080
aatgcaggga tctaccgctg cattggccag gggcagaggg gcccacccat catcctggaa    1140
gccacacttc acctagcaga gattgaagac atgccgctat ttgagccacg ggtgtttaca    1200 gctgcagcg aggagcgtgt gacctgcctt cccccaagg gtctgccaga gcccagcgtg      1260
tggtgggagc acgcgggagt ccggctgccc acccatggca gggtctacca gaagggccac    1320
gagctggtgt tggccaatat tgctgaaagt gatgctggtg tctacacctg ccacgcggcc    1380
aacctggctg gtcagcggag acaggatgtc aacatcactg tggccactgt gccctcctgg    1440
ctgaagaagc cccaagacag ccagctggag gagggcaaac ccggctactt ggattgcctg    1500
acccaggcca caccaaaacc tacagttgtc tggtacagaa accagatgct catctcagag    1560
gactcacggt tcgaggtctt caagaatggg accttgcgca tcaacagcgt ggaggtgtat    1620
gatgggacat ggtaccgttg tatgagcagc accccagccg gcagcatcga ggcgcaagcc    1680
cgtgtccaag tgctggaaaa gctcaagttc acaccaccac cccagccaca gcagtgcatg    1740
gagtttgaca aggaggccac ggtgccctgt tcagccacag gccgagagaa gcccactatt    1800
aagtgggaac gggcagatgg gagcagcctc ccagagtggg tgacagacaa cgctgggacc    1860
ctgcattttg cccgggtgac tcgagatgac gctggcaact acacttgcat tgcctccaac    1920
gggccgcagg ccagattcg tgcccatgtc cagctcactg tggcagtttt tatcaccttc    1980
aaagtggaac cagagcgtac gactgtgtac cagggccaca cagccctact gcagtgcgag    2040
gcccaggggg accccaagcc gctgattcag tggaaaggca aggaccgcat cctggacccc    2100
accaagctgg acccaggat gcacatcttc cagaatggct ccctggtgat ccatgacgtg    2160
gcccctgagg actcaggccg ctacacctgc attgcaggca cagctgcaa catcaagcac    2220 acggaggccc ccctctatgt cgtggacaag cctgtgccgg aggagtcgga gggccctggc    2280
agccctcccc cctacaagat gatccagacc attgggttgt cggtgggtgc cgctgtggcc    2340
tacatcattg ccgtgctggg cctcatgttc tactgcaaga agcgctgcaa agccaagcgg    2400
ctgcagaagc agcccgaggg cgaggagcca gagatggaat gcctcaacgg tgggcctttg    2460
cagaacgggc agccctcagc agagatccaa gaagaagtgg ccttgaccag cttgggctcc    2520
ggccccgcgg ccaccaacaa cgccacagc acaagtgata agatgcactt cccacggtct    2580
agcctgcagc ccatcaccac gctggggaag agtgagtttg gggaggtgtt cctggcaaag    2640
gctcagggct tggaggaggg agtggcagag accctggtac ttgtgaagag cctgcagagc    2700
aaggatgagc agcagcagct ggacttccgg agggagttgg agatgtttgg gaagctgaac    2760
cacgccaacg tggtgcggct cctggggctg tgccggagg ctgagcccca ctacatggtg    2820
ctggaatatg tggatctggg agacctcaag cagttcctga ggatttccaa gagcaaggat    2880
```

-continued

```
gaaaaattga agtcacagcc cctcagcacc aagcagaagg tggccctatg cacccaggta      2940
gccctgggca tggagcacct gtccaacaac cgctttgtgc ataaggactt ggctgcgcgt      3000
aactgcctgg tcagtgccca gagacaagtg aaggtgtctg ccctgggcct cagcaaggat      3060
gtgtacaaca gtgagtacta ccacttccgc caggcctggg tgccgctgcg ctggatgtcc      3120
cccgaggcca tcctggaggg tgacttctct accaagtctg atgtctgggc cttcggtgtg      3180
ctgatgtggg aagtgtttac acatggagag atgccccatg gtgggcaggc agatgatgaa      3240
gtactggcag atttgcaggc tgggaaggct agacttcctc agcccgaggg ctgcccttcc      3300
aaactctatc ggctgatgca gcgctgctgg ggccctcagcc ccaaggaccg gccctccttc      3360
agtgagattg ccagcgccct gggagacagc accgtggaca gcaagccgtg aggagggagc      3420
ccgctcagga tggcctgggc aggggaggac atctctagag ggaagctcac agcatgatgg      3480
gcaagatccc tgtcctcctg ggccctgagg cccctgccct agtgcaacag gcattgctga      3540
ggtctgagca gggcctggcc tttcctcctc ttcctcaccc tcatcctttg ggaggctgac      3600
ttggacccaa actgggcgac tagggctttg agctggcag ttttccctgc cacctcttcc      3660
tctatcaggg acagtgtggg tgccacaggt aaccccaatt tctggccttc aacttctccc      3720
cttgaccggg tccaactctg ccactcatct gccaactttg cctggggagg gctaggcttg      3780
ggatgagctg ggtttgtggg gagttcctta atattctcaa gttctgggca cacagggtta      3840
atgagtctct tggcccactg gtcccacttg ggggtctaga ccaggattat agaggacaca      3900
gcaagtgagt cctccccact ctgggcttgt gcacactgac ccagacccac gtcttcccca      3960
cccttctctc ctttcctcat cctaagtgcc tggcagatga aggagttttc aggagctttt      4020
gacactatat aaaccgccct ttttgtatgc accacgggcg gctttatat gtaattgcag      4080 cgtggggtgg gtgggcatgg gaggtagggg tgggccctgg agatgaggag ggtgggccat      4140
ccttacccca cactttatt gttgtcgttt tttgtttgtt ttgttttttt gttttttgttt     4200 ttgtttttac actcgctgct ctcaataaat aagcctttt tacaacctg                  4249
```

<210> SEQ ID NO 2
<211> LENGTH: 1070
<212> TYPE: PRT
<213> ORGANISM: Homo sapiens

<400> SEQUENCE: 2

```
Met Gly Ala Ala Arg Gly Ser Pro Ala Arg Pro Arg Arg Leu Pro Leu
1               5                   10                  15

Leu Ser Val Leu Leu Pro Leu Leu Gly Gly Thr Gln Thr Ala Ile
            20                  25                  30

Val Phe Ile Lys Gln Pro Ser Ser Gln Asp Ala Leu Gln Gly Arg Arg
        35                  40                  45

Ala Leu Leu Arg Cys Glu Val Glu Ala Pro Gly Pro Val His Val Tyr
    50                  55                  60

Trp Leu Leu Asp Gly Ala Pro Val Gln Asp Thr Glu Arg Arg Phe Ala
65                  70                  75                  80

Gln Gly Ser Ser Leu Ser Phe Ala Ala Val Asp Arg Pro Gln Asp Ser
                85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125
```

-continued

```
Val Val Leu Lys His Pro Ala Ser Glu Ala Glu Ile Gln Pro Gln Thr
        130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
                180                 185                 190

Glu His Ser Gly Leu Tyr Ser Cys Cys Ala His Ser Ala Phe Gly Gln
                195                 200                 205

Ala Cys Ser Ser Gln Asn Phe Thr Leu Ser Ile Ala Asp Glu Ser Phe
210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Ser Leu
                245                 250                 255

Gln Trp Leu Phe Glu Asp Glu Thr Pro Ile Thr Asn Arg Ser Arg Pro
                260                 265                 270

Pro His Leu Arg Arg Ala Thr Val Phe Ala Asn Gly Ser Leu Leu Leu
    275                 280                 285

Thr Gln Val Arg Pro Arg Asn Ala Gly Ile Tyr Arg Cys Ile Gly Gln
    290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
                340                 345                 350

Ser Val Trp Trp Glu His Ala Gly Val Arg Leu Pro Thr His Gly Arg
    355                 360                 365

Val Tyr Gln Lys Gly His Glu Leu Val Leu Ala Asn Ile Ala Glu Ser
    370                 375                 380

Asp Ala Gly Val Tyr Thr Cys His Ala Ala Asn Leu Ala Gly Gln Arg
385                 390                 395                 400

Arg Gln Asp Val Asn Ile Thr Val Ala Thr Val Pro Ser Trp Leu Lys
                405                 410                 415

Lys Pro Gln Asp Ser Gln Leu Glu Glu Gly Lys Pro Gly Tyr Leu Asp
                420                 425                 430

Cys Leu Thr Gln Ala Thr Pro Lys Pro Thr Val Val Trp Tyr Arg Asn
                435                 440                 445

Gln Met Leu Ile Ser Glu Asp Ser Arg Phe Glu Val Phe Lys Asn Gly
    450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Arg Val
                485                 490                 495

Gln Val Leu Glu Lys Leu Lys Phe Thr Pro Pro Gln Pro Gln Gln
                500                 505                 510

Cys Met Glu Phe Asp Lys Glu Ala Thr Val Pro Cys Ser Ala Thr Gly
                515                 520                 525

Arg Glu Lys Pro Thr Ile Lys Trp Glu Arg Ala Asp Gly Ser Ser Leu
530                 535                 540

Pro Glu Trp Val Thr Asp Asn Ala Gly Thr Leu His Phe Ala Arg Val
```

```
               545                 550                 555                 560

Thr Arg Asp Asp Ala Gly Asn Tyr Thr Cys Ile Ala Ser Asn Gly Pro
                    565                 570                 575

Gln Gly Gln Ile Arg Ala His Val Gln Leu Thr Val Ala Val Phe Ile
                    580                 585                 590

Thr Phe Lys Val Glu Pro Glu Arg Thr Thr Val Tyr Gln Gly His Thr
                    595                 600                 605

Ala Leu Leu Gln Cys Glu Ala Gln Gly Asp Pro Lys Pro Leu Ile Gln
            610                 615                 620

Trp Lys Gly Lys Asp Arg Ile Leu Asp Pro Thr Lys Leu Gly Pro Arg
625                 630                 635                 640

Met His Ile Phe Gln Asn Gly Ser Leu Val Ile His Asp Val Ala Pro
                    645                 650                 655

Glu Asp Ser Gly Arg Tyr Thr Cys Ile Ala Gly Asn Ser Cys Asn Ile
                    660                 665                 670

Lys His Thr Glu Ala Pro Leu Tyr Val Val Asp Lys Pro Val Pro Glu
                    675                 680                 685

Glu Ser Glu Gly Pro Gly Ser Pro Pro Pro Tyr Lys Met Ile Gln Thr
            690                 695                 700

Ile Gly Leu Ser Val Gly Ala Ala Val Ala Tyr Ile Ile Ala Val Leu
705                 710                 715                 720

Gly Leu Met Phe Tyr Cys Lys Lys Arg Cys Lys Ala Lys Arg Leu Gln
                    725                 730                 735

Lys Gln Pro Glu Gly Glu Glu Pro Glu Met Glu Cys Leu Asn Gly Gly
                    740                 745                 750

Pro Leu Gln Asn Gly Gln Pro Ser Ala Glu Ile Gln Glu Glu Val Ala
            755                 760                 765

Leu Thr Ser Leu Gly Ser Gly Pro Ala Ala Thr Asn Lys Arg His Ser
            770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                    805                 810                 815

Gly Leu Glu Glu Gly Val Ala Glu Thr Leu Val Leu Val Lys Ser Leu
                    820                 825                 830

Gln Ser Lys Asp Glu Gln Gln Leu Asp Phe Arg Arg Glu Leu Glu
            835                 840                 845

Met Phe Gly Lys Leu Asn His Ala Asn Val Val Arg Leu Leu Gly Leu
850                 855                 860

Cys Arg Glu Ala Glu Pro His Tyr Met Val Leu Glu Tyr Val Asp Leu
865                 870                 875                 880

Gly Asp Leu Lys Gln Phe Leu Arg Ile Ser Lys Ser Lys Asp Glu Lys
                    885                 890                 895

Leu Lys Ser Gln Pro Leu Ser Thr Lys Gln Lys Val Ala Leu Cys Thr
                    900                 905                 910

Gln Val Ala Leu Gly Met Glu His Leu Ser Asn Asn Arg Phe Val His
            915                 920                 925

Lys Asp Leu Ala Ala Arg Asn Cys Leu Val Ser Ala Gln Arg Gln Val
930                 935                 940

Lys Val Ser Ala Leu Gly Leu Ser Lys Asp Val Tyr Asn Ser Glu Tyr
945                 950                 955                 960

Tyr His Phe Arg Gln Ala Trp Val Pro Leu Arg Trp Met Ser Pro Glu
                    965                 970                 975
```

```
Ala Ile Leu Glu Gly Asp Phe Ser Thr Lys Ser Asp Val Trp Ala Phe
            980                 985                 990

Gly Val Leu Met Trp Glu Val Phe Thr His Gly Glu Met Pro His Gly
            995                 1000                1005

Gly Gln Ala Asp Asp Glu Val Leu Ala Asp Leu Gln Ala Gly Lys
        1010                1015                1020

Ala Arg Leu Pro Gln Pro Glu Gly Cys Pro Ser Lys Leu Tyr Arg
        1025                1030                1035

Leu Met Gln Arg Cys Trp Ala Leu Ser Pro Lys Asp Arg Pro Ser
        1040                1045                1050

Phe Ser Glu Ile Ala Ser Ala Leu Gly Asp Ser Thr Val Asp Ser
        1055                1060                1065

Lys Pro
    1070

<210> SEQ ID NO 3
<211> LENGTH: 1070
<212> TYPE: PRT
<213> ORGANISM: Homo sapiens

<400> SEQUENCE: 3

Met Gly Ala Ala Arg Gly Ser Pro Ala Arg Pro Arg Arg Leu Pro Leu
1               5                   10                  15

Leu Ser Val Leu Leu Leu Pro Leu Leu Gly Gly Thr Gln Thr Ala Ile
            20                  25                  30

Val Phe Ile Lys Gln Pro Ser Ser Gln Asp Ala Leu Gln Gly Arg Arg
        35                  40                  45

Ala Leu Leu Arg Cys Glu Val Glu Ala Pro Gly Pro Val His Val Tyr
    50                  55                  60

Trp Leu Leu Asp Gly Ala Pro Val Gln Asp Thr Glu Arg Arg Phe Ala
65                  70                  75                  80

Gln Gly Ser Ser Leu Ser Phe Ala Ala Val Asp Arg Leu Gln Asp Ser
                85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125

Val Val Leu Lys His Pro Ala Ser Glu Ala Glu Ile Gln Pro Gln Thr
    130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Gly Gln
        195                 200                 205

Ala Cys Ser Ser Gln Asn Phe Thr Leu Ser Ile Ala Asp Glu Ser Phe
    210                 215                 220

Ala Arg Val Val Leu Ala Pro Gln Asp Val Val Val Ala Arg Tyr Glu
225                 230                 235                 240

Glu Ala Met Phe His Cys Gln Phe Ser Ala Gln Pro Pro Pro Ser Leu
                245                 250                 255

Gln Trp Leu Phe Glu Asp Glu Thr Pro Ile Thr Asn Arg Ser Arg Pro
```

-continued

```
                260                 265                 270
Pro His Leu Arg Arg Ala Thr Val Phe Ala Asn Gly Ser Leu Leu Leu
        275                 280                 285
Thr Gln Val Arg Pro Arg Asn Ala Gly Ile Tyr Arg Cys Ile Gly Gln
290                 295                 300
Gly Gln Arg Gly Pro Pro Ile Ile Leu Glu Ala Thr Leu His Leu Ala
305                 310                 315                 320
Glu Ile Glu Asp Met Pro Leu Phe Glu Pro Arg Val Phe Thr Ala Gly
                325                 330                 335
Ser Glu Glu Arg Val Thr Cys Leu Pro Pro Lys Gly Leu Pro Glu Pro
            340                 345                 350
Ser Val Trp Trp Glu His Ala Gly Val Arg Leu Pro Thr His Gly Arg
        355                 360                 365
Val Tyr Gln Lys Gly His Glu Leu Val Leu Ala Asn Ile Ala Glu Ser
    370                 375                 380
Asp Ala Gly Val Tyr Thr Cys His Ala Ala Asn Leu Ala Gly Gln Arg
385                 390                 395                 400
Arg Gln Asp Val Asn Ile Thr Val Ala Thr Val Pro Ser Trp Leu Lys
                405                 410                 415
Lys Pro Gln Asp Ser Gln Leu Glu Glu Gly Lys Pro Gly Tyr Leu Asp
            420                 425                 430
Cys Leu Thr Gln Ala Thr Pro Lys Pro Thr Val Trp Tyr Arg Asn
        435                 440                 445
Gln Met Leu Ile Ser Glu Asp Ser Arg Phe Glu Val Phe Lys Asn Gly
    450                 455                 460
Thr Leu Arg Ile Asn Ser Val Glu Val Tyr Asp Gly Thr Trp Tyr Arg
465                 470                 475                 480
Cys Met Ser Ser Thr Pro Ala Gly Ser Ile Glu Ala Gln Ala Arg Val
                485                 490                 495
Gln Val Leu Glu Lys Leu Lys Phe Thr Pro Pro Pro Gln Pro Gln Gln
            500                 505                 510
Cys Met Glu Phe Asp Lys Glu Ala Thr Val Pro Cys Ser Ala Thr Gly
        515                 520                 525
Arg Glu Lys Pro Thr Ile Lys Trp Glu Arg Ala Asp Gly Ser Ser Leu
    530                 535                 540
Pro Glu Trp Val Thr Asp Asn Ala Gly Thr Leu His Phe Ala Arg Val
545                 550                 555                 560
Thr Arg Asp Asp Ala Gly Asn Tyr Thr Cys Ile Ala Ser Asn Gly Pro
                565                 570                 575
Gln Gly Gln Ile Arg Ala His Val Gln Leu Thr Val Ala Val Phe Ile
            580                 585                 590
Thr Phe Lys Val Glu Pro Glu Arg Thr Thr Val Tyr Gln Gly His Thr
        595                 600                 605
Ala Leu Leu Gln Cys Glu Ala Gln Gly Asp Pro Lys Pro Leu Ile Gln
    610                 615                 620
Trp Lys Gly Lys Asp Arg Ile Leu Asp Pro Thr Lys Leu Gly Pro Arg
625                 630                 635                 640
Met His Ile Phe Gln Asn Gly Ser Leu Val Ile His Asp Val Ala Pro
                645                 650                 655
Glu Asp Ser Gly Arg Tyr Thr Cys Ile Ala Gly Asn Ser Cys Asn Ile
            660                 665                 670
Lys His Thr Glu Ala Pro Leu Tyr Val Val Asp Lys Pro Val Pro Glu
        675                 680                 685
```

```
Glu Ser Glu Gly Pro Gly Ser Pro Pro Tyr Lys Met Ile Gln Thr
    690                 695                 700

Ile Gly Leu Ser Val Gly Ala Ala Val Ala Tyr Ile Ile Ala Val Leu
705                 710                 715                 720

Gly Leu Met Phe Tyr Cys Lys Lys Arg Cys Lys Ala Lys Arg Leu Gln
                725                 730                 735

Lys Gln Pro Glu Gly Glu Pro Glu Met Glu Cys Leu Asn Gly Gly
            740                 745                 750

Pro Leu Gln Asn Gly Gln Pro Ser Ala Glu Ile Gln Glu Glu Val Ala
        755                 760                 765

Leu Thr Ser Leu Gly Ser Gly Pro Ala Ala Thr Asn Lys Arg His Ser
770                 775                 780

Thr Ser Asp Lys Met His Phe Pro Arg Ser Ser Leu Gln Pro Ile Thr
785                 790                 795                 800

Thr Leu Gly Lys Ser Glu Phe Gly Glu Val Phe Leu Ala Lys Ala Gln
                805                 810                 815

Gly Leu Glu Glu Gly Val Ala Glu Thr Leu Val Leu Val Lys Ser Leu
            820                 825                 830

Gln Ser Lys Asp Glu Gln Gln Leu Asp Phe Arg Arg Glu Leu Glu
        835                 840                 845

Met Phe Gly Lys Leu Asn His Ala Asn Val Val Arg Leu Leu Gly Leu
850                 855                 860

Cys Arg Glu Ala Glu Pro His Tyr Met Val Leu Glu Tyr Val Asp Leu
865                 870                 875                 880

Gly Asp Leu Lys Gln Phe Leu Arg Ile Ser Lys Ser Lys Asp Glu Lys
                885                 890                 895

Leu Lys Ser Gln Pro Leu Ser Thr Lys Gln Lys Val Ala Leu Cys Thr
            900                 905                 910

Gln Val Ala Leu Gly Met Glu His Leu Ser Asn Asn Arg Phe Val His
        915                 920                 925

Lys Asp Leu Ala Ala Arg Asn Cys Leu Val Ser Ala Gln Arg Gln Val
930                 935                 940

Lys Val Ser Ala Leu Gly Leu Ser Lys Asp Val Tyr Asn Ser Glu Tyr
945                 950                 955                 960

Tyr His Phe Arg Gln Ala Trp Val Pro Leu Arg Trp Met Ser Pro Glu
                965                 970                 975

Ala Ile Leu Glu Gly Asp Phe Ser Thr Lys Ser Asp Val Trp Ala Phe
            980                 985                 990

Gly Val Leu Met Trp Glu Val Phe Thr His Gly Glu Met Pro His Gly
        995                 1000                1005

Gly Gln Ala Asp Asp Glu Val Leu Ala Asp Leu Gln Ala Gly Lys
        1010                1015                1020

Ala Arg Leu Pro Gln Pro Glu Gly Cys Pro Ser Lys Leu Tyr Arg
        1025                1030                1035

Leu Met Gln Arg Cys Trp Ala Leu Ser Pro Lys Asp Arg Pro Ser
        1040                1045                1050

Phe Ser Glu Ile Ala Ser Ala Leu Gly Asp Ser Thr Val Asp Ser
        1055                1060                1065

Lys Pro
    1070

<210> SEQ ID NO 4
<211> LENGTH: 1014
```

<212> TYPE: PRT
<213> ORGANISM: Homo sapiens

<400> SEQUENCE: 4

```
Met Gly Ala Ala Arg Gly Ser Pro Ala Arg Pro Arg Leu Pro Leu
1               5                   10                  15

Leu Ser Val Leu Leu Pro Leu Leu Gly Thr Gln Thr Ala Ile
            20                  25                  30

Val Phe Ile Lys Gln Pro Ser Ser Gln Asp Ala Leu Gln Gly Arg Arg
            35                  40                  45

Ala Leu Leu Arg Cys Glu Val Glu Ala Pro Gly Pro Val His Val Tyr
50                  55                  60

Trp Leu Leu Asp Gly Ala Pro Val Gln Asp Thr Glu Arg Arg Phe Ala
65                      70                  75                  80

Gln Gly Ser Ser Leu Ser Phe Ala Ala Val Asp Arg Leu Gln Asp Ser
                85                  90                  95

Gly Thr Phe Gln Cys Val Ala Arg Asp Asp Val Thr Gly Glu Glu Ala
            100                 105                 110

Arg Ser Ala Asn Ala Ser Phe Asn Ile Lys Trp Ile Glu Ala Gly Pro
        115                 120                 125

Val Val Leu Lys His Pro Ala Ser Glu Ala Glu Ile Gln Pro Gln Thr
130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Gly Gln
        195                 200                 205

Ala Cys Ser Ser Gln Asn Phe Thr Leu Ser Ile Ala Asp Glu Ser Phe
210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Ser Leu
                245                 250                 255

Gln Trp Leu Phe Glu Asp Glu Thr Pro Ile Thr Asn Arg Ser Arg Pro
            260                 265                 270

Pro His Leu Arg Arg Ala Thr Val Phe Ala Asn Gly Ser Leu Leu Leu
        275                 280                 285

Thr Gln Val Arg Pro Arg Asn Ala Gly Ile Tyr Arg Cys Ile Gly Gln
290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
            340                 345                 350

Ser Val Trp Trp Glu His Ala Gly Val Arg Leu Pro Thr His Gly Arg
        355                 360                 365

Val Tyr Gln Lys Gly His Glu Leu Val Leu Ala Asn Ile Ala Glu Ser
370                 375                 380

Asp Ala Gly Val Tyr Thr Cys His Ala Ala Asn Leu Ala Gly Gln Arg
385                 390                 395                 400
```

-continued

```
Arg Gln Asp Val Asn Ile Thr Val Ala Thr Val Pro Ser Trp Leu Lys
                405                 410                 415
Lys Pro Gln Asp Ser Gln Leu Glu Glu Gly Lys Pro Gly Tyr Leu Asp
            420                 425                 430
Cys Leu Thr Gln Ala Thr Pro Lys Pro Thr Val Trp Tyr Arg Asn
            435                 440                 445
Gln Met Leu Ile Ser Glu Asp Ser Arg Phe Glu Val Phe Lys Asn Gly
        450                 455                 460
Thr Leu Arg Ile Asn Ser Val Glu Val Tyr Asp Gly Thr Trp Tyr Arg
465                 470                 475                 480
Cys Met Ser Ser Thr Pro Ala Gly Ser Ile Glu Ala Gln Ala Arg Val
                485                 490                 495
Gln Val Leu Glu Lys Leu Lys Phe Thr Pro Pro Gln Pro Gln Gln
            500                 505                 510
Cys Met Glu Phe Asp Lys Glu Ala Thr Val Pro Cys Ser Ala Thr Gly
            515                 520                 525
Arg Glu Lys Pro Thr Ile Lys Trp Glu Arg Ala Asp Gly Ser Ser Leu
        530                 535                 540
Pro Glu Trp Val Thr Asp Asn Ala Gly Thr Leu His Phe Ala Arg Val
545                 550                 555                 560
Thr Arg Asp Asp Ala Gly Asn Tyr Thr Cys Ile Ala Ser Asn Gly Pro
                565                 570                 575
Gln Gly Gln Ile Arg Ala His Val Gln Leu Thr Val Ala Val Phe Ile
            580                 585                 590
Thr Phe Lys Val Glu Pro Glu Arg Thr Thr Val Tyr Gln Gly His Thr
            595                 600                 605
Ala Leu Leu Gln Cys Glu Ala Gln Gly Asp Pro Lys Pro Leu Ile Gln
        610                 615                 620
Trp Lys Asp Lys Pro Val Pro Glu Glu Ser Glu Gly Pro Gly Ser Pro
625                 630                 635                 640
Pro Pro Tyr Lys Met Ile Gln Thr Ile Gly Leu Ser Val Gly Ala Ala
                645                 650                 655
Val Ala Tyr Ile Ile Ala Val Leu Gly Leu Met Phe Tyr Cys Lys Lys
            660                 665                 670
Arg Cys Lys Ala Lys Arg Leu Gln Lys Gln Pro Glu Gly Glu Glu Pro
        675                 680                 685
Glu Met Glu Cys Leu Asn Gly Gly Pro Leu Gln Asn Gly Gln Pro Ser
        690                 695                 700
Ala Glu Ile Gln Glu Glu Val Ala Leu Thr Ser Leu Gly Ser Gly Pro
705                 710                 715                 720
Ala Ala Thr Asn Lys Arg His Ser Thr Ser Asp Lys Met His Phe Pro
                725                 730                 735
Arg Ser Ser Leu Gln Pro Ile Thr Thr Leu Gly Lys Ser Glu Phe Gly
            740                 745                 750
Glu Val Phe Leu Ala Lys Ala Gln Gly Leu Glu Glu Gly Val Ala Glu
            755                 760                 765
Thr Leu Val Leu Val Lys Ser Leu Gln Ser Lys Asp Glu Gln Gln Gln
        770                 775                 780
Leu Asp Phe Arg Arg Glu Leu Glu Met Phe Gly Lys Leu Asn His Ala
785                 790                 795                 800
Asn Val Val Arg Leu Leu Gly Leu Cys Arg Glu Ala Glu Pro His Tyr
                805                 810                 815
```

```
Met Val Leu Glu Tyr Val Asp Leu Gly Asp Leu Lys Gln Phe Leu Arg
            820             825             830

Ile Ser Lys Ser Lys Asp Glu Lys Leu Lys Ser Gln Pro Leu Ser Thr
835             840             845

Lys Gln Lys Val Ala Leu Cys Thr Gln Val Ala Leu Gly Met Glu His
    850             855             860

Leu Ser Asn Asn Arg Phe Val His Lys Asp Leu Ala Ala Arg Asn Cys
865             870             875             880

Leu Val Ser Ala Gln Arg Gln Val Lys Val Ser Ala Leu Gly Leu Ser
            885             890             895

Lys Asp Val Tyr Asn Ser Glu Tyr Tyr His Phe Arg Gln Ala Trp Val
    900             905             910

Pro Leu Arg Trp Met Ser Pro Glu Ala Ile Leu Glu Gly Asp Phe Ser
        915             920             925

Thr Lys Ser Asp Val Trp Ala Phe Gly Val Leu Met Trp Glu Val Phe
    930             935             940

Thr His Gly Glu Met Pro His Gly Gly Gln Ala Asp Asp Glu Val Leu
945             950             955             960

Ala Asp Leu Gln Ala Gly Lys Ala Arg Leu Pro Gln Pro Glu Gly Cys
            965             970             975

Pro Ser Lys Leu Tyr Arg Leu Met Gln Arg Cys Trp Ala Leu Ser Pro
        980             985             990

Lys Asp Arg Pro Ser Phe Ser Glu  Ile Ala Ser Ala Leu  Gly Asp Ser
        995            1000             1005

Thr Val  Asp Ser Lys Pro
    1010

<210> SEQ ID NO 5
<211> LENGTH: 1030
<212> TYPE: PRT
<213> ORGANISM: Homo sapiens

<400> SEQUENCE: 5

Met Gly Ala Ala Arg Gly Ser Pro Ala Arg Pro Arg Arg Leu Pro Leu
1               5              10              15

Leu Ser Val Leu Leu Leu Pro Leu Leu Gly Gly Thr Gln Thr Ala Ile
            20              25              30

Val Phe Ile Lys Gln Pro Ser Ser Gln Asp Ala Leu Gln Gly Arg Arg
        35              40              45

Ala Leu Leu Arg Cys Glu Val Glu Ala Pro Gly Pro Val His Val Tyr
    50              55              60

Trp Leu Leu Asp Gly Ala Pro Val Gln Asp Thr Glu Arg Arg Phe Ala
65              70              75              80

Gln Gly Ser Ser Leu Ser Phe Ala Ala Val Asp Arg Leu Gln Asp Ser
            85              90              95

Gly Thr Phe Gln Cys Val Ala Arg Asp Asp Val Thr Gly Glu Glu Ala
        100             105             110

Arg Ser Ala Asn Ala Ser Phe Asn Ile Lys Trp Ile Glu Ala Gly Pro
    115             120             125

Val Val Leu Lys His Pro Ala Ser Glu Ala Glu Ile Gln Pro Gln Thr
    130             135             140

Gln Val Thr Leu Arg Cys His Ile Asp Gly His Pro Arg Pro Thr Tyr
145             150             155             160

Gln Trp Phe Arg Asp Gly Thr Pro Leu Ser Asp Gly Gln Ser Asn His
            165             170             175
```

```
Thr Val Ser Ser Lys Glu Arg Asn Leu Thr Leu Arg Pro Ala Gly Pro
            180                 185                 190

Glu His Ser Gly Leu Tyr Ser Cys Ala His Ser Ala Phe Gly Gln
        195                 200                 205

Ala Cys Ser Ser Gln Asn Phe Thr Leu Ser Ile Ala Asp Glu Ser Phe
210                 215                 220

Ala Arg Val Val Leu Ala Pro Gln Asp Val Val Ala Arg Tyr Glu
225                 230                 235                 240

Glu Ala Met Phe His Cys Gln Phe Ser Ala Gln Pro Pro Ser Leu
                245                 250                 255

Gln Trp Leu Phe Glu Asp Glu Thr Pro Ile Thr Asn Arg Ser Arg Pro
        260                 265                 270

Pro His Leu Arg Arg Ala Thr Val Phe Ala Asn Gly Ser Leu Leu Leu
        275                 280                 285

Thr Gln Val Arg Pro Arg Asn Ala Gly Ile Tyr Arg Cys Ile Gly Gln
        290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
        340                 345                 350

Ser Val Trp Trp Glu His Ala Gly Val Arg Leu Pro Thr His Gly Arg
        355                 360                 365

Val Tyr Gln Lys Gly His Glu Leu Val Leu Ala Asn Ile Ala Glu Ser
        370                 375                 380

Asp Ala Gly Val Tyr Thr Cys His Ala Ala Asn Leu Ala Gly Gln Arg
385                 390                 395                 400

Arg Gln Asp Val Asn Ile Thr Val Ala Thr Val Pro Ser Trp Leu Lys
                405                 410                 415

Lys Pro Gln Asp Ser Gln Leu Glu Glu Gly Lys Pro Gly Tyr Leu Asp
        420                 425                 430

Cys Leu Thr Gln Ala Thr Pro Lys Pro Thr Val Val Trp Tyr Arg Asn
        435                 440                 445

Gln Met Leu Ile Ser Glu Asp Ser Arg Phe Glu Val Phe Lys Asn Gly
        450                 455                 460

Thr Leu Arg Ile Asn Ser Val Glu Val Tyr Asp Gly Thr Trp Tyr Arg
465                 470                 475                 480

Cys Met Ser Ser Thr Pro Ala Gly Ser Ile Glu Ala Gln Ala Arg Val
                485                 490                 495

Gln Val Leu Asp Gly Ser Ser Leu Pro Glu Trp Val Thr Asp Asn Ala
        500                 505                 510

Gly Thr Leu His Phe Ala Arg Val Thr Arg Asp Asp Ala Gly Asn Tyr
        515                 520                 525

Thr Cys Ile Ala Ser Asn Gly Pro Gln Gly Gln Ile Arg Ala His Val
        530                 535                 540

Gln Leu Thr Val Ala Val Phe Ile Thr Phe Lys Val Glu Pro Glu Arg
545                 550                 555                 560

Thr Thr Val Tyr Gln Gly His Thr Ala Leu Leu Gln Cys Glu Ala Gln
                565                 570                 575

Gly Asp Pro Lys Pro Leu Ile Gln Trp Lys Gly Lys Asp Arg Ile Leu
        580                 585                 590
```

-continued

Asp Pro Thr Lys Leu Gly Pro Arg Met His Ile Phe Gln Asn Gly Ser
            595                 600                 605

Leu Val Ile His Asp Val Ala Pro Glu Asp Ser Gly Arg Tyr Thr Cys
    610                 615                 620

Ile Ala Gly Asn Ser Cys Asn Ile Lys His Thr Glu Ala Pro Leu Tyr
625                 630                 635                 640

Val Val Asp Lys Pro Val Pro Glu Glu Ser Glu Gly Pro Gly Ser Pro
            645                 650                 655

Pro Pro Tyr Lys Met Ile Gln Thr Ile Gly Leu Ser Val Gly Ala Ala
            660                 665                 670

Val Ala Tyr Ile Ile Ala Val Leu Gly Leu Met Phe Tyr Cys Lys Lys
            675                 680                 685

Arg Cys Lys Ala Lys Arg Leu Gln Lys Gln Pro Glu Gly Glu Glu Pro
            690                 695                 700

Glu Met Glu Cys Leu Asn Gly Gly Pro Leu Gln Asn Gly Gln Pro Ser
705                 710                 715                 720

Ala Glu Ile Gln Glu Glu Val Ala Leu Thr Ser Leu Gly Ser Gly Pro
            725                 730                 735

Ala Ala Thr Asn Lys Arg His Ser Thr Ser Asp Lys Met His Phe Pro
            740                 745                 750

Arg Ser Ser Leu Gln Pro Ile Thr Thr Leu Gly Lys Ser Glu Phe Gly
            755                 760                 765

Glu Val Phe Leu Ala Lys Ala Gln Gly Leu Glu Glu Gly Val Ala Glu
            770                 775                 780

Thr Leu Val Leu Val Lys Ser Leu Gln Ser Lys Asp Glu Gln Gln Gln
785                 790                 795                 800

Leu Asp Phe Arg Arg Glu Leu Glu Met Phe Gly Lys Leu Asn His Ala
            805                 810                 815

Asn Val Val Arg Leu Leu Gly Leu Cys Arg Glu Ala Glu Pro His Tyr
            820                 825                 830

Met Val Leu Glu Tyr Val Asp Leu Gly Asp Leu Lys Gln Phe Leu Arg
            835                 840                 845

Ile Ser Lys Ser Lys Asp Glu Lys Leu Lys Ser Gln Pro Leu Ser Thr
850                 855                 860

Lys Gln Lys Val Ala Leu Cys Thr Gln Val Ala Leu Gly Met Glu His
865                 870                 875                 880

Leu Ser Asn Asn Arg Phe Val His Lys Asp Leu Ala Ala Arg Asn Cys
            885                 890                 895

Leu Val Ser Ala Gln Arg Gln Val Lys Val Ser Ala Leu Gly Leu Ser
            900                 905                 910

Lys Asp Val Tyr Asn Ser Glu Tyr Tyr His Phe Arg Gln Ala Trp Val
            915                 920                 925

Pro Leu Arg Trp Met Ser Pro Glu Ala Ile Leu Glu Gly Asp Phe Ser
            930                 935                 940

Thr Lys Ser Asp Val Trp Ala Phe Gly Val Leu Met Trp Glu Val Phe
945                 950                 955                 960

Thr His Gly Glu Met Pro His Gly Gly Gln Ala Asp Asp Glu Val Leu
            965                 970                 975

Ala Asp Leu Gln Ala Gly Lys Ala Arg Leu Pro Gln Pro Glu Gly Cys
            980                 985                 990

Pro Ser Lys Leu Tyr Arg Leu Met Gln Arg Cys Trp Ala Leu Ser Pro
            995                 1000                1005

Lys Asp Arg Pro Ser Phe Ser Glu Ile Ala Ser Ala Leu Gly Asp

Ser Thr Val Asp Ser Lys Pro
     1025              1030

<210> SEQ ID NO 6
<211> LENGTH: 940
<212> TYPE: PRT
<213> ORGANISM: Homo sapiens

<400> SEQUENCE: 6

Met Gly Ala Ala Arg Gly Ser Pro Ala Arg Pro Arg Leu Pro Leu
1               5                   10                  15

Leu Ser Val Leu Leu Pro Leu Leu Gly Thr Gln Thr Ala Ile
            20                  25                  30

Val Phe Ile Lys Gln Pro Ser Ser Gln Asp Ala Leu Gln Gly Arg Arg
                35                  40                  45

Ala Leu Leu Arg Cys Glu Val Glu Ala Pro Gly Pro Val His Val Tyr
50                  55                  60

Trp Leu Leu Asp Gly Ala Pro Val Gln Asp Thr Glu Arg Arg Phe Ala
65                  70                  75                  80

Gln Gly Ser Ser Leu Ser Phe Ala Ala Val Asp Arg Leu Gln Asp Ser
                85                  90                  95

Gly Thr Phe Gln Cys Val Ala Arg Asp Asp Val Thr Gly Glu Glu Ala
                100                 105                 110

Arg Ser Ala Asn Ala Ser Phe Asn Ile Lys Trp Ile Glu Ala Gly Pro
            115                 120                 125

Val Val Leu Lys His Pro Ala Ser Glu Ala Glu Ile Gln Pro Gln Thr
130                 135                 140

Gln Val Thr Leu Arg Cys His Ile Asp Gly His Pro Arg Pro Thr Tyr
145                 150                 155                 160

Gln Trp Phe Arg Asp Gly Thr Pro Leu Ser Asp Gly Gln Ser Asn His
                165                 170                 175

Thr Val Ser Ser Lys Glu Arg Asn Leu Thr Leu Arg Pro Ala Gly Pro
            180                 185                 190

Glu His Ser Gly Leu Tyr Ser Cys Cys Ala His Ser Ala Phe Gly Gln
            195                 200                 205

Ala Cys Ser Ser Gln Asn Phe Thr Leu Ser Ile Ala Asp Glu Ser Phe
210                 215                 220

Ala Arg Val Val Leu Ala Pro Gln Asp Val Val Ala Arg Tyr Glu
225                 230                 235             240

Glu Ala Met Phe His Cys Gln Phe Ser Ala Gln Pro Pro Pro Ser Leu
                245                 250                 255

Gln Trp Leu Phe Glu Asp Glu Thr Pro Ile Thr Asn Arg Ser Arg Pro
            260                 265                 270

Pro His Leu Arg Arg Ala Thr Val Phe Ala Asn Gly Ser Leu Leu Leu
        275                 280                 285

Thr Gln Val Arg Pro Arg Asn Ala Gly Ile Tyr Arg Cys Ile Gly Gln
290                 295                 300

Gly Gln Arg Gly Pro Pro Ile Ile Leu Glu Ala Thr Leu His Leu Ala
305                 310                 315                 320

Glu Ile Glu Asp Met Pro Leu Phe Glu Pro Arg Val Phe Thr Ala Gly
                325                 330                 335

Ser Glu Glu Arg Val Thr Cys Leu Pro Pro Lys Gly Leu Pro Glu Pro
            340                 345                 350

```
Ser Val Trp Glu His Ala Gly Val Arg Leu Pro Thr His Gly Arg
    355                 360                 365
Val Tyr Gln Lys Gly His Glu Leu Val Leu Ala Asn Ile Ala Glu Ser
370                 375                 380
Asp Ala Gly Val Tyr Thr Cys His Ala Ala Asn Leu Ala Gly Gln Arg
385                 390                 395                 400
Arg Gln Asp Val Asn Ile Thr Val Ala Asn Gly Ser Ser Leu Pro Glu
                405                 410                 415
Trp Val Thr Asp Asn Ala Gly Thr Leu His Phe Ala Arg Val Thr Arg
            420                 425                 430
Asp Asp Ala Gly Asn Tyr Thr Cys Ile Ala Ser Asn Gly Pro Gln Gly
        435                 440                 445
Gln Ile Arg Ala His Val Gln Leu Thr Val Ala Val Phe Ile Thr Phe
    450                 455                 460
Lys Val Glu Pro Glu Arg Thr Thr Val Tyr Gln Gly His Thr Ala Leu
465                 470                 475                 480
Leu Gln Cys Glu Ala Gln Gly Asp Pro Lys Pro Leu Ile Gln Trp Lys
                485                 490                 495
Gly Lys Asp Arg Ile Leu Asp Pro Thr Lys Leu Gly Pro Arg Met His
            500                 505                 510
Ile Phe Gln Asn Gly Ser Leu Val Ile His Asp Val Ala Pro Glu Asp
        515                 520                 525
Ser Gly Arg Tyr Thr Cys Ile Ala Gly Asn Ser Cys Asn Ile Lys His
    530                 535                 540
Thr Glu Ala Pro Leu Tyr Val Val Asp Lys Pro Val Pro Glu Glu Ser
545                 550                 555                 560
Glu Gly Pro Gly Ser Pro Pro Tyr Lys Met Ile Gln Thr Ile Gly
                565                 570                 575
Leu Ser Val Gly Ala Ala Val Ala Tyr Ile Ile Ala Val Leu Gly Leu
            580                 585                 590
Met Phe Tyr Cys Lys Lys Arg Cys Lys Ala Lys Arg Leu Gln Lys Gln
        595                 600                 605
Pro Glu Gly Glu Glu Pro Glu Met Glu Cys Leu Asn Gly Gly Pro Leu
    610                 615                 620
Gln Asn Gly Gln Pro Ser Ala Glu Ile Gln Glu Glu Val Ala Leu Thr
625                 630                 635                 640
Ser Leu Gly Ser Gly Pro Ala Ala Thr Asn Lys Arg His Ser Thr Ser
                645                 650                 655
Asp Lys Met His Phe Pro Arg Ser Ser Leu Gln Pro Ile Thr Thr Leu
            660                 665                 670
Gly Lys Ser Glu Phe Gly Glu Val Phe Leu Ala Lys Ala Gln Gly Leu
        675                 680                 685
Glu Glu Gly Val Ala Glu Thr Leu Val Leu Val Lys Ser Leu Gln Ser
    690                 695                 700
Lys Asp Glu Gln Gln Gln Leu Asp Phe Arg Arg Glu Leu Glu Met Phe
705                 710                 715                 720
Gly Lys Leu Asn His Ala Asn Val Val Arg Leu Leu Gly Leu Cys Arg
                725                 730                 735
Glu Ala Glu Pro His Tyr Met Val Leu Glu Tyr Val Asp Leu Gly Asp
            740                 745                 750
Leu Lys Gln Phe Leu Arg Ile Ser Lys Ser Lys Asp Glu Lys Leu Lys
        755                 760                 765
Ser Gln Pro Leu Ser Thr Lys Gln Lys Val Ala Leu Cys Thr Gln Val
```

```
                    770               775               780
Ala Leu Gly Met Glu His Leu Ser Asn Asn Arg Phe Val His Lys Asp
785                 790               795               800

Leu Ala Ala Arg Asn Cys Leu Val Ser Ala Gln Arg Gln Val Lys Val
                805               810               815

Ser Ala Leu Gly Leu Ser Lys Asp Val Tyr Asn Ser Glu Tyr Tyr His
            820               825               830

Phe Arg Gln Ala Trp Val Pro Leu Arg Trp Met Ser Pro Glu Ala Ile
        835               840               845

Leu Glu Gly Asp Phe Ser Thr Lys Ser Asp Val Trp Ala Phe Gly Val
850               855               860

Leu Met Trp Glu Val Phe Thr His Gly Glu Met Pro His Gly Gly Gln
865               870               875               880

Ala Asp Asp Glu Val Leu Ala Asp Leu Gln Ala Gly Lys Ala Arg Leu
                885               890               895

Pro Gln Pro Glu Gly Cys Pro Ser Lys Leu Tyr Arg Leu Met Gln Arg
            900               905               910

Cys Trp Ala Leu Ser Pro Lys Asp Arg Pro Ser Phe Ser Glu Ile Ala
        915               920               925

Ser Ala Leu Gly Asp Ser Thr Val Asp Ser Lys Pro
    930               935               940
```

```
<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 7

His His His His His His
1               5

<210> SEQ ID NO 8
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 8xHis tag"

<400> SEQUENCE: 8

His His His His His His His His
1               5

<210> SEQ ID NO 9
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gccattgtct tcatcaagca gcc                                          23

<210> SEQ ID NO 10
<211> LENGTH: 23
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ctggatcatc ttgtaggggg gag                                              23

<210> SEQ ID NO 11
<211> LENGTH: 8
<212> TYPE: PRT
<213> ORGANISM: Unknown
<220> FEATURE:
<221> NAME/KEY: source
<223> OTHER INFORMATION: /note="Description of Unknown: motif peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 11

Gly Xaa Gly Xaa Phe Gly Xaa Val
1               5

<210> SEQ ID NO 12
<211> LENGTH: 8
<212> TYPE: PRT
<213> ORGANISM: Unknown
<220> FEATURE:
<221> NAME/KEY: source
<223> OTHER INFORMATION: /note="Description of Unknown: motif peptide"
<220> FEATURE:
<221> NAME/KEY: MOD_RES
<222> LOCATION: (5)..(7)
<223> OTHER INFORMATION: Any amino acid

<400> SEQUENCE: 12

His Arg Asp Leu Xaa Xaa Xaa Asn
1               5

<210> SEQ ID NO 13
<211> LENGTH: 7
<212> TYPE: PRT
<213> ORGANISM: Unknown
<220> FEATURE:
<221> NAME/KEY: source
<223> OTHER INFORMATION: /note="Description of Unknown: motif peptide"
<220> FEATURE:
<221> NAME/KEY: MOD_RES
<222> LOCATION: (6)..(6)
<223> OTHER INFORMATION: Any amino acid

<400> SEQUENCE: 13

Ser Asp Val Trp Ser Xaa Gly
1               5

<210> SEQ ID NO 14

<400> SEQUENCE: 14

000
```

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 112
<212> TYPE: PRT
<213> ORGANISM: Mus sp.

<400> SEQUENCE: 20

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Phe
            20                  25                  30

Gly Asn Ser Phe Met His Trp Tyr Gln Gln Lys Pro Gly Gln Pro Pro
        35                  40                  45

Lys Leu Leu Ile Tyr Ala Ala Ser Asn Leu Gly Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ser Ala Met Tyr Phe Cys Gln Gln Ser Lys
                85                  90                  95

Glu Val Pro Arg Thr Phe Gly Gly Gly Ser Arg Leu Glu Ile Lys Arg
            100                 105                 110

<210> SEQ ID NO 21
<211> LENGTH: 113
<212> TYPE: PRT
<213> ORGANISM: Mus sp.

<400> SEQUENCE: 21

Gln Val Gln Met Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

```
Trp Ile Glu Trp Val Lys Gln Arg Pro Gly His Gly Leu Glu Trp Ile
         35                  40                  45

Gly Glu Ile Leu Pro Gly Ser Gly Arg Ser Asn Ser Asn Glu Lys Phe
 50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Glu Asp Ser Ala Ile Tyr Tyr Cys
             85                  90                  95

Ala Arg Gly Lys Leu Ser Trp Gly Gln Gly Thr Leu Val Thr Val Ser
             100                 105                 110

Ala
```

<210> SEQ ID NO 22
<211> LENGTH: 108
<212> TYPE: PRT
<213> ORGANISM: Mus sp.

<400> SEQUENCE: 22

```
Asp Ile Val Met Thr Gln Ser Gln Lys Phe Met Ser Thr Ser Val Gly
 1               5                  10                  15

Asp Arg Val Asn Val Thr Cys Lys Ala Ser Gln Asn Val Gly Thr Asn
             20                  25                  30

Val Val Trp Tyr Gln Gln Lys Thr Gly Gln Ser Pro Lys Ala Leu Ile
         35                  40                  45

His Ser Ala Ser Tyr Arg Tyr Ser Gly Val Pro Asp Arg Phe Thr Gly
 50                  55                  60

Ser Gly Ser Gly Thr Asp Phe Thr Leu Thr Leu Ser Asn Val Gln Ser
 65                  70                  75                  80

Glu Asp Leu Ala Glu Tyr Phe Cys Gln His Tyr Asn Ser Phe Pro Tyr
             85                  90                  95

Thr Phe Gly Gly Gly Thr Lys Leu Glu Ile Lys Arg
             100                 105
```

<210> SEQ ID NO 23
<211> LENGTH: 115
<212> TYPE: PRT
<213> ORGANISM: Mus sp.

<400> SEQUENCE: 23

```
Gln Val Gln Leu Gln Gln Ser Gly Ala Glu Leu Val Arg Pro Gly Val
 1               5                  10                  15

Ser Val Lys Ile Ser Cys Lys Gly Ser Gly Tyr Arg Phe Thr Asp Tyr
             20                  25                  30

Pro Ile His Trp Val Lys Gln Ser His Ala Lys Ser Leu Glu Trp Ile
         35                  40                  45

Gly Ile Ile Ser Thr Tyr Tyr Gly Asp Val Thr Asn Asn Pro Lys Phe
 50                  55                  60

Arg Gly Lys Ala Thr Met Thr Val Asp Lys Ser Ser Thr Thr Ala Tyr
 65                  70                  75                  80

Met Glu Leu Ala Arg Leu Thr Ser Glu Asp Ser Ala Ile Tyr Tyr Cys
             85                  90                  95

Ala Arg Asn Asp Leu Phe Ala Tyr Trp Gly Gln Gly Thr Leu Val Thr
             100                 105                 110

Val Ser Ala
     115
```

```
<210> SEQ ID NO 24
<211> LENGTH: 94
<212> TYPE: PRT
<213> ORGANISM: Mus sp.

<400> SEQUENCE: 24

Leu Gly Gly Arg Val Thr Ile Thr Cys Lys Ala Ser Asp His Ile Asn
1               5                   10                  15

Asn Trp Leu Ala Trp Tyr Gln Gln Lys Pro Gly Asn Ala Pro Arg Leu
            20                  25                  30

Leu Ile Ser Gly Ala Thr Thr Leu Glu Thr Gly Val Pro Ser Arg Phe
        35                  40                  45

Ser Gly Ser Gly Ser Gly Lys Asp Tyr Thr Leu Ser Ile Thr Ser Leu
50                  55                  60

Gln Thr Glu Asp Val Ala Thr Tyr Tyr Cys Gln Gln Tyr Trp Ser Ile
65                  70                  75                  80

Pro Tyr Thr Phe Gly Gly Gly Thr Lys Leu Glu Ile Lys Arg
                85                  90

<210> SEQ ID NO 25
<211> LENGTH: 123
<212> TYPE: PRT
<213> ORGANISM: Mus sp.

<400> SEQUENCE: 25

Ser Asp Val Gln Leu Gln Glu Ser Gly Pro Gly Leu Val Lys Pro Ser
1               5                   10                  15

Gln Ser Leu Ser Leu Thr Cys Thr Val Thr Gly Tyr Ser Ile Thr Ser
            20                  25                  30

Asp Tyr Ala Trp Asn Trp Ile Arg Gln Phe Pro Gly Asn Lys Leu Glu
        35                  40                  45

Trp Met Val Ser Tyr Ser Gly Tyr Thr Asn Tyr Asn Pro Ser Leu Lys
50                  55                  60

Ser Arg Ile Ser Ile Thr Arg Asp Thr Ser Lys Asn Gln Phe Phe Leu
65                  70                  75                  80

Gln Leu Ile Ser Val Thr Thr Glu Asp Thr Ala Thr Tyr Tyr Cys Ala
                85                  90                  95

Arg Gly Asp Ala Tyr Asp Val Arg Arg Ser Thr Tyr Tyr Phe Asp Tyr
            100                 105                 110

Trp Gly Gln Gly Thr Thr Leu Thr Val Ser Ser
        115                 120

<210> SEQ ID NO 26
<211> LENGTH: 108
<212> TYPE: PRT
<213> ORGANISM: Mus sp.

<400> SEQUENCE: 26

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Val Ser Asn Asn
            20                  25                  30

Leu His Trp Tyr Gln Gln Lys Ser His Ala Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Leu Ser Ile Asn Ser Val Glu Thr
65                  70                  75                  80
```

```
Glu Asp Phe Gly Met Tyr Phe Cys Gln Gln Ser Tyr Ser Trp Pro Arg
                85                  90                  95

Thr Phe Gly Gly Gly Thr Lys Leu Glu Ile Lys Arg
            100                 105

<210> SEQ ID NO 27
<211> LENGTH: 114
<212> TYPE: PRT
<213> ORGANISM: Mus sp.

<400> SEQUENCE: 27

Gln Leu Glu Glu Ser Gly Ala Glu Leu Met Gln Pro Gly Ala Ser Val
1               5                   10                  15

Lys Val Ser Cys Lys Ala Thr Leu Glu Glu Gly Tyr Thr Phe Thr Val
            20                  25                  30

Tyr Trp Ile Glu Trp Val Lys Gln Arg Pro Gly His Gly Leu Glu Trp
        35                  40                  45

Ile Gly Glu Ile Leu Pro Gly Ser Gly Ser Thr Asp Tyr Asn Glu Lys
    50                  55                  60

Phe Lys Gly Lys Ala Thr Phe Thr Ala Asp Ser Ser Ser Asn Thr Ala
65                  70                  75                  80

Tyr Met Gln Leu Ser Ser Leu Thr Thr Glu Asp Ser Ala Ile Tyr Tyr
                85                  90                  95

Cys Ala Arg Gly Lys Leu His Trp Gly Gln Gly Thr Leu Val Thr Val
            100                 105                 110

Ser Ala

<210> SEQ ID NO 28
<211> LENGTH: 114
<212> TYPE: PRT
<213> ORGANISM: Mus sp.

<400> SEQUENCE: 28

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Gly
            20                  25                  30

Gly Asn Gln Gln Asn Ser Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Ser Ser Val Gln Ala Glu Asp Leu Ala Val Tyr Tyr Cys Gln Asn
                85                  90                  95

Asp His Thr Tyr Pro Tyr Thr Phe Gly Gly Gly Thr Glu Leu Glu Ile
            100                 105                 110

Lys Arg

<210> SEQ ID NO 29
<211> LENGTH: 118
<212> TYPE: PRT
<213> ORGANISM: Mus sp.

<400> SEQUENCE: 29

Glu Val Lys Leu Leu Glu Ser Gly Gly Gly Leu Val Gln Pro Gly Gly
1               5                   10                  15
```

```
Ser Leu Lys Leu Ser Cys Ala Ala Ser Gly Phe Asp Phe Lys Asp
            20                  25                  30

Trp Met Ser Trp Val Arg Gln Ala Pro Gly Lys Gly Leu Glu Trp Ile
            35                  40                  45

Gly Glu Ile Asn Pro Asp Ser Arg Thr Ile Asn Tyr Ala Pro Ser Leu
 50                  55                  60

Lys Asp Lys Phe Ile Ile Ser Arg Glu Asn Ala Lys Asn Thr Leu Tyr
 65                  70                  75                  80

Leu Gln Met Ser Lys Val Arg Ser Glu Asp Thr Ala Leu Tyr Tyr Cys
                85                  90                  95

Ala Arg Trp Asp Tyr Asp Gly Gly Met Asp Tyr Trp Gly Gln Gly Thr
            100                 105                 110

Ser Val Thr Val Ser Ser
            115
```

```
<210> SEQ ID NO 30
<211> LENGTH: 116
<212> TYPE: PRT
<213> ORGANISM: Mus sp.

<400> SEQUENCE: 30

Asp Ile Gln Met Thr Gln Ser Pro Ala Ser Leu Ser Ala Ser Val Gly
 1               5                  10                  15

Glu Thr Val Thr Ile Thr Cys Arg Thr Ser Glu Asn Ile Tyr Ser Tyr
            20                  25                  30

Leu Ala Trp Tyr Gln Gln Lys Gln Leu Ala Trp Tyr Gln Gln Lys Gln
            35                  40                  45

Gly Lys Ser Pro Gln Leu Leu Val His Asn Ala Asn Thr Leu Ala Glu
 50                  55                  60

Gly Val Pro Ser Arg Phe Ser Gly Ser Gly Ser Gly Thr Gln Phe Ser
 65                  70                  75                  80

Leu Arg Ile Asn Ser Leu Gln Pro Glu Asp Phe Gly Ser Tyr Tyr Cys
                85                  90                  95

Gln His His Tyr Gly Ile Pro Phe Thr Phe Gly Gly Gly Thr Lys Leu
            100                 105                 110

Glu Val Glu Arg
            115
```

```
<210> SEQ ID NO 31
<211> LENGTH: 118
<212> TYPE: PRT
<213> ORGANISM: Mus sp.

<400> SEQUENCE: 31

Glu Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                85                  90                  95
```

-continued

```
Ala Arg Pro Gly Tyr Gly Asn Leu Phe Ala Tyr Trp Gly Gln Gly Thr
            100                 105                 110

Leu Val Thr Val Ser Ala
        115

<210> SEQ ID NO 32
<211> LENGTH: 111
<212> TYPE: PRT
<213> ORGANISM: Mus sp.

<400> SEQUENCE: 32

Asp Ile Val Leu Thr Gln Ser Pro Ala Ser Leu Ala Val Ser Leu Gly
1               5                   10                  15

Gln Arg Ala Thr Val Phe Cys Arg Ala Ser Gln Thr Val Asp Tyr Asn
            20                  25                  30

Gly Met Ser Tyr Met His Trp Phe Gln Gln Lys Pro Gly Gln Pro Pro
        35                  40                  45

Lys Leu Leu Ile Tyr Ala Ala Ser Asn Leu Asp Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Cys Ile
                85                  90                  95

Glu Asp Pro Leu Thr Phe Gly Ala Gly Thr Met Leu Glu Val Lys
            100                 105                 110

<210> SEQ ID NO 33
<211> LENGTH: 122
<212> TYPE: PRT
<213> ORGANISM: Mus sp.

<400> SEQUENCE: 33

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Ile His Trp Val Lys Gln Lys Pro Gly Gln Gly Leu Glu Trp Ile
        35                  40                  45

Gly Tyr Ile Ile Asn Pro Phe Ser Asp Gly Thr Lys Phe Thr Glu Lys
    50                  55                  60

Phe Lys Gly Lys Ala Ser Leu Thr Ser Asp Lys Ser Ser Thr Ala
65                  70                  75                  80

Tyr Met Glu Leu Asn Ser Leu Thr Ser Glu Asp Ser Ala Val Tyr Tyr
                85                  90                  95

Cys Ala Arg Arg Gly Pro Tyr Tyr Tyr Gly Thr Ala Met Asp Tyr Trp
            100                 105                 110

Gly Gln Gly Thr Ser Val Thr Val Ser Ser
        115                 120

<210> SEQ ID NO 34
<211> LENGTH: 107
<212> TYPE: PRT
<213> ORGANISM: Mus sp.

<400> SEQUENCE: 34

Asp Ile Gln Met Thr Gln Ser Pro Ala Ser Leu Ser Val Ser Val Gly
1               5                   10                  15
```

```
Glu Thr Val Thr Ile Thr Cys Arg Ala Ser Glu Asn Ile Tyr Ser Asn
             20                  25                  30

Leu Ala Trp Tyr Gln Gln Lys Gln Gly Lys Ser Pro Gln Leu Leu Val
         35                  40                  45

Asn Ala Ala Thr Asn Leu Ala Asp Gly Val Ser Ser Arg Phe Arg Gly
 50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Ile Thr Pro Phe
                 85                  90                  95

Thr Phe Gly Ser Gly Thr Lys Leu Glu Arg Lys
                100                 105
```

<210> SEQ ID NO 35
<211> LENGTH: 122
<212> TYPE: PRT
<213> ORGANISM: Mus sp.

<400> SEQUENCE: 35

```
Gln Val Gln Leu Gln Gln Ser Gly Ala Glu Leu Gly Arg Pro Gly Ala
 1               5                  10                  15

Ser Val Lys Leu Ser Cys Lys Asp Ser Gly Tyr Thr Ile Thr Ile Tyr
             20                  25                  30

Trp Met Gln Trp Val Lys Gln Arg Pro Gly Gln Gly Leu Glu Trp Ile
         35                  40                  45

Gly Ala Ile Tyr Pro Gly Asp Gly Asp Thr Arg Tyr Pro Gln Lys Phe
 50                  55                  60

Lys Gly Lys Ser Thr Leu Ser Ala Asp Lys Ser Ser Asn Thr Ala Ser
 65                  70                  75                  80

Met His Leu Ser Ser Leu Ala Ser Asp Ser Ala Val Tyr Tyr Cys
                 85                  90                  95

Ser Arg Gly Gly Ser Thr Asn Tyr Asp Tyr Asp Gly Phe Ala Tyr Trp
                100                 105                 110

Gly Gln Gly Thr Leu Val Thr Val Ser Ala
            115                 120
```

<210> SEQ ID NO 36
<211> LENGTH: 111
<212> TYPE: PRT
<213> ORGANISM: Mus sp.

<400> SEQUENCE: 36

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Asn Tyr
             20                  25                  30

Gly Ile Ser Phe Met His Trp Phe Gln Gln Lys Pro Gly Gln Pro Pro
         35                  40                  45

Lys Leu Leu Ile Tyr Ala Ala Ser Asn Leu Gly Ser Gly Val Pro Ala
 50                  55                  60

Arg Phe Ser Gly Ser Gly Ser Gly Thr Asp Phe Ser Leu Asn Ile His
 65                  70                  75                  80

Pro Leu Glu Glu Ala Asp Thr Ala Met Tyr Phe Cys Gln Gln Ser Lys
                 85                  90                  95

Glu Val Pro Arg Thr Phe Gly Gly Gly Thr Lys Leu Glu Ile Lys
                100                 105                 110
```

<210> SEQ ID NO 37
<211> LENGTH: 113
<212> TYPE: PRT
<213> ORGANISM: Mus sp.

<400> SEQUENCE: 37

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Arg Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Lys Gln Tyr Trp Gly Gln Gly Thr Thr Leu Thr Val Ser
            100                 105                 110

Ser

<210> SEQ ID NO 38
<211> LENGTH: 108
<212> TYPE: PRT
<213> ORGANISM: Mus sp.

<400> SEQUENCE: 38

Ser Ile Val Leu Thr Gln Ser Leu Lys Phe Leu Leu Val Ser Ala Gly
1               5                   10                  15

Asp Arg Val Thr Met Thr Cys Lys Ala Ser Gln Ser Val Thr Asn Asp
            20                  25                  30

Val Ala Trp Tyr Gln Gln Lys Pro Gly Gln Ser Pro Lys Leu Leu Ile
        35                  40                  45

Tyr Tyr Ala Ser Lys His Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys Arg
            100                 105

<210> SEQ ID NO 39
<211> LENGTH: 120
<212> TYPE: PRT
<213> ORGANISM: Mus sp.

<400> SEQUENCE: 39

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Ser Asn Tyr Asn Glu Lys Phe
    50                  55                  60

```
Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala His Tyr Tyr Asp Gly Ser Tyr Gly Phe Phe Asp Tyr Trp Gly Gln
            100                 105                 110

Gly Thr Thr Leu Thr Val Ser Ser
        115                 120

<210> SEQ ID NO 40
<211> LENGTH: 111
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Gln Ser Val Ser Thr Ser
             20                  25                  30

Thr Ser Ile Tyr Met His Trp Tyr Gln Gln Lys Pro Gly Gln Pro Pro
         35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Glu Ile Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Trp Thr Phe Gly Gly Gly Thr Lys Leu Glu Ile Lys
            100                 105                 110

<210> SEQ ID NO 41
<211> LENGTH: 118
<212> TYPE: PRT
<213> ORGANISM: Mus sp.

<400> SEQUENCE: 41

Glu Val Lys Leu Leu Glu Ser Gly Gly Gly Leu Val Gln Pro Gly Gly
  1               5                  10                  15

Ser Leu Lys Val Ser Cys Thr Ala Ser Gly Phe Asp Phe Ser Arg Tyr
             20                  25                  30

Trp Met Ser Trp Val Arg Gln Ala Pro Gly Lys Gly Leu Glu Trp Ile
         35                  40                  45

Gly Glu Ile Asn Pro Asp Ser Ser Thr Ile Asn Tyr Thr Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Arg Pro Gly Tyr Gly Asn Leu Phe Val Tyr Trp Gly Gln Gly Thr
            100                 105                 110

Leu Val Thr Val Ser Ser
        115

<210> SEQ ID NO 42
<211> LENGTH: 114
<212> TYPE: PRT
<213> ORGANISM: Mus sp.
```

<400> SEQUENCE: 42

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Pro Lys Asn Tyr Leu Ala Trp Tyr Gln Gln Lys Pro Gly Gln
        35                  40                  45

Pro Pro Lys Leu Leu Ile Tyr Gly Ala Ser Thr Arg Gly Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Thr Phe Pro Tyr Thr Phe Gly Gly Thr Lys Leu Glu Ile
            100                 105                 110

Lys Arg

<210> SEQ ID NO 43
<211> LENGTH: 116
<212> TYPE: PRT
<213> ORGANISM: Mus sp.

<400> SEQUENCE: 43

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Lys Asp
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ala Leu
50                  55                  60

Lys Asp Lys Phe Ile Ile Ser Arg Glu Asn Ala Lys Asn Thr Leu Tyr
65                  70                  75                  80

Leu Gln Met Asn Lys Val Arg Ser Glu Asp Thr Ala Leu Tyr Tyr Cys
                85                  90                  95

Ala Arg Trp Ser Thr Gly Leu Asp Tyr Trp Gly Gln Gly Thr Thr Leu
            100                 105                 110

Thr Val Ser Ser
        115

<210> SEQ ID NO 44
<211> LENGTH: 107
<212> TYPE: PRT
<213> ORGANISM: Mus sp.

<400> SEQUENCE: 44

Asp Ile Gln Met Thr Gln Thr Pro Ser Ser Leu Ser Ala Ser Leu Gly
1               5                   10                  15

Asp Arg Val Thr Ile Asn Cys Arg Ala Ser Gln Gly Leu Ser Asn Tyr
            20                  25                  30

Leu Asn Trp Tyr Gln Gln Lys Pro Asp Gly Thr Val Lys Leu Leu Ile
        35                  40                  45

Tyr Tyr Ala Ser Ile Leu His Ser Gly Val Pro Ser Arg Phe Thr Gly
50                  55                  60

Ser Gly Ser Gly Thr Asp Tyr Ser Leu Thr Ile Ser Thr Leu Glu Gln

```
                     65                  70                  75                  80
Glu Asp Ile Gly Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 45
<211> LENGTH: 116
<212> TYPE: PRT
<213> ORGANISM: Mus sp.

<400> SEQUENCE: 45

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Pro Phe Ser Thr Ser
                20                  25                  30

Trp Met Asn Trp Val Lys Gln Arg Pro Gly Lys Gly Leu Glu Trp Ile
                35                  40                  45

Gly Arg Ile Tyr Leu Gly Asp Gly Asp Thr Asn Tyr Asn Gly Lys Phe
            50                  55                  60

Thr Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Phe Cys
                85                  90                  95

Ala Arg Trp Arg Gly Asp Tyr Asp Tyr Trp Gly Gln Gly Thr Thr Leu
                100                 105                 110

Thr Val Ser Ser
            115
```

<210> SEQ ID NO 46
<211> LENGTH: 113
<212> TYPE: PRT
<213> ORGANISM: Mus sp.

<400> SEQUENCE: 46

```
Asp Ile Val Met Ser Gln Ser Pro Ser Ser Leu Ala Val Ser Val Gly
1               5                   10                  15

Glu Lys Val Thr Leu Ser Cys Lys Ser Ser Gln Ser Leu Leu Tyr Ser
                20                  25                  30

Ser Thr Gln Asn Asn Tyr Leu Ala Trp Tyr Gln Gln Thr Pro Gly Gln
                35                  40                  45

Ser Pro Lys Leu Leu Ile Tyr Trp Ala Ser Thr Arg Glu Ser Gly Val
            50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Trp Thr Phe Gly Gly Gly Thr Lys Leu Glu Ile
                100                 105                 110

Lys
```

<210> SEQ ID NO 47
<211> LENGTH: 118
<212> TYPE: PRT
<213> ORGANISM: Mus sp.

<400> SEQUENCE: 47

```
Ser Asp Val Gln Leu Gln Glu Ser Gly Pro Gly Leu Val Lys Pro Ser
1               5                   10                  15

Gln Thr Leu Ser Leu Thr Cys Ser Val Pro Asp Tyr Ser Ile Thr Ser
            20                  25                  30

Asp Tyr His Trp His Trp Ile Arg Gln Phe Pro Gly Asn Lys Leu Glu
        35                  40                  45

Trp Met Gly Tyr Ile Ser Ser Arg Gly Ser Thr Asn Tyr Asn Pro Ser
    50                  55                  60

Leu Lys Asn Arg Ile Ser Ile Thr His Asp Thr Ser Glu Asn Gln Phe
65                  70                  75                  80

Phe Leu Lys Leu Thr Ser Val Thr Thr Glu Asp Ser Ala Thr Tyr Tyr
                85                  90                  95

Cys Ala Gly Leu Ser Gln Leu Ala Leu Asp Tyr Trp Gly Gln Gly Thr
                100                 105                 110

Thr Leu Thr Val Ser Ser
            115
```

<210> SEQ ID NO 48
<211> LENGTH: 107
<212> TYPE: PRT
<213> ORGANISM: Mus sp.

<400> SEQUENCE: 48

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Tyr Pro Tyr
            20                  25                  30

Leu Asn Trp Phe Gln Gln Lys Pro Gly Lys Ser Pro Lys Thr Leu Ile
        35                  40                  45

Tyr Arg Thr Asn Arg Leu Leu Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
                100                 105
```

<210> SEQ ID NO 49
<211> LENGTH: 120
<212> TYPE: PRT
<213> ORGANISM: Mus sp.

<400> SEQUENCE: 49

```
Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Asn Met Gly Val Gly Trp Ile Arg Gln Pro Ser Gly Lys Gly Leu Glu
        35                  40                  45

Trp Leu Ala His Ile Trp Trp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Glu Asp Thr Ala Thr Tyr Tyr
                85                  90                  95
```

```
Cys Val Arg Ser Asn Tyr Gly Tyr Ala Trp Phe Ala Tyr Trp Gly Gln
                100                 105                 110

Gly Thr Leu Val Thr Val Ser Ala
        115                 120

<210> SEQ ID NO 50
<211> LENGTH: 111
<212> TYPE: PRT
<213> ORGANISM: Mus sp.

<400> SEQUENCE: 50

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Lys Ser Phe Met His Trp Tyr Gln Gln Arg Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Trp Thr Phe Gly Gly Gly Thr Lys Leu Glu Ile Lys
                100                 105                 110

<210> SEQ ID NO 51
<211> LENGTH: 119
<212> TYPE: PRT
<213> ORGANISM: Mus sp.

<400> SEQUENCE: 51

Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Val His Trp Val Lys Leu Ser His Ala Lys Ser Leu Glu Trp Ile
        35                  40                  45

Gly Val Ile Ser Thr Tyr Asn Asp Tyr Thr Tyr Asn Asn Gln Asp Phe
    50                  55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Asn Ser Tyr Phe Tyr Ala Leu Asp Tyr Trp Gly Gln Gly
                100                 105                 110

Thr Ser Val Thr Val Ser Ser
        115

<210> SEQ ID NO 52
<211> LENGTH: 111
<212> TYPE: PRT
<213> ORGANISM: Mus sp.

<400> SEQUENCE: 52

Asp Ile Ala Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Ser
```

```
                    20                  25                  30

Gly Ile Cys Phe Val Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
        50                  55                  60

Arg Phe Ser Gly Ser Gly Ser Gly Thr Asp Phe Ser Leu Asn Ile His
65                  70                  75                  80

Pro Met Glu Lys Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
                100                 105                 110

<210> SEQ ID NO 53
<211> LENGTH: 121
<212> TYPE: PRT
<213> ORGANISM: Mus sp.

<400> SEQUENCE: 53

Gln Val Gln Leu Gln Gln Ser Gly Ala Glu Leu Ala Ser Pro Gly Thr
1               5                   10                  15

Ser Val Lys Leu Ser Cys Lys Ala Ser Gly Tyr Thr Phe Thr Phe Tyr
            20                  25                  30

Gly Ile Ser Trp Val Lys Gln Lys Thr Gly Gln Gly Leu Glu Trp Ile
        35                  40                  45

Gly Glu Ile Tyr Pro Gly Ser Tyr Asn Ala Tyr Tyr Asn Asp Lys Phe
    50                  55                  60

Lys Gly Lys Ala Thr Leu Thr Ala Asp Arg Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Asp Tyr Gly Asp Pro Tyr Tyr Tyr Ala Met Asp Tyr Trp Gly
                100                 105                 110

Gln Gly Thr Ser Val Thr Val Ser Ser
            115                 120

<210> SEQ ID NO 54
<211> LENGTH: 111
<212> TYPE: PRT
<213> ORGANISM: Mus sp.

<400> SEQUENCE: 54

Asp Ile Val Leu Thr Gln Ser Pro Ala Ser Leu Thr Val Ser Leu Gly
1               5                   10                  15

Gln Arg Ala Thr Ile Ser Cys Arg Ala Ser Gln Ser Val Ser Thr Ser
            20                  25                  30

Thr Phe Asn Tyr Met Asn Trp Tyr Gln Gln Lys Leu Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ile Ala Thr Tyr Tyr Cys Gln His Ser Trp
                85                  90                  95

Glu Ile Pro Trp Thr Phe Gly Gly Gly Thr Lys Leu Glu Ile Lys
                100                 105                 110
```

-continued

<210> SEQ ID NO 55
<211> LENGTH: 118
<212> TYPE: PRT
<213> ORGANISM: Mus sp.

<400> SEQUENCE: 55

Glu Val Lys Leu Leu Glu Ser Gly Gly Gly Leu Val Gln Pro Gly Gly
1               5                   10                  15

Ser Gln Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Val Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Gly Tyr Gly Asn Leu Phe Val Tyr Trp Gly Gln Gly Thr
            100                 105                 110

Leu Val Thr Val Ser Ala
        115

<210> SEQ ID NO 56
<211> LENGTH: 113
<212> TYPE: PRT
<213> ORGANISM: Mus sp.

<400> SEQUENCE: 56

Asp Ile Val Leu Thr Gln Ala Thr Pro Ser Val Pro Val Thr Pro Gly
1               5                   10                  15

Glu Ser Val Ser Ile Ser Cys Arg Ser Ser Lys Ser Leu Leu His Thr
            20                  25                  30

Lys Gly Asp Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Val Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Ser Gly Thr Lys Leu Glu Ile Lys
            100                 105                 110

Arg

<210> SEQ ID NO 57
<211> LENGTH: 118
<212> TYPE: PRT
<213> ORGANISM: Mus sp.

<400> SEQUENCE: 57

Glu Val Gln Leu Gln Gln Ser Gly Ala Glu Ser Val Arg Ser Gly Ala
1               5                   10                  15

Ser Val Lys Leu Ser Cys Thr Ala Ser Gly Leu Asn Ile Lys Asp Tyr
            20                  25                  30

Tyr Met His Trp Val Asn Leu Arg Pro Glu Gln Gly Leu Glu Trp Ile
        35                  40                  45

Gly Trp Ile Asp Pro Glu Asn Gly Asp Thr Glu Tyr Ala Pro Glu Phe
            50                  55                  60
Gln Gly Lys Ala Thr Met Thr Ala Asp Thr Ser Ser Asn Thr Ala Tyr
 65                  70                  75                  80
Leu Gln Leu Ser Ser Leu Thr Ser Glu Asp Thr Ala Val Tyr Tyr Cys
                 85                  90                  95
Asn Ala Cys Asn Tyr Gly Ser Ala Tyr Gly Tyr Trp Gly Gln Gly Thr
            100                 105                 110
Thr Leu Thr Val Ser Ser
            115

<210> SEQ ID NO 58
<211> LENGTH: 107
<212> TYPE: PRT
<213> ORGANISM: Mus sp.

<400> SEQUENCE: 58

Glu Thr Thr Val Thr Gln Ser Pro Ala Ser Leu Ser Met Ala Ile Gly
 1               5                  10                  15
Glu Lys Val Thr Ile Arg Cys Ile Thr Asn Thr Asp Ile Asp Asp Asp
                 20                  25                  30
Met Asn Trp Tyr Gln Gln Lys Pro Gly Glu Pro Pro Lys Leu Leu Ile
             35                  40                  45
Ser Glu Gly Asn Gly Leu Arg Pro Gly Val Pro Ser Arg Phe Ser Ser
         50                  55                  60
Ser Gly Tyr Gly Thr Asp Phe Val Phe Thr Ile Glu Asn Met Leu Ser
 65                  70                  75                  80
Glu Asp Val Ala Asp Tyr Tyr Cys Leu Gln Ser Asp Asn Leu Pro Leu
                 85                  90                  95
Thr Phe Gly Ser Gly Thr Lys Leu Glu Ile Lys
            100                 105

<210> SEQ ID NO 59
<211> LENGTH: 120
<212> TYPE: PRT
<213> ORGANISM: Mus sp.

<400> SEQUENCE: 59

Glu Val Lys Leu Leu Glu Ser Gly Gly Gly Leu Val Gln Pro Gly Gly
 1               5                  10                  15
Ser Leu Lys Leu Ser Cys Ala Ala Ser Gly Phe Asp Phe Ser Arg Tyr
                 20                  25                  30
Trp Met Ser Trp Val Arg Gln Ala Pro Gly Lys Gly Leu Glu Trp Ile
             35                  40                  45
Gly Asp Leu Asn Pro Asp Ser Ser Ala Ile Asn Tyr Thr Pro Ser Leu
         50                  55                  60
Lys Asp Lys Phe Ile Ile Ser Arg Asp Asn Ala Lys Asn Thr Leu Tyr
 65                  70                  75                  80
Leu Gln Met Ser Lys Val Arg Ser Glu Asp Thr Ala Leu Tyr Tyr Cys
                 85                  90                  95
Thr Leu Ile Thr Thr Leu Val Pro Tyr Thr Met Asp Phe Trp Gly Gln
            100                 105                 110
Gly Thr Ser Val Thr Val Ser Ser
            115                 120

<210> SEQ ID NO 60
<211> LENGTH: 113

```
<212> TYPE: PRT
<213> ORGANISM: Mus sp.

<400> SEQUENCE: 60

Asp Ile Val Met Thr Gln Ser Pro Ser Ser Leu Thr Val Thr Ala Gly
1               5                   10                  15

Val Lys Val Thr Met Ser Cys Lys Ser Ser Gln Ser Leu Leu Asn Ser
            20                  25                  30

Gly Asp Gln Lys Asn Cys Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 61
<211> LENGTH: 120
<212> TYPE: PRT
<213> ORGANISM: Mus sp.

<400> SEQUENCE: 61

Glu Ile His Leu Val Glu Ser Gly Gly Gly Leu Val Lys Pro Gly Gly
1               5                   10                  15

Ser Leu Lys Val Ser Cys Ala Ala Ser Gly Phe Thr Phe Ser Arg Tyr
            20                  25                  30

Ala Met Ser Trp Val Arg Gln Thr Pro Glu Lys Arg Leu Glu Trp Val
        35                  40                  45

Ala Thr Ile Ser Gly Gly Gly Arg Tyr Thr Tyr Tyr Pro Asp Leu Val
    50                  55                  60

Lys Gly Arg Phe Thr Ile Ser Arg Asp Ile Ala Arg Thr Thr Leu Tyr
65                  70                  75                  80

Leu Gln Met Ser Ser Leu Arg Ser Glu Asp Thr Ala Met Tyr Tyr Cys
                85                  90                  95

Ala Arg Thr Ala Arg Ala Ser Asn Tyr Ala Met Asp Tyr Trp Gly Gln
            100                 105                 110

Gly Thr Ser Val Thr Val Ser Ser
        115                 120

<210> SEQ ID NO 62
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Tyr Pro Tyr
            20                  25                  30

Leu Asn Trp Phe Gln Gln Lys Pro Gly Lys Ala Pro Lys Thr Leu Ile
```

```
                35                  40                  45

Tyr Arg Thr Asn Arg Leu Leu Asp Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Leu Gln Tyr Asp Glu Phe Pro Leu
                 85                  90                  95

Thr Phe Gly Ala Gly Thr Lys Leu Glu Ile Lys Arg
            100                 105

<210> SEQ ID NO 63
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
                20                  25                  30

Asn Met Gly Val Gly Trp Ile Arg Gln Pro Pro Gly Lys Ala Leu Glu
            35                  40                  45

Trp Leu Ala His Ile Trp Trp Asp Asp Asp Lys Tyr Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Val Arg Ser Asn Tyr Gly Tyr Ala Trp Phe Ala Tyr Trp Gly Gln
            100                 105                 110

Gly Thr Leu Val Thr Val Ser Ser
        115                 120

<210> SEQ ID NO 64
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Glu Ser Val Asp Ser Tyr
                20                  25                  30

Gly Lys Ser Phe Met His Trp Tyr Gln Gln Lys Pro Gly Gln Ala Pro
            35                  40                  45

Arg Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln Gln Ser Asn
                 85                  90                  95
```

Glu Asp Pro Trp Thr Phe Gly Gly Gly Thr Lys Leu Glu Ile Lys Arg
            100                 105                 110

<210> SEQ ID NO 65
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Val His Trp Val Arg Gln Ala Pro Gly Lys Arg Leu Glu Trp Ile
        35                  40                  45

Gly Val Ile Ser Thr Tyr Asn Asp Tyr Thr Tyr Asn Asn Gln Asp Phe
    50                  55                  60

Lys Gly Arg Val Thr Met Thr Arg Asp Thr Ser Ala Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Gly Asn Ser Tyr Phe Tyr Ala Leu Asp Tyr Trp Gly Gln Gly
            100                 105                 110

Thr Ser Val Thr Val Ser Ser
        115

<210> SEQ ID NO 66
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Thr
            20                  25                  30

Lys Gly Asp Thr Tyr Leu Tyr Trp Phe Leu Gln Lys Pro Gly Gln Ser
        35                  40                  45

Pro Gln Leu Leu Ile Tyr Arg Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gln Gly Thr Lys Leu Glu Ile Lys
            100                 105                 110

Arg

<210> SEQ ID NO 67
<211> LENGTH: 118
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Glu Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Asn Ala Cys Asn Tyr Gly Ser Ala Tyr Gly Tyr Trp Gly Gln Gly Thr
            100                 105                 110

Thr Leu Thr Val Ser Ser
            115

<210> SEQ ID NO 68
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Glu Thr Thr Leu Thr Gln Ser Pro Ala Phe Met Ser Ala Thr Pro Gly
1               5                   10                  15

Asp Lys Val Asn Ile Ser Cys Ile Thr Asn Thr Asp Ile Asp Asp Asp
            20                  25                  30

Met Asn Trp Tyr Gln Gln Lys Pro Gly Glu Ala Ala Ile Leu Leu Ile
        35                  40                  45

Ser Glu Gly Asn Gly Leu Arg Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln Ser Asp Asn Leu Pro Leu
                85                  90                  95

Thr Phe Gly Ser Gly Thr Lys Leu Glu Ile Lys Arg
            100                 105

<210> SEQ ID NO 69
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Asp Leu Asn Pro Asp Ser Ser Ala Ile Asn Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Leu Ile Thr Thr Leu Val Pro Tyr Thr Met Asp Phe Trp Gly Gln
            100                 105                 110

Gly Thr Ser Val Thr Val Ser Ser
            115                 120

<210> SEQ ID NO 70
<211> LENGTH: 434
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Ala Ile Val Phe Ile Lys Gln Pro Ser Ser Gln Asp Ala Leu Gln Gly
1               5                   10                  15

Arg Arg Ala Leu Leu Arg Cys Glu Val Glu Ala Pro Gly Pro Val His
            20                  25                  30

Val Tyr Trp Leu Leu Asp Gly Ala Pro Val Gln Asp Thr Glu Arg Arg
        35                  40                  45

Phe Ala Gln Gly Ser Ser Leu Ser Phe Ala Ala Val Asp Arg Leu Gln
    50                  55                  60

Asp Ser Gly Thr Phe Gln Cys Val Ala Arg Asp Asp Val Thr Gly Glu
65                  70                  75                  80

Glu Ala Arg Ser Ala Asn Ala Ser Phe Asn Ile Lys Trp Ile Glu Ala
                85                  90                  95

Gly Pro Val Val Leu Lys His Pro Ala Ser Glu Ala Glu Ile Gln Pro
            100                 105                 110

Gln Thr Gln Val Thr Leu Arg Cys His Ile Asp Gly His Pro Arg Pro
            115                 120                 125

Thr Tyr Gln Trp Phe Arg Asp Gly Thr Pro Leu Ser Asp Gly Gln Ser
    130                 135                 140

Asn His Thr Val Ser Ser Lys Glu Arg Asn Leu Thr Leu Arg Pro Ala
145                 150                 155                 160

Gly Pro Glu His Ser Gly Leu Tyr Ser Cys Cys Ala His Ser Ala Phe
                165                 170                 175

Gly Gln Ala Cys Ser Ser Gln Asn Phe Thr Leu Ser Ile Ala Asp Glu
            180                 185                 190

Ser Phe Ala Arg Val Val Leu Ala Pro Gln Asp Val Val Val His Pro
        195                 200                 205

Val Arg Ser Val Glu Cys Pro Pro Cys Pro Ala Pro Pro Val Ala Gly
    210                 215                 220

Pro Ser Val Phe Leu Phe Pro Pro Lys Pro Lys Asp Thr Leu Met Ile
225                 230                 235                 240
```

```
Ser Arg Thr Pro Glu Val Thr Cys Val Val Asp Val Ser His Glu
            245                 250                 255

Asp Pro Glu Val Gln Phe Asn Trp Tyr Val Asp Gly Val Glu Val His
        260                 265                 270

Asn Ala Lys Thr Lys Pro Arg Glu Glu Gln Phe Asn Ser Thr Phe Arg
            275                 280                 285

Val Val Ser Val Leu Thr Val His Gln Asp Trp Leu Asn Gly Lys
        290                 295                 300

Glu Tyr Lys Cys Lys Val Ser Asn Lys Gly Leu Pro Ala Pro Ile Glu
305                 310                 315                 320

Lys Thr Ile Ser Lys Thr Lys Gly Gln Pro Arg Glu Pro Gln Val Tyr
                325                 330                 335

Thr Leu Pro Pro Ser Arg Glu Glu Met Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Met
370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys

<210> SEQ ID NO 71
<211> LENGTH: 702
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 71

Ala Pro Gln Asp Val Val Ala Arg Tyr Glu Glu Ala Met Phe His
1               5                   10                  15

Cys Gln Phe Ser Ala Gln Pro Pro Ser Leu Gln Trp Leu Phe Glu
            20                  25                  30

Asp Glu Thr Pro Ile Thr Asn Arg Ser Arg Pro Pro His Leu Arg Arg
        35                  40                  45

Ala Thr Val Phe Ala Asn Gly Ser Leu Leu Leu Thr Gln Val Arg Pro
    50                  55                  60

Arg Asn Ala Gly Ile Tyr Arg Cys Ile Gly Gln Gly Arg Gly Pro
65                  70                  75                  80

Pro Ile Ile Leu Glu Ala Thr Leu His Leu Ala Glu Ile Glu Asp Met
                85                  90                  95

Pro Leu Phe Glu Pro Arg Val Phe Thr Ala Gly Ser Glu Glu Arg Val
            100                 105                 110

Thr Cys Leu Pro Pro Lys Gly Leu Pro Glu Pro Ser Val Trp Trp Glu
        115                 120                 125

His Ala Gly Val Arg Leu Pro Thr His Gly Arg Val Tyr Gln Lys Gly
    130                 135                 140

His Glu Leu Val Leu Ala Asn Ile Ala Glu Ser Asp Ala Gly Val Tyr
145                 150                 155                 160
```

```
Thr Cys His Ala Ala Asn Leu Ala Gly Gln Arg Arg Gln Asp Val Asn
            165                 170                 175
Ile Thr Val Ala Thr Val Pro Ser Trp Leu Lys Lys Pro Gln Asp Ser
            180                 185                 190
Gln Leu Glu Glu Gly Lys Pro Gly Tyr Leu Asp Cys Leu Thr Gln Ala
            195                 200                 205
Thr Pro Lys Pro Thr Val Val Trp Tyr Arg Asn Gln Met Leu Ile Ser
        210                 215                 220
Glu Asp Ser Arg Phe Glu Val Phe Lys Asn Gly Thr Leu Arg Ile Asn
225                 230                 235                 240
Ser Val Glu Val Tyr Asp Gly Thr Trp Tyr Arg Cys Met Ser Ser Thr
                245                 250                 255
Pro Ala Gly Ser Ile Glu Ala Gln Ala Arg Val Gln Val Leu Glu Lys
                260                 265                 270
Leu Lys Phe Thr Pro Pro Gln Pro Gln Gln Cys Met Glu Phe Asp
        275                 280                 285
Lys Glu Ala Thr Val Pro Cys Ser Ala Thr Gly Arg Glu Lys Pro Thr
        290                 295                 300
Ile Lys Trp Glu Arg Ala Asp Gly Ser Ser Leu Pro Glu Trp Val Thr
305                 310                 315                 320
Asp Asn Ala Gly Thr Leu His Phe Ala Arg Val Thr Arg Asp Asp Ala
                325                 330                 335
Gly Asn Tyr Thr Cys Ile Ala Ser Asn Gly Pro Gln Gly Gln Ile Arg
                340                 345                 350
Ala His Val Gln Leu Thr Val Ala Val Phe Ile Thr Phe Lys Val Glu
                355                 360                 365
Pro Glu Arg Thr Thr Val Tyr Gln Gly His Thr Ala Leu Leu Gln Cys
        370                 375                 380
Glu Ala Gln Gly Asp Pro Lys Pro Leu Ile Gln Trp Lys Gly Lys Asp
385                 390                 395                 400
Arg Ile Leu Asp Pro Thr Lys Leu Gly Pro Arg Met His Ile Phe Gln
                405                 410                 415
Asn Gly Ser Leu Val Ile His Asp Val Ala Pro Glu Asp Ser Gly Arg
                420                 425                 430
Tyr Thr Cys Ile Ala Gly Asn Ser Cys Asn Ile Lys His Thr Glu Ala
            435                 440                 445
Pro Leu Tyr Val Val Asp Lys Pro Val Pro Glu Glu Ser Glu Gly Pro
        450                 455                 460
Gly Ser Pro Pro Pro Tyr Lys Met Ile Gln His Pro Val Arg Ser Val
465                 470                 475                 480
Glu Cys Pro Pro Cys Pro Ala Pro Pro Val Ala Gly Pro Ser Val Phe
                485                 490                 495
Leu Phe Pro Pro Lys Pro Lys Asp Thr Leu Met Ile Ser Arg Thr Pro
                500                 505                 510
Glu Val Thr Cys Val Val Val Asp Val Ser His Glu Asp Pro Glu Val
            515                 520                 525
Gln Phe Asn Trp Tyr Val Asp Gly Val Glu Val His Asn Ala Lys Thr
        530                 535                 540
Lys Pro Arg Glu Glu Gln Phe Asn Ser Thr Phe Arg Val Val Ser Val
545                 550                 555                 560
Leu Thr Val Val His Gln Asp Trp Leu Asn Gly Lys Glu Tyr Lys Cys
                565                 570                 575
```

-continued

```
Lys Val Ser Asn Lys Gly Leu Pro Ala Pro Ile Glu Lys Thr Ile Ser
            580                 585                 590

Lys Thr Lys Gly Gln Pro Arg Glu Pro Gln Val Tyr Thr Leu Pro Pro
        595                 600                 605

Ser Arg Glu Glu Met Thr Lys Asn Gln Val Ser Leu Thr Cys Leu Val
    610                 615                 620

Lys Gly Phe Tyr Pro Ser Asp Ile Ala Val Glu Trp Glu Ser Asn Gly
625                 630                 635                 640

Gln Pro Glu Asn Asn Tyr Lys Thr Thr Pro Pro Met Leu Asp Ser Asp
                645                 650                 655

Gly Ser Phe Phe Leu Tyr Ser Lys Leu Thr Val Asp Lys Ser Arg Trp
            660                 665                 670

Gln Gln Gly Asn Val Phe Ser Cys Ser Val Met His Glu Ala Leu His
        675                 680                 685

Asn His Tyr Thr Gln Lys Ser Leu Ser Leu Ser Pro Gly Lys
    690                 695                 700
```

<210> SEQ ID NO 72
<211> LENGTH: 708
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Ala Ile Val Phe Ile Lys Gln Pro Ser Ser Gln Asp Ala Leu Gln Gly
1               5                   10                  15

Arg Arg Ala Leu Leu Arg Cys Glu Val Glu Ala Pro Gly Pro Val His
            20                  25                  30

Val Tyr Trp Leu Leu Asp Gly Ala Pro Val Gln Asp Thr Glu Arg Arg
        35                  40                  45

Phe Ala Gln Gly Ser Ser Leu Ser Phe Ala Ala Val Asp Arg Leu Gln
    50                  55                  60

Asp Ser Gly Thr Phe Gln Cys Val Ala Arg Asp Asp Val Thr Gly Glu
65                  70                  75                  80

Glu Ala Arg Ser Ala Asn Ala Ser Phe Asn Ile Lys Trp Ile Glu Ala
                85                  90                  95

Gly Pro Val Val Leu Lys His Pro Ala Ser Glu Ala Glu Ile Gln Pro
            100                 105                 110

Gln Thr Gln Val Thr Leu Arg Cys His Ile Asp Gly His Pro Arg Pro
        115                 120                 125

Thr Tyr Gln Trp Phe Arg Asp Gly Thr Pro Leu Ser Asp Gly Gln Ser
    130                 135                 140

Asn His Thr Val Ser Ser Lys Glu Arg Asn Leu Thr Leu Arg Pro Ala
145                 150                 155                 160

Gly Pro Glu His Ser Gly Leu Tyr Ser Cys Cys Ala His Ser Ala Phe
                165                 170                 175

Gly Gln Ala Cys Ser Ser Gln Asn Phe Thr Leu Ser Ile Ala Asp Glu
            180                 185                 190

Ser Phe Ala Arg Val Val Leu Ala Pro Gln Asp Val Val Ala Arg
        195                 200                 205

Tyr Glu Glu Ala Met Phe His Cys Gln Phe Ser Ala Gln Pro Pro Pro
    210                 215                 220

Ser Leu Gln Trp Leu Phe Glu Asp Glu Thr Pro Ile Thr Asn Arg Ser
```

```
                225                 230                 235                 240
Arg Pro Pro His Leu Arg Arg Ala Thr Val Phe Ala Asn Gly Ser Leu
                    245                 250                 255

Leu Leu Thr Gln Val Arg Pro Arg Asn Ala Gly Ile Tyr Arg Cys Ile
                260                 265                 270

Gly Gln Gly Gln Arg Gly Pro Ile Ile Leu Glu Ala Thr Leu His
                275                 280                 285

Leu Ala Glu Ile Glu Asp Met Pro Leu Phe Glu Pro Arg Val Phe Thr
            290                 295                 300

Ala Gly Ser Glu Glu Arg Val Thr Cys Leu Pro Pro Lys Gly Leu Pro
305                 310                 315                 320

Glu Pro Ser Val Trp Trp Glu His Ala Gly Val Arg Leu Pro Thr His
                    325                 330                 335

Gly Arg Val Tyr Gln Lys Gly His Glu Leu Val Leu Ala Asn Ile Ala
                340                 345                 350

Glu Ser Asp Ala Gly Val Tyr Thr Cys His Ala Ala Asn Leu Ala Gly
            355                 360                 365

Gln Arg Arg Gln Asp Val Asn Ile Thr Val Ala Thr Val Pro Ser Trp
        370                 375                 380

Leu Lys Lys Pro Gln Asp Ser Gln Leu Glu Glu Gly Lys Pro Gly Tyr
385                 390                 395                 400

Leu Asp Cys Leu Thr Gln Ala Thr Pro Lys Pro Thr Val Val Trp Tyr
                405                 410                 415

Arg Asn Gln Met Leu Ile Ser Glu Asp Ser Arg Phe Glu Val Phe Lys
                420                 425                 430

Asn Gly Thr Leu Arg Ile Asn Ser Val Glu Val Tyr Asp Gly Thr Trp
            435                 440                 445

Tyr Arg Cys Met Ser Ser Thr Pro Ala Gly Ser Ile Glu Ala Gln Ala
        450                 455                 460

Arg Val Gln Val Leu Glu Lys Leu Lys Phe Thr Pro Pro Pro Gln Pro
465                 470                 475                 480

His Pro Val Arg Ser Val Glu Cys Pro Pro Cys Pro Ala Pro Pro Val
                485                 490                 495

Ala Gly Pro Ser Val Phe Leu Phe Pro Pro Lys Pro Lys Asp Thr Leu
                500                 505                 510

Met Ile Ser Arg Thr Pro Glu Val Thr Cys Val Val Asp Val Ser
            515                 520                 525

His Glu Asp Pro Glu Val Gln Phe Asn Trp Tyr Val Asp Gly Val Glu
        530                 535                 540

Val His Asn Ala Lys Thr Lys Pro Arg Glu Glu Gln Phe Asn Ser Thr
545                 550                 555                 560

Phe Arg Val Val Ser Val Leu Thr Val Val His Gln Asp Trp Leu Asn
                565                 570                 575

Gly Lys Glu Tyr Lys Cys Lys Val Ser Asn Lys Gly Leu Pro Ala Pro
                580                 585                 590

Ile Glu Lys Thr Ile Ser Lys Thr Lys Gly Gln Pro Arg Glu Pro Gln
            595                 600                 605

Val Tyr Thr Leu Pro Pro Ser Arg Glu Glu Met Thr Lys Asn Gln Val
        610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655
```

```
Pro Met Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
            675                 680                 685

Met His Glu Ala Leu His Asn His Tyr Thr Gln Lys Ser Leu Ser Leu
            690                 695                 700

Ser Pro Gly Lys
705

<210> SEQ ID NO 73
<211> LENGTH: 429
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Lys Phe Thr Pro Pro Gln Pro Gln Gln Cys Met Glu Phe Asp Lys
1               5                   10                  15

Glu Ala Thr Val Pro Cys Ser Ala Thr Gly Arg Glu Lys Pro Thr Ile
            20                  25                  30

Lys Trp Glu Arg Ala Asp Gly Ser Ser Leu Pro Glu Trp Val Thr Asp
            35                  40                  45

Asn Ala Gly Thr Leu His Phe Ala Arg Val Thr Arg Asp Asp Ala Gly
        50                  55                  60

Asn Tyr Thr Cys Ile Ala Ser Asn Gly Pro Gln Gly Gln Ile Arg Ala
65                  70                  75                  80

His Val Gln Leu Thr Val Ala Val Phe Ile Thr Phe Lys Val Glu Pro
                85                  90                  95

Glu Arg Thr Thr Val Tyr Gln Gly His Thr Ala Leu Leu Gln Cys Glu
            100                 105                 110

Ala Gln Gly Asp Pro Lys Pro Leu Ile Gln Trp Lys Gly Lys Asp Arg
            115                 120                 125

Ile Leu Asp Pro Thr Lys Leu Gly Pro Arg Met His Ile Phe Gln Asn
        130                 135                 140

Gly Ser Leu Val Ile His Asp Val Ala Pro Glu Asp Ser Gly Arg Tyr
145                 150                 155                 160

Thr Cys Ile Ala Gly Asn Ser Cys Asn Ile Lys His Thr Glu Ala Pro
                165                 170                 175

Leu Tyr Val Val Asp Lys Pro Val Pro Glu Glu Ser Glu Gly Pro Gly
            180                 185                 190

Ser Pro Pro Pro Tyr Lys Met Ile Gln His Pro Val Arg Ser Val Glu
            195                 200                 205

Cys Pro Pro Cys Pro Ala Pro Val Ala Gly Pro Ser Val Phe Leu
        210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Gln
                245                 250                 255

Phe Asn Trp Tyr Val Asp Gly Val Glu Val His Asn Ala Lys Thr Lys
            260                 265                 270

Pro Arg Glu Glu Gln Phe Asn Ser Thr Phe Arg Val Val Ser Val Leu
            275                 280                 285
```

Thr Val Val His Gln Asp Trp Leu Asn Gly Lys Glu Tyr Lys Cys Lys
290                     295                 300

Val Ser Asn Lys Gly Leu Pro Ala Pro Ile Glu Lys Thr Ile Ser Lys
305                 310                 315                 320

Thr Lys Gly Gln Pro Arg Glu Pro Gln Val Tyr Thr Leu Pro Pro Ser
                325                 330                 335

Arg Glu Glu Met Thr Lys Asn Gln Val Ser Leu Thr Cys Leu Val Lys
                340                 345                 350

Gly Phe Tyr Pro Ser Asp Ile Ala Val Glu Trp Glu Ser Asn Gly Gln
                355                 360                 365

Pro Glu Asn Asn Tyr Lys Thr Thr Pro Pro Met Leu Asp Ser Asp Gly
370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
                405                 410                 415

His Tyr Thr Gln Lys Ser Leu Ser Leu Ser Pro Gly Lys
                420                 425

<210> SEQ ID NO 74
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Glu Ala Arg Ser Ala Asn Ala Ser Phe Asn Ile Lys Trp Ile Glu
1               5                   10                  15

Ala Gly Pro Val Val Leu Lys His Pro Ala Ser Glu Ala Glu Ile Gln
                20                  25                  30

Pro Gln Thr Gln Val Thr Leu Arg Cys His Ile Asp Gly His Pro Arg
            35                  40                  45

Pro Thr Tyr Gln Trp Phe Arg Asp Gly Thr Pro Leu Ser Asp Gly Gln
50                  55                  60

Ser Asn His Thr Val Ser Ser Lys Glu Arg Asn Leu Thr Leu Arg Pro
65                  70                  75                  80

Ala Gly Pro Glu His Ser Gly Leu Tyr Ser Cys Cys Ala His Ser Ala
                85                  90                  95

Phe Gly Gln Ala Cys Ser Ser Gln Asn Phe Thr Leu Ser Ile Ala Asp
                100                 105                 110

Glu Ser Phe Ala Arg Val Val Leu Ala Pro Gln Asp Val Val Val Ala
            115                 120                 125

Arg Tyr Glu Glu Ala Met Phe His Cys Gln Phe Ser Ala Gln Pro Pro
130                 135                 140

Pro Ser Leu Gln Trp Leu Phe Glu Asp Glu Thr Pro Ile Thr Asn Arg
145                 150                 155                 160

Ser Arg Pro Pro His Leu Arg Arg Ala Thr Val Phe Ala Asn Gly Ser
                165                 170                 175

Leu Leu Leu Thr Gln Val Arg Pro Arg Asn Ala Gly Ile Tyr Arg Cys
                180                 185                 190

Ile Gly Gln Gly Gln Arg Gly Pro Pro Ile Ile Leu Glu Ala Thr Leu
            195                 200                 205

His Leu Ala Glu His Pro Val Arg Ser Val Glu Cys Pro Pro Cys Pro

```
            210                 215                 220
Ala Pro Pro Val Ala Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Phe Arg Val Val Ser Val Leu Thr Val Val His Gln
        290                 295                 300

Asp Trp Leu Asn Gly Lys Glu Tyr Lys Cys Lys Val Ser Asn Lys Gly
305                 310                 315                 320

Leu Pro Ala Pro Ile Glu Lys Thr Ile Ser Lys Thr Lys Gly Gln Pro
                325                 330                 335

Arg Glu Pro Gln Val Tyr Thr Leu Pro Pro Ser Arg Glu Glu Met Thr
                340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
        370                 375                 380

Lys Thr Thr Pro Pro Met Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
                405                 410                 415

Ser Cys Ser Val Met His Glu Ala Leu His Asn His Tyr Thr Gln Lys
            420                 425                 430

Ser Leu Ser Leu Ser Pro Gly Lys
        435                 440

<210> SEQ ID NO 75
<211> LENGTH: 607
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Ala Ile Val Phe Ile Lys Gln Pro Ser Ser Gln Asp Ala Leu Gln Gly
1               5                   10                  15

Arg Arg Ala Leu Leu Arg Cys Glu Val Glu Ala Pro Gly Pro Val His
            20                  25                  30

Val Tyr Trp Leu Leu Asp Gly Ala Pro Val Gln Asp Thr Glu Arg Arg
        35                  40                  45

Phe Ala Gln Gly Ser Ser Leu Ser Phe Ala Ala Val Asp Arg Leu Gln
    50                  55                  60

Asp Ser Gly Thr Phe Gln Cys Val Ala Arg Asp Asp Val Thr Gly Glu
65                  70                  75                  80

Glu Ala Arg Ser Ala Asn Ala Ser Phe Asn Ile Lys Trp Ile Glu Ala
                85                  90                  95

Gly Pro Val Val Leu Lys His Pro Ala Ser Glu Ala Glu Ile Gln Pro
            100                 105                 110

Gln Thr Gln Val Thr Leu Arg Cys His Ile Asp Gly His Pro Arg Pro
        115                 120                 125
```

```
Thr Tyr Gln Trp Phe Arg Asp Gly Thr Pro Leu Ser Asp Gly Gln Ser
    130                 135                 140

Asn His Thr Val Ser Ser Lys Glu Arg Asn Leu Thr Leu Arg Pro Ala
145                 150                 155                 160

Gly Pro Glu His Ser Gly Leu Tyr Ser Cys Cys Ala His Ser Ala Phe
                165                 170                 175

Gly Gln Ala Cys Ser Ser Gln Asn Phe Thr Leu Ser Ile Ala Asp Glu
                180                 185                 190

Ser Phe Ala Arg Val Val Leu Ala Pro Gln Asp Val Val Ala Arg
                195                 200                 205

Tyr Glu Glu Ala Met Phe His Cys Gln Phe Ser Ala Gln Pro Pro Pro
    210                 215                 220

Ser Leu Gln Trp Leu Phe Glu Asp Glu Thr Pro Ile Thr Asn Arg Ser
225                 230                 235                 240

Arg Pro Pro His Leu Arg Arg Ala Thr Val Phe Ala Asn Gly Ser Leu
                245                 250                 255

Leu Leu Thr Gln Val Arg Pro Arg Asn Ala Gly Ile Tyr Arg Cys Ile
                260                 265                 270

Gly Gln Gly Gln Arg Gly Pro Pro Ile Ile Leu Glu Ala Thr Leu His
                275                 280                 285

Leu Ala Glu Ile Glu Asp Met Pro Leu Phe Glu Pro Arg Val Phe Thr
    290                 295                 300

Ala Gly Ser Glu Glu Arg Val Thr Cys Leu Pro Pro Lys Gly Leu Pro
305                 310                 315                 320

Glu Pro Ser Val Trp Trp Glu His Ala Gly Val Arg Leu Pro Thr His
                325                 330                 335

Gly Arg Val Tyr Gln Lys Gly His Glu Leu Val Leu Ala Asn Ile Ala
                340                 345                 350

Glu Ser Asp Ala Gly Val Tyr Thr Cys His Ala Ala Asn Leu Ala Gly
    355                 360                 365

Gln Arg Arg Gln Asp Val Asn Ile Thr Val Ala His Pro Val Arg Ser
    370                 375                 380

Val Glu Cys Pro Pro Cys Pro Ala Pro Pro Val Ala Gly Pro Ser Val
385                 390                 395                 400

Phe Leu Phe Pro Pro Lys Pro Lys Asp Thr Leu Met Ile Ser Arg Thr
                405                 410                 415

Pro Glu Val Thr Cys Val Val Val Asp Val Ser His Glu Asp Pro Glu
                420                 425                 430

Val Gln Phe Asn Trp Tyr Val Asp Gly Val Glu Val His Asn Ala Lys
                435                 440                 445

Thr Lys Pro Arg Glu Glu Gln Phe Asn Ser Thr Phe Arg Val Val Ser
    450                 455                 460

Val Leu Thr Val Val His Gln Asp Trp Leu Asn Gly Lys Glu Tyr Lys
465                 470                 475                 480

Cys Lys Val Ser Asn Lys Gly Leu Pro Ala Pro Ile Glu Lys Thr Ile
                485                 490                 495

Ser Lys Thr Lys Gly Gln Pro Arg Glu Pro Gln Val Tyr Thr Leu Pro
                500                 505                 510

Pro Ser Arg Glu Glu Met Thr Lys Asn Gln Val Ser Leu Thr Cys Leu
    515                 520                 525

Val Lys Gly Phe Tyr Pro Ser Asp Ile Ala Val Glu Trp Glu Ser Asn
530                 535                 540
```

```
Gly Gln Pro Glu Asn Asn Tyr Lys Thr Thr Pro Met Leu Asp Ser
545                 550                 555                 560

Asp Gly Ser Phe Phe Leu Tyr Ser Lys Leu Thr Val Asp Lys Ser Arg
                565                 570                 575

Trp Gln Gln Gly Asn Val Phe Ser Cys Ser Val Met His Glu Ala Leu
            580                 585                 590

His Asn His Tyr Thr Gln Lys Ser Leu Ser Leu Ser Pro Gly Lys
            595                 600                 605

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85
```

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

```
<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
```

<400> SEQUENCE: 119

000

<210> SEQ ID NO 120
<211> LENGTH: 336
<212> TYPE: DNA
<213> ORGANISM: Mus sp.

<400> SEQUENCE: 120

| gacattgtgc tgacccaatc tccagcttct ttggctgtgt ctctagggca gagggccacc | 60 |
| atatcctgca gagccagtga aagtgttgat agttttggca atagtttat gcactggtac | 120 |
| cagcagaaac caggacagcc acccaaactc ctcatctatg ctgcatccaa cctaggatcc | 180 |
| ggggtccctg ccaggtttag tggcagtggg tctgggacag acttcagcct caacatccat | 240 |
| cctgtggagg aggatgattc tgcaatgtat ttctgtcagc aaagtaagga ggttcctcgg | 300 |
| acgttcggtg aggctccag gctggaaatc aaacgg | 336 |

<210> SEQ ID NO 121
<211> LENGTH: 339
<212> TYPE: DNA
<213> ORGANISM: Mus sp.

<400> SEQUENCE: 121

| caggtccaaa tgcagcagtc tggagctgag ctgatgaagc ctggggcctc agtgaagctt | 60 |
| tcctgcaagg ctactggcta cacattcact ggctactgga ttgagtgggt aaagcagagg | 120 |
| cctggacatg gccttgagtg gattggagag attttacctg gaagtggtcg ttctaactcc | 180 |
| aatgagaagt tcaagggcaa ggccacattc actgctgata catcctccaa cacagcctac | 240 |
| atgcaactca gcagcctgac aactgaggac tctgccatct attactgtgc aagagggaag | 300 |
| ctttcctggg gccaagggac tctggtcact gtctctgca | 339 |

<210> SEQ ID NO 122
<211> LENGTH: 324
<212> TYPE: DNA
<213> ORGANISM: Mus sp.

<400> SEQUENCE: 122

| gacattgtga tgacccagtc tcaaaaattc atgtccacat cagtaggaga cagggtcaac | 60 |
| gtcacctgca aggccagtca gaatgtgggt actaatgtag tctggtatca acagaaaaca | 120 |
| gggcaatctc ctaaagcact gattcactcg gcatcctacc ggtacagtgg agtccctgat | 180 |
| cgcttcacag gcagtggatc tgggacagat ttcactctca ccctcagcaa tgtacagtct | 240 |
| gaagacttgg cagagtattt ctgtcagcac tataacagct ttccgtacac gttcggaggg | 300 |
| gggaccaagc tggaaataaa acgg | 324 |

<210> SEQ ID NO 123
<211> LENGTH: 345
<212> TYPE: DNA
<213> ORGANISM: Mus sp.

<400> SEQUENCE: 123

| caggtccagc tgcagcagtc tggggctgaa ctggtgaggc ctggggtctc agtgaagatt | 60 |
| tcctgcaagg gttctggcta cagattcact gattatccta tacactgggt gaagcagagt | 120 |
| catgcaaaga gtctagagtg gattggaatt attagtactt actatggtga tgttaccaac | 180 |
| aacccgaagt tcagggggcaa ggccacaatg actgtagaca atcctccac cacagcctat | 240 |

```
atggaacttg ccagactgac atctgaggat tctgccatct attactgtgc aagaaatgat      300 cttttgctt actggggcca agggactctg gtcactgtct ctgca                       345

<210> SEQ ID NO 124
<211> LENGTH: 282
<212> TYPE: DNA
<213> ORGANISM: Mus sp.

<400> SEQUENCE: 124
ctaggaggca gagtcaccat tacttgcaag gcaagtgacc acattaataa ttggttagcc      60
tggtatcagc agaaaccagg aaatgctcct aggctcttaa tatctggtgc taccactttg     120
gaaactgggg ttccttcaag attcagtggc agtggatctg gaaggatta cactctcagc      180 ataaccagtc ttcagactga agatgttgct acttattact gtcaacagta ttggagtatt     240
ccgtacacgt tcggagggg gaccaagctg gaaataaaac gg                         282

<210> SEQ ID NO 125
<211> LENGTH: 375
<212> TYPE: DNA
<213> ORGANISM: Mus sp.

<400> SEQUENCE: 125
tctgatgtgc agcttcagga gtcgggacct ggcctggtga aaccttctca gtctctgtcc      60
ctcacctgca ctgtcactgg ctactcaatc accagtgatt atgcctggaa ctggatccgg     120
cagtttccag gaaacaaact ggagtggatg ggctacataa gctacagtgg ttacactaac     180
tacaacccat ctctcaaaag tcgaatctct atcactcgag acacatccaa gaaccagttc     240
ttcctgcagt tgatttctgt gactactgag gacacagcca catattactg tgcaagaggg     300
gatgcttacg acgtccggag aagtacgtac tactttgact actggggcca aggcaccact     360
ctcacagtct cctcg                                                       375

<210> SEQ ID NO 126
<211> LENGTH: 324
<212> TYPE: DNA
<213> ORGANISM: Mus sp.

<400> SEQUENCE: 126
gatattgtgc taactcagtc tccagccacc ctgtcggtga ctccaggaga tagcgtcagt      60
ctttcctgca gggccagcca aagtgttagc aacaacctac actggtatca acaaaaatca     120
catgcgtctc caaggcttct catcaagtat gcttcccagt ccatctctgg gatccctcc      180 aggttcagtg gcagtggatc agggacagat ttcactctca gtatcaacag tgtggagact     240
gaagattttg gaatgtattt ctgtcaacag agttacagct ggcctcggac gttcggtgga     300
ggcaccaagc tggaaatcaa acgg                                             324

<210> SEQ ID NO 127
<211> LENGTH: 333
<212> TYPE: DNA
<213> ORGANISM: Mus sp.

<400> SEQUENCE: 127
cagctggagg agtcaggtgc tgagctgatg cagcctgggg cctcagtgaa ggtttcctgc      60
aaggccactg gctacacatt cactgtctac tggatagagt gggtaaaaca gaggcctgga     120
catggccttg aatggattgg agagatttta cctggaagtg gtagtactga ttacaatgag     180
```
aagttcaagg gcaaggccac attcactgca gattcatcct ccaacacagc ctacatgcaa    240
ctcagcagcc tgacaactga ggactctgcc atctattact gtgcaagagg gaagcttcac    300
tggggccaag ggactctggt cacagtctct gca    333

<210> SEQ ID NO 128
<211> LENGTH: 341
<212> TYPE: DNA
<213> ORGANISM: Mus sp.

<400> SEQUENCE: 128
gacattgtga tgacacagtc tccatcctcc ctgagtgtgt cagcaggaga gaaggtcact     60
atgagctgca agtccagtca gagtctgtta acggtggaa atcaacagaa ctccttggcc    120
tggtaccagc agaaaccagg gcagcctcct aaactgttga tctacggggc ttccactagg    180
gaatctgggg tccctgatcg cttcacaggc agtggatctg gaaccgattt cgctcttacc    240
atcagcagtg tgcaggctga agacctgca gtttattact gtcagaatga tcatacttat    300
ccgtacacgt tcggaggggg gaccgagctg gaaataaaac g    341

<210> SEQ ID NO 129
<211> LENGTH: 354
<212> TYPE: DNA
<213> ORGANISM: Mus sp.

<400> SEQUENCE: 129
gaggtgaagc ttctcgagtc tggaggtggc ctggtgcagc ctggaggatc cctgaaactc     60
tcctgtgcag cctcaggatt cgattttagt aaagactgga tgagttgggt ccggcaggct    120
ccagggaaag gctagaatg gattggagaa attaatccag atagccgtac gataaattat    180
gcaccatctc taaggataa attcatcatc tccagagaga cgccaaaaa tacgctgtac    240 ctgcaaatga gtaaagtgag atctgaggac acagcccttt attactgtgc aagatgggat    300
tacgacggtg gtatggacta ctggggtcaa ggaacctcag tcaccgtctc ctca    354

<210> SEQ ID NO 130
<211> LENGTH: 323
<212> TYPE: DNA
<213> ORGANISM: Mus sp.

<400> SEQUENCE: 130
gacatccaga tgactcagtc tccagcctcc ctatctgcat ctgtgggaga aactgtcacc     60
atcacatgtc gaacaagtga gaatatttac agttatttag catggtatca gcagaaacag    120
ggaaaatctc ctcagctcct ggtccacaat gcaaacacct tagcagaagg tgtgccatca    180
aggttcagtg gcagtggatc aggcacacag ttttctctga ggatcaacag cctgcagcct    240
gaagattttg ggagttatta ttgtcagcat cattatggta ttccgttcac gttcggaggg    300
gggaccaagc tggaagtaga acg    323

<210> SEQ ID NO 131
<211> LENGTH: 354
<212> TYPE: DNA
<213> ORGANISM: Mus sp.

<400> SEQUENCE: 131
gaggtgaagc ttctcgagtc tggaggtggc ctggtgcagc ctggaggatc cctgaaactc     60
tcctgtgcag cctcaggatt cgattttagt agatactgga tgagttgggt ccggcaggct    120
ccagggaaag gctagaatg gattggagaa attaatccag atagcagtac gataaactat    180

```
acgccatctc taaaggataa attcatcatc tccagagaca acgccaaaaa tacgctgtac    240
ctgcaaatga gcaaagtgag atctgaggac acagccettt attactgtgc aagaccggga    300
tatggtaact tgtttgctta ctggggccaa gggactctgg tcactgtctc tgca           354
```

<210> SEQ ID NO 132
<211> LENGTH: 334
<212> TYPE: DNA
<213> ORGANISM: Mus sp.

<400> SEQUENCE: 132

```
gacattgtgc tgacccaatc tccagcttct ttggctgtgt ctctaggaca gagagccact     60
gtcttctgca gagccagcca gactgtcgat tataatggaa tgagttatat gcactggttc    120
caacagaaac caggacagcc acccaaactc ctcatctatg ctgcatccaa cctagattct    180
gggatccctg ccaggttcag tggcagtggg tctgggacag acttcaccct caacatccat    240
cctgtggagg aggaagatgc tgcaacctat tactgtcagc aatgtattga ggatccgctc    300
acgttcggtg ctgggaccat gctggaggtg aaac                                334
```

<210> SEQ ID NO 133
<211> LENGTH: 363
<212> TYPE: DNA
<213> ORGANISM: Mus sp.

<400> SEQUENCE: 133

```
gaggtccagc tgcagcagtc tggacctgag ctggtaaagc ctggggcttc agtgaagatg     60
tcctgcaagg cttctggata cacattcact agctatgtta cactgggt gaagcagaag     120 cctgggcagg gccttgagtg gattggatat attaatcctt tcagtgatgg tactaagttt    180
actgagaagt tcaaaggcaa ggcctcactg acttcagaca aatcgtccag cacagcctac    240
atggagctca acagcctgac ctctgaggac tctgcggtct attactgtgc aagaagaggt    300
ccttattatt acggtaccgc tatggactac tggggtcaag gaacctcagt caccgtctcc    360
tca                                                                  363
```

<210> SEQ ID NO 134
<211> LENGTH: 322
<212> TYPE: DNA
<213> ORGANISM: Mus sp.

<400> SEQUENCE: 134

```
cacatccaga tgactcagtc tccagcctcc ctatctgtat ctgtgggaga aactgtcacc     60
atcacatgtc gagcaagtga gaatatttac agtaatttag catggtatca acagaaacag    120
ggaaaatctc ctcagctcct ggtcaatgct gcaacaaact tagcagatgg tgtgtcatcg    180
aggttccgtg gcagtggatc aggcacacag tattccctca agatcaacag cctgcagtct    240
gaagattttg ggagttatta ttgtcaacat ttttggatta ctccattcac gttcggctcg    300
gggacaaagt tggaaagaaa ac                                             322
```

<210> SEQ ID NO 135
<211> LENGTH: 366
<212> TYPE: DNA
<213> ORGANISM: Mus sp.

<400> SEQUENCE: 135

```
caggttcagc tccagcagtc aggggctgag ctggaagac ctggggcttc agtgaaactg      60
```

```
tcctgcaagg attctggcta caccattact atctactgga tgcagtgggt aaaacagagg     120
cctggacagg gtctggaatg gattggggct atttatcctg agatggtgaa tactaggtac     180
cctcagaagt tcaagggcaa gtccacattg tctgcagata atcctccaa cacagcctcc     240 atgcacctca gcagcttggc atctgatgac tctgcggtct attactgttc aagaggaggg     300
tcaaccaact atgattacga cggatttgct tactggggcc aagggactct ggtcactgtc     360
tctgca                                                                366

<210> SEQ ID NO 136
<211> LENGTH: 334
<212> TYPE: DNA
<213> ORGANISM: Mus sp.

<400> SEQUENCE: 136
gacattgtgc tgacccaatc tccagcttct ttggctgtgt ctctagggca gagggccacc     60
atctcctgca gagccagcga aagtgttgat aattatggca ttagttttat gcactggttc     120
caacagaaac caggacagcc acccaaactc ctcatctatg ctgcatccaa cctaggatcc     180
ggggtccctg ccaggtttag tggcagtggg tctgggacag acttcagcct caacatccat     240 cctctgagg aggctgatac tgcaatgtat ttctgtcagc agagtaagga ggttcctcgg     300
acgttcggtg aggcaccaa gctggaaatc aaac                                  334

<210> SEQ ID NO 137
<211> LENGTH: 339
<212> TYPE: DNA
<213> ORGANISM: Mus sp.

<400> SEQUENCE: 137
caggttcagc tgcagcagtc tggagctgaa ctgatgaagc ctggggcctc agtgaagata     60
tcctgcaagg ctactggcta cacattcagt aactactgga tagagtgggt aaagcagagg     120
cctggacatg gccttgagtg gattggagag attttacctg aaggggtag tactaactac     180 aatgagaagt tcaagggcaa ggccacattc actgcagata cttcctccaa cacagcctac     240
atgcaactca gcagcctgac ctctgaggac tctgccgtct attactgtgc aagagggaaa     300
caatactggg gccaaggcac cactctcaca gtctcctca                            339

<210> SEQ ID NO 138
<211> LENGTH: 323
<212> TYPE: DNA
<213> ORGANISM: Mus sp.

<400> SEQUENCE: 138
agtattgtgc tgacccagtc tctcaaattc ctgcttgtgt cagcaggaga cagggttacc     60
atgacctgca aggccagtca gagtgtgact aatgatgtag cttggtacca acagaagcca     120 ggcagtctc ctaaactgct gatatactat gcatccaaac actacactgg agtccctgat     180
cgcttcactg gcagtggata tgggacggat ttcactttca ccatcagcac tgtgcaggct     240
gaagacctgg cagtttattt ctgtcagcag gattatagct ctccgtacac gttcggaggg     300
gggaccaagc tggaaataaa acg                                             323

<210> SEQ ID NO 139
<211> LENGTH: 360
<212> TYPE: DNA
<213> ORGANISM: Mus sp.

<400> SEQUENCE: 139
```

```
caggtccaac tgcagcagcc tggggctgaa ctagtgaagc ctgggcttca agtgaagctg    60
tcctgcaagg cttctggcta caccttcacc agctactgga tgcactgggt gaagcagagg   120
cctggacaag gccttgagtg gattggagag attaatccta gcaacggtcg ttctaactac   180
aatgagaagt tcaagagcaa ggccacactg actgtagaca atcctccag cacagcctac    240 atgcaactca gcagcctgac atctgaggac tctgcggtct atttctgtgc acattactac   300
gatggtagtt acgggttctt tgactattgg ggccaaggca ccactctcac agtctcctca   360
```

<210> SEQ ID NO 140
<211> LENGTH: 334
<212> TYPE: DNA
<213> ORGANISM: Mus sp.

<400> SEQUENCE: 140

```
gacattgtgc tgacacagtc tcctgcttcc ttagctgtat ctctggggca gagggccacc    60
atctcatgca gggccagcca aagtgtcagt acatctacct ctatttatat gcactggtac   120
caacagaaac caggacagcc acccaaactc ctcatcaagt atgcatccaa cctagaatct   180
ggggtccctg ccaggttcag tggcagtggg tctgggacag aaatcaccct caacatccat   240
cctgtggagg aggaggatac tgcaacatat tactgtcagc acagttggga gattccgtgg   300
acgttcggtg gaggcaccaa gctggaaatc aaac                               334
```

<210> SEQ ID NO 141
<211> LENGTH: 354
<212> TYPE: DNA
<213> ORGANISM: Mus sp.

<400> SEQUENCE: 141

```
gaggtgaagc ttctcgagtc tggaggtggc ctggtgcagc ctggaggatc cctgaaagtc    60
tcctgtacag cctcaggatt cgatttagt agatattgga tgagttgggt ccggcaggct   120
ccagggaaag gctagaatg gattggagaa attaatccag atagcagtac gataaactat   180
acgccatctc tgaaggataa attcatcatc tccagagaca acgccaaaaa tacgctgtac   240
ctgcaaatga gcaaagtgag atctgaggac acagcccttt attactgtgc aagaccggga   300
tatggtaacc tctttgttta ctggggccaa gggactctgg tcactgtctc ctca         354
```

<210> SEQ ID NO 142
<211> LENGTH: 341
<212> TYPE: DNA
<213> ORGANISM: Mus sp.

<400> SEQUENCE: 142

```
gacattgtga tgacacagtc tccatcctcc ctgagtgtgt cagcaggaga gaaggtcact    60
atgagctgca gtccagtca gagtctgtta acagtggaa atccaaagaa ctacttggcc     120
tggtaccagc agaagccagg gcagcctcct aaactgttga tctacggggc atccactagg   180
ggatctgggg tccctgatcg cttcacaggc agtggatctg ggaccgattt cactcttacc   240
atcagcagtg tgcaggctga agacctggca gtttactact gtcagaatga tcatactttt   300
ccgtacacgt tcggagggg gaccaagctg gaaataaaac g                        341
```

<210> SEQ ID NO 143
<211> LENGTH: 348
<212> TYPE: DNA
<213> ORGANISM: Mus sp.

<400> SEQUENCE: 143

```
gaggtgaagc ttctcgagtc tggaggtggc ctggtgcagc ctggaggatc cctgagactc    60
tcctgtgcag cctcaggatt cgattttagt aaagactgga tgagttgggt ccggcaggct   120
ccagggaaag ggctagaatg gattggagaa attaatccag acagtagtac gataaactat   180
gcaccagctc taaaggataa attcatcatc tccagagaga cgccaaaaa tacgctgtac    240
ctgcaaatga acaaagtgag atctgaggac acagcccttt attactgtgc aagatggtca   300
actgggcttg actactgggg ccaaggcacc actctcacag tctcctca               348
```

<210> SEQ ID NO 144
<211> LENGTH: 321
<212> TYPE: DNA
<213> ORGANISM: Mus sp.

<400> SEQUENCE: 144

```
gatatccaga tgacacagac tccatcctcc ctgtctgcct ctctgggaga cagagtcacc    60
atcaattgca gggcaagtca gggcctcagc aattatttaa actggtatca gcagaaacca   120
gatggaactg ttaaactcct gatctactac gcatcaatat tacactcagg agtcccatca   180
aggttcactg gcagtgggtc tggaacagat tattctctca ccattagcac cctggagcaa   240
gaggatattg cacttacttt tgccaacag gtaatacgc ttccgtggac gttcggtgga    300
ggcaccaaac tggaaatcaa c                                             321
```

<210> SEQ ID NO 145
<211> LENGTH: 348
<212> TYPE: DNA
<213> ORGANISM: Mus sp.

<400> SEQUENCE: 145

```
caggttcaac tgcagcagtc tggacctgag ctggtgaagc ctggggcctc agtgaagatt    60
tcctgcaagg cttctggcta tccattcagt acctcctgga tgaactgggt gaagcagagg   120
cctggaaagg gtcttgagtg gattggacgg atttatcttg agatggaga tactaactac    180
aatgggaagt tcacgggcaa ggccacactg actgcagaca atcctccag cacagtttac   240
atgcaactca gcagcctgac atctgaggac tctgcggtct acttctgtgc aagatggagg   300
ggtgactacg actactgggg ccaaggcacc actctcacag tctcctca               348
```

<210> SEQ ID NO 146
<211> LENGTH: 340
<212> TYPE: DNA
<213> ORGANISM: Mus sp.

<400> SEQUENCE: 146

```
gacattgtga tgtcacagtc tccatcctcc ctagctgtgt cagttggaga aaggttact    60
ctgagctgca gtccagtca gagccttta tatagtagca ctcaaaacaa ctacttggcc    120
tggtaccagc agacaccagg gcagtctcct aaactgctga tttactgggc atccactagg   180
gaatctgggg tccctgatcg cttcacaggc agtggatctg ggacagattt cactctcacc   240
atcagcagtg tgaaggctga agacctggca gtttattact gtcagcaata ttatagctat   300
ccgtggacgt tcggtggagg caccaagctg gaaatcaaac                         340
```

<210> SEQ ID NO 147
<211> LENGTH: 354
<212> TYPE: DNA
<213> ORGANISM: Mus sp.

<400> SEQUENCE: 147

```
tctgatgtgc agcttcagga gtcaggacct ggcctcgtga accttctca gactctgtct      60
ctcacctgct ctgtccctga ctactccatc accagtgatt atcactggca ctggatcagg    120
cagtttccag gaaacaaact ggagtggatg ggatacataa gctcaagggg tagtactaac    180
tacaacccat ctctcaaaaa tcgaatctcc atcactcatg acacatctga gaatcagttc    240
ttcctgaaat tgacttctgt gactactgag gactcagcca catattattg tgcaggcttg    300
tcccagttag ctcttgacta ctggggccaa ggcaccactc tcacagtctc ctca          354
```

<210> SEQ ID NO 148
<211> LENGTH: 322
<212> TYPE: DNA
<213> ORGANISM: Mus sp.

<400> SEQUENCE: 148

```
gacatcaaga tgacccagtc tccatcttcc atgtatgcat ctctaggaga gagagtcact     60
atcacttgca aggcgagtca ggacatttat ccctatttaa actggttcca acaaaaacca    120
gggaaatctc ctaagaccct gatctatcgt acaaatagat tgctagatgg ggtcccatca    180
aggttcagtg gcagtggatc tggacaagat tattctctca ccatcagcag cctggactat    240
gaagatatgg gaatttatta ttgtctacag tatgatgagt ttccgctcac gttcggtgct    300
gggaccaagc tggagctgaa ac                                              322
```

<210> SEQ ID NO 149
<211> LENGTH: 360
<212> TYPE: DNA
<213> ORGANISM: Mus sp.

<400> SEQUENCE: 149

```
caagttactc taaaagagtc tggccctggg atattgaagc cctcacagac cctcagtctg     60
acttgttctt tctctggggtt tcactgagc acttctaata tgggtgtagg ctggattcgt    120
cagccttcag ggaagggtct ggagtggctg gcacacatt ggtgggatga tgataagtat    180
tataacccat ccctgaagag ccagctcaca atctccaagg atacctccag aaaccaggtc    240
ttcctcaaga tcaccagtgt ggacactgaa gatactgcca cttactactg tgttcgaagt    300
aactatggtt acgcctggtt tgcttactgg ggccaaggga ctctggtcac tgtctctgca    360
```

<210> SEQ ID NO 150
<211> LENGTH: 334
<212> TYPE: DNA
<213> ORGANISM: Mus sp.

<400> SEQUENCE: 150

```
gacattgtgc tgacccaatc tccagcttct ttggctgtgt ctctagggca gagggccacc     60
atatcctgca gagccagtga aagtgttgat agctatgcca aaagttttat gcactggtac    120
cagcagagac caggacagcc acccaaactc ctcatctatc gtgcatccaa cctagaatct    180
gggatccctg ccaggttcag tggcagtggg tctaggacag acttcaccct caccattaat    240
cctgtggagg ctgatgatgt tgcaacctat tactgtcaac aaagtaatga ggatccgtgg    300
acgttcggtg gaggcaccaa gctggaaatc aaac                                 334
```

<210> SEQ ID NO 151
<211> LENGTH: 357
<212> TYPE: DNA

<213> ORGANISM: Mus sp.

<400> SEQUENCE: 151

```
caggtccagt tgcagcagtc tgggcctgag gtggtgaggc ctggggtctc agtgaagatt    60
tcctgcaagg gttccggcta cacattcact gattatgctg tgcactgggt gaagctgagt   120
catgcaaaga gtctggagtg gattggagtt attagtactt acaatgatta tacatacaac   180
aaccaggatt ttaagggcaa ggccacaatg actgtagaca atcctccag cacagcctat    240
atggaacttg ccagattgac atctgaggat tctgccatct attactgtgc aagaggtaac   300
tcctacttct atgctttgga ctactggggt caaggaacct cagtcaccgt ctcctca      357
```

<210> SEQ ID NO 152
<211> LENGTH: 334
<212> TYPE: DNA
<213> ORGANISM: Mus sp.

<400> SEQUENCE: 152

```
gacattgcgc tgacccaatc tccagcttct ttggctgtgt ctctggggca gagggccacc    60
atttcctgca gagccagcga aagtgttgat aattctggca tttgttttgt gaactggttc   120
caacagaaac caggacagcc acccaaactc ctcatctatg ctgcatccaa ccaaggatcc   180
ggggtccctg ccaggtttag tggcagtggg tctgggacag acttcagcct caacatccat   240
cctatggaga aggatgatac tgcaatgtat ttctgtcagc aaagtaagga ggttccgtgg   300
acgttcggtg gaggcaccaa gctggaaatc aaac                               334
```

<210> SEQ ID NO 153
<211> LENGTH: 363
<212> TYPE: DNA
<213> ORGANISM: Mus sp.

<400> SEQUENCE: 153

```
caggttcagc tgcagcagtc tggagctgag ctggcgagcc tgggacttc agtgaagctg     60
tcctgcaagg cttctggata caccttcaca ttctatggta aagctgggt gaagcagaaa    120
actggacagg gccttgagtg gattggagag atttatcctg gaagttataa tgcttactac   180
aatgacaagt tcaagggcaa ggccacactg actgcagaca atcctccag cacagcctac    240
atgcagctca gcagcctgac atctgaggac tctgccgtct atttctgtgc cagagactat   300
ggtgacccgt attactatgc tatggactac tggggtcaag gaacctcagt caccgtctcc   360
tca                                                                 363
```

<210> SEQ ID NO 154
<211> LENGTH: 334
<212> TYPE: DNA
<213> ORGANISM: Mus sp.

<400> SEQUENCE: 154

```
gacattgtgc tgacacagtc tcctgcttcc ttaactgtgt ctctggggca gagggccacc    60
atctcatgca gggccagcca aagtgtcagt acatctacct taattatat gaactggtac    120
caacagaaac taggacagcc acccaaactc ctcatcaagt atgcatccaa cctagaatct   180
ggggtccctg ccaggttcag tggcagtggg tctgggacag acttcaccct caacatccat   240
cctgtggagg aggaggatat tgcaacatat tactgtcagc acagttggga gattccgtgg   300
acgttcggtg gaggcaccaa gctggaaatc aaac                               334
```

```
<210> SEQ ID NO 155
<211> LENGTH: 354
<212> TYPE: DNA
<213> ORGANISM: Mus sp.

<400> SEQUENCE: 155
gaggtgaagc ttctcgagtc tggaggtggc ctggtgcagc ctggaggatc ccagaaactc    60
tcctgtgcag cctcaggatt cgatttcagt agatactgga tgagttgggt ccggcaggct   120
ccagggaaag ggctagaatg gattggagaa attaatccag atagcagtac ggtaaactat   180
acgccatctc taaaggataa attcatcatc tccagagaca cgccaaaaa tacgctgtac    240 ctgcaaatga gtaaagtgag atctgaggac acagcccttt attactgtgc aagaccggga   300
tatggtaacc tctttgttta ctggggccaa gggactctgg tcactgtctc ctca         354

<210> SEQ ID NO 156
<211> LENGTH: 337
<212> TYPE: DNA
<213> ORGANISM: Mus sp.

<400> SEQUENCE: 156
gatattgtgt tgactcaggc tacaccctct gtacctgtca ctcctggaga gtcagtatcc    60
atctcctgca ggtctagtaa gagtctcctg catactaagg gcgacactta cttgtattgg   120
ttcctgcaga ggccaggcca gtctcctcag ctcctgatat atcggatgtc caaccttgcc   180
tcaggagtcc cagacaggtt cagtggcagt gggtcaggaa ctgttttcac actgagaatc   240
agtagagtgg aggctgagga tgtgggtgtt tattactgta tgcaacatct agaatatcca   300
ttcacgttcg gctcggggac aaagttggaa ataaaac                            337

<210> SEQ ID NO 157
<211> LENGTH: 354
<212> TYPE: DNA
<213> ORGANISM: Mus sp.

<400> SEQUENCE: 157
gaggttcagc tgcagcagtc tggggcagag tctgtgaggt caggggcctc agtcaagttg    60
tcctgcaccg cttctggcct caatattaaa gactactata tgcactgggt gaacctgagg   120
cctgaacagg gcctgagtg gattggatgg attgatcctg agaatggtga tactgaatat   180
gccccggagt tccagggcaa ggccactatg actgcagaca tcttccaa cacagcctac     240 ctgcagctca gcagcctgac atctgaggac actgccgtct attactgtaa tgcttgcaac   300
tacggtagtg cctacggcta ctggggccaa ggcaccactc tcacagtctc ctca         354

<210> SEQ ID NO 158
<211> LENGTH: 322
<212> TYPE: DNA
<213> ORGANISM: Mus sp.

<400> SEQUENCE: 158
gaaacaactg tgacccagtc tccagcatcc ctgtccatgg ctataggaga aaaagtcacc    60
atcagatgca taaccaacac tgatattgat gatgatatga actggtacca gcagaagcca   120
ggggaacctc ctaagctcct tatttcagaa ggcaatggtt tcgtcctgg agtcccatcc    180 cgattctcca gcagtggcta tgcacagat tttgttttta caattgaaaa catgctctca    240
gaagatgttg cagattacta ctgtttgcaa agtgataact tgcctctcac gttcggctcg   300
gggacaaagt tggaaataaa ac                                            322
```

<210> SEQ ID NO 159
<211> LENGTH: 360
<212> TYPE: DNA
<213> ORGANISM: Mus sp.

<400> SEQUENCE: 159

```
gaggtgaagc ttctcgagtc tggaggtggc ctggtgcagc ctggaggatc cctgaaactc      60
tcctgtgcag cctcaggatt cgattttagt agatactgga tgagttgggt ccggcaggct     120
ccagggaaag gactagaatg gattggagat cttaatccag atagcagtgc gataaactat     180
acgccatctc taaaggataa attcatcatc tccagagaca cgccaaaaa tacgctgtac      240
ctgcaaatga gcaaagtgag atctgaggac acagcccttt attactgtac actcattact     300
acgttagtac cctatactat ggacttctgg ggtcaaggaa cctcagtcac cgtctcctca     360
```

<210> SEQ ID NO 160
<211> LENGTH: 340
<212> TYPE: DNA
<213> ORGANISM: Mus sp.

<400> SEQUENCE: 160

```
gacattgtga tgactcagtc tccatcctcc ctgactgtga cagcaggagt gaaggtcact      60
atgagctgca gtccagtca gagtctgtta aacagtggag atcaaaagaa ctgcttgact      120
tggtaccagc agaaaccagg gcagccacct aaactgttga tctactgggc atccactagg     180
gaatctgggg tccctgatcg cttcacaggc agtggatctg gaacagattt cactctcacc     240
atcagcagtg tgcaggctga agacctggca gtttattact gtcagaatga ttatagttat     300
ccgctcacgt tcggtgctgg gaccaagctg gagctgaaac                            340
```

<210> SEQ ID NO 161
<211> LENGTH: 360
<212> TYPE: DNA
<213> ORGANISM: Mus sp.

<400> SEQUENCE: 161

```
gaaatacatc tggtggagtc tgggggaggc ttagtgaagc ctggagggtc cctgaaagtc      60
tcctgtgcag cctctggatt cactttcagt aggtatgcca tgtcttgggt tcgccagact     120
ccggagaaga ggctggagtg ggtcgcaacc attagtggtg gtggtcgtta cacctactat     180
ccagaccttg tgaagggtcg attcaccatc tccagagaca ttgccaggac caccctgtac     240
ctgcaaatga gcagtctgag gtctgaggac acggccatgt attactgtgc aagaacagct     300
cgggcttcga attatgctat ggactactgg ggtcaaggaa cctcagtcac cgtctcctca     360
```

<210> SEQ ID NO 162
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 162

```
gacatccaga tgacccagtc tccatcttcc ctgtctgcat ctgtaggaga tagagtcact      60
atcacttgca aggcgagtca ggacatttat ccctatttaa actggttcca acaaaaacca     120
gggaaagctc ctaagaccct gatctatcgt acaaatagat tgctagatgg ggtcccatca     180
aggttcagtg gcagtggatc tggaacagat tttactttca ccatcagcag cctgcaacct     240
```

```
gaagatattg caacttatta ttgtctacag tatgatgagt ttccgctcac gttcggtgct      300
gggaccaagc tggaaatcaa ac                                              322
```

<210> SEQ ID NO 163
<211> LENGTH: 361
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 163

```
cagatcacct tgaaggagtc tggtcctacg ctggtgaaac ccacacagac cctcacgctg       60
acctgcacct tctctgggtt ctcactcagc actagtaaca tgggtgtggg ctggatccgt      120
cagcccccag gaaaggccct ggagtggctt gcacacattt ggtgggatga tgataagtac      180
tacagcccat ctctgaagag caggctcacc atcaccaagg acacctccaa aaaccaggtg      240
gtccttacaa tgaccaacat ggaccctgtg gacacagcca catattactg tgttcgaagt      300
aactatggtt acgcctggtt tgcttactgg ggccaaggga ctctggtcac tgtctcttca      360
g                                                                      361
```

<210> SEQ ID NO 164
<211> LENGTH: 334
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 164

```
gaaattgtgt tgacacagtc tccagccacc ctgtctttgt ctccagggga aagagccacc       60
ctctcctgca gggccagtga gagtgttgac agctatggca aaagttttat gcactggtac      120
caacagaaac tggccaggc tcccaggctc ctcatctata ggcatccaa cctggaatct       180 ggcatcccag ccaggttcag tggcagtggg tctgggacag acttcactct caccatcagc      240
agcctagagc ctgaagattt tgcagtttat tactgtcagc agagtaatga ggatccgtgg      300
acgttcggtg gaggcaccaa gctggaaatc aaac                                  334
```

<210> SEQ ID NO 165
<211> LENGTH: 358
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 165

```
caggtccagc ttgtgcagtc tgggcctgag gtgaagaagc ctggggcctc agtgaaggtt       60
tcctgcaagg cttctggata caccttcact gactatgctg tgcattgggt gcgccaggcc      120
cccggaaaaa ggcttgagtg gattggagtg atcagcactt acaatgatta cacatacaat      180
aaccaggact tcaagggcag agtcaccatg accagggaca tccgcgagac acagcctac       240 atggagctga gcagactgag atctgaagac acggctgtgt attactgtgc gagaggtaac      300
tcctacttct atgctttgga ctactggggt caaggaacct cagtcaccgt ctcctcag       358
```

<210> SEQ ID NO 166
<211> LENGTH: 337
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 166
gatattgtga tgactcagtc tccactctcc ctgcccgtca cccctggaga gccggcctcc      60
atctcctgca ggtctagtaa gagcctcctg catactaaag agacaccta tttgtattgg     120 ttcctgcaga agccagggca gtctccacag ctcctgatct atcggatgtc taatcgggcc     180
tccggggtcc ctgacaggtt cagtggcagt ggatcaggca cagattttac actgaaaatc     240
agcagagtgg aggctgagga tgttggggtt tattactgta tgcaacatct agaatatcca     300
ttcacgttcg gccaggggac aaagttggaa atcaaac                             337

<210> SEQ ID NO 167
<211> LENGTH: 355
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 167
caggtgcagc tggtgcagtc tggggctgag gtgaagaagc ctggggcctc agtgaaggtt      60
tcctgcaagg catctggata caccttcaaa gactactata tgcactgggt gcgacaggcc     120
cctggacaag gcttgagtg gatgggatgg atcgaccctg aaaatggtga cacagaatac     180
gcaccggagt tccagggcag agtcaccatg accagggaca cgtccacgag cacagtctac     240
atggagctga gcagcctgag atctgaggac acggccgtgt attactgtaa tgcttgcaac     300
tacggtagtg cctacggcta ctggggccaa ggcaccactc tcaccgtctc ctcag          355

<210> SEQ ID NO 168
<211> LENGTH: 322
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 168
gaaacgacac tcacgcagtc tccagcattc atgtcagcga ctccaggaga caaagtcaac      60
atctcctgca taaccaacac agacattgat gatgatatga actggtacca acagaaacca     120
ggagaagctg ctattctcct tatttcagaa ggtaatggtc tccgtcctgg aatcccacct     180
cgattcagtg gcagcgggta tggaacagat tttacccctca caattaataa catagaatct     240
gaggatgctg catattactt ctgtctacaa agtgataact gcctctcac gttcggctcg     300 gggacaaagt tggaaataaa ac                                             322

<210> SEQ ID NO 169
<211> LENGTH: 361
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 169

```
gaggtgcagc tggtggagtc tgggggaggc ttggtccagc ctgggggtc cctgagactc      60
tcctgtgcag cctctggatt cgactttagt agatattgga tgagctgggt ccgccaggct    120
ccagggaagg ggctggagtg gatcggcgac ctaaacccag attcaagtgc gataaactat    180
gtggactctg tgaagggccg attcaccatc tccagagaca acgccaagaa ctcactgtat    240
ctgcaaatga acagcctgag agccgaggac acggctgtgt attactgtac actcattact    300
acgttagtac cctatactat ggacttctgg ggtcaaggaa cctcagtcac cgtctcctca    360
g                                                                    361
```

<210> SEQ ID NO 170
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 170

```
Thr Ser Asn Met Gly Val Gly
1               5
```

<210> SEQ ID NO 171
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 171

```
His Ile Trp Trp Asp Asp Asp Lys Tyr Tyr Ser Pro Ser Leu Lys Ser
1               5                   10                  15
```

<210> SEQ ID NO 172
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 172

```
Ser Asn Tyr Gly Tyr Ala Trp Phe Ala Tyr
1               5                   10
```

<210> SEQ ID NO 173
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 173

```
Lys Ala Ser Gln Asp Ile Tyr Pro Tyr Leu Asn
1               5                   10
```

```
<210> SEQ ID NO 174
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 174

Arg Thr Asn Arg Leu Leu Asp
1               5

<210> SEQ ID NO 175
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 175

Leu Gln Tyr Asp Glu Phe Pro Leu Thr
1               5

<210> SEQ ID NO 176
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 176

Asp Tyr Ala Val His
1               5

<210> SEQ ID NO 177
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 177

Val Ile Ser Thr Tyr Asn Asp Tyr Thr Tyr Asn Asn Gln Asp Phe Lys
1               5                   10                  15

Gly

<210> SEQ ID NO 178
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 178

Gly Asn Ser Tyr Phe Tyr Ala Leu Asp Tyr
1               5                   10

<210> SEQ ID NO 179
```

```
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 179

Arg Ala Ser Glu Ser Val Asp Ser Tyr Gly Lys Ser Phe Met His
1               5                   10                  15

<210> SEQ ID NO 180
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 180

Arg Ala Ser Asn Leu Glu Ser
1               5

<210> SEQ ID NO 181
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 181

Gln Gln Ser Asn Glu Asp Pro Trp Thr
1               5

<210> SEQ ID NO 182
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 182

Gly Phe Ser Leu Ser Thr Ser Asn Met
1               5

<210> SEQ ID NO 183
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 183

Trp Trp Asp Asp Asp
1               5

<210> SEQ ID NO 184
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 184

Gly Tyr Thr Phe Thr Asp Tyr
1               5

<210> SEQ ID NO 185
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 185

Ser Thr Tyr Asn Asp Tyr
1               5

<210> SEQ ID NO 186
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 186

Ser Thr Ser Asn Met Gly Val Gly
1               5

<210> SEQ ID NO 187
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 187

Trp Leu Ala His Ile Trp Trp Asp Asp Asp Lys Tyr
1               5                   10

<210> SEQ ID NO 188
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 188

Val Arg Ser Asn Tyr Gly Tyr Ala Trp Phe Ala
1               5                   10

<210> SEQ ID NO 189
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 189

Tyr Pro Tyr Leu Asn Trp Phe
1               5

<210> SEQ ID NO 190
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 190

Thr Leu Ile Tyr Arg Thr Asn Arg Leu Leu
1               5                   10

<210> SEQ ID NO 191
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 191

Leu Gln Tyr Asp Glu Phe Pro Leu
1               5

<210> SEQ ID NO 192
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 192

Thr Asp Tyr Ala Val His
1               5

<210> SEQ ID NO 193
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 193

Trp Ile Gly Val Ile Ser Thr Tyr Asn Asp Tyr Thr Tyr
1               5                   10

<210> SEQ ID NO 194
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 194

Ala Arg Gly Asn Ser Tyr Phe Tyr Ala Leu Asp
1               5                   10
```

```
<210> SEQ ID NO 195
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 195

Asp Ser Tyr Gly Lys Ser Phe Met His Trp Tyr
1               5                   10

<210> SEQ ID NO 196
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 196

Leu Leu Ile Tyr Arg Ala Ser Asn Leu Glu
1               5                   10

<210> SEQ ID NO 197
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 197

Gln Gln Ser Asn Glu Asp Pro Trp
1               5
```